US012600754B2

(12) United States Patent
Abe et al.

(10) Patent No.: US 12,600,754 B2
(45) Date of Patent: Apr. 14, 2026

(54) PROTEIN FIBER PRODUCTION METHOD

(71) Applicant: Spiber Inc., Yamagata (JP)

(72) Inventors: Yunosuke Abe, Tsuruoka (JP);
Hirotada Ando, Kariya (JP); Koichi Kotaka, Tsuruoka (JP)

(73) Assignee: Spiber Inc., Yamagata (JP)

( * ) Notice: Subject to any disclaimer, the term of this patent is extended or adjusted under 35 U.S.C. 154(b) by 934 days.

(21) Appl. No.: 17/279,564

(22) PCT Filed: Sep. 30, 2019

(86) PCT No.: PCT/JP2019/038637
§ 371 (c)(1),
(2) Date: Mar. 24, 2021

(87) PCT Pub. No.: WO2020/067574
PCT Pub. Date: Apr. 2, 2020

(65) Prior Publication Data
US 2021/0395317 A1     Dec. 23, 2021

(30) Foreign Application Priority Data
Sep. 28, 2018     (JP) ................................. 2018-185598

(51) Int. Cl.
| | |
|---|---|
| *C07K 14/435* | (2006.01) |
| *C07K 14/47* | (2006.01) |
| *D01D 5/06* | (2006.01) |
| *D01F 4/00* | (2006.01) |
| *D01F 4/02* | (2006.01) |

(52) U.S. Cl.
CPC .... *C07K 14/43518* (2013.01); *C07K 14/4741* (2013.01); *D01D 5/06* (2013.01); *D01F 4/00* (2013.01); *D01F 4/02* (2013.01); *D10B 2211/01* (2013.01); *D10B 2211/04* (2013.01)

(58) Field of Classification Search
None
See application file for complete search history.

(56) References Cited

U.S. PATENT DOCUMENTS

| | | | |
|---|---|---|---|
| 5,252,285 A | 10/1993 | Lock | |
| 9,187,537 B2 * | 11/2015 | Cha .................. | C07K 14/43595 |
| 11,505,654 B2 * | 11/2022 | Widmaier ............... | D01D 5/00 |
| 2005/0054830 A1 † | 3/2005 | Islam | |
| 2012/0231499 A1 | 9/2012 | Lee et al. | |
| 2014/0058066 A1 | 2/2014 | Sekiyama et al. | |
| 2014/0326165 A1 | 11/2014 | Saleh | |
| 2015/0292120 A1 | 10/2015 | Lewis et al. | |
| 2018/0193524 A1 | 7/2018 | Shoseyov et al. | |
| 2019/0002644 A1 | 1/2019 | Ohta et al. | |
| 2022/0127755 A1 * | 4/2022 | Ando ......................... | D01F 4/00 |

FOREIGN PATENT DOCUMENTS

| | | | | | |
|---|---|---|---|---|---|
| CN | 1078509 | A | 11/1993 | | |
| CN | 1664183 | A † | 9/2005 | | |
| CN | 102477592 | A | 5/2012 | | |
| CN | 103320886 | A | 9/2013 | | |
| CN | 103739691 | A | 4/2014 | | |
| CN | 106048765 | A | 10/2016 | | |
| CN | 106245134 | A | 12/2016 | | |
| CN | 106928729 | A | 7/2017 | | |
| JP | 2005-515309 | A | 5/2005 | | |
| JP | 2013-528568 | A | 7/2013 | | |
| JP | 5540154 | B2 | 7/2014 | | |
| JP | 5584932 | B2 | 9/2014 | | |
| JP | 2018-512407 | A | 5/2018 | | |
| KR | 10-2007-0000892 | A | 1/2007 | | |
| KR | 10-0796099 | B1 | 1/2008 | | |
| WO | 93/015244 | A1 | 8/1993 | | |
| WO | 9315244 | A1 † | 8/1993 | | |
| WO | 03/060207 | A1 | 7/2003 | | |
| WO | WO-2004090205 | A2 * | 10/2004 | ............... | D01F 4/00 |
| WO | 2013/065651 | A1 | 5/2013 | | |
| WO | 2016/149414 | A1 | 9/2016 | | |
| WO | 2017/110922 | A1 | 6/2017 | | |
| WO | 2018/164234 | A1 | 9/2018 | | |

OTHER PUBLICATIONS

Goujon et al., "Effect of solvent on Ionic Liquid dissolved regenerated Antheraea assamensis Silk Fibroin", J. Appl. Polym. Sci. DOI: 10.1002/APP.38666 pp. 4411-4416 (Year: 2012).*

Yan et al., "Wet-spinning of regenerated silk fiber from aqueous silk fibroin solution: discussion of spinning parameters", Biomacromolecules 11: 1-5 (Year: 2010).*

Reddy et al., "Wet Cross-linking Gliadin fibers with citric acid and a quantitative relationship between cross-linking conditions and mechanical properties", J. Agric. Food Chem. 57: 90-98 (Year: 2009).*

Um et al., "Wet spinning of silk polymer I. Effect of coagulation conditions on the morphological feature of filament," International Journal of Biological Macromolecules, 34: 89-105 (2004).

Xia et al., "Native-sized recombinant spider silk protein produced in metabolically engineered *Escherichia coli* results in strong fiber," PNAS, 107 (32): 14059-14063 (2010).

International Search Report issued in corresponding International Patent Application No. PCT/JP2019/038637 dated Dec. 24, 2019.

(Continued)

*Primary Examiner* — Anand U Desai
(74) *Attorney, Agent, or Firm* — Studebaker Brackett PLLC

(57)     ABSTRACT

Disclosed is a method for producing a protein fiber, the method including: bringing a spinning dope containing a protein and an organic solvent into contact with a coagulation liquid to coagulate the protein, wherein a content of the protein in the spinning dope is more than 10% by mass based on a total amount of the spinning dope, and the coagulation liquid contains water or an aqueous solution of pH 0.25 or more and pH 10.00 or less.

20 Claims, 5 Drawing Sheets
Specification includes a Sequence Listing.

(56)        References Cited

OTHER PUBLICATIONS

International Preliminary Report on Patentability and Written Opinion issued in corresponding International Patent Application No. PCT/JP2019/038637 dated Apr. 8, 2021.

Heidebrecht et al., "Biomimetic fibers made of recombinant spidroins with the same toughness as natural spider silk," Advanced Materials, 27: 2189-2194 (2015).

Notification of Third Party Observation filed in counterpart European Patent Application No. 19866282.7 dated Aug. 17, 2022.

Extended European Search Report issued in corresponding European Patent Application No. 19866282.7 dated Jul. 1, 2022.

Heidebrecht, Aniela, Lukas Eisoldt, Johannes Diehl, Andreas Schmidt, Martha Geffers, Gregor Lang, and Thomas Scheibel. Biomimetic fibers made of recombinant spidroins with the same toughness as natural spider silk. Advanced materials 27, No. 13 (2015): 2189-2194.†

\* cited by examiner
† cited by third party

AAAA (SEQ ID NO: 63)

AAAA (SEQ ID NO: 63)
GPGXX (SEQ ID NO: 64)

PROTEIN FIBER PRODUCTION METHOD

SEQUENCE LISTING SUBMISSION VIA EFS-WEB

A computer readable text file, entitled "SequenceListing.txt," created on or about Mar. 24, 2021 with a file size of about 348 kb contains the sequence listing for this application and is hereby incorporated by reference in its entirety.

TECHNICAL FIELD

The present invention relates to a method for producing a protein fiber.

BACKGROUND ART

As a method for producing a protein fiber containing a structural protein as a main component, a wet spinning method and dry wet spinning method have been conventionally known including discharging a spinning dope from a nozzle into a coagulation bath to coagulate the spinning dope, thus forming a fiber.

In the wet spinning method and dry wet spinning method of the protein fiber, it has been reported that a protein fiber is obtained by using, as a spinning dope (dope solution), a protein solution in which a protein is dissolved in a solvent; extruding the spinning dope from a nozzle into a coagulation liquid; and removing the solvent from the spinning dope to form a fiber, thus forming an undrawn yarn (see, for example, Patent Literature 1, Patent Literature 2, Non-Patent Literature 1, and Non-Patent Literature 2).

As the solvent used for the coagulation liquid in the production of the protein fiber, lower alcohols such as methanol, ethanol, and 2-propanol, and ketones such as acetone have been generally used. For example, a method including dissolving regenerated silk protein (regenerated silk fibroin) in formic acid, and introducing the dope into a coagulation liquid such as lower alcohol or acetone to form regenerated silk fibroin fiber (Non-Patent Literature 1), a method including dissolving a spider silk fibroin having an amino acid sequence derived from Masp1 of *Nephila clavipes* into hexafluoroisopropanol (HFIP), and introducing the dope into a methanol coagulation liquid to form a spider silk fibroin fiber (Non-Patent Literature 2), and the like have been reported.

CITATION LIST

Patent Literature

Patent Literature 1: JP 5540154 B
Patent Literature 2: JP 5584932 B

Non Patent Literature

Non Patent Literature 1: Int. J. Biol. Macromol., vol. 34, 2004, pp. 89-105
Non Patent Literature 2: PNAS, Aug. 10, 2010, vol. 107, No. 32, pp. 14059-14063

SUMMARY OF INVENTION

Technical Problem

When a protein fiber is produced by using a high molecular weight structural protein, which is a material extremely useful in the future, for example, silk fibroin, spider silk fibroin, keratin, and the like, by the wet spinning method and dry wet spinning method, the coagulation liquid for forming such a protein fiber is extremely limited. Among these coagulation liquids, lower alcohols such as methanol, ethanol, and 2-propanol, and ketones such as acetone, which are procurable with relatively low cost and have a fiber-forming property, are generally used as a coagulation liquid for a structural protein.

However, these coagulation solvents are designated as the hazardous materials Class 4 under the Fire Defense Law and have a risk of explosion, fire, and the like. Therefore, these coagulation solvents are difficult to consider to be suitable as a coagulation solvent which is most consumed in a large amount in the production process from the viewpoint of safety. Further reduction in load has been desired from the viewpoint of production cost and environmental load.

In view of the problems of the above-described conventional art, an object of the present invention is to provide a method for producing a protein fiber formed by using a coagulation liquid containing water or an aqueous solution.

Solution to Problem

The present inventors conducted intensive studies to solve the above-described problems of the conventional art. As a result, the present inventors found that a protein fiber can be produced by combining a spinning dope containing a protein and an organic solvent with a coagulation liquid containing water or an aqueous solution of pH 0.25 or more and pH 10.00 or less.

That is, the present invention relates to, for example, the following inventions.

[1]

A method for producing a protein fiber, the method including:

bringing a spinning dope containing a protein and an organic solvent into contact with a coagulation liquid to coagulate the protein, wherein a content of the protein in the spinning dope is more than 10% by mass based on a total amount of the spinning dope, and the coagulation liquid contains water or an aqueous solution of pH 0.25 or more and pH 10.00 or less.

[2]

The method according to [1], wherein a content of water or aqueous solution in the coagulation liquid is 60% by mass or more based on a total amount of the coagulation liquid.

[3]

The method according to [1] or [2], wherein the aqueous solution is a salt aqueous solution, an acid aqueous solution, or a mixed solution thereof.

[4]

The method according to [3], wherein the acid aqueous solution is a carboxylic acid aqueous solution.

[5]

The method according to [3] or [4], wherein a content of salt in the coagulation liquid is 0.1% by mass or more based on a total amount of the coagulation liquid.

[6]

The method according to [5], wherein the salt includes at least one type selected from the group consisting of carboxylate and an inorganic salt.

[7]

The method according to [6], wherein the inorganic salt includes at least one type selected from the group consisting of a sulfate, a chloride, a nitrate, an iodide salt, a carbonate, a hydrogen sulfate, a hydrogen phosphate, a bicarbonate, and a thiocyanate.

[8]

The method according to [6] or [7], wherein the inorganic salt includes at least one type selected from the group consisting of a sulfate, a chloride, a hydrogen phosphate, and a bicarbonate.

[9]

The method according to [7] or [8], wherein the chloride includes at least one type selected from the group consisting of sodium chloride, calcium chloride, ammonium chloride, potassium chloride, lithium chloride, magnesium chloride, and guanidinium chloride.

[10]

The method according to any of [7] to [9], wherein the sulfate includes at least one type selected from the group consisting of ammonium sulfate, potassium sulfate, sodium sulfate, lithium sulfate, magnesium sulfate, and calcium sulfate.

[11]

The method according to any of [3] to [10], wherein the salt aqueous solution includes at least one type selected from the group consisting of a sodium sulfate aqueous solution, a sodium chloride aqueous solution, brackish water, and sea water.

[12]

The method according to any of [3] to [11], wherein a content of an organic solvent dissolved from a spinning dope in contact with a coagulation liquid in the coagulation liquid is 40% by mass or less based on 100% by mass of total content of the salt aqueous solution in the coagulation liquid and the organic solvent dissolved in the coagulation liquid.

[13]

The method according to any of [1] to [12], wherein an average hydropathy index of the protein is more than −1.3.

[14]

The method according to any of [1] to [13], wherein the protein includes at least one type selected from the group consisting of spider silk protein, silk protein, collagen protein, resilin protein, elastin protein, and keratin protein.

[15]

The method according to any of [1] to [14], wherein the protein is keratin protein or spider silk protein.

[16]

The method according to any of [1] to [15], wherein the protein is spider silk protein.

[17]

The method according to any of [1] to [16], wherein the average hydropathy index of the protein is more than −0.8.

[18]

The method according to any of [1] to [17], further including drawing the coagulated protein.

[19]

The method according to any of [1] to [18], wherein the organic solvent includes at least one type selected from the group consisting of formic acid, dimethyl sulfoxide, and hexafluoroisopropanol.

[20]

The method according to any one of [1] to [19], wherein the organic solvent includes at least one type selected from the group consisting of formic acid and dimethyl sulfoxide.

[21]

The method according to any of [1] to [20], wherein the spinning dope further contains a dissolution promoter.

[22]

A method for producing a protein fiber, the method including:

bringing a spinning dope containing a protein and a solvent into contact with a coagulation liquid to coagulate the protein, wherein a content of the protein in the spinning dope is more than 10% by mass based on a total amount of the spinning dope, and the coagulation liquid contains water or an aqueous solution of pH 0.25 or more and pH 2.50 or less, or pH 7.50 or more and pH 10.00 or less.

Advantageous Effects of Invention

The present invention can provide a method for producing a protein fiber formed by using a coagulation liquid containing water or an aqueous solution. Use of a coagulation liquid containing water or an aqueous solution can reduce a risk of explosion, fire, and the like, production cost, and environmental load.

DESCRIPTION OF EMBODIMENTS

Figure 1:
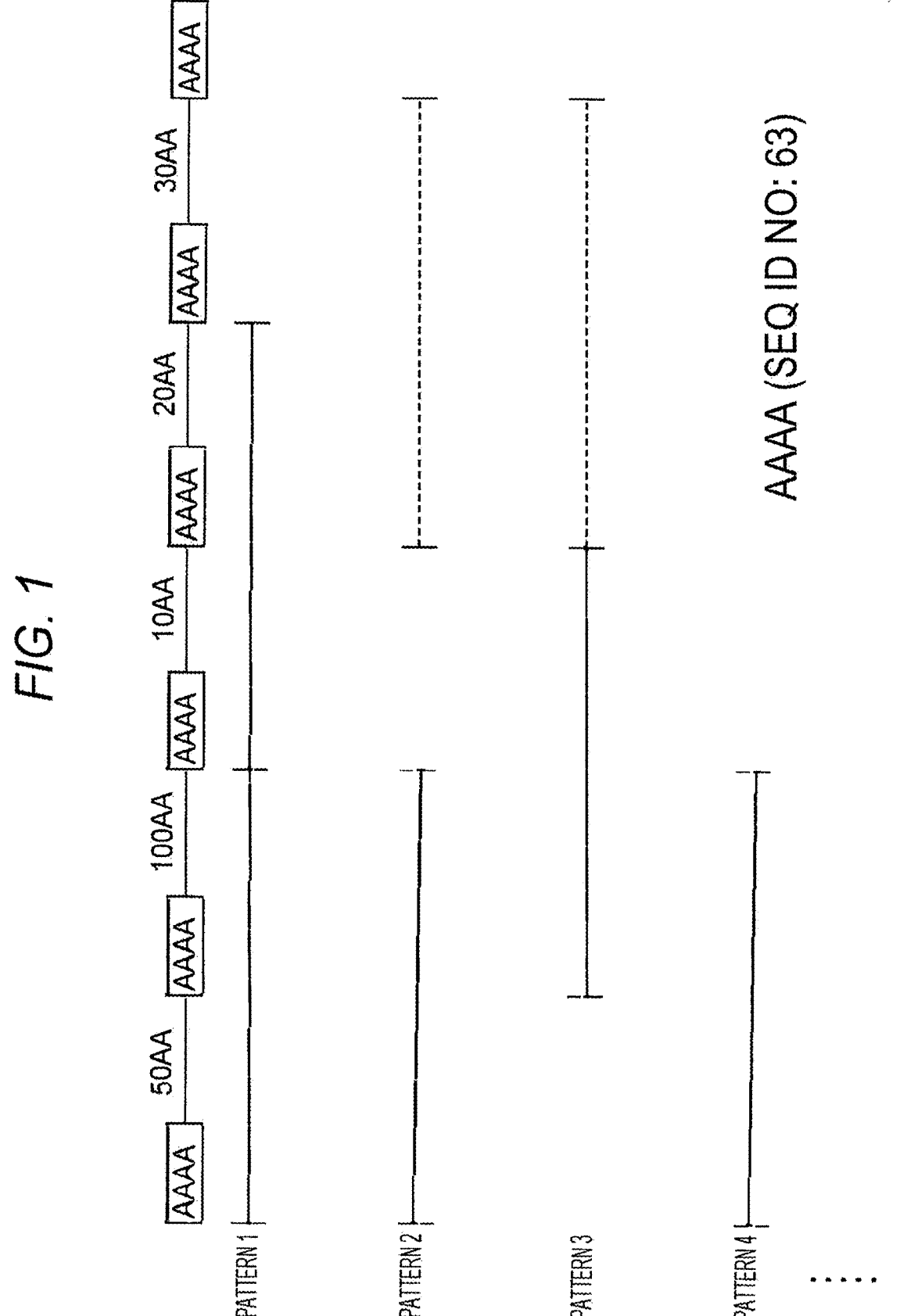
FIG. 1 is a schematic view illustrating an example of a domain sequence of a spider fibroin comprising the amino acid sequence set forth in SEQ ID NO: 63 (AAAA).

Hereinafter, embodiments of the present invention will be described in detail. However, the present invention is not limited to the following embodiments.

[Method for Producing Protein Fiber]

The method for producing a protein fiber of the present embodiment includes a process of bringing a spinning dope containing a protein and an organic solvent into contact with a coagulation liquid to coagulate the protein. Here, the content of protein in the spinning dope is more than 10% by mass based on the total amount of the spinning dope. Further, the coagulation liquid contains water or an aqueous solution of pH 0.25 or more and pH 10.00 or less. The method for producing a protein fiber of the present embodiment can be performed in accordance with a publicly known spinning method such as wet spinning and dry wet spinning.

<Spinning Dope>

The spinning dope according to the present embodiment contains a protein and an organic solvent.

(Protein)

The protein fiber produced according to the production method of the present embodiment contains a protein as a main component. The protein contained in the spinning dope of the present embodiment is an artificially produced protein (artificial protein), but is not natural protein or a purified product thereof. The method for artificially producing a protein is not particularly limited. The protein may be those produced by microorganisms or the like by a gene recombination technology, or may be those produced through synthesis.

The protein may be, for example, a structural protein or an artificial structural protein derived from the structural protein. The structural protein means a protein that forms or maintains its structure, form, and the like in vivo.

Examples of the structural protein include spider silk protein (spider silk fibroin, for example), silk protein, collagen protein, resilin protein, elastin protein, and keratin protein.

The spider silk protein of the present embodiment includes naturally occurring spider silk protein and modified spider silk protein (hereinafter, also referred to as "modified fibroin"). The term "naturally occurring spider silk protein" as used herein means a spider silk protein having the same amino acid sequence as a naturally occurring spider silk protein (spider silk fibroin, for example), and the "modified spider silk protein" or the "modified fibroin" means a spider silk protein having an amino acid sequence different from that of the naturally occurring spider silk protein.

Examples of the naturally occurring spider silk protein include spider fibroins produced by spiders, such as major dragline silk proteins, flagelliform silk proteins, and minor ampullate gland proteins. The major dragline silk has a repetitive region composed of crystal regions and noncrystal regions (also referred to as amorphous region), and therefore has high stress and stretchability. The spider flagelliform silk does not have crystal regions, but have a repetitive region composed of amorphous regions. The flagelliform silk has high stretchability, although its stress is inferior to that of the major dragline silk.

The major dragline silk protein is produced in the major ampullate glands of spiders, and has a feature of being excellent in toughness. Examples of the major dragline silk protein include major ampullate spidroins MaSp1 and MaSp2 derived from *Nephila clavipes* and ADF3 and ADF4 derived from *Araneus diadematus*. ADF3 is one of the two major dragline silk proteins of *Araneus diadematus*. The spider silk protein may be a spider silk protein derived from these dragline silk proteins. The spider silk protein derived from ADF3 is relatively easy to synthesize and has excellent characteristics in terms of strength elongation and toughness.

The flagelliform silk protein is produced in flagelliform glands of spiders. Examples of the flagelliform silk protein include flagelliform silk proteins derived from *Nephila clavipes*.

Examples of the spider fibroin produced by spiders include spider silk proteins produced by spiders belonging to the genus *Araneus* such as *Araneus ventricosus, Araneus diadematus, Araneus pinguis, Araneus pentagrammicus,* and *Araneus nojimai*; spiders belonging to the genus *Neoscona* such as *Neoscona scylla, Neoscona nautica, Neoscona adianta,* and *Neoscona scylloides*; spiders belonging to the genus *Pronus* such as *Pronous minutes*; spiders belonging to the genus *Cyrtarachne* such as *Cyrtarachne bufo* and *Cyrtarachne inaequalis*; spiders belonging to the genus *Gasteracantha* such as *Gasteracantha kuhli* and *Gasteracantha mammosa*; spiders belonging to the genus *Ordgarius* such as *Ordgarius hobsoni* and *Ordgarius sexspinosus*; spiders belonging to the genus *Argiope* such as *Argiope amoena, Argiope minuta,* and *Argiope bruennich*; spiders belonging to the genus *Arachnura* such as *Arachnura logio*; spiders belonging to the genus *Acusilas* such as *Acusilas coccineus*; spiders belonging to the genus *Cytophora* such as *Cyrtophora moluccensis, Cyrtophora exan-*

*thematica,* and *Cyrtophora unicolor*; spiders belonging to the genus *Poltys* such as *Poltys illepidus*; spiders belonging to the genus *Cyclosa* such as *Cyclosa octotuberculata, Cyclosa sedeculata, Cyclosa vallata,* and *Cyclosa atrata*; and spiders belonging to the genus *Chorizopes* such as *Chorizopes nipponicus*; and spider silk proteins produced by spiders belonging to the genus *Tetragnatha* such as *Tetragnatha praedonia, Tetragnatha maxillosa, Tetragnatha extensa,* and *Tetragnatha squamata*; spiders belonging to the genus *Leucauge* such as *Leucauge magnifwca, Leucauge blanda,* and *Leucauge subblanda*; spiders belonging to the genus *Nephila* such as *Nephila clavate* and *Nephila pilipes*; spiders belonging to the genus *Menosira* such as *Menosira ornata*; spiders belonging to the genus *Dyschiriognatha* such as *Dyschiriognatha tenera*; spiders belonging to the genus *Latrodectus* such as *Latrodectus mactans, Latrodectus hasseltii, Latrodectus geometricus,* and *Latrodectus tredecimguttatus*; and spiders belonging to the family Tetragnathidae such as spiders belonging to the genus *Euprosthenops.*

More specific examples of the spider silk protein produced by spiders include fibroin-3 (adf-3) [derived from *Araneus diadematus*] (GenBank Accession No. AAC47010 (amino acid sequence), U47855 (base sequence)), fibroin-4 (adf-4) [derived from *Araneus diadematus*] (GenBank Accession No. AAC47011 (amino acid sequence), U47856 (base sequence)), dragline silk protein spidroin 1 [derived from *Nephila clavipes*] (GenBank Accession No. AAC04504 (amino acid sequence), U37520 (base sequence)), major ampullate spidroin 1 [derived from *Latrodectus hesperus*] (GenBank Accession No. ABR68856 (amino acid sequence), EF595246 (base sequence)), dragline silk protein spidroin 2 [derived from *Nephila clavata*] (GenBank Accession No. AAL32472 (amino acid sequence), AF441245 (base sequence)), major ampullate spidroin 1 [derived from *Euprosthenops australis*](GenBank Accession No. CAJ00428 (amino acid sequence), AJ973155 (base sequence)), and major ampullate spidroin 2 [*Euprosthenops australis*] (GenBank Accession No. CAM32249.1 (amino acid sequence), AM490169 (base sequence)), minor ampullate silk protein 1 [*Nephila clavipes*] (GenBank Accession No. AAC14589.1 (amino acid sequence)), minor ampullate silk protein 2 [*Nephila clavipes*] (GenBank Accession No. AAC14591.1 (amino acid sequence)), and minor ampullate spidroin-like protein [*Nephilengys cruentata*] (GenBank Accession No. ABR37278.1 (amino acid sequence).

The spider silk protein of the present embodiment may be, for example, a protein including a domain sequence represented by Formula 1: $[(A)_n$ motif-REP$]_m$ or Formula 2: $[(A)_n$ motif-REP$]_m$-$(A)_n$ motif. In the spider silk protein of the present embodiment, an amino acid sequence (N-terminal sequence and C-terminal sequence) may be further added to either or both of the N-terminal side and C-terminal side of the domain sequence. The N-terminal sequence and the C-terminal sequence are not limited thereto, but, typically are regions having no repetitions of amino acid motifs characterized in fibroin, and each consist of amino acids of approximately 100 residues.

The term "domain sequence" as used herein is an amino acid sequence that produces a crystal region (typically, corresponding to the $(A)_n$ motif of the amino acid sequence) and an amorphous region (typically, corresponding to the REP of the amino acid sequence) specific to fibroin, and means an amino acid sequence represented by Formula 1: $[(A)_n$ motif-REP$]_m$ or Formula 2: $[(A)_n$ motif-REP$]_m$-$(A)_n$ motif. Here, the $(A)_n$ motif represents an amino acid sequence mainly consisting of alanine residues, and the number of amino acid residues is 2 to 27. The number of amino acid residues of the $(A)_n$ motif may be 2 to 20, 4 to 27, 4 to 20, 8 to 20, 10 to 20, 4 to 16, 8 to 16, or 10 to 16. Further, the proportion of the number of alanine residues relative to the total number of amino acid residues in the $(A)_n$ motif may be 40% or more, 60% or more, 70% or more, 80% or more, 83% or more, 85% or more, 86% or more, 90% or more, 95% or more, or 100% (which means that the $(A)_n$ motif consists of only alanine residues). At least seven of a plurality of $(A)_n$ motifs in the domain sequence may consist of only alanine residues. The REP represents an amino acid sequence consisting of 2 to 200 amino acid residues. The REP may be an amino acid sequence consisting of 10 to 200 amino acid residues, or may be an amino acid sequence consisting of 10 to 40, 10 to 60, 10 to 80, 10 to 100, 10 to 120, 10 to 140, 10 to 160, or 10 to 180 amino acid residues. m represents an integer of 2 to 300, or may be an integer of 8 to 300, 10 to 300, 10 to 300, 20 to 300, 40 to 300, 60 to 300, 80 to 300, 10 to 200, 20 to 200, 20 to 180, 20 to 160, 20 to 140, or 20 to 120. A plurality of $(A)_n$ motifs may be the same amino acid sequences or different amino acid sequences. A plurality of REPs may be the same amino acid sequences or different amino acid sequences.

The modified spider silk protein (modified fibroin) may be, for example, those obtained by modifying an amino acid sequence derived from naturally occurring spider fibroin (for example, those obtained by modifying the gene sequence of cloned naturally occurring spider fibroin to modify the amino acid sequence thereof), or may be those obtained by being artificially designed and synthesized rather than depending on naturally occurring spider fibroin (for example, those having a desired amino acid sequence obtained by chemically synthesizing a nucleic acid encoding the designed amino acid sequence). Incidentally, in the present embodiment, a modified spider silk fibroin, which is excellent in the heat retention property, moisture-absorptive heat generation property, and/or flame retardancy, is preferably used as the modified fibroin.

The modified fibroin can be obtained by, for example, performing modification of the amino acid sequence corresponding to, for example, substitution, deletion, insertion, and/or addition of one or a plurality of amino acid residues, with respect to the gene sequence of cloned naturally occurring spider fibroin. The substitution, deletion, insertion, and/or addition of amino acid residues can be performed by a method known to those skilled in the art such as site-directed mutagenesis. Specifically, the modification may be performed according to a method described in literatures such as Nucleic Acid Res. 10, 6487 (1982), and Methods in Enzymology, 100, 448 (1983).

Specific examples of the modified fibroin include a modified fibroin derived from major dragline silk proteins produced in major ampullate glands of spiders (first modified fibroin), a modified fibroin having a reduced content of glycine residue (second modified fibroin), a modified fibroin having a reduced content of $(A)_n$ motif (third modified fibroin), a modified fibroin having a reduced content of glycine residue and a reduced content of $(A)_n$ motif (fourth modified fibroin), a modified fibroin having a domain sequence including a region with locally high hydropathy index (fifth modified fibroin), and a modified fibroin having a domain sequence having a reduced content of glutamine residue (sixth modified fibroin).

The modified fibroin derived from major dragline silk proteins produced in major ampullate glands of spiders (first modified fibroin) includes a protein including a domain sequence represented by Formula 1: $[(A)_n \text{ motif-REP}]_m$. In the first modified fibroin, in Formula 1, n is preferably an integer of 3 to 20, more preferably an integer of 4 to 20, still more preferably an integer of 8 to 20, even still more preferably an integer of 10 to 20, still further preferably an integer of 4 to 16, particularly preferably an integer of 8 to 16, and most preferably an integer of 10 to 16. In the first modified fibroin, in Formula 1, the number of amino acid residues constituting the REP is preferably 10 to 200, more preferably 10 to 150, still more preferably 20 to 100, and even still more preferably 20 to 75. In the first modified fibroin, the total number of glycine residues, serine residues, and alanine residues included in the amino acid sequence represented by Formula 1: $[(A)_n \text{ motif-REP}]_m$ is preferably 40% or more, more preferably 60% or more, and still more preferably 70% or more, relative to the total number of amino acid residues.

The first modified fibroin may be a protein which includes units of an amino acid sequence represented by Formula 1: $[(A)_n \text{ motif-REP}]_m$ and whose C-terminal sequence is an amino acid sequence set forth in any of SEQ ID NO: 1 to 3 or an amino acid sequence having a homology of 90% or more with the amino acid sequence set forth in any of SEQ ID NO: 1 to 3.

The amino acid sequence set forth in SEQ ID NO: 1 is identical to an amino acid sequence consisting of 50 amino acid residues of the C-terminal of an amino acid sequence of ADF3 (GI: 1263287, NCBI). The amino acid sequence set forth in SEQ ID NO: 2 is identical to an amino acid sequence set forth in SEQ ID NO: 1 in which 20 amino acid residues have been removed from the C-terminal. The amino acid sequence set forth in SEQ ID NO: 3 is identical to an amino acid sequence set forth in SEQ ID NO: 1 in which 29 amino acid residues have been removed from the C-terminal.

More specific examples of the first modified fibroin include modified fibroins including (1-i) the amino acid sequence set forth in SEQ ID NO: 4, or (1-ii) an amino acid sequence having a sequence identity of 90% or more with the amino acid sequence set forth in SEQ ID NO: 4. The sequence identity is preferably 95% or more.

The amino acid sequence set forth in SEQ ID NO: 4 is an amino acid sequence obtained by the following mutation: in an amino acid sequence of ADF3 in which an amino acid sequence (SEQ ID NO: 5) consisting of a start codon, a His 10-tag and an HRV3C protease (Human rhinovirus 3C protease) recognition site is added to the N-terminal, the 1st to 13th repetitive regions are about doubled and the translation ends at the 1154th amino acid residue. The C-terminal amino acid sequence of the amino acid sequence set forth in SEQ ID NO: 4 is identical to the amino acid sequence set forth in SEQ ID NO: 3.

The modified fibroin of (1-i) may consist of the amino acid sequence set forth in SEQ ID NO: 4.

The modified fibroin having a reduced content of glycine residue (second modified fibroin) has a domain sequence having an amino acid sequence having a reduced content of glycine residue, as compared to naturally occurring spider fibroin. The second modified fibroin may have an amino acid sequence corresponding to an amino acid sequence in which at least one or a plurality of glycine residues in REP are substituted with another amino acid residue, as compared to naturally occurring spider fibroin.

The second modified fibroin may have a domain sequence having an amino acid sequence corresponding to an amino acid sequence in which, in at least one motif sequence selected from GGX and GPGXX (where G represents a glycine residue, P represents a proline residue, and X represents an amino acid residue other than glycine) in REP, one glycine residue in at least one or a plurality of the motif sequences is substituted with another amino acid residue, as compared to naturally occurring spider fibroin.

In the second modified fibroin, the proportion of the motif sequence in which the glycine residue has been substituted with another amino acid residue may be 10% or more relative to the entire motif sequence.

The second modified fibroin includes a domain sequence represented by Formula 1: $[(A)_n \text{ motif-REP}]_m$, and may have an amino acid sequence in which z/w is 30% or more, 40% or more, 50% or more, or 50.9% or more in a case where the total number of amino acid residues in the amino acid sequence consisting of XGX (where X represents an amino acid residue other than glycine) contained in all REPs in a sequence excluding the sequence from the $(A)_n$ motif located at the most C-terminal side to the C-terminal of the domain sequence from the domain sequence is defined as z, and the total number of amino acid residues in a sequence excluding the sequence from the $(A)_n$ motif located at the most C-terminal side to the C-terminal of the domain sequence from the domain sequence is defined as w. The number of alanine residues relative to the total number of amino acid residues in the $(A)_n$ motif may be 83% or more, preferably 86% or more, more preferably 90% or more, still more preferably 95% or more, and even still more preferably 100% (which means that the $(A)_n$ motif consists of only alanine residues).

The second modified fibroin is preferably one in which the content ratio of the amino acid sequence consisting of XGX is increased by substituting one glycine residue of the GGX motif with another amino acid residue. In the second modified fibroin, the content ratio of the amino acid sequence consisting of GGX in the domain sequence is preferably 30% or less, more preferably 20% or less, still more preferably 10% or less, even still more preferably 6% or less, still further preferably 4% or less, and particularly preferably 2% or less. The content ratio of the amino acid sequence consisting of GGX in the domain sequence can be calculated by the same method as the calculation method of the content ratio (z/w) of the amino acid sequence consisting of XGX described below.

The calculation method of z/w will be described in more detail. First, in a spider fibroin (modified fibroin or naturally occurring spider fibroin) including a domain sequence represented by Formula 1: $[(A)_n \text{ motif-REP}]_m$, an amino acid sequence consisting of XGX is extracted from all REPs contained in a sequence excluding the sequence from the $(A)_n$ motif located at the most C-terminal side to the C-terminal of the domain sequence from the domain sequence. The total number of amino acid residues constituting XGX is z. For example, in a case where 50 amino acid sequences consisting of XGX are extracted (there is no overlap), z is $50\times3=150$. Also, for example, in a case where X (central X) contained in two XGXs exists as in a case of the amino acid sequence consisting of XGXGX, z is calculated by subtracting the overlapping portion (in a case of XGXGX, it is 5 amino acid residues). w is the total number of amino acid residues contained in a sequence excluding the sequence from the $(A)_n$ motif located at the most C-terminal side to the C-terminal of the domain sequence from the domain sequence. For example, in a case of the domain sequence shown in FIG. 1, w is $4+50+4+100+4+10+4+20+4+30=230$ (excluding the $(A)_n$ motif located at the most C-terminal side). Next, z/w (%) can be calculated by dividing z by w.

In the second modified fibroin, z/w is preferably 50.9% or more, more preferably 56.1% or more, still more preferably 58.7% or more, even still more preferably 70% or more, and still further preferably 80% or more. The upper limit of z/w is not particularly limited, but may be 95% or less, for example.

The second modified fibroin can be obtained by, for example, substituting and modifying at least a part of a base sequence encoding a glycine residue from the gene sequence of cloned naturally occurring spider fibroin so as to encode another amino acid residue. At this time, one glycine residue in the GGX motif and GPGXX motif may be selected as a glycine residue to be modified, and substitution may be performed so that z/w is 50.9% or more. Alternatively, the second modified fibroin can also be obtained by, for example, designing an amino acid sequence satisfying each of the above embodiments from the amino acid sequence of naturally occurring spider fibroin, and chemically synthesizing a nucleic acid encoding the designed amino acid sequence. In any case, in addition to modification corresponding to substitution of a glycine residue in REP with another amino acid residue from the amino acid sequence of naturally occurring spider fibroin, modification of the amino acid sequence corresponding to substitution, deletion, insertion, and/or addition of one or a plurality of amino acid residues may be further performed.

The above-described another amino acid residue is not particularly limited as long as it is an amino acid residue other than a glycine residue, but is preferably a hydrophobic amino acid residue such as a valine (V) residue, a leucine (L) residue, an isoleucine (I) residue, a methionine (M) residue, a proline (P) residue, a phenylalanine (F) residue, and a tryptophan (W) residue; and a hydrophilic amino acid residue such as a glutamine (Q) residue, an asparagine (N) residue, a serine (S) residue, a lysine (K) residue, and a glutamic acid (E) residue. Among them, a valine (V) residue, a leucine (L) residue, an isoleucine (I) residue, and a glutamine (Q) residue are more preferable, and a glutamine (Q) residue is still more preferable.

More specific examples of the second modified fibroin include modified fibroins including (2-i) the amino acid sequence set forth in SEQ ID NO: 6, SEQ ID NO: 7, SEQ ID NO: 8, or SEQ ID NO: 9, or (2-ii) an amino acid sequence having a sequence identity of 90% or more with the amino acid sequence set forth in SEQ ID NO: 6, SEQ ID NO: 7, SEQ ID NO: 8, or SEQ ID NO: 9.

The modified fibroin of (2-i) will be described. The amino acid sequence set forth in SEQ ID NO: 6 is an amino acid sequence obtained by substituting all GGX in REP of the amino acid sequence set forth in SEQ ID NO: 10 corresponding to naturally occurring spider fibroin with GQX. The amino acid sequence set forth in SEQ ID NO: 7 is an amino acid sequence obtained by deleting the $(A)_n$ motif every other two positions from the N-terminal side to the C-terminal side from the amino acid sequence set forth in SEQ ID NO: 6, and further inserting one $[(A)_n \text{ motif-REP}]$ before the C-terminal sequence. The amino acid sequence set forth in SEQ ID NO: 8 is an amino acid sequence obtained by inserting two alanine residues on the C-terminal side of each $(A)_n$ motif of the amino acid sequence set forth in SEQ ID NO: 7, and further substituting a part of glutamine (Q) residues with a serine (S) residue, and deleting a part of amino acids on the N-terminal side so that the molecular weight thereof is approximately the same as that of SEQ ID NO: 7. The amino acid sequence set forth in SEQ ID NO: 9 is an amino acid sequence obtained by adding a His tag to the C-terminal of the sequence having four repeating regions of 20 domain sequences existing in the amino acid residue set forth in SEQ ID NO: 11 (where several amino acid residues on the C-terminal side of the region are substituted).

The value of z/w in the amino acid sequence set forth in SEQ ID NO: 10 (corresponding to naturally occurring spider fibroin) is 46.8%. The values of z/w of the amino acid sequence set forth in SEQ ID NO: 6, the amino acid sequence set forth in SEQ ID NO: 7, the amino acid sequence set forth in SEQ ID NO: 8, and the amino acid sequence set forth in SEQ ID NO: 9 are respectively 58.7%, 70.1%, 66.1%, and 70.0%. Additionally, the values of x/y at the Giza ratio (described later) of 1:1.8 to 11.3 of the amino acid sequences set forth in SEQ ID NO: 10, SEQ ID NO: 6, SEQ ID NO: 7, SEQ ID NO: 8, and SEQ ID NO: 9 are respectively 15.0%, 15.0%, 93.4%, 92.7%, and 89.3%.

The modified fibroin of (2-i) may consist of the amino acid sequence set forth in SEQ ID NO: 6, SEQ ID NO: 7, SEQ ID NO: 8, or SEQ ID NO: 9.

The modified fibroin of (2-ii) includes an amino acid sequence having a sequence identity of 90% or more with the amino acid sequence set forth in SEQ ID NO: 6, SEQ ID NO: 7, SEQ ID NO: 8, or SEQ ID NO: 9. The modified fibroin of (2-ii) is also a protein including a domain sequence represented by Formula 1: $[(A)_n$ motif-REP$]_m$. The sequence identity is preferably 95% or more.

It is preferred that the modified fibroin of (2-ii) has a sequence identity of 90% or more with the amino acid sequence set forth in SEQ ID NO: 6, SEQ ID NO: 7, SEQ ID NO: 8, or SEQ ID NO: 9, and z/w is 50.9% or more in a case where the total number of amino acid residues in the amino acid sequence consisting of XGX (where X represents an amino acid residue other than glycine) included in REP is defined as z, and the total number of amino acid residues of REP in the domain sequence is defined as w.

The second modified fibroin may include a tag sequence at either or both of the N-terminal and the C-terminal. This enables the modified fibroin to be isolated, immobilized, detected and visualized.

The tag sequence may be, for example, an affinity tag utilizing specific affinity (binding property, affinity) with another molecule. A specific example of the affinity tag includes a histidine tag (His tag). The His tag is a short peptide in which about 4 to 10 histidine residues are arranged, and has a property of specifically binding to a metal ion such as nickel, and thus can be used for isolation of modified fibroin by chelating metal chromatography. A specific example of the tag sequence may be, for example, the amino acid sequence set forth in SEQ ID NO: 12 (amino acid sequence including a His tag and a hinge sequence).

Also, a tag sequence such as glutathione-S-transferase (GST) that specifically binds to glutathione, and a maltose binding protein (MBP) that specifically binds to maltose can also be utilized.

Further, an "epitope tag" utilizing an antigen-antibody reaction can also be utilized. Adding a peptide (epitope) exhibiting antigenicity as a tag sequence allows an antibody against the epitope to be bound. Examples of the epitope tag include an HA (peptide sequence of hemagglutinin of influenza virus) tag, a myc tag, and a FLAG tag. The modified fibroin can easily be purified with high specificity by utilizing an epitope tag.

Moreover, it is possible to use a tag sequence which can be cleaved with a specific protease. The modified fibroin cleaved from the tag sequence can be recovered by treating a protein adsorbed through the tag sequence with protease.

More specific examples of the second modified fibroin including a tag sequence include modified fibroins including (2-iii) the amino acid sequence set forth in SEQ ID NO: 13, SEQ ID NO: 11, SEQ ID NO: 14, or SEQ ID NO: 15, or (2-iv) an amino acid sequence having a sequence identity of 90% or more with the amino acid sequence set forth in SEQ ID NO: 13, SEQ ID NO: 11, SEQ ID NO: 14, or SEQ ID NO: 15.

The amino acid sequences set forth in SEQ ID NO: 16, SEQ ID NO: 17, SEQ ID NO: 13, SEQ ID NO: 11, SEQ ID NO: 14, and SEQ ID NO: 15 are an amino acid sequence obtained by adding the amino acid sequence set forth in SEQ ID NO: 12 (including a His tag sequence and a hinge sequence) to the N-terminal of each of the amino acid sequences set forth in SEQ ID NO: 10, SEQ ID NO: 18, SEQ ID NO: 6, SEQ ID NO: 7, SEQ ID NO: 8, and SEQ ID NO: 9.

The modified fibroin of (2-iii) may consist of the amino acid sequence set forth in SEQ ID NO: 13, SEQ ID NO: 11, SEQ ID NO: 14, or SEQ ID NO: 15.

The modified fibroin of (2-iv) includes an amino acid sequence having a sequence identity of 90% or more with the amino acid sequence set forth in SEQ ID NO: 13, SEQ ID NO: 11, SEQ ID NO: 14, or SEQ ID NO: 15. The modified fibroin of (2-iv) is also a protein including a domain sequence represented by Formula 1: $[(A)_n$ motif-REP$]_m$. The sequence identity is preferably 95% or more.

It is preferred that the modified fibroin of (2-iv) has a sequence identity of 90% or more with the amino acid sequence set forth in SEQ ID NO: 13, SEQ ID NO: 11, SEQ ID NO: 14, or SEQ ID NO: 15, and z/w is 50.9% or more in a case where the total number of amino acid residues in the amino acid sequence consisting of XGX (where X represents an amino acid residue other than glycine) contained in REP is defined as z, and the total number of amino acid residues of REP in the domain sequence is defined as w.

The second modified fibroin may include a secretory signal for releasing the protein produced in the recombinant protein production system to the outside of a host. The sequence of the secretory signal can be appropriately set depending on the type of the host.

The modified fibroin having a reduced content of $(A)_n$ motif (third modified fibroin) has a domain sequence having an amino acid sequence having a reduced content of $(A)_n$ motif, as compared to naturally occurring spider fibroin. The domain sequence of the third modified fibroin may have an amino acid sequence corresponding to an amino acid sequence in which at least one or a plurality of $(A)_n$ motifs are deleted, as compared to naturally occurring spider fibroin.

The third modified fibroin may have an amino acid sequence corresponding to an amino acid sequence in which 10 to 40% of the $(A)_n$ motif is deleted from naturally occurring spider fibroin.

The third modified fibroin may have a domain sequence having an amino acid sequence corresponding to an amino acid sequence in which at least one $(A)_n$ motif every one to three $(A)_n$ motifs from the N-terminal side to the C-terminal side is deleted, as compared to naturally occurring spider fibroin.

The third modified fibroin may have a domain sequence having an amino acid sequence corresponding to an amino acid sequence in which at least two consecutive $(A)_n$ motif deletions and one $(A)_n$ motif deletion are repeated in this order from the N-terminal side to the C-terminal side, as compared to naturally occurring spider fibroin.

The third modified fibroin may have a domain sequence having an amino acid sequence corresponding to an amino acid sequence in which at least $(A)_n$ motif every other two positions is deleted from the N-terminal side to the C-terminal side.

The third modified fibroin has a domain sequence represented by Formula 1: $[(A)_n \text{ motif-REP}]_m$, and may have an amino acid sequence in which x/y is 20% or more, 30% or more, 40% or more, or 50% or more in a case where the number of amino acid residues in REPs of two adjacent $[(A)_n \text{ motif-REP}]$ units is sequentially compared from the N-terminal side to the C-terminal side, and the number of amino acid residues in REP having a smaller number of amino acid residues is defined as 1, the maximum value of the total value of the number of amino acid residues in the two adjacent $[(A)_n \text{ motif-REP}]$ units where the ratio of the number of amino acid residues in the other REP is 1.8 to 11.3 is defined as x, and the total number of amino acid residues of the domain sequence is defined as y. The number of alanine residues relative to the total number of amino acid residues in the $(A)_n$ motif may be 83% or more, preferably 86% or more, more preferably 90% or more, still more preferably 95% or more, and even still more preferably 100% (which means that the $(A)_n$ motif consists of only alanine residues).

A method of calculating x/y will be described in more detail with reference to FIG. 1. FIG. 1 shows a domain sequence excluding the N-terminal sequence and the C-terminal sequence from spider fibroin. The domain sequence has a sequence of $(A)_n$ motif-first REP (50 amino acid residues)-$(A)_n$ motif-second REP (100 amino acid residues)-$(A)_n$ motif-third REP (10 amino acid residues)-$(A)_n$ motif-fourth REP (20 amino acid residues)-$(A)_n$ motif-fifth REP (30 amino acid residues)-$(A)_n$ motif from the N-terminal side (left side).

The two adjacent $[(A)_n \text{ motif-REP}]$ units are sequentially selected from the N-terminal side to the C-terminal side so as not to overlap. At this time, an unselected $[(A)_n \text{ motif-REP}]$ unit may exist. FIG. 1 shows a pattern 1 (a comparison between the first REP and the second REP, and a comparison between the third REP and the fourth REP), a pattern 2 (a comparison between the first REP and the second REP, and a comparison between the fourth REP and the fifth REP), a pattern 3 (a comparison between the second REP and the third REP, and a comparison between the fourth REP and the fifth REP), and a pattern 4 (a comparison between the first REP and the second REP). There are other selection methods besides this.

Subsequently, the number of amino acid residues of each REP in the selected two adjacent $[(A)_n \text{ motif-REP}]$ units is compared for each pattern. The comparison is performed by determining the ratio of the number of amino acid residues of the other REP in a case where one REP having a smaller number of amino acid residues is defined as 1. For example, in a case of comparing the first REP (50 amino acid residues) and the second REP (100 amino acid residues), the ratio of the number of amino acid residues of the second REP is 100/50=2 in a case where the first REP having a smaller number of amino acid residues is defined as 1. Similarly, in a case of comparing the fourth REP (20 amino acid residues) and the fifth REP (30 amino acid residues), the ratio of the number of amino acid residues of the fifth REP is 30/20=1.5 in a case where the fourth REP having a smaller number of amino acid residues is defined as 1.

In FIG. 1, a set of $[(A)_n \text{ motif-REP}]$ units in which the ratio of the number of amino acid residues of the other REP is 1.8 to 11.3 in a case where one REP having a smaller number of amino acid residues is defined as 1 is indicated by a solid line. Hereinafter, such a ratio is referred to as a Giza ratio. A set of $[(A)_n \text{ motif-REP}]$ units in which the ratio of the number of amino acid residues of the other REP is less than 1.8 or more than 11.3 in a case where one REP having a smaller number of amino acid residues is defined as 1 is indicated by a broken line.

In each pattern, the number of all amino acid residues of two adjacent $[(A)_n \text{ motif-REP}]$ units indicated by solid lines (including not only the number of amino acid residues of the REP but also the number of amino acid residues of the $(A)_n$ motif) is combined. Then, the total values combined are compared, and the total value of the pattern whose total value is the maximum (the maximum value of the total value) is defined as x. In the example shown in FIG. 1, the total value of the pattern 1 is the maximum.

Then, x/y (%) can be calculated by dividing x by the total number of amino acid residues y of the domain sequence.

In the third modified fibroin, x/y is preferably 50% or more, more preferably 60% or more, still more preferably 65% or more, even still more preferably 70% or more, still further preferably 75% or more, and particularly preferably 80% or more. The upper limit of x/y is not particularly limited, but may be 100% or less, for example. In a case where the Giza ratio is 1:1.9 to 11.3, x/y is preferably 89.6% or more; in a case where the Giza ratio is 1:1.8 to 3.4, x/y is preferably 77.1% or more; in a case where the Giza ratio is 1:1.9 to 8.4, x/y is preferably 75.9% or more; and in a case where the Giza ratio is 1:1.9 to 4.1, x/y is preferably 64.2% or more.

In a case where the third modified fibroin is a modified fibroin in which at least seven of a plurality of $(A)_n$ motifs in the domain sequence consist of only alanine residues, x/y is preferably 46.4% or more, more preferably 50% or more, still more preferably 55% or more, even still more preferably 60% or more, still further preferably 70% or more, and particularly preferably 80% or more. The upper limit of x/y is not particularly limited, but is only required to be 100% or less.

The third modified fibroin can be obtained by, for example, deleting one or a plurality of sequences encoding the $(A)_n$ motif from the gene sequence of cloned naturally occurring spider fibroin so that x/y is 64.2% or more. Alternatively, the third modified fibroin can also be obtained by, for example, designing an amino acid sequence corresponding to an amino acid sequence in which one or a plurality of $(A)_n$ motifs are deleted from the amino acid sequence of naturally occurring spider fibroin so that x/y is 64.2% or more, and chemically synthesizing a nucleic acid encoding the designed amino acid sequence. In any case, in addition to modification corresponding to deletion of the $(A)_n$ motif from the amino acid sequence of naturally occurring spider fibroin, modification of the amino acid sequence corresponding to substitution, deletion, insertion, and/or addition of one or a plurality of amino acid residues may be further performed.

More specific examples of the third modified fibroin include modified fibroins including (3-i) the amino acid sequence set forth in SEQ ID NO: 18, SEQ ID NO: 7, SEQ ID NO: 8, or SEQ ID NO: 9, or (3-ii) an amino acid sequence having a sequence identity of 90% or more with the amino acid sequence set forth in SEQ ID NO: 18, SEQ ID NO: 7, SEQ ID NO: 8, or SEQ ID NO: 9.

The modified fibroin of (3-i) will be described. The amino acid sequence set forth in SEQ ID NO: 18 is an amino acid sequence obtained by deleting the $(A)_n$ motif every other two positions from the N-terminal side to the C-terminal side from the amino acid sequence set forth in SEQ ID NO: 10 corresponding to naturally occurring spider fibroin, and further inserting one [(A)$_n$ motif-REP] before the C-terminal sequence. The amino acid sequence set forth in SEQ ID NO: 7 is an amino acid sequence obtained by substituting all GGXs in REP of the amino acid sequence set forth in SEQ ID NO: 18 with GQX. The amino acid sequence set forth in SEQ ID NO: 8 is an amino acid sequence obtained by inserting two alanine residues on the C-terminal side of each (A)$_n$ motif of the amino acid sequence set forth in SEQ ID NO: 7, and further substituting a part of glutamine (Q) residues with a serine (S) residue, and deleting a part of amino acids on the N-terminal side so that the molecular weight thereof is approximately the same as that of SEQ ID NO: 7. The amino acid sequence set forth in SEQ ID NO: 9 is an amino acid sequence obtained by adding a His tag to the C-terminal of the sequence having four repeating regions of 20 domain sequences existing in the amino acid residue set forth in SEQ ID NO: 11 (where several amino acid residues on the C-terminal side of the region are substituted).

The value of x/y at the Giza ratio of 1:1.8 to 11.3 of the amino acid sequence set forth in SEQ ID NO: 10 (corresponding to naturally occurring spider fibroin) is 15.0%. The values of x/y of the amino acid sequence set forth in SEQ ID NO: 18 and the amino acid sequence set forth in SEQ ID NO: 7 are both 93.4%. The value of x/y of the amino acid sequence set forth in SEQ ID NO: 8 is 92.7%. The value of x/y of the amino acid sequence set forth in SEQ ID NO: 9 is 89.3%. The values of z/w of the amino acid sequences set forth in SEQ ID NO: 10, SEQ ID NO: 18, SEQ ID NO: 7, SEQ ID NO: 8, and SEQ ID NO: 9 are respectively 46.8%, 56.2%, 70.1%, 66.1%, and 70.0%.

The modified fibroin of (3-i) may consist of the amino acid sequence set forth in SEQ ID NO: 18, SEQ ID NO: 7, SEQ ID NO: 8, or SEQ ID NO: 9.

The modified fibroin of (3-ii) includes an amino acid sequence having a sequence identity of 90% or more with the amino acid sequence set forth in SEQ ID NO: 18, SEQ ID NO: 7, SEQ ID NO: 8, or SEQ ID NO: 9. The modified fibroin of (3-ii) is also a protein including a domain sequence represented by Formula 1: [(A)$_n$ motif-REP]$_m$. The sequence identity is preferably 95% or more.

It is preferred that the modified fibroin of (3-ii) has a sequence identity of 90% or more with the amino acid sequence set forth in SEQ ID NO: 18, SEQ ID NO: 7, SEQ ID NO: 8, or SEQ ID NO: 9, and x/y is 64.2% or more in a case where the number of amino acid residues in REPs of two adjacent [(A)$_n$ motif-REP] units is sequentially compared from the N-terminal side to the C-terminal side, and the number of amino acid residues in REP having a smaller number of amino acid residues is defined as 1, the maximum value of the total value of the number of amino acid residues in the two adjacent [(A)$_n$ motif-REP] units where the ratio of the number of amino acid residues in the other REP is 1.8 to 11.3 (the Giza ratio is 1:1.8 to 11.3) is defined as x, and the total number of amino acid residues of the domain sequence is defined as y.

The third modified fibroin may include the above-described tag sequence at either or both of the N-terminal and the C-terminal.

More specific examples of the third modified fibroin including a tag sequence include modified fibroins including (3-iii) the amino acid sequence set forth in SEQ ID NO: 17, SEQ ID NO: 11, SEQ ID NO: 14, or SEQ ID NO: 15, or (3-iv) an amino acid sequence having a sequence identity of 90% or more with the amino acid sequence set forth in SEQ ID NO: 17, SEQ ID NO: 11, SEQ ID NO: 14, or SEQ ID NO: 15.

The amino acid sequences set forth in SEQ ID NO: 16, SEQ ID NO: 17, SEQ ID NO: 13, SEQ ID NO: 11, SEQ ID NO: 14, and SEQ ID NO: 15 are an amino acid sequence obtained by adding the amino acid sequence set forth in SEQ ID NO: 12 (including a His tag sequence and a hinge sequence) to the N-terminal of each of the amino acid sequences set forth in SEQ ID NO: 10, SEQ ID NO: 18, SEQ ID NO: 6, SEQ ID NO: 7, SEQ ID NO: 8, and SEQ ID NO: 9.

The modified fibroin of (3-iii) may consist of the amino acid sequence set forth in SEQ ID NO: 17, SEQ ID NO: 11, SEQ ID NO: 14, or SEQ ID NO: 15.

The modified fibroin of (3-iv) includes an amino acid sequence having a sequence identity of 90% or more with the amino acid sequence set forth in SEQ ID NO: 17, SEQ ID NO: 11, SEQ ID NO: 14, or SEQ ID NO: 15. The modified fibroin of (3-iv) is also a protein including a domain sequence represented by Formula 1: [(A)$_n$ motif-REP]$_m$. The sequence identity is preferably 95% or more.

It is preferred that the modified fibroin of (3-iv) has a sequence identity of 90% or more with the amino acid sequence set forth in SEQ ID NO: 17, SEQ ID NO: 11, SEQ ID NO: 14, or SEQ ID NO: 15, and x/y is 64.2% or more in a case where the number of amino acid residues in REPs of two adjacent [(A)$_n$ motif-REP] units is sequentially compared from the N-terminal side to the C-terminal side, and the number of amino acid residues in REP having a smaller number of amino acid residues is defined as 1, the maximum value of the total value of the number of amino acid residues in the two adjacent [(A)$_n$ motif-REP] units where the ratio of the number of amino acid residues in the other REP is 1.8 to 11.3 is defined as x, and the total number of amino acid residues of the domain sequence is defined as y.

The third modified fibroin may include a secretory signal for releasing the protein produced in the recombinant protein production system to the outside of a host. The sequence of the secretory signal can be appropriately set depending on the type of the host.

The modified fibroin having a reduced content of glycine residue and a reduced content of (A)$_n$ motif (fourth modified fibroin) has a domain sequence having an amino acid sequence having a reduced content of glycine residue, in addition to having a reduced content of (A)$_n$ motif, as compared to naturally occurring spider fibroin. The fourth modified fibroin may have a domain sequence having an amino acid sequence corresponding to an amino acid sequence in which, in addition to deletion of at least one or a plurality of (A)$_n$ motifs, at least one or a plurality of glycine residues in REP are substituted with another amino acid residue, as compared to naturally occurring spider fibroin. That is, the fourth modified fibroin is a modified fibroin having characteristic of both the modified fibroin having a reduced content of glycine residue (second modified fibroin) and the modified fibroin having a reduced content of (A)$_n$ motif (third modified fibroin) described above. Specific embodiments thereof, and the like are as in the descriptions for the second modified fibroin and the third modified fibroin.

More specific examples of the fourth modified fibroin include modified fibroins including (4-i) the amino acid sequence set forth in SEQ ID NO: 7, SEQ ID NO: 8, SEQ ID NO: 9, SEQ ID NO: 11, SEQ ID NO: 14, SEQ ID NO: 15, SEQ ID NO: 50, SEQ ID NO: 51, SEQ ID NO: 52, SEQ ID NO: 53, SEQ ID NO: 54, or SEQ ID NO: 57, or (4-ii) an amino acid sequence having a sequence identity of 90% or more with the amino acid sequence set forth in SEQ ID NO: 7, SEQ ID NO: 8, SEQ ID NO: 9, SEQ ID NO: 11, SEQ ID NO: 14, SEQ ID NO: 15, SEQ ID NO: 50, SEQ ID NO: 51, SEQ ID NO: 52, SEQ ID NO: 53, SEQ ID NO: 54, or SEQ ID NO: 57. Specific embodiments of the modified fibroin including the amino acid sequence set forth in SEQ ID NO: 7, SEQ ID NO: 8, SEQ ID NO: 9, SEQ ID NO: 11, SEQ ID NO: 14, SEQ ID NO: 15, SEQ ID NO: 50, SEQ ID NO: 51, SEQ ID NO: 52, SEQ ID NO: 53, SEQ ID NO: 54, or SEQ ID NO: 57 are as described above.

The modified fibroin including a domain sequence having a region with locally high hydropathy index (fifth modified fibroin) may have a domain sequence having an amino acid sequence including a region with locally high hydropathy index, corresponding to an amino acid sequence in which one or a plurality of amino acid residues in REP are substituted with an amino acid residue with a high hydropathy index and/or one or a plurality of amino acid residues with a high hydropathy index are inserted in REP, as compared to naturally occurring spider fibroin.

The region with locally high hydropathy index preferably consists of consecutive two to four amino acid residues.

The above-described amino acid residue with a high hydropathy index is more preferably an amino acid residue selected from isoleucine (I), valine (V), leucine (L), phenylalanine (F), cysteine (C), methionine (M), and alanine (A).

In the fifth modified fibroin, in addition to modifications corresponding to substitution of one or a plurality of amino acid residues in REP with an amino acid residue with a high hydropathy index and/or insertion of one or a plurality of amino acid residues with a high hydropathy index into REP, as compared to naturally occurring spider fibroin, there may be further modification of an amino acid sequence corresponding to substitution, deletion, insertion, and/or addition of one or a plurality of amino acid residues as compared to naturally occurring spider fibroin.

The fifth modified fibroin can be obtained by, for example, substituting one or a plurality of hydrophilic amino acid residues in REP (for example, amino acid residues having a negative hydropathy index) with a hydrophobic amino acid residue (for example, an amino acid residue having a positive hydropathy index), and/or inserting one or a plurality of hydrophobic amino acid residues into REP, from the gene sequence of cloned naturally occurring spider fibroin. Alternatively, the fifth modified fibroin can be obtained by, for example, designing an amino acid sequence corresponding to an amino acid sequence in which one or a plurality of hydrophilic amino acid residues in REP are substituted with a hydrophobic amino acid residue and/or one or a plurality of hydrophobic amino acid residues are inserted into REP, from the amino acid sequence of naturally occurring spider fibroin, and chemically synthesizing a nucleic acid encoding the designed amino acid sequence. In any case, in addition to modifications corresponding to substitution of one or a plurality of hydrophilic amino acid residues in REP with a hydrophobic amino acid residue, and/or insertion of one or a plurality of hydrophobic amino acid residues into REP, from the amino acid sequence of naturally occurring spider fibroin, modification of the amino acid sequence corresponding to substitution, deletion, insertion, and/or addition of one or a plurality of amino acid residues may be further performed.

The fifth modified fibroin includes a domain sequence represented by Formula 1: $[(A)_n \text{ motif-REP}]_m$, and may have an amino acid sequence in which p/q is 6.2% or more in a case where in all REPs included in a sequence excluding the sequence from the $(A)_n$ motif located at the most C-terminal side to the C-terminal of the domain sequence from the domain sequence, the total number of amino acid residues included in a region where the average value of hydropathy indices of four consecutive amino acid residues is 2.6 or more is defined as p, and the total number of amino acid residues included in a sequence excluding the sequence from the $(A)_n$ motif located at the most C-terminal side to the C-terminal of the domain sequence from the domain sequence is defined as q.

For the hydropathy index of the amino acid residue, a publicly known index (Hydropathy index: Kyte J, & Doolittle R (1982) "A simple method for displaying the hydropathic character of a protein", J. Mol. Biol., 157, pp. 105-132) is used. Specifically, the hydropathy index (hereinafter, also referred to as "HI") of each amino acid is as shown in Table 1 below.

TABLE 1

| Amino acid | HI |
| --- | --- |
| Isoleucine (Ile) | 4.5 |
| Valine (Val) | 4.2 |
| Leucine (Leu) | 3.8 |
| Phenylalanine (Phe) | 2.8 |
| Cysteine (Cys) | 2.5 |
| Methionine (Met) | 1.9 |
| Alanine (Ala) | 1.8 |
| Glycine (Gly) | −0.4 |
| Threonine (Thr) | −0.7 |
| Serine (Ser) | −0.8 |
| Tryptophan (Trp) | −0.9 |
| Tyrosine (Tyr) | −1.3 |
| Proline (Pro) | −1.6 |
| Histidine (His) | −3.2 |
| Asparagine (Asn) | −3.5 |
| Aspartic acid (Asp) | −3.5 |
| Glutamine (Gln) | −3.5 |
| Glutamic acid (Glu) | −3.5 |
| Lysine (Lys) | −3.9 |
| Arginine (Arg) | −4.5 |

The calculation method of p/q will be described in more detail. In the calculation, a sequence excluding the sequence from the $(A)_n$ motif located at the most C-terminal side to the C-terminal of the domain sequence from the domain sequence represented by Formula 1 $[(A)_n \text{ motif-REP}]_m$ (hereinafter also referred to as "sequence A") is used. First, in all REPs included in the sequence A, the average values of hydropathy indices of four consecutive amino acid residues are calculated. The average value of the hydropathy indices is determined by dividing the total sum of HIs of respective amino acid residues included in the four consecutive amino acid residues by 4 (number of amino acid residues). The average value of the hydropathy indices is determined for all of the four consecutive amino acid residues (each of the amino acid residues is used for calculating the average value 1 to 4 times). Then, a region where the average value of the hydropathy indices of the four consecutive amino acid residues is 2.6 or more is specified. Even in a case where a certain amino acid residue corresponds to the "four consecutive amino acid residues having an average value of the hydropathy indices of 2.6 or more" multiple times, the amino acid residue is included as one amino acid residue in the region. The total number of amino acid residues included in the region is p. Also, the total number of amino acid residues included in the sequence A is q.

Figure 2:
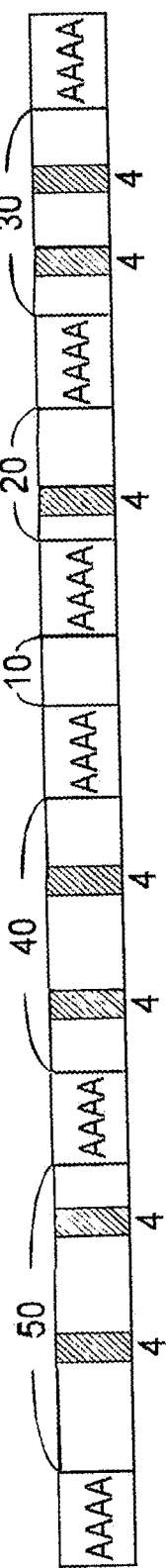
FIG. 2 is a schematic view illustrating an example of a domain sequence of a spider fibroin comprising the amino acid sequence set forth in SEQ ID NO: 63 (AAAA).

For example, in a case where the "four consecutive amino acid residues having an average value of the hydropathy indices of 2.6 or more" are extracted from 20 places (no overlap), in the region where the average value of the hydropathy indices of four consecutive amino acid residues is 2.6 or more, 20 of the four consecutive amino acid residues (no overlap) are included, and thus p is 20×4=80. Further, for example, in a case where two of the "four consecutive amino acid residues having an average value of the hydropathy indices of 2.6 or more" overlap by one amino acid residue, in the region where the average value of the hydropathy indices of the four consecutive amino acid residues is 2.6 or more, seven amino acid residues are included (p=2×4−1=7. "−1" is the deduction of overlap). For example, in a case of the domain sequence shown in FIG. 2, there are seven "four consecutive amino acid residues having an average value of the hydropathy indices of 2.6 or more" without overlapping, and thus p is 7×4=28. For example, in a case of the domain sequence shown in FIG. 2, q is 4+50+4+40+4+10+4+20+4+30=170 (not including the $(A)_n$ motif located at the end of the C-terminal side). Next, p/q (%) can be calculated by dividing p by q. In a case of FIG. 2, p/q is 28/170=16.47%.

In the fifth modified fibroin, p/q is preferably 6.2% or more, more preferably 7% or more, still more preferably 10% or more, even still more preferably 20% or more, and still further preferably 30% or more. The upper limit of p/q is not particularly limited, but may be 45% or less, for example.

The fifth modified fibroin can be obtained by, for example, substituting one or a plurality of hydrophilic amino acid residues in REP (for example, amino acid residues having a negative hydropathy index) with a hydrophobic amino acid residue (for example, an amino acid residue having a positive hydropathy index), and/or inserting one or a plurality of hydrophobic amino acid residues into REP, so as to satisfy the condition of the above p/q, thereby modifying the amino acid sequence of cloned naturally occurring spider fibroin into an amino acid sequence including a region with locally high hydropathy index. Alternatively, the fifth modified fibroin can also be obtained by, for example, designing an amino acid sequence satisfying the condition of the above p/q from the amino acid sequence of naturally occurring spider fibroin, and chemically synthesizing a nucleic acid encoding the designed amino acid sequence. In any case, in addition to modifications corresponding to substitution of one or a plurality of amino acid residues in REP with an amino acid residue with a high hydropathy index, and/or insertion of one or a plurality of amino acid residues with a high hydropathy index into REP, as compared to naturally occurring spider fibroin, modification corresponding to substitution, deletion, insertion, and/or addition of one or a plurality of amino acid residues may be further performed.

The amino acid residue with a high hydropathy index is not particularly limited, but is preferably isoleucine (I), valine (V), leucine (L), phenylalanine (F), cysteine (C), methionine (M), and alanine (A), and more preferably valine (V), leucine (L), and isoleucine (I).

More specific examples of the fifth modified fibroin include modified fibroins including (5-i) the amino acid sequence set forth in SEQ ID NO: 19, SEQ ID NO: 20, or SEQ ID NO: 21, or (5-ii) an amino acid sequence having a sequence identity of 90% or more with the amino acid sequence set forth in SEQ ID NO: 19, SEQ ID NO: 20, or SEQ ID NO: 21.

The modified fibroin of (5-i) will be described. The amino acid sequence set forth in SEQ ID NO: 22 is an amino acid sequence obtained by deleting alanine residues in the $(A)_n$ motif of the amino acid sequence of naturally occurring spider fibroin so that the number of the consecutive alanine residues is five. The amino acid sequence set forth in SEQ ID NO: 19 is an amino acid sequence obtained by inserting an amino acid sequence consisting of three amino acid residues (VLI) at two sites for each REP into the amino acid sequence set forth in SEQ ID NO: 22, and deleting a part of amino acids on the C-terminal side so that the molecular weight thereof is approximately the same as that of the amino acid sequence set forth in SEQ ID NO: 22. The amino acid sequence set forth in SEQ ID NO: 23 is an amino acid sequence obtained by inserting two alanine residues at the C-terminal side of each $(A)_n$ motif of the amino acid sequence set forth in SEQ ID NO: 22, further substituting a part of glutamine (Q) residues with a serine (S) residue, and deleting a part of amino acids on the C-terminal side so that the molecular weight thereof is approximately the same as that of the amino acid sequence set forth in SEQ ID NO: 22. The amino acid sequence set forth in SEQ ID NO: 20 is an amino acid sequence obtained by inserting an amino acid sequence consisting of three amino acid residues (VLI) at one site for each REP into the amino acid sequence set forth in SEQ ID NO: 23. The amino acid sequence set forth in SEQ ID NO: 21 is an amino acid sequence obtained by inserting an amino acid sequence consisting of three amino acid residues (VLI) at two sites for each REP into the amino acid sequence set forth in SEQ ID NO: 23.

The modified fibroin of (5-i) may consist of the amino acid sequence set forth in SEQ ID NO: 19, SEQ ID NO: 20, or SEQ ID NO: 21.

The modified fibroin of (5-ii) includes an amino acid sequence having a sequence identity of 90% or more with the amino acid sequence set forth in SEQ ID NO: 19, SEQ ID NO: 20, or SEQ ID NO: 21. The modified fibroin of (5-ii) is also a protein including a domain sequence represented by Formula 1: $[(A)_n$ motif-REP$]_m$. The sequence identity is preferably 95% or more.

It is preferred that the modified fibroin of (5-ii) has a sequence identity of 90% or more with the amino acid sequence set forth in SEQ ID NO: 19, SEQ ID NO: 20, or SEQ ID NO: 21, and p/q is 6.2% or more in a case where in all REPs included in a sequence excluding the sequence from the $(A)_n$ motif located at the most C-terminal side to the C-terminal of the domain sequence from the domain sequence, the total number of amino acid residues included in a region where the average value of hydropathy indices of four consecutive amino acid residues is 2.6 or more is defined as p, and the total number of amino acid residues included in a sequence excluding the sequence from the $(A)_n$ motif located at the most the C-terminal side to the C-terminal of the domain sequence from the domain sequence is defined as q.

The fifth modified fibroin may include a tag sequence at either or both of the N-terminal and the C-terminal.

More specific examples of the fifth modified fibroin including a tag sequence include modified fibroins including (5-iii) the amino acid sequence set forth in SEQ ID NO: 24, SEQ ID NO: 25, or SEQ ID NO: 26, or (5-iv) an amino acid sequence having a sequence identity of 90% or more with the amino acid sequence set forth in SEQ ID NO: 24, SEQ ID NO: 25, or SEQ ID NO: 26.

The amino acid sequences set forth in SEQ ID NO: 24, SEQ ID NO: 25, and SEQ ID NO: 26 are an amino acid sequence obtained by adding the amino acid sequence set forth in SEQ ID NO: 12 (including a His tag sequence and a hinge sequence) to the N-terminal of each of the amino acid sequences set forth in SEQ ID NO: 19, SEQ ID NO: 20, and SEQ ID NO: 21.

The modified fibroin of (5-iii) may consist of the amino acid sequence set forth in SEQ ID NO: 24, SEQ ID NO: 25, or SEQ ID NO: 26.

The modified fibroin of (5-iv) includes an amino acid sequence having a sequence identity of 90% or more with the amino acid sequence set forth in SEQ ID NO: 24, SEQ ID NO: 25, or SEQ ID NO: 26. The modified fibroin of (5-iv) is also a protein including a domain sequence represented by Formula 1: $[(A)_n$ motif-REP$]_m$. The sequence identity is preferably 95% or more.

It is preferred that the modified fibroin of (5-iv) has a sequence identity of 90% or more with the amino acid sequence set forth in SEQ ID NO: 24, SEQ ID NO: 25, or SEQ ID NO: 26, and p/q is 6.2% or more in a case where in all REPs included in a sequence excluding the sequence from the $(A)_n$ motif located at the most C-terminal side to the C-terminal of the domain sequence from the domain sequence, the total number of amino acid residues included in a region where the average value of hydropathy indices of four consecutive amino acid residues is 2.6 or more is defined as p, and the total number of amino acid residues included in a sequence excluding the sequence from the $(A)_n$ motif located at the most the C-terminal side to the C-terminal of the domain sequence from the domain sequence is defined as q.

The fifth modified fibroin may include a secretory signal for releasing the protein produced in the recombinant protein production system to the outside of a host. The sequence of the secretory signal can be appropriately set depending on the type of the host.

The modified fibroin, which has a domain sequence having a reduced content of glutamine residue (sixth modified fibroin), has an amino acid sequence having a reduced content of glutamine residue, as compared to naturally occurring spider fibroin.

In the sixth modified fibroin, at least one motif selected from a GGX motif and a GPGXX motif is preferably included in the amino acid sequence of REP.

In a case where the sixth modified fibroin includes the GPGXX motif in REP, the GPGXX motif content is usually 1% or more, may also be 5% or more, and preferably 10% or more. The upper limit of the GPGXX motif content is not particularly limited, and may be 50% or less, or may also be 30% or less.

In the present specification, the "GPGXX motif content" is a value calculated by the following method.

The GPGXX motif content is calculated as s/t in a case where in all REPs included in a sequence excluding the sequence from the $(A)_n$ motif located at the most C-terminal side to the C-terminal of the domain sequence in spider fibroin including a domain sequence represented by Formula 1: $[(A)_n$ motif-REP$]_m$ or Formula 2: $[(A)_n$ motif -REP$]_m$-$(A)_n$ motif, a number three times the total number of GPGXX motifs included in this region is defined as s (that is, a number corresponding to the total number of G and P in the GPGXX motif), and the total number of amino acid residues in all REPs excluding the sequence excluding the sequence from the $(A)_n$ motif located at the most C-terminal side to the C-terminal of the domain sequence from the domain sequence and further excluding the $(A)_n$ motifs is defined as t.

In the calculation of the GPGXX motif content, the "sequence excluding the sequence from the $(A)_n$ motif located at the most C-terminal side to the C-terminal of the domain sequence from the domain sequence" is used as a target. In "the sequence from the $(A)_n$ motif located at the most C-terminal side to the C-terminal of the domain sequence" (the sequence corresponding to REP), a sequence having low correlation with a sequence characteristic of spider fibroin is included in some cases, and in a case where m is small, (that is, the domain sequence is short), such a sequence affects the calculation result of the GPGXX motif content. The reason for targeting the sequence is for eliminating this influence. Incidentally, in a case where the "GPGXX motif" is located at the C-terminal of REP, even when "XX" is "AA", for example, it is treated as the "GPGXX motif".

Figure 3:
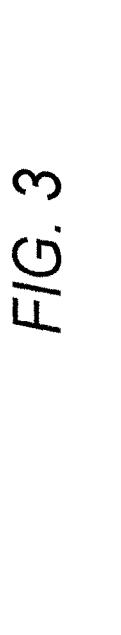
FIG. 3 is a schematic view illustrating an example of a domain sequence of a spider fibroin comprising the amino acid sequences set forth in SEQ ID NO: 63 (AAAA) and SEQ ID NO: 64 (GPGXX).
Figure 3:
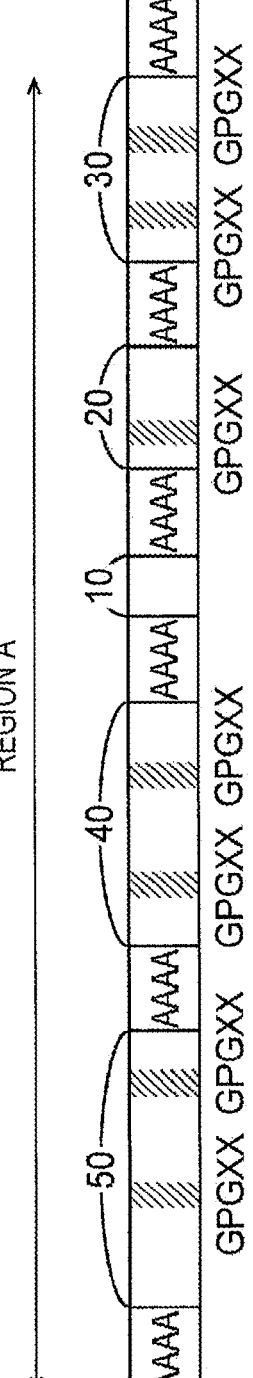

FIG. 3 is a schematic view illustrating the domain sequence of spider fibroin. The calculation method of the GPGXX motif content will be specifically described with reference to FIG. 3. First, in the domain sequence of the spider fibroin shown in FIG. 3 ("$[(A)_n$ motif-REP$]_m$-$(A)_n$ motif" type), all REPs are included in the "sequence excluding the sequence from the $(A)_n$ motif located at the most C-terminal side to the C-terminal of the domain sequence from the domain sequence" (the sequence indicated by the "region A" in FIG. 3). Thus, the number of GPGXX motifs for calculating s is 7, and s is 7×3=21. Similarly, all REPs are included in the sequence excluding the sequence from the $(A)_n$ motif located at the most C-terminal side to the C-terminal of the domain sequence from the domain sequence" (the sequence indicated by the "region A" in FIG. 3). Thus, the total number t of amino acid residues in all REPs further excluding the $(A)_n$ motifs from the sequence is 50+40+10+20+30=150. Then, s/t (%) can be calculated by dividing s by t, and in a case of the fibroin in FIG. 3, s/t is 21/150=14.0%.

In the sixth modified fibroin, the glutamine residue content is preferably 9% or less, more preferably 7% or less, still more preferably 4% or less, and particularly preferably 0%.

In the present specification, the "glutamine residue content" is a value calculated by the following method.

The glutamine residue content is calculated as u/t in a case where in all REPs included in a sequence excluding the sequence from the $(A)_n$ motif located at the most C-terminal side to the C-terminal of the domain sequence from the domain sequence (the sequence correspond to the "region A" in FIG. 3) in spider fibroin including a domain sequence represented by Formula 1: $[(A)_n$ motif-REP$]_m$ or Formula 2: $[(A)_n$ motif -REP$]_m$-$(A)_n$ motif, the total number of glutamine residues included in this region is defined as u, and the total number of amino acid residues in all REPs excluding the sequence from the $(A)_n$ motif located at the most C-terminal side to the C-terminal of the domain sequence from the domain sequence and further excluding the $(A)_n$ motifs is defined as t. In the calculation of the glutamine residue content, the reason for targeting the "sequence excluding the sequence from the $(A)_n$ motif located at the most C-terminal side to the C-terminal of the domain sequence from the domain sequence" is the same as the reason descried above.

The sixth modified fibroin may have a domain sequence having an amino acid sequence corresponding to an amino acid sequence in which one or a plurality of glutamine residues in REP are deleted, or substituted with another amino acid residue, as compared to naturally occurring spider fibroin.

The "another amino acid residue" may be an amino acid residue other than the glutamine residue, but is preferably an amino acid residue with a higher hydropathy index than that of the glutamine residue. The hydropathy index of the amino acid residue is as shown in Table 1.

As shown in Table 1, examples of the amino acid residue with a higher hydropathy index than that of the glutamine residue include amino acid residues selected from isoleucine (I), valine (V), leucine (L), phenylalanine (F), cysteine (C), methionine (M), alanine (A), glycine (G), threonine (T), serine (S), tryptophan (W), tyrosine (Y), proline (P), and histidine (H). Among them, the amino acid residue is more preferably an amino acid residue selected from isoleucine (I), valine (V), leucine (L), phenylalanine (F), cysteine (C), methionine (M), and alanine (A), and still more preferably an amino acid residue selected from isoleucine (I), valine (V), leucine (L), and phenylalanine (F).

In the sixth modified fibroin, the hydrophobicity of REP is preferably −0.8 or more, more preferably −0.7 or more, still more preferably 0 or more, even still more preferably 0.3 or more, and particularly preferably 0.4 or more. The upper limit of REP is not particularly limited, and may be 1.0 or less, or may also be 0.7 or less.

In the present specification, the "hydrophobicity of REP" is a value calculated by the following method.

The hydrophobicity of REP is calculated as v/t in a case where in all REPs included in a sequence excluding the sequence from the $(A)_n$ motif located at the most C-terminal side to the C-terminal of the domain sequence from the domain sequence (the sequence corresponding to the "region A" in FIG. 3) in spider fibroin including the domain sequence represented by Formula 1: $[(A)_n \text{ motif-REP}]_m$ or Formula 2: $[(A)_n \text{ motif -REP}]_m\text{-}(A)_n$ motif, the total sum of the hydropathy indices of each of amino acid residues in this region is defined as v, and the total number of amino acid residues in all REPs excluding the sequence from the $(A)_n$ motif located at the most C-terminal side to the C-terminal of the domain sequence from the domain sequence and further excluding the $(A)_n$ motifs is defined as t. In the calculation of the hydrophobicity of REP, the reason for targeting the "sequence excluding the sequence from the $(A)_n$ motif located at the most C-terminal side to the C-terminal of the domain sequence from the domain sequence" is the same as the reason descried above.

In the domain sequence of the sixth modified fibroin, in addition to modifications corresponding to deletion of one or a plurality of glutamine residues in REP and/or substitution of one or a plurality of glutamine residues in REP with another amino acid residue, as compared to naturally occurring spider fibroin, there may be further modification of the amino acid sequence corresponding to substitution, deletion, insertion, and/or addition of one or a plurality of amino acid residues.

The sixth modified fibroin can be obtained by, for example, deleting one or a plurality of glutamine residues in REP and/or substituting one or a plurality of glutamine residues in REP with another amino acid residue, from the gene sequence of cloned naturally occurring spider fibroin. Alternatively, the sixth modified fibroin can be obtained by, for example, designing an amino acid sequence corresponding to an amino acid sequence in which one or a plurality of glutamine residues in REP are deleted and/or one or a plurality of glutamine residues in REP are substituted with another amino acid residue, from the amino acid sequence of naturally occurring spider fibroin, and chemically synthesizing a nucleic acid encoding the designed amino acid sequence.

More specific examples of the sixth modified fibroin include modified fibroins including (6-i) the amino acid sequence set forth in SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 43, or (6-ii) an amino acid sequence having a sequence identity of 90% or more with the amino acid sequence set forth in SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 43.

The modified fibroin of (6-i) will be described.

The amino acid sequence set forth in SEQ ID NO: 7 (Met-PRT410) is an amino acid sequence obtained by, performing modification of amino acid for improving productivity, such as modification in which an amino acid sequence having consecutive alanine residues in the $(A)_n$ motif is modified so that the number of the consecutive alanine residues becomes five, based on the base sequence and amino acid sequence of Nephila clavipes (GenBank Accession No.: P46804.1, GI: 1174415) which is naturally occurring fibroin. Meanwhile, modification for the glutamine residue (Q) is not performed in Met-PRT410, and thus the glutamine residue content thereof is approximately the same as the glutamine residue content of naturally occurring fibroin.

The amino acid sequence set forth in SEQ ID NO: 27 (M_PRT888) is an amino acid sequence obtained by substituting all QQs in Met-PRT410 (SEQ ID NO: 7) with VL.

The amino acid sequence set forth in SEQ ID NO: 28 (M_PRT965) is an amino acid sequence obtained by substituting all QQs in Met-PRT410 (SEQ ID NO: 7) with TS, and substituting the remaining Q with A.

The amino acid sequence set forth in SEQ ID NO: 29 (M_PRT889) is an amino acid sequence obtained by substituting all QQs in Met-PRT410 (SEQ ID NO: 7) with VL, and substituting the remaining Q with I.

The amino acid sequence set forth in SEQ ID NO: 30 (M_PRT916) is an amino acid sequence obtained by substituting all QQs in Met-PRT410 (SEQ ID NO: 7) with VI, and substituting the remaining Q with L.

The amino acid sequence set forth in SEQ ID NO: 31 (M_PRT918) is an amino acid sequence obtained by substituting all QQs in Met-PRT410 (SEQ ID NO: 7) with VF, and substituting the remaining Q with I.

The amino acid sequence set forth in SEQ ID NO: 34 (M_PRT525) is an amino acid sequence obtained by, with respect to Met-PRT410 (SEQ ID NO: 7), inserting two alanine residues into a region $(A_5)$ having consecutive alanine residues, deleting two domain sequences on the C-terminal side so that the molecular weight thereof is approximately the same as that of Met-PRT410, and substituting glutamine residues (Q) at 13 sites with a serine residue (S) or a proline residue (P).

The amino acid sequence set forth in SEQ ID NO: 32 (M_PRT699) is an amino acid sequence obtained by substituting all QQs in M_PRT525 (SEQ ID NO: 34) with VL.

The amino acid sequence set forth in SEQ ID NO: 33 (M_PRT698) is an amino acid sequence obtained by substituting all QQs in M_PRT525 (SEQ ID NO: 34) with VL, and substituting the remaining Q with I.

The amino acid sequence set forth in SEQ ID NO: 43 (Met-PRT966) is an amino acid sequence obtained by substituting all QQs in the amino acid sequence set forth in SEQ ID NO: 9 (amino acid sequence before the amino acid sequence set forth in SEQ ID NO: 42 is added to the C-terminal thereof) with VF, and substituting the remaining Q with I.

In all the amino acid sequences set forth in SEQ ID NO: 27, SEQ ID NO: 28, SEQ ID NO: 29, SEQ ID NO: 30, SEQ ID NO: 31, SEQ ID NO: 32, SEQ ID NO: 33, and SEQ ID NO: 43, the glutamine residue content is 9% or less (Table 2).

TABLE 2

| Modified Fibroin | Glutamine residue content | GPGXX motif content | Hydrophobicity of REP |
|---|---|---|---|
| Met-PRT410 (SEQ ID NO: 7) | 17.7% | 27.9% | −1.52 |
| M_PRT888 (SEQ ID NO: 27) | 6.3% | 27.9% | −0.07 |
| M_PRT965 (SEQ ID NO: 28) | 0.0% | 27.9% | −0.65 |
| M_PRT889 (SEQ ID NO: 29) | 0.0% | 27.9% | 0.35 |
| M_PRT916 (SEQ ID NO: 30) | 0.0% | 27.9% | 0.47 |
| M_PRT918 (SEQ ID NO: 31) | 0.0% | 27.9% | 0.45 |
| M_PRT525 (SEQ ID NO: 34) | 13.7% | 26.4% | −1.24 |
| M_PRT699 (SEQ ID NO: 32) | 3.6% | 26.4% | −0.78 |
| M_PRT698 (SEQ ID NO: 33) | 0.0% | 26.4% | −0.03 |
| Met-PRT966 (SEQ ID NO: 43) | 0.0% | 28.0% | 0.35 |

The modified fibroin of (6-i) may consist of the amino acid sequence set forth in SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 43.

The modified fibroin of ((6-ii) includes an amino acid sequence having a sequence identity of 90% or more with the amino acid sequence set forth in SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 43. The modified fibroin of (6-ii) is also a protein including a domain sequence represented by Formula 1: $[(A)_n$ motif-REP$]_m$ or Formula 2: $[(A)_n$ motif-REP$]_m$-$(A)_n$ motif. The sequence identity is preferably 95% or more.

In the modified fibroin of (6-ii), the glutamine residue content is preferably 9% or less. In the modified fibroin of (6-ii), the GPGXX motif content is preferably 10% or more.

The sixth modified fibroin may include a tag sequence at either or both of the N-terminal and the C-terminal. This enables the modified fibroin to be isolated, immobilized, detected and visualized.

More specific examples of the sixth modified fibroin including a tag sequence include modified fibroins including (6-iii) the amino acid sequence set forth in SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 44, SEQ ID NO: 55, or SEQ ID NO: 56, or (6-iv) an amino acid sequence having a sequence identity of 90% or more with the amino acid sequence set forth in SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 44, SEQ ID NO: 55, or SEQ ID NO: 56.

The amino acid sequences set forth in SEQ ID NO: 35, SEQ ID NO: 36, SEQ ID NO: 37, SEQ ID NO: 38, SEQ ID NO: 39, SEQ ID NO: 40, SEQ ID NO: 41, and SEQ ID NO: 44 are an amino acid sequence obtained by adding the amino acid sequence set forth in SEQ ID NO: 12 (including a His tag sequence and a hinge sequence) to the N-terminal of each of the amino acid sequences set forth in SEQ ID NO: 27, SEQ ID NO: 28, SEQ ID NO: 29, SEQ ID NO: 30, SEQ ID NO: 31, SEQ ID NO: 32, SEQ ID NO: 33, and SEQ ID NO: 43. Since these amino acid sequences are obtained by only adding a tag sequence at the N-terminal, the glutamine residue content does not change, and in all the amino acid sequences set forth in SEQ ID NO: 35, SEQ ID NO: 36, SEQ ID NO: 37, SEQ ID NO: 38, SEQ ID NO: 39, SEQ ID NO: 40, SEQ ID NO: 41, and SEQ ID NO: 44, the glutamine residue content is 9% or less (Table 3).

The amino acid sequence set forth in SEQ ID NO: 55 (PRT1107) is an amino acid sequence obtained by substituting a serine residue (S) of the amino acid sequence set forth in SEQ ID NO: 31 (Met-PRT918) with an alanine residue (A), a valine residue (V), a leucine residue (L), or an isoleucine residue (I), and further adding a tag sequence to the N-terminal of thereof.

The amino acid sequence set forth in SEQ ID NO: 56 (PRT1083) is an amino acid sequence obtained by substituting a proline residue (P) of the amino acid sequence set forth in SEQ ID NO: 31 (Met-PRT918) with a threonine residue (T) or a leucine residue (L), and further adding a tag sequence to the N-terminal thereof.

TABLE 3

| Modified Fibroin | Glutamine residue content | GPGXX motif content | Hydrophobicity of REP |
|---|---|---|---|
| PRT888 (SEQ ID NO: 35) | 6.3% | 27.9% | −0.07 |
| PRT965 (SEQ ID NO: 36) | 0.0% | 27.9% | −0.65 |
| PRT889 (SEQ ID NO: 37) | 0.0% | 27.9% | 0.35 |
| PRT916 (SEQ ID NO: 38) | 0.0% | 27.9% | 0.47 |
| PRT918 (SEQ ID NO: 39) | 0.0% | 27.9% | 0.45 |
| PRT699 (SEQ ID NO: 40) | 3.6% | 26.4% | −0.78 |
| PRT698 (SEQ ID NO: 41) | 0.0% | 26.4% | −0.03 |
| PRT966 (SEQ ID NO: 44) | 0.0% | 28.0% | 0.35 |

The modified fibroin of (6-iii) may consist of the amino acid sequence set forth in SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 44, SEQ ID NO: 55, or SEQ ID NO: 56.

The modified fibroin of (6-iv) includes an amino acid sequence having a sequence identity of 90% or more with the amino acid sequence set forth in SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 44, SEQ ID NO: 55, or SEQ ID NO: 56. The modified fibroin of (6-iv) is also a protein including a domain sequence represented by Formula 1: $[(A)_n$ motif-REP$]_m$ or Formula 2: $[(A)_n$ motif-REP$]_m$-$(A)_n$ motif. The sequence identity is preferably 95% or more.

In the modified fibroin of (6-iv), the glutamine residue content is preferably 9% or less. In the modified fibroin of (6-iv), the GPGXX motif content is preferably 10% or more.

The sixth modified fibroin may include a secretory signal for releasing the protein produced in the recombinant protein production system to the outside of a host. The sequence of the secretory signal can be appropriately set depending on the type of the host.

The modified fibroin may also be a modified fibroin having at least two or more characteristics among the characteristics of the first modified fibroin, the second modified fibroin, the third modified fibroin, the fourth modified fibroin, the fifth modified fibroin, and the sixth modified fibroin.

The spider silk protein may be a hydrophilic spider silk protein or a hydrophobic spider silk protein. The hydrophobic spider silk protein is a spider silk protein in which a value (average HI) obtained by determining the total sum of hydropathy indices (HI) of all amino acid residues constituting spider silk protein and then dividing the sum by the total number of amino acid residues is more than −0.8. The hydrophobic spider silk protein has preferably an average HI of −0.6 or more, more preferably −0.4 or more, still more preferably −0.2 or more, and particularly preferably 0 or more. The hydropathy index is as shown in Table 1. The hydrophilic spider silk protein is a spider silk protein having the above average HI of −0.8 or less. The average hydropathy index (HI) of the protein related to the present embodiment is preferably −1.3 or more, preferably −1.0 or more, preferably −0.8 or more, preferably more than −0.8, prefer-
ably −0.7 or more, preferably −0.6 or more, more preferably
−0.5 or more, preferably −0.4 or more, preferably −0.3 or
more, preferably −0.2 or more, preferably −0.1 or more,
more preferably 0 or more, more preferably 0.1 or more,
more preferably 0.2 or more, still more preferably 0.3 or
more, and particularly preferably 0.4 or more.

The HI of each of the amino acid sequences set forth in
SEQ ID NO: 11, SEQ ID NO: 15, SEQ ID NO: 35, SEQ ID
NO: 36, SEQ ID NO: 37, SEQ ID NO: 38, SEQ ID NO: 39,
SEQ ID NO: 40, and SEQ ID NO: 41 is as shown in Table
4. In the calculation of the HI of each amino acid sequence,
calculation was performed excluding a sequence having no
relationship with the modified fibroin (that is, a sequence
corresponding to the amino acid sequence set forth in SEQ
ID NO: 12).

TABLE 4

| Amino acid sequence | Hydrophobicity |
| --- | --- |
| Amino acid sequence set forth in SEQ ID NO: 11 | −0.8 |
| Amino acid sequence set forth in SEQ ID NO: 15 | −0.8 |
| Amino acid sequence set forth in SEQ ID NO: 35 | 0.07 |
| Amino acid sequence set forth in SEQ ID NO: 36 | −0.16 |
| Amino acid sequence set forth in SEQ ID NO: 37 | 0.55 |
| Amino acid sequence set forth in SEQ ID NO: 38 | 0.54 |
| Amino acid sequence set forth in SEQ ID NO: 39 | 0.49 |
| Amino acid sequence set forth in SEQ ID NO: 40 | 0.21 |
| Amino acid sequence set forth in SEQ ID NO: 41 | 0.48 |
| Amino acid sequence set forth in SEQ ID NO: 45 | −0.74 |
| Amino acid sequence set forth in SEQ ID NO: 47 | −1.2 |
| Amino acid sequence set forth in SEQ ID NO: 48 | 0.47 |
| Amino acid sequence set forth in SEQ ID NO: 49 | −0.531 |

Examples of the hydrophobic spider silk protein include
the sequence of the first modified fibroin, the sequence of the
second modified fibroin, the sequence of the third modified
fibroin, the sequence of the fifth modified fibroin, and the
sequence of the sixth modified fibroin. More specific
examples of the hydrophobic spider silk protein include
spider silk proteins including the amino acid sequence set
forth in SEQ ID NO: 27, SEQ ID NO: 28, SEQ ID NO: 29,
SEQ ID NO: 30, SEQ ID NO: 31, SEQ ID NO: 32, SEQ ID
NO: 33, or SEQ ID NO: 43, or the amino acid sequence set
forth in SEQ ID NO: 35, SEQ ID NO: 37, SEQ ID NO: 38,
SEQ ID NO: 39, SEQ ID NO: 40, SEQ ID NO: 41, or SEQ
ID NO: 44.

The hydrophilic spider silk protein may be, for example,
the sequence of the fourth modified fibroin described above.
More specific examples of the hydrophilic spider silk protein
include spider silk proteins including the amino acid
sequence set forth in SEQ ID NO: 4, the amino acid
sequence set forth in SEQ ID NO: 6, SEQ ID NO: 7, SEQ
ID NO: 8, or SEQ ID NO: 9, the amino acid sequence set
forth in SEQ ID NO: 13, SEQ ID NO: 11, SEQ ID NO: 14,
or SEQ ID NO: 15, the amino acid sequence set forth in SEQ
ID NO: 18, SEQ ID NO: 7, SEQ ID NO: 8, or SEQ ID NO:
9, the amino acid sequence set forth in SEQ ID NO: 17, SEQ
ID NO: 11, SEQ ID NO: 14, or SEQ ID NO: 15, the amino
acid sequence set forth in SEQ ID NO: 19, SEQ ID NO: 20,
SEQ ID NO: 21, or SEQ ID NO: 47.

One type of the above-descried spider silk protein can be
used alone, or two or more types thereof can be used in
combination.

The spider silk protein can be produced by, for example,
by using a host transformed with an expression vector
having a nucleic acid sequence encoding the spider silk protein and one or a plurality of regulatory sequences
operably linked to the nucleic acid sequence to express the
nucleic acid.

A method for producing a nucleic acid encoding the
spider silk protein is not particularly limited. The nucleic
acid can be produced by, for example, a method of perform-
ing cloning through amplification of gene encoding natural
spider silk protein by polymerase chain reaction (PCR), or
a method of producing the nucleic acid by chemical syn-
thesis. The method of chemically synthesizing nucleic acid
is not particularly limited, and gene can be chemically
synthesized by, for example, based on amino acid sequence
information of the spider silk protein obtained from the
NCBI web data base, according to a method of linking
oligonucleotides automatically synthesized by AKTA oligo-
pilot plus 10/100 (GE Healthcare, Japan), and the like by
PCR, for example. At this time, in order to facilitate puri-
fication and/or confirmation of the spider silk protein, a
nucleic acid encoding spider silk protein consisting of an
amino acid sequence in which an amino acid sequence
consisting of a start codon and a His 10-tag are added to the
N-terminal may be synthesized.

The regulatory sequence is a sequence that controls the
expression of a recombinant protein in a host (for example,
a promoter, an enhancer, a ribosome binding sequence, and
a transcription termination sequence), and can be appropri-
ately selected depending on the type of the host. As the
promoter, an inducible promoter that functions in a host cell,
and can induce the expression of a desired spider silk protein
may be used. The inducible promoter is a promoter that can
control transcription by presence of an inducer (expression
inducer), absence of a repressor molecule, or physical fac-
tors such as increase or decrease in the temperature, osmotic
pressure, pH value, or the like.

The type of the expression vector such as a plasmid
vector, a viral vector, a cosmid vector, a fosmid vector, or an
artificial chromosome vector can be appropriately selected
depending on the type of the host. As the expression vector,
an expression vector that can autonomously replicate in a
host cell or can be incorporated into a chromosome of a host,
and contains a promoter at a position capable of transcribing
a nucleic acid encoding spider silk protein is suitably used.

Both prokaryotes, and eukaryotes such as yeast, filamen-
tous fungi, insect cells, animal cells, and plant cells can be
suitably used as the host.

In a case where a prokaryote such as bacteria is used as
the host, the expression vector is preferably an expression
vector that can autonomously replicate in the prokaryote,
and contains a promoter, a ribosome binding sequence, a
nucleic acid encoding spider silk protein, and a transcription
termination sequence. The expression vector may contain
gene that controls the promoter.

Examples of the prokaryote include microorganisms
belonging to the genus *Escherichia, Brevibacillus, Serratia,*
*Bacillus, Microbacterium, Brevibacterium, Corynebacte-*
*rium,* and *Pseudomonas.* Examples of the microorganism
belonging to the genus *Escherichia* include *Escherichia coli,*
and the like. Examples of the microorganism belonging to
the genus *Brevibacillus* include *Brevibacillus agri,* and the
like. Examples of the microorganism belonging to the genus
*Serratia* include *Serratia liquefacience,* and the like.
Examples of the microorganism belonging to the genus
*Bacillus* include *Bacillus subtilis,* and the like. Examples of
the microorganism belonging to the genus *Microbacterium*
include *Microbacterium ammoniaphilum,* and the like.
Examples of the microorganism belonging to the genus
*Brevibacterium* include *Brevibacterium divaricatum,* and

US 12,600,754 B2

29
30 the like. Examples of the microorganism belonging to the genus *Corynebacterium* include *Corynebacterium ammoniagenes*, and the like. Examples of the microorganism belonging to the genus *Pseudomonas* include *Pseudomonas putida*, and the like.

In a case where a prokaryote is used as the host, examples of a vector into which a nucleic acid encoding spider silk protein is introduced include pBTrp2 (manufactured by Boehringer Ingelheim GmbH), pGEX (manufactured by Pharmacia), pUC18, pBluescriptII, pSupex, pET22b, pCold, pUB110, and pNCO2 (JP 2002-238569 A).

Examples of the eukaryotic host include yeasts, and filamentous fungi (mold and the like). Examples of the yeast include yeasts belonging to the genus *Saccharomyces, Pichia*, and *Schizosaccharomyces*. Examples of the filamentous fungi include fungi belonging to the genus *Aspergillus, Penicillium*, and *Trichoderma*.

In a case where a eukaryote is used as the host, examples of a vector into which a nucleic acid encoding spider silk protein is introduced include YEp13 (ATCC37115), and YEp24 (ATCC37051). As a method for introducing an expression vector into the host cell, any method can be used as long as it introduces DNA into the host cell. Examples thereof include a method using calcium ions [Proc. Natl. Acad. Sci. USA, 69, 2110 (1972)], an electroporation method, a spheroplast method, a protoplast method, a lithium acetate method, and a competent method.

As a method for expressing a nucleic acid in a host transformed with an expression vector, secretory production, fusion protein expression, and the like, in addition to direct expression, can be performed according to the method described in Molecular Cloning, 2nd edition.

The spider silk protein can be produced by, for example, culturing a transformed host in a culture medium, producing and accumulating spider silk protein in the culture medium, and then collecting the spider silk protein from the culture medium. The method for culturing a transformed host in a culture medium can be performed according to a method commonly used for culturing a host.

In a case where the host is a prokaryote such as *Escherichia coli* or a eukaryote such as yeast, any of a natural medium and a synthetic medium may be used as a culture medium as long as it contains a carbon source, a nitrogen source, an inorganic salt, or the like which can be assimilated by the host and it enables the host to be efficiently cultured.

Any carbon source that can be assimilated by the host may be used as the carbon source. Examples thereof include carbohydrates such as glucose, fructose, sucrose, and molasses, starch, and starch hydrolyzates containing them, organic acids such as acetic acid and propionic acid, and alcohols such as ethanol and propanol.

Examples of the nitrogen source that can be used include ammonium salts of inorganic or organic acids such as ammonia, ammonium chloride, ammonium sulfate, ammonium acetate, and ammonium phosphate, other nitrogen-containing compounds, peptone, meat extract, yeast extract, corn steep liquor, casein hydrolyzate, soybean cake, and soybean cake hydrolyzate, various fermented bacterial cells, and digested products thereof.

Examples of the inorganic salt that can be used include monopotassium phosphate, dipotassium phosphate, magnesium phosphate, magnesium sulfate, sodium chloride, ferrous sulfate, manganese sulfate, copper sulfate, and calcium carbonate.

Prokaryotes such as *Escherichia coli* or eukaryotes such as yeast can be cultured, for example, under aerobic conditions such as shaking culture or aeration agitation submerged culture. The culture temperature is, for example, 15 to 40° C. The culture time is usually 16 hours to 7 days. The pH of the culture medium during culture is preferably maintained at 3.0 to 9.0. The pH of the culture medium can be adjusted by using an inorganic acid, an organic acid, an alkali solution, urea, calcium carbonate, ammonia, or the like.

Moreover, antibiotics such as ampicillin and tetracycline may be added to the culture medium during culture as necessary. In a case of culturing a microorganism transformed with an expression vector using an inducible promoter as a promoter, an inducer may be added to the culture medium as necessary. For example, in a case of culturing a microorganism transformed with an expression vector using a lac promoter, isopropyl-β-D-thiogalactopyranoside or the like may be added to the medium, and in a case of culturing a microorganism transformed with an expression vector using a trp promoter, indole acrylic acid or the like may be added to the culture medium.

The spider silk protein produced by a transformed host can be isolated and purified by a method commonly used for protein isolation and purification. For example, in a case where the spider silk protein is expressed in a dissolved state in cells, the host cells are recovered by centrifugation after completion of culture, suspended in an aqueous buffer solution, and then disrupted using an ultrasonicator, a French press, a Manton-Gaulin homogenizer, a Dyno-Mill, or the like to obtain a cell-free extract. A purified preparation can be obtained from the supernatant obtained by centrifuging the cell-free extract, according to a method commonly used for protein isolation and purification, that is, a solvent extraction method, a salting-out method using ammonium sulfate or the like, a desalting method, a precipitation method using an organic solvent, an anion exchange chromatography method using a resin such as diethylaminoethyl (DEAE)-sepharose or DIAION HPA-75 (manufactured by Mitsubishi Kasei Kogyo Kabushiki Kaisha), a cation exchange chromatography method using a resin such as S-sepharose FF (manufactured by Pharmacia Corporation), a hydrophobic chromatography method using a resin such as butyl sepharose and phenyl sepharose, a gel filtration method using a molecular sieve, an affinity chromatography method, a chromatofocusing method, an electrophoresis method such as isoelectric focusing phoresis and the like, alone or in combination thereof.

As the chromatography, column chromatography using phenyl-TOYOPEARL (Tosoh Corporation), DEAE-TOYOPEARL (Tosoh Corporation), and Sephadex G-150 (Pharmacia Biotech Inc.) is preferably used.

In a case where the spider silk protein is expressed with formation of an insoluble matter in cells, similarly, host cells are recovered, disrupted, and centrifuged to recover the insoluble matter of the spider silk protein as a precipitated fraction. The recovered insoluble matter of the spider silk protein can be solubilized with a protein denaturing agent. After this operation, a purified preparation of the spider silk protein can be obtained by the same isolation and purification method as described above.

In a case where the spider silk protein is secreted extracellularly, the spider silk protein can be recovered from a culture supernatant. That is, the culture supernatant is obtained by treating a culture by a technique such as centrifugation, and a purified preparation can be obtained from the culture supernatant by using the same isolation and purification method as described above.

A structural protein derived from collagen (collagen protein) is, for example, a structural protein including a domain sequence represented by Formula 3: [REP3]$_p$ (in Formula 3, p represents an integer of 5 to 300, REP3 represents an amino acid sequence consisting of Gly-X-Y, X and Y each represent an optional amino acid residue other than Gly, and a plurality of REP3s may be the same or different amino acid sequences). Specifically, a structural protein including the amino acid sequence set forth in SEQ ID NO: 45 can be exemplified. The amino acid sequence set forth in SEQ ID NO: 45 is an amino acid sequence obtained by adding the amino acid sequence set forth in SEQ ID NO: 46 (tag sequence and hinge sequence) to the N-terminal of an amino acid sequence from the 301th residue to the 540th residue corresponding to repeated portions and motifs of a partial sequence of human collagen type 4 (NCBI Genbank Accession No.: CAA56335.1, GI: 3702452) obtained from the NCBI data base. As a structural protein derived from collagen, a structural protein including the amino acid sequence set forth in SEQ ID NO: 59 can be exemplified.

A structural protein derived from resilin (resilin protein) includes a structural protein including a domain sequence represented by Formula 4: [REP4]$_q$ (in Formula 4, q represents an integer of 4 to 300, REP4 represents an amino acid sequence consisting of Ser-J-J-Tyr-Gly-U-Pro, J represents an optional amino acid residue and is particularly preferably an amino acid residue selected from the group consisting of Asp, Ser, and Thr, U represents an optional amino acid residue and is particularly preferably an amino acid residue selected from the group consisting of Pro, Ala, Thr, and Ser, and a plurality of REP4s may be the same or different amino acid sequences). Specifically, a structural protein including the amino acid sequence set forth in SEQ ID NO: 47 can be exemplified. The amino acid sequence set forth in SEQ ID NO: 47 is an amino acid sequence obtained by adding the amino acid sequence set forth in SEQ ID NO: 46 (tag sequence and hinge sequence) to the N-terminal of an amino acid sequence from the 19th residue to the 321th residue, obtained by substituting Thr of the 87th residue with Ser and substituting Asn of the 95th residue with Asp in the amino acid sequence of resilin (NCBI Genbank Accession No.: NP 611157, GI: 24654243). As a structural protein derived from resilin, a structural protein including the amino acid sequence set forth in SEQ ID NO: 60 can also be exemplified.

Examples of a structural protein derived from elastin protein (elastin protein) include structural proteins having amino acid sequences such as NCBI Genbank Accession No. AAC98395 (human), 147076 (sheep), and NP786966 (cow). Specifically, a structural protein including the amino acid sequence set forth in SEQ ID NO: 48 can be exemplified. The amino acid sequence set forth in SEQ ID NO: 48 is an amino acid sequence obtained by adding the amino acid sequence set forth in SEQ ID NO: 46 (tag sequence and hinge sequence) to the N-terminal of an amino acid sequence from the 121th residue to the 390th residue of the amino acid sequence of NCBI Genbank Accession No. AAC98395.

As a structural protein derived from keratin (keratin protein), a type I keratin and the like of Capra hircus can be exemplified. Specifically, a structural protein including the amino acid sequence set forth in SEQ ID NO: 49 (amino acid sequence of NCBI Genbank Accession No. ACY30466) can be exemplified. The amino acid sequence set forth in SEQ ID NO: 49 is an amino acid sequence obtained by adding the amino acid sequence set forth in SEQ ID NO: 46 (tag sequence and hinge sequence) to the N-terminal of the amino acid sequence of NCBI Genbank Accession No. ACY30466. As a structural protein derived from keratin, a structural protein including having the amino acid sequence set forth in SEQ ID NO: 58 can be exemplified. The amino acid sequence set forth in SEQ ID NO: 58 has an amino acid sequence obtained by substituting leucine or valine with alanine or glycine in an amino acid sequence consisting of the 1st to 292nd amino acid residues from the N-terminal of SEQ ID NO: 49 to obtain an amino acid sequence, and further substituting three amino acid residues in the 1st to 246th amino acid residues from the N-terminal of the obtained amino acid sequence and inserting an amino acid sequence consisting of GAAAAAG (SEQ ID NO: 62) therein.

The collagen protein, resilin protein, elastin protein, and keratin protein may be a hydrophilic protein or may be a hydrophobic protein. The hydrophobic protein is a protein in which a value (average HI) obtained by determining the total sum of hydropathy indices (HI) of all amino acid residues constituting the protein and then dividing the sum by the total number of amino acid residues is more than −0.8. The hydrophobic protein has preferably an average HI of −0.6 or more, more preferably −0.4 or more, still more preferably −0.2 or more, and particularly preferably 0 or more. The hydropathy index is as shown in Table 1. The hydrophilic protein is a protein having the above average HI of −0.8 or less.

The hydrophobic collagen protein, hydrophobic resilin protein, hydrophobic elastin protein, and hydrophobic keratin protein include a protein including the amino acid sequence set forth in SEQ ID NO: 45, SEQ ID NO: 48, or SEQ ID NO: 49 described above.

The hydrophilic collagen protein, hydrophilic resilin protein, hydrophilic elastin protein, and hydrophilic keratin protein include a protein including the amino acid sequence set forth in SEQ ID NO: 47.

The HI of each of the amino acid sequences set forth in SEQ ID NO: 45, SEQ ID NO: 47, SEQ ID NO: 48, and SEQ ID NO: 49 is as shown in Table 4. In the calculation of the HI of each amino acid sequence, calculation was performed excluding a sequence having no relationship with collagen protein, resilin protein, elastin protein, and keratin protein (that is, a sequence corresponding to the amino acid sequence set forth in SEQ ID NO: 12).

Also, the structural protein contains a hydrophobic protein and a polypeptide that tends to cause self-aggregation in a polar solvent, and is preferably a hydrophobic protein. One type of structural protein or structural protein derived therefrom can be used alone, or two or more types thereof can be used in combination. By combining two or more types of structural proteins, the entire hydrophobicity may be adjusted to a desired value. The hydrophobicity can be calculated by the method described above.

(Organic Solvent)

As the organic solvent of the spinning dope according to the present embodiment, any organic solvent that can dissolve artificial protein can be used. Examples of the organic solvent include hexafluoroisopropanol (HFIP), hexafluoroacetone (HFA), dimethyl sulfoxide (DMSO), N,N-dimethylformamide (DMF), N,N-dimethylacetamide (DMA), 1,3-dimethyl-2-imidazolidone (DMI), N-methyl-2-pyrolidone (NMP), acetonitrile, N-methylmorpholine N-oxide (NMO), and formic acid. One type of these solvent may be used alone, or two or more types thereof can be mixed and used. For example, the organic solvent may contain at least one type selected from the group consisting of formic acid, DMSO, and HFIP, may be at least one type selected from the group consisting of formic acid, DMSO, and HFIP, or may also be formic acid. These organic solvents may contain water.

The content of protein in the spinning dope according to the present embodiment is preferably 10 to 40% by mass, more preferably 10 to 35% by mass, more preferably 12 to 35% by mass, more preferably 15 to 35% by mass, more preferably 15 to 30% by mass, still more preferably 20 to 35% by mass, and particularly preferably 20 to 30% by mass based on 100% by mass of the total amount of the spinning dope. When the content of the structural protein is 10% by mass or more, fibers formed in the coagulation bath can further reduce influence of an accompanying flow occurred in the coagulation bath, thus improving productivity. When the content of the structural protein is 40% by mass or less, the spinning dope can be even more stably discharged from the spinneret, thus improving productivity.

(Dissolution promoter) The spinning dope according to the present embodiment may further contain a dissolution promoter. Inclusion of the dissolution promoter facilitates preparation of the spinning dope.

The dissolution promoter may be an inorganic salt composed of the following Lewis acid and Lewis base. Examples of the Lewis base include halide ions. Examples of the Lewis acid include metal ions such as alkaline metal ions, and halide alkaline earth metal ions. Examples of the inorganic salt include alkaline metal halides, and alkaline earth metal halides. Specific examples of the alkaline metal halide include lithium chloride and lithium bromide. Specific examples of the alkaline earth halide include magnesium chloride and calcium chloride. One type of dissolution promoter can be used alone, or two or more types thereof can be used in combination.

These inorganic salts can be used as a dissolution promoter for structural protein against formic acid or DMSO, and lithium chloride and calcium chloride are particularly preferable. Inclusion of the dissolution promoter (the above inorganic salts) in the spinning dope allows the structural protein to be dissolved at a high concentration in the spinning dope. With this, the production efficiency of the protein fiber is further improved, and improvement in quality of the protein fiber, improvement of physical properties such as stress, and the like can be expected.

The content of the dissolution promoter may be 0.1% by mass or more, 1% by mass or more, 2% by mass or more, 3% by mass or more, 4% by mass or more, 7% by mass or more, 10% by mass or more, or 15% by mass or more; or may be 20% by mass or less, 16% by mass or less, 12% by mass or less, or 9% by mass or less based on the total amount of the spinning dope.

(Various additives) The spinning dope may further contain various types of additives as necessary. Examples of the additive include a plasticizer, a leveling agent, a crosslinking agent, a nucleating agent, an antioxidant, an ultraviolet absorber, a coloring agent, a filler, and a synthetic resin. The content of the additive may be 50 parts by mass or less based on 100 parts by mass of total amount of protein in the spinning dope.

The viscosity of the spinning dope according to the present embodiment may be appropriately set depending on the application of the fiber to be produced, the spinning method, and the like. The viscosity at 20° C. may be 60,000 to 130,000 mPa·sec, or 65,000 to 125,000 mPa·sec, for example. The viscosity at 35° C. may be 500 to 35,000 mPa·sec, 1,000 to 35,000 mPa·sec, 3,000 to 30,000 mPa·sec, 500 to 20,000 mPa·sec, 500 to 15,000 mPa·sec, 1,000 to 15,000 mPa sec, 1,000 to 12,000 mPa sec, 1,500 to 12,000 mPa sec, 1,500 to 10,000 mPa sec, or 1,500 to 8,000 mPa·sec, for example. The viscosity at 40° C. may be 500 to 35,000 mPa sec, 1,000 to 35,000 mPa sec, 5,000 to 35,000 mPa sec, 10,000 to 30,000 mPa sec, 12,000 to 30,000 mPa·sec, or 12,000 to 28,000 mPa sec, for example. The viscosity at 70° C. may be 1,000 to 6,000 mPa sec, or 1,500 to 5,000 mPa sec, for example. The viscosity of the spinning dope can be measured by using, for example, an "EMS viscometer" (trade name) manufactured by Kyoto Electronics Manufacturing Co., Ltd.

The spinning dope may be stirred or shaken for a certain period of time in order to promote dissolution. At this time, the spinning dope may be heated, as necessary, to a temperature at which the spinning dope can be dissolved, depending on a structural protein and solvent to be used. The dope solution may be heated to 30° C. or more, 40° C. or more, 50° C. or more, 60° C. or more, 70° C. or more, 80° C. or more, or 90° C. or more, for example. From the viewpoint of preventing decomposition of the artificial protein, the heating temperature is preferably 40° C. The upper limit of the heating temperature is, for example, a temperature equal to or less than the boiling point of the solvent.

<Coagulation Liquid>

The coagulation liquid according to the present embodiment contains water or an aqueous solution of PH 0.25 or more and PH 10.00 or less. This enables a method of producing a protein fiber with reduced risk of explosion, fire and the like, reduced production cost, and reduced environmental load to be provided. The aqueous solution may be a salt aqueous solution, an acid aqueous solution, or a mixed solution of a salt aqueous solution and an acid aqueous solution, may be a salt aqueous solution, or a mixed solution of a salt aqueous solution and an acid aqueous solution, or may be a salt aqueous solution. Here, the mixed solution of a salt aqueous solution and an acid aqueous solution is not limited to a solution in which a salt aqueous solution and an acid aqueous solution are mixed. The mixed solution includes a solution in which an acid is added to a salt aqueous solution, a solution in which a salt is added to an acid aqueous solution, and a solution in which a salt and an acid are dissolved in water.

(Acid Aqueous Solution)

Examples of the acid aqueous solution include aqueous solutions of carboxylic acid, and the like. Specific examples of the carboxylic acid include formic acid, acetic acid, propionic acid, citric acid, and oxalic acid. One type of these solvent may be used alone, or two or more types thereof may be mixed and used as an aqueous solution. The acid aqueous solution may be, for example, a citric acid aqueous solution or a formic acid aqueous Solution (Salt Aqueous Solution)

Examples of the salt aqueous solution include a salt aqueous solution of an organic salt or an inorganic salt, and a mixed aqueous solution of an organic salt and an inorganic salt.

Examples of the organic salt include carboxylate and the like. Specific examples of the carboxylate include a formate, an acetate, a propionate, a citrate, and an oxalate. The organic salt may be, for example, a formate, an acetate, and a citrate.

Specific examples of the formate include ammonium formate, potassium formate, sodium formate, lithium formate, magnesium formate, and calcium formate.

Specific examples of the acetate include ammonium acetate, potassium acetate, sodium acetate, lithium acetate, magnesium acetate, and calcium acetate.

Specific examples of the propionate include ammonium propionate, potassium propionate, sodium propionate, lithium propionate, magnesium propionate, and calcium propionate.

Specific examples of the citrate include ammonium citrate, potassium citrate, sodium citrate, lithium citrate, magnesium citrate, and calcium citrate. For example, the citrate may include at least one type selected from the group consisting of ammonium citrate, potassium citrate, sodium citrate, magnesium citrate, and calcium citrate. The citrate may include at least one type selected from the group consisting of ammonium citrate, potassium citrate, and sodium citrate. The citrate may include at least one type selected from the group consisting of potassium citrate and sodium citrate. The citrate may be sodium citrate.

Specific examples of the oxalate include ammonium oxalate, potassium oxalate, sodium oxalate, lithium oxalate, magnesium oxalate, and calcium oxalate. The carboxylate is more preferably a sodium carboxylate, and specific examples of the sodium carboxylate include sodium formate, sodium acetate, sodium propionate, and sodium oxalate.

Specific examples of the inorganic salt include a normal salt, an acid salt, and a basic salt.

Specific examples of the normal salt include a sulfate, a chloride, a nitrate, an iodide salt, a thiocyanate, and a carbonate.

Specific examples of the sulfate include ammonium sulfate, potassium sulfate, sodium sulfate, lithium sulfate, magnesium sulfate, and calcium sulfate. For example, the sulfate may include at least one type selected from the group consisting of ammonium sulfate, sodium sulfate, magnesium sulfate, and calcium sulfate. The sulfate may include at least one type selected from the group consisting of ammonium sulfate and sodium sulfate. The sulfate may be sodium sulfate.

Specific examples of the chloride include ammonium chloride, potassium chloride, sodium chloride, lithium chloride, magnesium chloride, calcium chloride, and guanidinium chloride. For example, the chloride may include at least one type selected from the group consisting of ammonium chloride, potassium chloride, sodium chloride, lithium chloride, calcium chloride, magnesium chloride, and guanidinium chloride. The chloride may include at least one type selected from the group consisting of ammonium chloride, potassium chloride, sodium chloride, lithium chloride, calcium chloride, and magnesium chloride. The chloride may include at least one type selected from the group consisting of potassium chloride, sodium chloride, and calcium chloride. The chloride may include at least one type selected from the group consisting of sodium chloride and calcium chloride. The chloride may be sodium chloride.

Specific examples of the nitrate include ammonium nitrate, potassium nitrate, sodium nitrate, lithium nitrate, magnesium nitrate, and calcium nitrate.

Specific examples of the iodide salt include ammonium iodide, potassium iodide, sodium iodide, lithium iodide, magnesium iodide, and calcium iodide.

Specific examples of the thiocyanate include ammonium thiocyanate, potassium thiocyanate, sodium thiocyanate, lithium thiocyanate, magnesium thiocyanate, calcium thiocyanate, and guanidine thiocyanate.

Specific examples of the carbonate include ammonium carbonate, potassium carbonate, sodium carbonate, lithium carbonate, magnesium carbonate, and calcium carbonate.

Specific examples of the acid salt include a hydrogen sulfate, a hydrogen phosphate, and a bicarbonate.

Specific examples of the hydrogen sulfate include ammonium hydrogen sulfate, potassium hydrogen sulfate, sodium hydrogen sulfate, lithium hydrogen sulfate, magnesium hydrogen sulfate, and calcium hydrogen sulfate.

Specific examples of the hydrogen phosphate include sodium dihydrogen phosphate, disodium hydrogen phosphate, potassium dihydrogen phosphate, dipotassium hydrogen phosphate, ammonium dihydrogen phosphate, ammonium dihydrogen phosphate, diammonium hydrogen phosphate, magnesium dihydrogen phosphate, dimagnesium hydrogen phosphate, calcium dihydrogenphosphate, and dicalcium hydrogen phosphate.

Specific examples of the bicarbonate include ammonium bicarbonate, potassium bicarbonate, sodium bicarbonate, lithium bicarbonate, lithium bicarbonate, magnesium bicarbonate, and calcium bicarbonate.

Specific examples of the basic salt include calcium hydroxide chloride, and magnesium hydroxide chloride.

One type of the above acid, acid aqueous solution, salt, and salt aqueous solution may be used alone, or two or more types thereof can be mixed and used.

Examples of the salt mixed aqueous solution in which two or more types of salts or salt aqueous solutions are mixed include a mixed aqueous solution of the organic salts, a mixed aqueous solution of the inorganic salts, and a mixed aqueous solution of the organic salt and the inorganic salt. Brackish water and sea water are particularly preferable from the viewpoint of reducing production cost. The brackish water and sea water are known to primarily contain potassium chloride, sodium chloride, magnesium chloride, magnesium sulfate, and calcium sulfate.

Preferably, the coagulation liquid preferably contains a salt aqueous solution, and more preferably, the coagulation liquid is a salt aqueous solution. Inclusion of salt can further improve solvent removal rate. The salt preferably includes at least one type selected from the group consisting of a carboxylate, a sulfate, a chloride, a hydrogen phosphate, and a bicarbonate. The salt more preferably includes at least one type selected from the group consisting of a carboxylate, a sulfate, and a chloride. The salt particularly preferably includes at least one type selected from the group consisting of a sulfate and a chloride. Inclusion of these salts can further improve the fiber-forming property, and thus can further improve elongation of the fiber to be obtained.

The carboxylate is more preferably sodium carboxylate. The sulfate is more preferably ammonium sulfate, sodium sulfate, magnesium sulfate, and calcium sulfate. The chloride is more preferably potassium chloride, sodium chloride, magnesium chloride, and calcium chloride. The bicarbonate is more preferably sodium bicarbonate. The mixed aqueous solution is particularly preferably brackish water and sea water. Use of these salts and mixed aqueous solutions can further reduce production cost, in addition to the effect of improving the fiber-forming property.

The content of the salt may be 0.1% by mass or more, 0.3% by mass or more, 0.5% by mass or more, 0.7% by mass or more, 1% by mass or more, 1.3% by mass or more, 1.5% by mass or more, 1.7% by mass or more, 2% by mass or more, 2.3% by mass or more, 2.5% by mass or more, 2.7% by mass or more, 3% by mass or more, 4% by mass or more, 5% by mass or more, 7% by mass or more, 10% by mass or more, 15% by mass or more, or 20% by mass or more, based on the total amount of the coagulation liquid. The upper limit thereof may be 30% by mass or less, 25% by mass or less, or less than or equal to the solubility. The content of the salt may be, for example, 0.1% by mass or more and 30% by mass or less, 0.3% by mass or more and 25% by mass or less, 1% by mass or more and 25% by mass or less, 3% by mass or more and 25% by mass or less, 5% by mass or more and 25% by mass or less, 8% by mass or more and 25% by mass or less, 10% by mass or more and 25% by mass or less, 1% by mass or more and 20% by mass or less, 3% by mass or more and 20% by mass or less, 5% by mass or more and 20% by mass or less, 8% by mass or more and 20% by mass or less, 10% by mass or more and 20% by mass or less, 15% by mass or more and 20% by mass or less, or 16% by mass or more and 20% by mass or less, based on the total amount of the coagulation liquid. The content of the salt is, for example, preferably 0.05 mol/L or more, may be 0.05 mol/L or more and 5.5 mol/L or less, may be 0.1 mol/L or more and 5.0 mol/L or less, may be 0.1 mol/L or more and 4.5 mol/L or less, or may be 0.1 mol/L or more and 4.0 mol/L or less, based on the total amount of the coagulation liquid.

The content of the salt in a case of using sodium chloride may be, for example, 0.1 mol/L or more and 5.0 mol/L or less, 0.1 mol/L or more and 4.5 mol/L or less, or 0.1 mol/L or more and 4.0 mol/L or less, based on the total amount of the coagulation liquid.

The content of the salt in a case of using potassium chloride may be, for example, 0.1 mol/L or more and 3.9 mol/L or less, based on the total amount of the coagulation liquid.

The content of the salt in a case of using calcium chloride may be, for example, 0.1 mol/L or more and 14.3 mol/L or less, 0.1 mol/L or more and 13.0 mol/L or less, 0.1 mol/L or more and 12.0 mol/L or less, 0.1 mol/L or more and 11.0 mol/L or less, 0.1 mol/L or more and 10.0 mol/L or less, 0.1 mol/L or more and 9.0 mol/L or less, 0.1 mol/L or more and 8.0 mol/L or less, 0.1 mol/L or more and 7.0 mol/L or less, 0.1 mol/L or more and 6.0 mol/L or less, 0.1 mol/L or more and 5.0 mol/L or less, 0.1 mol/L or more and 4.0 mol/L or less, 0.1 mol/L or more and 3.0 mol/L or less, or 0.1 mol/L or more and 2.0 mol/L or less, based on the total amount of the coagulation liquid.

The content of the salt in a case of using sodium sulfate may be, for example, 0.1 mol/L or more and 3.4 mol/L or less, 0.1 mol/L or more and 3.0 mol/L or less, 0.1 mol/L or more and 2.5 mol/L or less, or 0.1 mol/L or more and 2.0 mol/L or less, based on the total amount of the coagulation liquid. The content may be, for example, 3% by mass or more and 28% by mass or less, 3% by mass or more and 25% by mass or less, 3% by mass or more and 20% by mass or less, 5% by mass or more and 20% by mass or less, or 8% by mass or more and 20% by mass or less, based on the total amount of the coagulation liquid. The content of the sodium sulfate relative to the total amount of the coagulation liquid is preferably 10% by mass or more and 20% by mass or less, preferably 11% by mass or more and 19% by mass or less, more preferably 11% by mass or more and 18% by mass or less, still more preferably 12% by mass or more and 18% by mass or less, and particularly preferably 12% by mass or more and 17% by mass or less. When the content of the sodium sulfate relative to the total amount of the coagulation liquid is 10% by mass or more, sufficient coagulation rate can be obtained, thus enabling cost increase due to facility investment to be prevented. When the content of the sodium sulfate relative to the total amount of the coagulation liquid is 20% by mass or less, the breakage of the yarn can be prevented that occurs at the interface between the dope solution and the coagulated yarn (fiber bundle) caused by rapid coagulation of the dope solution. The content of water relative to the total amount of the coagulation liquid in the above case is preferably 60% by mass or more and 80% by mass or less, and more preferably 60% by mass or more and 70% by mass or less from the viewpoint of improving the recovery efficiency of the solvent. The concentration of the sodium sulfate aqueous solution in a case of using sodium sulfate is preferably 10% by mass or more and 22% by mass or less, preferably 10% by mass or more and 20% by mass or less, more preferably 12% by mass or more and 20% by mass or less, still more preferably 14% by mass or more and 20% by mass or less, and particularly preferably 16% by mass or more and 20% by mass or less. When the concentration of the sodium sulfate aqueous solution is 10% by mass or more, sufficient coagulation rate can be obtained, thus enabling cost increase due to facility investment to be prevented. When the content of the sodium sulfate aqueous solution is 22% by mass or less, the breakage of the yarn can be prevented that occurs at the interface between the dope solution and the coagulated yarn (fiber bundle) caused by rapid coagulation of the dope solution.

The content of the salt in a case of using sodium citrate may be, for example, 0.1 mol/L or more and 1.6 mol/L or less, or 0.1 mol/L or more and 1.3 mol/L or less, based on the total amount of the coagulation liquid.

The aqueous solution contained in the coagulation liquid of the present embodiment may be selected from the group consisting of, for example, a carboxylic acid aqueous solution, a bicarbonate aqueous solution, a formate aqueous solution, an acetate aqueous solution, a chloride aqueous solution, a sulfate aqueous solution, a hydrogen phosphate aqueous solution, a citrate aqueous solution, brackish water, sea water, and a mixed solution thereof. The aqueous solution contained in the coagulation liquid of the present embodiment may be selected from the group consisting of, for example, citric acid aqueous solution, formic acid aqueous solution, sodium bicarbonate aqueous solution, sodium formate aqueous solution, sodium acetate aqueous solution, sodium chloride aqueous solution, sodium sulfate aqueous solution, ammonium sulfate aqueous solution, potassium hydrogen phosphate aqueous solution, calcium chloride aqueous solution, sodium citrate aqueous solution, brackish water, sea water, and a mixed solution thereof.

The coagulation liquid before contact with the spinning dope may or may not contain an organic solvent. Even in a case where the coagulation liquid before contact with the spinning dope contains no organic solvent, there may be a case where the organic solvent is dissolved from the spinning dope in contact with the coagulation liquid in the coagulation liquid in a process of bringing the spinning dope into contact with the coagulation liquid. The content of the organic solvent contained in the coagulation liquid (including a case where the organic solvent is dissolved from the spinning dope in contact with the coagulation liquid to the coagulation liquid) is preferably 0% by mass or more and 40% by mass or less, 0% by mass or more and 30% by mass or less, 5% by mass or more and 30% by mass or less, 5% by mass or more and 25% by mass or less, 0% by mass or more and 20% by mass or less, 5% by mass or more and 20% by mass or less, 5% by mass or more and 15% by mass or less, 10% by mass or more and 40% by mass or less, 15% by mass or more and 40% by mass or less, 20% by mass or more and 40% by mass or less, 10% by mass or more and 30% by mass or less, 10% by mass or more and 20% by mass or less, 0% by mass or more and 10% by mass or less, 0% by mass or more and 5% by mass or less, and 0% by mass or more and 2% by mass or less, based on 100% by mass of the total mass of the coagulation liquid (in a case where the organic solvent is dissolved from the spinning dope to the coagulation liquid, the total content of the coagulation liquid before contact with the spinning dope and the organic solvent dissolved from the spinning dope to the coagulation liquid). When the content of the organic solvent is within the above-described range, the effect of the invention of the present application is remarkably exhibited. The content of the organic solvent contained in the coagulation liquid may be 10% by mass or more and 40% by mass or less, 15% by mass or more and 40% by mass or less, or 20% by mass or more and 40% by mass or less, based on 100% by mass of the total mass of the coagulation liquid. When the content of the organic solvent is within the above-described range, the fiber-forming property of the structural protein is further improved. As the organic solvent, formic acid, DMSO or HFIP is preferable, and formic acid is more preferable.

The pH of the aqueous solution contained in the coagulation liquid may be 0.25 to 10.00, or 0.25 to 9.50.

The pH of the acid aqueous solution in the coagulation liquid may be, for example, less than 0.25 to 7.00, less than 0.50 to 7.00, less than 1.00 to 7.00, less than 1.50 to 7.00, less than 2.00 to 7.00, or less than 3.00 to 7.00.

The pH of the salt aqueous solution in the coagulation liquid may be, for example, 0.50 to 10.00, 1.00 to 10.00, 2.00 to 10.00, 3.00 to 10.00, 3.50 to 10.00, 4.00 to 10.00, 4.50 to 10.00, 5.00 to 10.00, 5.50 to 10.00, 6.00 to 10.00, 6.50 to 10.00, or 6.50 to 9.50.

The content of the water or the aqueous solution in the coagulation liquid is preferably 60% by mass or more, more preferably 70% by mass or more, more preferably 80% by mass or more, still more preferably 90% by mass or more, and particularly preferably 95% by mass or more, based on the total amount of the coagulation liquid. When the content of the water or the aqueous solution is within the above-described range, the fiber-forming property of the structural protein is further improved. The content of the water or the aqueous solution in the coagulation liquid may be, for example, 60% by mass or more and 100% by mass or less, 70% by mass or more and 100% by mass or less, 80% by mass or more and 100% by mass or less, or 95% by mass or more and 100% by mass or less, based on the total amount of the coagulation liquid.

The coagulation liquid may contain formic acid. The content of the formic acid relative to the total amount of the coagulation liquid is preferably 15 to 25% by mass, more preferably 16 to 25% by mass, still more preferably 16 to 24% by mass, and particularly preferably 18 to 24% by mass from the viewpoint of improving the recovery efficiency of the solvent.

The temperature of the coagulation liquid may be room temperature, 0° C. to 90° C., 0° C. to 80° C., 5° C. to 80° C., 10° C. to 80° C., 15° C. to 80° C., 20° C. to 80° C., 25° C. to 80° C., 30° C. to 80° C., 40° C. to 80° C., 50° C. to 80° C., 60° C. to 80° C., 70° C. to 80° C., 20° C. to 70° C., 30° C. to 70° C., 40° C. to 70° C., 50° C. to 70° C., 20° C. to 60° C., 30° C. to 60° C., 40° C. to 60° C., or 50° C. to 60° C. The lower limit of the temperature of the coagulation liquid may be equal to or more than the melting point of the organic solvent contained in the spinning dope. The upper limit of the temperature may be equal to or less than the boiling point of the organic solvent contained in the spinning dope. By setting the temperature of the coagulation liquid to a higher temperature, the solvent removal rate of the spinning dope can be increased. Also, the temperature of the coagulation liquid is preferably 55° C. to 65° C., more preferably 45° C. to 55° C., and sill more preferably 35° C. to 45° C. When the temperature of the coagulation liquid is 35° C. or more, an appropriate solvent removal rate can be obtained, thus enabling productivity to be further improved. When the temperature of the coagulation liquid is 65° C. or less, rapid softening caused by the dope solution being heated in the coagulation liquid can be prevented.

The coagulation liquid may further contain the above-described dissolution promoter that can be added to the spinning dope.

[Spinning Process]

The method for producing a protein fiber according to the present embodiment can be produced by a publicly known wet spinning method and dry wet spinning method. That is, in the spinning process, the spinning dope is brought into contact with the coagulation liquid to coagulate protein. The method for producing a protein fiber of the present embodiment, including the spinning process, can be performed by, for example, using the spinning apparatus shown in FIG. 4.

Figure 4:
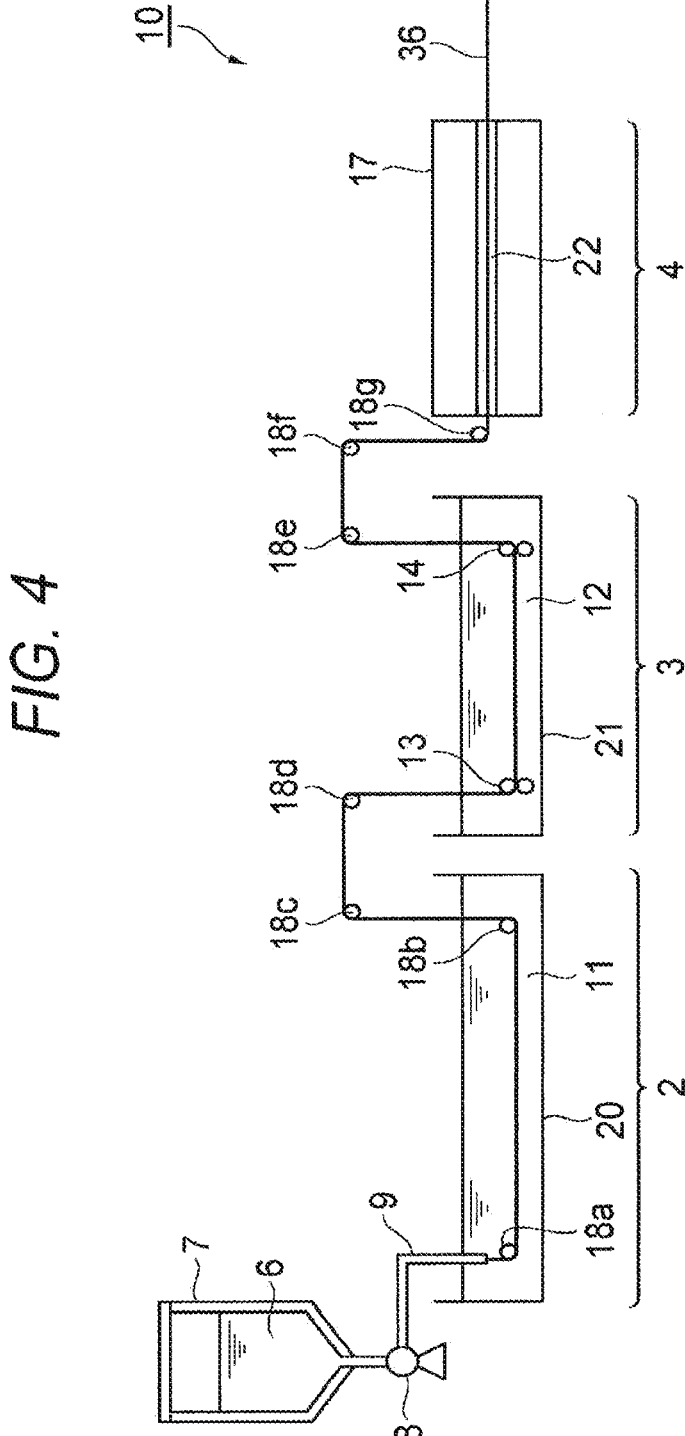
FIG. 4 is an explanatory view illustrating an example of a spinning apparatus for producing a protein fiber.

FIG. 4 is an explanatory view illustrating an example of a spinning apparatus for producing a protein fiber. The spinning apparatus 10 shown in FIG. 4 is an example of the spinning apparatus for wet spinning, and has an extrusion apparatus 1, a coagulation bath 20, a washing bath (drawing bath) 21, and a drying apparatus 4 from the upstream side in this order.

The extrusion apparatus 1 has a storage tank 7 that stores a spinning dope (dope solution) 6. The coagulation bath 20 stores a coagulation liquid 11. The spinning dope 6 is extruded from a nozzle 9 provided in the coagulation liquid 11 by a gear pump 8 attached to the lower end portion of the storage tank 7. The extruded spinning dope 6 is supplied (introduced) to the coagulation liquid 11 in the coagulation bath 20. The solvent is removed from the spinning dope in the coagulation liquid 11, and the spider silk protein coagulates. The coagulated spider silk protein is introduced into a washing bath 21, washed with a washing solution 12 in the washing bath 21, then sent to the drying apparatus 4 by a first nip roller 13 and a second nip roller 14 provided in the washing bath 21. At this time, when the rotational speed of the second nip roller 14 is made faster than the rotational speed of the first nip roller 13, for example, a protein fiber 36 drawn at a ratio corresponding to the rotational speed ratio is obtained. The protein fiber drawn in the washing solution 12 is taken out from the washing bath 21, dried at the time of passing through inside of the drying apparatus 4, and then wound by a winder. In this way, in the spinning apparatus 10, the protein fiber is finally wound as a wound roll 5 by the winder. Incidentally, reference numerals 18*a* to 18*g* are yarn guides.

The temperature of the coagulation liquid 11 is not particularly limited, but may be 80° C. or less, 70° C. or less, 60° C. or less, 50° C. or less, 40° C. or less, 30° C. or less, 25° C. or less, 20° C. or less, 10° C. or less, or 5° C. or less. The temperature is preferably 0° C. or more from the viewpoint of workability, cooling cost, and the like. Additionally, the temperature of the coagulation liquid 11 can be adjusted by, for example, using the spinning apparatus 10 having the coagulation bath 20 including a heat exchanger inside thereof and a coolant circulation device. For example, a cooled medium, which has been cooled to a predetermined temperature by the coolant circulation device, is allowed to flow through the heat exchanger provided in the coagulation bath. Whereby, the temperature can be adjusted to a temperature within the above range by heat exchange between the coagulation liquid 11 and the heat exchanger. In this case, more efficient cooling can be achieved by circulating, as a medium, a solvent used for the coagulation liquid 11.

A plurality of coagulation baths storing the coagulation liquid may be provided.

The coagulated artificial structural protein removed from the coagulation bath or the washing bath may be wound as is by the winder, or may be dried by being allowed to pass through the drying apparatus and then wound by the winder.

The distance for which the coagulated artificial structural protein passes through the coagulation liquid may be any distance as long as the solvent can be efficiently removed. The distance may be determined depending on, for example, the extrusion speed (discharge speed) of the spinning dope from the nozzle. The residence time of the coagulated artificial structural protein (or spinning dope) in the coagulation liquid may be determined depending on the distance for which the coagulated artificial structural protein passes through the coagulation liquid, the extrusion speed of the spinning dope from the nozzle, and the like.

[Drawing Process]

The method for producing an artificial structural protein of the present embodiment may further include a process of drawing the coagulated artificial structural protein fiber (drawing process). Examples of the drawing method include wet heat drawing, dry heat drawing and the like. The drawing process may be performed by, for example, in the coagulation bath 20, or in the washing bath 21. The drawing process can also be performed in the air.

The drawing in the washing bath 21 may be drawing in hot water, in a solution in which an organic solvent is added to hot water, or the like, that is, wet heat drawing. The temperature for wet heat drawing is preferably 50 to 90° C. When this temperature is 50° C. or more, the pore diameter of the yarn can be stably made small. Also, when the temperature is 90° C. or less, temperature setting is easy, and thus spinning stability is improved. The temperature is more preferably 75 to 85° C.

The wet heat drawing can be performed in hot water, in a solution in which an organic solvent or the like is added to hot water, or in a heated steam. The temperature may be, for example, 40 to 200° C., 50 to 180° C., 50 to 150° C., or 75 to 90° C. The draw ratio in the wet heat drawing may be, for example, 1 to 30 times, 2 to 25 times, 2 to 20 times, 2 to 15 times, 2 to 10 times, 2 to 8 times, 2 to 6 times, or 2 to 4 times, with respect to the undrawn yarn (or pre-drawing yarn). However, the draw ratio is not limited as long as characteristics such as a desired fiber thickness and mechanical properties can be obtained.

The dry heat drawing can be performed by using an apparatus such as a contact-type hot plate and a non-contact type furnace, but is not particularly limited thereto. Any apparats can be used that increases the temperature of the fiber to a desired temperature and allows drawing at a predetermined draw ratio. The temperature for dry heat drawing may be, for example, 100° C. to 270° C., 140° C. to 230° C., 140° C. to 200° C., 160° C. to 200° C., or 160° C. to 180° C.

The draw ratio in the dry heat drawing process may be, for example, 1 to 30 times, may be 2 to 30 times, may be 2 to 20 times, may be 3 to 15 times, preferably 3 to 10 times, more preferably 3 to 8 times, and still more preferably 4 to 8 times, with respect to the undrawn yarn (or pre-drawing yarn). However, the draw ratio is not limited as long as characteristics such as a desired fiber thickness and mechanical properties can be obtained.

The drawing process may be a process that performs each of wet heat drawing and dry heat drawing separately, or a process that performs these drawings in multiple stages or in combination. That is, as the drawing process, wet heat drawing and dry heat drawing can be appropriately combined and performed as follows: wet heat drawing is performed at a first drawing stage and then dry heat drawing is performed at a second drawing stage, or wet heat drawing is performed at a first drawing stage, then wet heat drawing is performed at a second drawing stage, and further dry heat drawing is performed at a third drawing stage, for example.

The lower limit of the final draw ratio of the artificial structural protein fiber subjected to the drawing process may be preferably any of 1 time, 2 times, 3 times, 4 times, 5 times, 6 times, 7 times, 8 times, and 9 times, with respect to the undrawn yarn (or pre-drawing yarn). The upper limit of the final draw ratio of the modified fibroin fiber subjected to the drawing process may be preferably any of 40 times, 30 times, 20 times, 15 times, 14 times, 13 times, 12 times, 11 times, and 10 times. The final draw ratio may be, for example, 3 to 40 times, 3 to 30 times, 5 to 30 times, 5 to 20 times, 5 to 15 times, or 5 to 13 times. However, the draw ratio is not limited as long as characteristics such as a desired fiber thickness and mechanical properties can be obtained.

In the spinning process, the shape of the spinneret, the shape of the hole, the number of holes is not particularly limited, and can be appropriately selected depending on a desired fiber diameter, the number of single yarns, and the like.

An oil agent may be applied to an undrawn yarn (or pre-drawing yarns) or drawn yarn, as necessary, for the purpose of imparting an antistatic property, convergence and lubricity, or the like before or after drying. The type of the oil agent applied and application amount thereof, and the like are not particularly limited, and can be appropriately adjusted in consideration of use application of the fiber, dealing of the fiber, and the like.

In a case where the hole shape of the spinneret is a circular shape, the hole diameter of the spinneret may be 0.01 mm or more and 0.6 mm or less, for example. When the hole diameter is 0.01 mm or more, the pressure loss can be reduced, and thus the facility cost can be suppressed. When the hole diameter is 0.6 mm or less, the necessity of the drawing operation for minimizing the fiber diameter can be reduced. Thus, a possibility of causing breakage on drawing during a period from discharge to winding can be reduced.

The temperature of the spinning dope when the spinning dope passes through the spinneret and the temperature of the spinneret are not particularly limited. The temperatures may be appropriately adjusted depending on the concentration and viscosity of the spinning dope to be used, the type of the organic solvent, and the like. The temperatures are preferably 30° C. to 100° C. from the viewpoint of preventing deterioration the structural protein, for example. Also, the upper limit of the temperature is preferably a temperature that does not reach the boiling point of a solvent to be used, from the viewpoint of reducing possibilities of pressure increase due to volatilization of the solvent and clogging in the conduit due to solidification of the spinning dope. This improves process stability.

The production method according to the present embodiment may further include a process of filtrating the spinning dope before discharging the spinning dope (filtration process) and/or a process of defoaming the spinning dope before discharging (defoaming process).

(Evaluation of Physical Properties of Fiber)

Measurement and evaluation of the physical properties of the artificial structural protein fiber can be performed as follows.

The fineness and strength elongation of randomly sampled fibers are measured by using "FAVIMAT" which is a single yarn strength elongation measuring instrument, manufactured by Textechno in an environment of a temperature of 20° C. and a relative humidity of 65%, and the average value is calculated. The conditions for strength elongation measurement are preferably set as follows: load cell capacity: 210 cN, gauge length: 20 mm, and tensile speed: 10 mm/min. A strength when the fiber is broken is defined as strength at break [g/d], and an elongation when the fiber is broken is defined as elongation at break [%]. Also, a value obtained by multiplying the numerical value of an area enclosed by a stress-strain curve where the horizontal axis is strain [%] and the vertical axis is stress [g/d], and the horizontal axis, by density [kg/m$^3$] is defined as toughness [MJ/m$^3$]. It is preferred that the measured value is calculated as, for example, the average value of the number of samples n=10.

(Evaluation of Fiber Shrinkage)

The artificial structural protein fiber has characteristics of shrinking by being brought into contact (wetting) with water of less than the boiling point. Preferably, such a shrinkage is as little as possible in the artificial structural protein fiber.

The shrinkage can be evaluated by, for example, using the shrinkage ratio as an indicator obtained by the following method.

A plurality of numbers of artificial structural protein fibers having a length of about 30 cm are bundled to form a fiber bundle with a fineness of 150 denier. A 0.8 g-lead weight is attached to this fiber bundle, and the fiber bundle is made shrunk by immersing the fiber bundle in this state in water at 40° C. for 90 seconds. Then, each fiber bundle is taken out from the water, and dried with the 0.8 g-lead weight attached thereto. Then, the length of each fiber bundle after drying is measured. The shrinkage ratio is calculated according to the following equation. Note that $L_0$ represents the length of a fiber before contact with water (after spinning) (herein, 30 cm), and $L_D$ represents the length of a fiber after shrinkage (dried fiber after impregnation treatment with water).

$$\text{shrinkage ratio[\%]} = \{1 - (L_D/L_0)\} \times 100 \qquad \text{Equation:}$$

[Product]

The protein fiber according to the present embodiment can be applied, as fibers (long fiber, short fiber, monofilament, or multifilament, for example) or yarns (spun yarn, twisted yarn, false-twisted yarn, processed yarn, combined filament yarn, or blended yarn, for example), to a woven fabric, a knitted fabric, a braided fabric, or a fabric such as a non-woven fabric, paper, and cotton, and the like. Also, the protein fiber according to the present embodiment can be applied to high strength applications such as ropes, surgical sutures, hemostatics, flexible stops for electrical components, and physiologically active materials for implantation (for example, artificial ligament and aortic band). These can be produced by a publicly known method.

EXAMPLES

Hereinafter, the present invention will be described more specifically based on Examples. However, the present invention is not limited to the following Examples.

[Production of Artificial Structural Protein]

(1) Production of Expression Vector

Based on the base sequence and amino acid sequence of fibroin derived from *Nephila clavipes* (GenBank Accession No.: P46804.1, GI:1174415), designed were an artificial structural protein having SEQ ID NO: 44 (modified fibroin)

(hereinafter, also referred to as "PRT966"), a modified fibroin having SEQ ID NO: 15 (hereinafter, referred to as "PRT799"), and a modified fibroin having SEQ ID NO: 37 (hereinafter, referred to as "PRT918"), a modified fibroin having SEQ ID NO: 50 (hereinafter, also referred to as "PRT705"), a modified fibroin having SEQ ID NO: 51 (hereinafter, also referred to as "PRT826"), a modified fibroin having SEQ ID NO: 52 (hereinafter, also referred to as "PRT853"), a modified fibroin having SEQ ID NO: 53 (hereinafter, also referred to as "PRT1103"), a modified fibroin having SEQ ID NO: 54 (hereinafter, also referred to as "PRT1104"), a modified fibroin having SEQ ID NO: 55 (hereinafter, also referred to as "PRT1107"), a modified fibroin having SEQ ID NO: 56 (hereinafter, also referred to as "PRT1083"), and a modified fibroin having SEQ ID NO: 57 (hereinafter, also referred to as "PRT1125"). Also, as an artificial structural protein, a keratin protein having SEQ ID NO: 58 (hereinafter, also referred to as "PRT855"), a collagen protein having SEQ ID NO: 59 (hereinafter, also referred to as "PRT537"), a resilin protein having SEQ ID NO: 60 (hereinafter, also referred to as "PRT366"), and an interferon γ having SEQ ID NO: 61 (hereinafter, also referred to as "PRT662").

Incidentally, the amino acid sequence set forth in SEQ ID NO: 44 has an amino acid sequence obtained by substituting all QQs with VF, substituting the remaining Q with I in the amino acid sequence set forth in SEQ ID NO: 9 (amino acid sequence before the amino acid sequence set forth in SEQ ID NO: 42 is added to the C-terminal thereof), for the purpose of improving hydrophobicity, and further adding the amino acid sequence set forth in SEQ ID NO: 12 to the N-terminal thereof.

Also, the amino acid sequence set forth in SEQ ID NO: 15 has an amino acid sequence obtained by substituting, inserting, and deleting amino acid residues with respect to the amino acid sequence of fibroin derived from *Nephila clavipes*, for the purpose of improving productivity, and further adding the amino acid sequence set forth in SEQ ID NO: 12 (tag sequence and hinge sequence) to the N-terminal thereof.

The amino acid sequence set forth in SEQ ID NO: 53 (PRT1103) is an amino acid sequence obtained by substituting a tyrosine residue (Y) of the amino acid sequence set forth in SEQ ID NO: 7 (Met-PRT410) with a phenylalanine residue (F), substituting a large part of serine residues (S) with an alanine residue (A) or a glycine residue (G), and further adding a tag sequence to the N-terminal of thereof.

The amino acid sequence set forth in SEQ ID NO: 54 (PRT1104) is an amino acid sequence obtained by substituting a large part of serine residues (S) of the amino acid sequence set forth in SEQ ID NO: 7 with an alanine residue (A) or a glycine residue (G), and further adding a tag sequence to the N-terminal thereof.

The amino acid sequence set forth in SEQ ID NO: 55 (PRT1107) is an amino acid sequence obtained by substituting a serine residue (S) of the amino acid sequence set forth in SEQ ID NO: 31 (Met-PRT918) with an alanine residue (A), a valine residue (V), a leucine residue (L), or an isoleucine residue (I), and further adding a tag sequence to the N-terminal of thereof.

The amino acid sequence set forth in SEQ ID NO: 56 (PRT1083) is an amino acid sequence obtained by substituting a proline residue (P) of the amino acid sequence set forth in SEQ ID NO: 31 (Met-PRT918) with a threonine residue (T) or a leucine residue (L), and further adding a tag sequence to the N-terminal thereof.

The amino acid sequence set forth in SEQ ID NO: 58 (PRT855) has an amino acid sequence obtained by substituting leucine or valine with alanine or glycine in an amino acid sequence consisting of the 1st to 292nd amino acid residues from the N-terminal of PRT798 (SEQ ID NO: 49) to obtain an amino acid sequence, and further substituting three amino acid residues in the 1st to 246th amino acid residues from the N-terminal of the obtained amino acid sequence and inserting an amino acid sequence consisting of GAAAAAG (SEQ ID NO: 62) therein.

Next, nucleic acids encoding the designed artificial structural proteins PRT966, PRT799, PRT918, PRT826, PRT853, PRT1104, PRT705, PRT1125, PRT1103, PRT1107, and PRT1083 (modified fibroins), PRT855 (keratin protein), PRT537 (collagen protein), PRT366 (resilin protein), and interferon γ (PRT662) were synthesized. In each of the nucleic acids, an NdeI site was added to the 5' end thereof, and an EcoRI site was added downstream of the stop codon thereof. The nucleic acid was each cloned into a cloning vector (pUC118). Then, the nucleic acid was excised by restriction enzyme treatment with NdeI and EcoRI, and then recombined into a protein expression vector pET-22b(+), thus obtaining an expression vector.

(2) Expression of Artificial Structural Protein

*Escherichia coli* BLR(DE3) was transformed with the expression vector obtained in (1). The transformed *Escherichia coli* was cultured in 2 mL of an LB culture medium containing ampicillin for 15 hours. The culture solution was added to 100 mL of a seed culture medium containing ampicillin (Table 5) so that the $OD_{600}$ reached 0.005. The temperature of the culture solution was maintained at 30° C., and the flask culture was performed (for about 15 hours) until the $OD_{600}$ reached 5, thus obtaining a seed culture solution.

TABLE 5

| Seed culture medium | |
| --- | --- |
| Reagent | Concentration (g/L) |
| Glucose | 5.0 |
| $KH_2PO_4$ | 4.0 |
| $K_2HPO_4$ | 9.3 |
| Yeast Extract | 6.0 |
| Ampicillin | 0.1 |

The seed culture solution was added to a jar fermenter to which 500 mL of a production medium (Table 6) has been added so that the $OD_{600}$ reached 0.05. Culture was performed while maintaining the temperature of the culture solution at 37° C. and keeping the pH constant at 6.9. Further, the dissolved oxygen concentration in the culture solution was maintained at 20% of the dissolved oxygen saturation concentration.

TABLE 6

| Production medium | |
| --- | --- |
| Reagent | Concentration (g/L) |
| Glucose | 12.0 |
| $KH_2PO_4$ | 9.0 |
| $MgSO_4 \cdot 7H_2O$ | 2.4 |
| Yeast Extract | 15 |
| $FeSO_4 \cdot 7H_2O$ | 0.04 |
| $MnSO_4 \cdot 5H_2O$ | 0.04 |
| $CaCl_2 \cdot 2H_2O$ | 0.04 |
| GD-113 (antifoaming agent) | 0.1 (mL/L) |

Immediately after glucose in the production medium was completely consumed, a feed solution (455 g/1 L of glucose, 120 g/1 L of Yeast Extract) was added at a rate of 1 mL/min. Culture was performed while maintaining the temperature of the culture solution at 37° C. and keeping the pH constant at 6.9. Further, the dissolved oxygen concentration in the culture solution was maintained at 20% of the dissolved oxygen saturation concentration, and culture was performed for 20 hours. Thereafter, 1 M isopropyl-β-thiogalactopyranoside (IPTG) was added to the culture solution so that the final concentration thereof was 1 mM, thus inducing the expression of the modified fibroin. 20 hours after the addition of IPTG, the culture solution was centrifuged to recover bacterial cells. SDS-PAGE was performed using the bacterial cells prepared from the culture solutions before and after the addition of IPTG, and the expression of a desired artificial structural protein was confirmed by the appearance of a band of a desired modified fibroin size depending on the addition of IPTG.

(3) Purification of Artificial Structural Protein

The bacterial cells recovered 2 hours after the addition of IPTG were washed with 20 mM Tris-HCl buffer (pH 7.4). The bacterial cells after washing were suspended in 20 mM Tris-HCl buffer (pH 7.4) containing about 1 mM PMSF, and the cells were disrupted with a high-pressure homogenizer (manufactured by GEA Niro Soavi). The disrupted cells were centrifuged to obtain a precipitate. The obtained precipitate was washed with 20 mM Tris-HCl buffer (pH 7.4) until the purity of the precipitate became high. The precipitate after washing was suspended in 8 M guanidine buffer (8 M guanidine hydrochloride, 10 mM sodium dihydrogen phosphate, 20 mM NaCl, 1 mM Tris-HCl, pH 7.0) so that the concentration thereof was 100 mg/mL, and dissolved by stirring with a stirrer for 30 minutes at 60° C. After dissolution, dialysis was performed with water using a dialysis tube (cellulose tube 36/32, manufactured by Sanko Junyaku Co., Ltd.). The white aggregated protein obtained after dialysis was recovered by centrifugation, the water content was removed by a freeze dryer, and a freeze-dried powder was recovered. Thus, modified fibroins (PRT966, PRT799, PRT918PRT826, PRT853, PRT1104, PRT705, PRT1125, PRT1103, PRT1107, and PRT1083), PRT855 (keratin protein), PRT537 (collagen protein), PRT366 (resilin protein), and PRT662 (interferon γ) were obtained.

[Evaluation of Fiber-Forming Property (Coagulation Liquid)]

(1-1) Preparation of Dope Solution

First, 26% by mass of a modified fibroin (PRT966) obtained in the production process of the artificial structural protein and 74% by mass of formic acid as a dissolving solvent (manufactured by Asahi Chemical Co., Ltd., purity: 98%) were mixed, and dissolved by heating the mixture by an aluminum block heater set at 70° C. for 1 hour with stirring. The obtained solution was defoamed by filtration with a metal filter having an opening of 1 μm, and thus a dope solution was obtained.

(1-2) Discharge Test of Dope Solution

The dope solution obtained in (1-1) was charged into a 10 ml-syringe, and then discharged from a nozzle having a nozzle diameter of 0.2 μm into the coagulation liquid, to coagulate the modified fibroin at room temperature. The coagulated raw fiber was wound up at a linear velocity of 2.39 m/min. The obtained raw fiber was observed, and the fiber-forming property was visually determined. The extrusion speed of the dope solution was 0.075 ml/min. The type of the coagulation liquid used is as shown in Table 7. Incidentally, the brackish water is collected from the estuary in Sakata city, Yamagata prefecture, and the sea water is collected from the ocean in Kamo city, Yamagata prefecture. The concentration of brackish water and sea water [wt %] indicates an approximate value of the concentration of the entire solutes. The mixed solutions of Test Examples 26 to 28 are a solution prepared based on an assumption that formic acid being in contact with the sodium chloride aqueous solution in the spinning dope is dissolved in the aqueous solution, and the proportion of the total mass of the coagulation liquid (mixed solution) is made such that the content of the sodium chloride aqueous solution is 60% by mass to 80% by mass, and the content of the formic acid is 20% by mass to 40% by mass. The formic acid aqueous solution of Test Example 29 was prepared on an assumption that formic acid being in contact with water in the spinning dope is dissolved in water, and the proportion of the total mass of the coagulation liquid (mixed solution) was made so that the content of water was 80% by mass and the content of formic acid was 20% by mass.

The evaluation result of the fiber-forming property was shown in Table 7. The evaluation criterion of the fiber-forming property is as follows.

⊙: Fiber is formed. The obtained fiber is flexible and homogeneous.

◯: Fiber is formed. The obtained fiber is flexible.

Δ: Fiber is formed.

X: Fiber is not formed.

TABLE 7

| No. | Coagulation liquid | Concentration [% by mass] | pH | Fiber-forming property |
|---|---|---|---|---|
| Test Example 1 | Water | 100 | 7.22 | ◯ |
| Test Example 2 | Citric acid hydrate | 10 | 1.35 | ◯ |
| Test Example 3 | aqueous solution | 20 | 1.09 | ◯ |
| Test Example 4 | Sodium bicarbonate aqueous solution | 2.5 | 8.4 | ⊙ |
| Test Example 5 | Formic acid | 5 | 7.36 | ⊙ |
| Test Example 6 | aqueous solution | 10 | 7.95 | ⊙ |
| Test Example 7 | | 20 | 8.42 | ⊙ |
| Test Example 8 | Sodium acetate | 10 | 8.78 | ⊙ |
| Test Example 9 | | 20 | 9.3 | ⊙ |
| Test Example 10 | Sodium citrate | 10 | 7.84 | ⊙ |
| Test Example 11 | | 20 | 7.7 | ⊙ |
| Test Example 12 | Potassium chloride aqueous solution | 6.5 | 5.4 | ⊙ |
| Test Example 13 | Sodium chloride | 5 | 5.97 | ⊙ |
| Test Example 14 | aqueous solution | 10 | 6.88 | ⊙ |
| Test Example 15 | | 15 | 6.55 | ⊙ |
| Test Example 16 | | 20 | 6.2 | ⊙ |
| Test Example 17 | Calcium chloride | 10 | 8.62 | ⊙ |
| Test Example 18 | | 20 | 8.71 | ⊙ |
| Test Example 19 | Sodium sulfate | 10 | 7.09 | ⊙ |
| Test Example 20 | aqueous solution | 20 | 6.78 | ⊙ |
| Test Example 21 | Ammonium sulfate | 5 | 4.89 | ⊙ |
| Test Example 22 | aqueous solution | 10 | 4.83 | ⊙ |
| Test Example 23 | | 20 | 4.75 | ⊙ |
| Test Example 24 | Buffer (1.5M potassium dihydrogen phosphate and 1.5M dipotassium hydrogen phosphate) | 20 | 7.5 | ⊙ |
| Test Example 25 | Brackish water | 1.6 | — | ⊙ |
| Test Example 26 | Sea water | 3.0 | — | ⊙ |
| Test Example 27 | Formic acid aqueous solution | 20 | 0.98 | ◯ |
| Test Example 28 | Mixed solution (0.9M sodium chloride aqueous solution:formic acid = 80:20) | — | 1.11 | ⊙ |

TABLE 7-continued

| No. | Coagulation liquid | Concentration [% by mass] | pH | Fiber-forming property |
|---|---|---|---|---|
| Test Example 29 | Mixed solution (0.9M sodium chloride aqueous solution:formic acid = 70:30) | — | 0.87 | ⊙ |
| Test Example 30 | Mixed solution (0.9M sodium chloride aqueous solution:formic acid = 60:40) | — | 0.57 | ⊙ |
| Comparative Example 1 | Methanol | 100 | — | ◯ |

As shown in Table 7, in a case of using any of water, an acid aqueous solution, a salt aqueous solution, and a mixed solution, flexible fibers could be formed (Test Examples 1 to 26). In a case of using a salt aqueous solution as a coagulation liquid, flexible and homogeneous fibers could be formed, and an extremely good fiber-forming property was shown (Test Examples 4 to 26). In particular, a large amount of production cost can be reduced by using, as a coagulation liquid, water, a sodium chloride aqueous solution, brackish water, and sea water, which are abundant and inexpensive resources. The result also shows that, even in a case where the organic solvent being in contact with the coagulation liquid in the spinning dope is dissolved in the coagulation liquid, flexible fibers could be formed (Test Examples 27 to 30). In particular, in a case where a coagulation liquid in which formic acid has been dissolved was a sodium chloride aqueous solution, flexible and homogeneous fibers could be formed (Test Examples 28 to 30).

[Evaluation of Fiber-Forming Property (Protein)]

(2-1) Preparation of Dope Solution

First, 26% by mass of each modified fibroin (PRT966, PRT826, PRT853, PRT1104, PRT705, PRT1125, PRT1103, PRT1107, and PRT1083), keratin protein (PRT855), collagen protein (PRT537), resilin protein (PRT366), or interferon γ (PRT662), produced in the production process of the artificial structural protein, or 26% by mass of MEDIGELATIN which is a commercially available structural protein (manufactured by Nippi, Inc.), egg white albumin, or casein, and 74% by mass of formic acid as a dissolving solvent or 74% by mass of a dimethyl sulfoxide solution containing lithium chloride (lithium chloride concentration: 4.0% by mass) were mixed, and dissolved by heating the mixture with an aluminum block heater set at 70° C. for 1 hour with stirring. The obtained solution was defoamed by filtration with a metal filter having an opening of 1 μm, and thus a dope solution was obtained. The prepared dope solution was shown in Table 8.

(2-2) Discharge Test of Dope Solution

The dope solution obtained in (2-1) was charged into a 10 ml-syringe, and then discharged from a nozzle having a nozzle diameter of 0.2 μm into the coagulation liquid (sodium sulfate aqueous solution with a concentration of 30%, or water), to coagulate the modified fibroin at room temperature. The obtained raw fiber was observed, and the fiber-forming property was visually determined. The extrusion speed of the dope solution was 0.075 ml/min. The evaluation criterion of the fiber-forming property is as follows. The evaluation result of the fiber-forming property was shown in Table 8. Incidentally, the average HI in Table 8 is a value calculated by determining the total sum of the hydropathy indices (HI) of all amino acid residues constituting the structural protein, and then dividing the sum by the total number of amino acid residues. The average HI is a value obtained by calculating the hydropathy index of the amino acid sequence set forth in the sequence listing (a sequence including a tag sequence and a hinge sequence).

⊙: Fiber is formed, and coagulability is good.

Δ: Fiber is formed, but coagulability is low.

X: Dope solution is gelated, or dissolution of the solute is impossible.

solution as a coagulation liquid, fibers were formed regardless of the type of the structural protein, and an excellent fiber-forming property was exhibited.

[Production and Evaluation of Artificial Structural Protein Fiber]

(1) Preparation of Dope Solution

A dope solution was prepared in the same procedure as in the dope solution prepared in evaluation of the fiber-forming property except that the concentration of the modified

TABLE 8

| Test Example | Coagulation liquid | Dope solvent | | Protein | Average HI | Evaluation result of fiber-forming property |
|---|---|---|---|---|---|---|
| Test Example 83 | 30% sodium sulfate | Formic acid | Modified fibroin | PRT826 | −0.804 | ○ |
| Test Example 84 | saturated aqueous | | Modified fibroin | PRT853 | −0.68 | ○ |
| Test Example 85 | solution | | Modified fibroin | PRT1104 | −0.653 | ○ |
| Test Example 86 | | | Modified fibroin | PRT705 | −0.57 | ○ |
| Test Example 87 | | | Modified fibroin | PRT1125 | −0.57 | ○ |
| Test Example 88 | | | Modified fibroin | PRT1103 | −0.37 | ○ |
| Test Example 89 | | | Modified fibroin | PRT966 | 0.466 | ○ |
| Test Example 90 | | | Modified fibroin | PRT1107 | 0.82 | ○ |
| Test Example 91 | | | Modified fibroin | PRT1083 | 0.95 | ○ |
| Test Example 92 | | | Resilin | PRT366 | −1.229 | Δ |
| Test Example 93 | | | Interferon γ | PRT662 | −0.941 | Δ |
| Test Example 94 | | | Collagen | PRT537 | −0.793 | Δ |
| Test Example 95 | | | Keratin | PRT855 | −0.55 | Δ |
| Test Example 96 | | | Gelatin | (Commercial product) | — | ○ |
| Test Example 97 | | | Egg white albumin | (Commercial product) | — | ○ |
| Test Example 98 | | 4 wt % LiCl/ | Resilin | PRT366 | −1.229 | ○ |
| Test Example 99 | | DMSO | Interferon γ | PRT662 | −0.941 | ○ |
| Test Example 100 | | | Modified fibroin | PRT826 | −0.804 | ○ |
| Test Example 101 | | | Collagen | PRT537 | −0.793 | ○ |
| Test Example 102 | | | Modified fibroin | PRT1104 | −0.653 | ○ |
| Test Example 103 | | | Keratin | PRT855 | −0.55 | ○ |
| Test Example 104 | | | Modified fibroin | PRT1103 | −0.37 | ○ |
| Test Example 105 | | | Casein | (Commercial product) | — | ○ |
| Test Example 106 | | | Gelatin | (Commercial product) | — | ○ |
| Test Example 107 | Water | Formic acid | Modified fibroin | PRT966 | 0.466 | ○ |
| Test Example 108 | | | Modified fibroin | PRT1107 | 0.82 | ○ |
| Test Example 109 | | | Modified fibroin | PRT1083 | 0.95 | ○ |

As shown in Table 8, in a case of using a sodium sulfate aqueous solution as a coagulation liquid, fibers were formed in all structural proteins having an average HI value of −1.229 to 0.95, and it was therefore confirmed that these structural proteins had the fiber-forming property (Test Examples 83 to 109). Further, in a case of using water as a coagulation liquid, fibers were formed in modified fibroins having an average HI value of 0.466 to 0.95, and it was therefore conformed that these modified fibroins had the fiber-forming property (Test Examples 107 to 109). The result shows that, in a case of using a sodium sulfate aqueous fibroin (PRT966) was 26% by mass and the concentration the formic acid was 74% by mass.

(2) Wet Spinning

The prepared dope solution was charged into a reserve tank and discharged, with a gear pump, from a mono-hole nozzle having a diameter of 0.2 mm into a coagulation bath by using a table-top spinning apparatus, thus forming an original yarn. Then, the coagulated original yarn was drawn in a water washing bath. After washing and drawing in the water washing bath, the obtained yarn was dried by using a dry heat plate, and the obtained modified fibroin fiber (artificial protein fiber) was wound up by a table-top spinning apparatus. The conditions for wet spinning are as follows, and the coagulation liquids used are as shown in Table 9.

Diameter of extrusion nozzle: 0.2 mm

Temperature of coagulation liquid: room temperature

Draw ratio in water washing bath: 3.5 to 5.5 times

Temperature of water washing bath: 40° C.

Dry temperature: 60° C.

(3) Evaluation of Physical Properties of Artificial Structural Protein Fiber

The physical properties of the fibers obtained in above (2) were measured by the following method. The fineness and strength elongation of ten randomly sampled fibers were measured by using "FAVIMAT" which is a single yarn strength elongation measuring instrument, manufactured by value when the value of elongation at break of the modified fibroin fiber of Comparative Example 2 (a fiber produced by using 100% methanol for a coagulation bath) is taken as 100. Incidentally, for the elongation at break of Test Example 33 (potassium chloride aqueous solution) and Test Example 36 (sodium sulfate aqueous solution) in Table 9, and the elongation at break in Table 10, a value when the temperature of the coagulation bath was 60° C. was shown.

The toughness value in Tables 11 and 12 is a relative value when the toughness of the modified fibroin fiber of Comparative Example 3 (a fiber produced by using 100% methanol for a coagulation bath) is taken as 100. Incidentally, for the relative value of the toughness of Test Example 44 (potassium chloride aqueous solution) and Test Example 47 (sodium sulfate aqueous solution) in Table 11, and the relative value of the toughness in Table 12, a value when the temperature of the coagulation bath was 60° C. was shown.

TABLE 9

| No. | Coagulation liquid | Molar concentration [mol/L] | Concentration [% by mass] | Draw ratio [time] | Relative value of elongation [%] | Elongation at break [%] |
|---|---|---|---|---|---|---|
| Test Example 31 | Sodium citrate aqueous solution | 0.9 | 21 | 3.5 | 176 | 70.7 |
| Test Example 32 | Sodium formate aqueous solution | 0.9 | 5 | 3.5 | 207 | 83.2 |
| Test Example 33 | Potassium chloride aqueous solution | 0.9 | 10 | 3.5 | 212 | 85.2 |
| Test Example 34 | Sodium chloride aqueous solution | 0.5 | 3 | 3.5 | 248 | 99.5 |
| Test Example 35 | Calcium chloride aqueous solution | 0.9 | 10 | 3.5 | 201 | 80.8 |
| Test Example 36 | Sodium sulfate aqueous solution | 0.9 | 12 | 3.5 | 231 | 93 |
| Test Example 37 | Ammonium sulfate aqueous solution | 0.9 | 5 | 5.5 | 141 | 56.7 |
| Test Example 38 | Buffer (1.5M potassium dihydrogen phosphate and 1.5M dipotassium hydrogen phosphate) | 1.5 | 20 | 4.5 | 171 | 68.7 |
| Test Example 39 | Brackish water | — | 1.6 | 3.5 | 232 | 93.3 |
| Test Example 40 | Sea water | — | 3.0 | 3.5 | 188 | 75.6 |
| Test Example 41 | Water | — | 100 | 3.5 | 297 | 119.2 |
| Comparative Example 2 | Methanol | — | 100 | 4.0 | 100 | 40.2 |

Textechno in an environment of a temperature of 20° C. and a relative humidity of 65% (sample number=10), and the average value was calculated. The conditions for strength elongation measurement were set as follows: load cell capacity: 210 cN, gauge length: 20 mm, and tensile speed: 10 mm/min. A strength when the fiber was broken was defined as strength at break [g/d], and an elongation when the fiber was broken was defined as elongation at break [%]. Further, a value obtained by multiplying the numerical value of an area enclosed by a stress-strain curve where the horizontal axis is strain [%] and the vertical axis is stress [g/d], and the horizontal axis, by density [kg/m³] was defined as toughness [MJ/m³]. The density of the modified fibroin (PRT966) was 1.34 [g/cm³].

The evaluation results of mechanical properties of respective modified fibroin fibers are shown in Tables 9, 10, 11, and 12. The value of elongation in Tables 9 and 10 is a relative As shown in Table 9, in all the modified fibroin fibers produced by using, as a coagulation liquid, a carboxylate aqueous solution (a sodium citrate aqueous solution and a sodium formate aqueous solution), a chloride aqueous solution (a potassium chloride aqueous solution, a sodium chloride aqueous solution, and a calcium chloride aqueous solution), a sulfate aqueous solution (a sodium sulfate aqueous solution and an ammonium sulfate aqueous solution), a hydrogen phosphate aqueous solution (buffer), and a mixed solution (brackish water and sea water) (Test Examples 31 to 40) and the modified fibroin fiber produced by using water as a coagulation liquid (Test Example 41), an effect of further improving elongation was observed compared to the modified fibroin fiber produced by using methanol as a coagulation liquid (Comparative Example 2), and an unexpected excellent result could be obtained.

TABLE 10

| No. | Coagulation liquid | Proportion of sodium chloride aqueous solution [%] | Proportion of water [%] | Proportion of formic acid [%] | Draw ratio [time] | Relative value of elongation [%] | Elongation at break [%] |
|---|---|---|---|---|---|---|---|
| Test Example 42 | 0.5M sodium chloride aqueous solution | 100 | 0 | 0 | 3.5 | 168 | 67.4 |
| Test Example 43 | Formic acid mixed aqueous solution 1 | 90 | 0 | 10 | 3.5 | 174 | 70.0 |
| Test Example 44 | Formic acid mixed aqueous solution 2 | 80 | 0 | 20 | 3.5 | 170 | 68.2 |
| Test Example 41 | Water | 0 | 100 | 0 | 3.5 | 297 | 119.2 |
| Test Example 45 | Formic acid aqueous solution 1 | 0 | 90 | 10 | 3.5 | 213 | 85.6 |
| Test Example 46 | Formic acid aqueous solution 2 | 0 | 80 | 20 | 4.5 | 166 | 66.6 |
| Comparative Example 2 | Methanol | 0 | 0 | 0 | 4.0 | 100 | 40.2 |

As shown in Table 10, in all the modified fibroin fibers produced by using, as a coagulation liquid, a mixed aqueous solution of a sodium chloride aqueous solution and formic acid (Test Examples 43 to 44), and the modified fibroin fibers produced by using, as a coagulation liquid, a mixed aqueous solution of water and formic acid (Test Examples 45 to 46), an effect of further improving elongation was observed in any mixing ratio, compared to the modified fibroin fiber produced by using methanol as a coagulation liquid (Comparative Example 2), and an unexpected excellent result could be obtained. This result shows that, even in a case where formic acid in the spinning dope is dissolved in a coagulation liquid of water (Test Example 41) and a coagulation liquid of a sodium chloride aqueous solution (Test Example 42), an excellent effect of improving elongation is observed.

As shown in Table 11, in all the modified fibroin fibers produced by using, as a coagulation liquid, a carboxylate aqueous solution (a sodium citrate aqueous solution and a sodium formate aqueous solution), a chloride aqueous solution (a potassium chloride aqueous solution and a sodium chloride aqueous solution), a sulfate aqueous solution (a sodium sulfate aqueous solution and an ammonium sulfate aqueous solution), a phosphoric acid water salt buffer, and a mixed solution (brackish water and sea water) (Test Examples 47 to 56) and the modified fibroin fiber produced by using water as a coagulation liquid (Test Example 56), an effect of further improving the toughness value was observed, compared to the modified fibroin fiber produced by using methanol as a coagulation liquid (Comparative Example 3), and an unexpected excellent result could be obtained.

TABLE 11

| No. | Coagulation liquid | Molar concentration [mol/L] | Concentration [% by mass] | Draw ratio [time] | Relative value of toughness [%] |
|---|---|---|---|---|---|
| Test Example 47 | Sodium citrate aqueous solution | 0.9 | 21.3 | 3.5 | 110 |
| Test Example 48 | Sodium formate aqueous solution | 0.9 | 5 | 5.0 | 119 |
| Test Example 49 | Potassium chloride aqueous solution | 0.9 | 6.5 | 3.5 | 116 |
| Test Example 50 | Sodium chloride aqueous solution | 0.9 | 5 | 3.5 | 276 |
| Test Example 51 | Ammonium sulfate aqueous solution | 0.9 | 5 | 5.5 | 166 |
| Test Example 52 | Sodium sulfate aqueous solution | 0.9 | 11.9 | 3.5 | 126 |
| Test Example 53 | Buffer (1.5M potassium dihydrogen phosphate and 1.5M dipotassium hydrogen phosphate) | 1.5 | 20 | 4.5 | 177 |
| Test Example 54 | Brackish water | — | 1.6 | 3.5 | 248 |
| Test Example 55 | Sea water | — | 3.0 | 3.5 | 194 |
| Test Example 56 | Water | — | 100 | 3.5 | 135 |
| Comparative Example 3 | Methanol | — | 100 | 3.5 | 100 |

TABLE 12

| No. | Coagulation liquid | Proportion of sodium chloride aqueous solution [%] | Proportion of water [%] | Proportion of formic acid [%] | Draw ratio [time] | Relative value of toughness [%] |
|---|---|---|---|---|---|---|
| Test Example 57 | 0.5M sodium chloride aqueous solution | 100 | 0 | 0 | 3.5 | 120 |
| Test Example 58 | Formic acid mixed aqueous solution 1 | 90 | 0 | 10 | 3.5 | 108 |
| Test Example 59 | Formic acid mixed aqueous solution 2 | 80 | 0 | 20 | 3.5 | 106 |
| Test Example 56 | Water | 0 | 100 | 0 | 3.5 | 135 |
| Test Example 60 | Formic acid aqueous solution 1 | 0 | 90 | 10 | 3.5 | 140 |
| Test Example 61 | Formic acid aqueous solution 2 | 0 | 80 | 20 | 3.5 | 108 |
| Comparative Example 3 | Methanol | 0 | 0 | 0 | 4.0 | 100 |

As shown in Table 12, in all the modified fibroin fibers produced by using, as a coagulation liquid, a mixed aqueous solution of a sodium chloride aqueous solution and formic acid (Test Examples 58 to 59), and the modified fibroin fiber produced by using, as a coagulation liquid, a mixed aqueous solution of water and formic acid (Test Examples 60 to 61), an effect of further improving the toughness value was observed in any mixing ratio, compared to the modified fibroin fiber produced by using methanol as a coagulation liquid (Comparative Example 3), and an unexpected excellent result could be obtained. This result shows that, even in a case where formic acid in the spinning dope is dissolved in a coagulation liquid of water (Test Example 41) and a coagulation liquid of a sodium chloride aqueous solution (Test Example 34), an excellent effect of improving the toughness value is observed.

(4) Evaluation of Shrinkage of Artificial Structural Protein Fiber

The lengths of the modified fibroin fibers obtained in the above (2) were adjusted to about 30 cm and bundled, and this was used as a fibroin fiber bundle with a fineness of 150D. A 0.8 g-lead weight was attached to each of the fibroin fiber bundles, and the fiber bundle was made shrunk by immersing the fiber bundle in this state in water at 40° C. for 90 seconds. Then, each fiber bundle was taken out from the water, and dried with the 0.8 g-lead weight attached thereto. Then, the length of each fiber bundle after drying was measured. The shrinkage ratio was calculated according to the following equation. Note that $L_0$ represents the length of a modified fibroin fiber before contact with water (after spinning) (herein, 30 cm), and $L_D$ represents the length of a fiber after shrinkage (dried fiber after impregnation treatment with water).

$$\text{shrinkage ratio[\%]} = \{1 - (L_D/L_0)\} \times 100 \qquad \text{Equation:}$$

The shrinkage ratio of each of the modified fibroin fibers is shown in Tables 11 and 12. The value of the shrinkage ratio in Tables 13 and 14 was shown as a relative value when the value of shrinkage ratio (17.0%) of the modified fibroin fiber of Comparative Example 4 (a fiber produced by using methanol for a coagulation bath) is taken as 100. Incidentally, for the shrinkage ratio of Test Example 64 (potassium chloride aqueous solution) and Test Example 73 (sodium sulfate aqueous solution) in Table 13, and the shrinkage ratio in Table 14, a value when the temperature of the coagulation bath was 60° C. was shown.

TABLE 13

| No. | Coagulation liquid | Concentration [% by mass] | Molar concentration [mol/l] | Draw ratio [time] | Relative value of shrinkage ratio [%] | Shrinkage ratio [%] |
|---|---|---|---|---|---|---|
| Test Example 62 | Sodium citrate aqueous solution | 21.3 | 0.9 | 3.5 | 75 | 12.8 |
| Test Example 63 | Sodium formate aqueous solution | 5 | 0.9 | 3.5 | 62 | 10.5 |
| Test Example 64 | Potassium chloride aqueous solution | 6.5 | 0.9 | 3.5 | 88 | 15.0 |
| Test Example 65 | Sodium chloride aqueous solution | 3 | 0.5 | 3.5 | 68 | 11.5 |
| Test Example 71 | Calcium chloride aqueous solution | 20 | 1.8 | 3.5 | 72 | 12.2 |
| Test Example 72 | Ammonium sulfate aqueous solution | 10 | 0.9 | 3.5 | 59 | 10.0 |
| Test Example 73 | Sodium sulfate aqueous solution | 11.9 | 0.9 | 3.5 | 65 | 11.0 |
| Test Example 74 | Buffer (1.5M potassium dihydrogen phosphate and 1.5M dipotassium hydrogen phosphate) | 20 | 1.5 | 3.5 | 62 | 10.5 |

TABLE 13-continued

| No. | Coagulation liquid | Concentration [% by mass] | Molar concentration [mol/l] | Draw ratio [time] | Relative value of shrinkage ratio [%] | Shrinkage ratio [%] |
|---|---|---|---|---|---|---|
| Test Example 75 | Brackish water | 1.6 | — | 3.5 | 69 | 11.8 |
| Test Example 76 | Sea water | 3.0 | — | 3.5 | 74 | 12.5 |
| Test Example 77 | Water | 100 | — | 3.5 | 58 | 9.8 |
| Comparative Example 4 | Methanol | 100 | — | 3.5 | 100 | 17.0 |

As shown in Table 13, in all the modified fibroin fibers produced by using, as a coagulation liquid, a carboxylate aqueous solution (a sodium citrate aqueous solution and a sodium formate aqueous solution), a chloride aqueous solution (a potassium chloride aqueous solution and a sodium chloride aqueous solution), a sulfate aqueous solution (a sodium sulfate aqueous solution and an ammonium sulfate aqueous solution), a phosphoric acid water salt aqueous solution, and a mixed solution (brackish water and sea water) (Test Examples 62 to 76) and the modified fibroin fiber produced by using water as a coagulation liquid (Test Example 77), an excellent effect of reducing the shrinkage ratio relative to water was observed, compared to the modified fibroin fiber produced by using methanol as a coagulation liquid (Comparative Example 4), and an unexpected excellent result was obtained.

In particular, an effect of improving elongation (see, Table 9), an effect of improving toughness (see, Table 11), and an effect of reducing shrinkage relative to water content (see, Table 13) can be further obtained, in addition to a large amount of reduction in production cost, by using, as a coagulation liquid, water, a sodium chloride aqueous solution, a sodium sulfate aqueous solution, brackish water, and sea water, which are abundant and inexpensive resources.

nol as a coagulation liquid (Comparative Example 4), and an unexpected excellent result was obtained. This result shows that, even in a case where formic acid in the spinning dope is dissolved in a coagulation liquid of water (Test Example 77) and a coagulation liquid of a sodium chloride aqueous solution (Test Example 65), an excellent effect of reducing the shrinkage ratio relative to water is observed.

Reference Example 1: Combustion Test of Modified Fibroin

A freeze-dried powder of the modified fibroin (PRT799) was added to a dimethyl sulfoxide solution of lithium chloride (concentration: 4.0% by mass) so that the concentration was 24% by mass, and then dissolved by mixing using a shaker for 3 hours. Thereafter, insoluble matters and foams were removed to obtain a modified fibroin solution (spinning dope).

The obtained spinning dope was heated to 90° C., and filtrated with a metal filter having an opening of 5 μm. Thereafter, the filtrate was allowed to stand in a 30 mL-stainless steel syringe to remove foams. The resulting spinning dope was discharged from a solid nozzle having a needle diameter of 0.2 mm into a 100% by mass methanol

TABLE 14

| No. | Coagulation liquid | Proportion of sodium chloride aqueous solution [%] | Proportion of water [%] | Proportion of formic acid [%] | Draw ratio [time] | Relative value of shrinkage ratio [%] | Shrinkage ratio [%] |
|---|---|---|---|---|---|---|---|
| Test Example 65 | Sodium chloride aqueous solution | 100 | 0 | 0 | 3.5 | 68 | 11.5 |
| Test Example 78 | Formic acid mixed aqueous solution 1 | 80 | 0 | 20 | 3.5 | 78 | 13.2 |
| Test Example 79 | Formic acid mixed aqueous solution 2 | 70 | 0 | 30 | 3.5 | 81 | 13.8 |
| Test Example 80 | Formic acid mixed aqueous solution 3 | 60 | 0 | 40 | 3.5 | 71 | 12.0 |
| Test Example 77 | Water | 0 | 100 | 0 | 3.5 | 58 | 9.8 |
| Test Example 81 | Formic acid aqueous solution 1 | 0 | 90 | 10 | 3.5 | 82 | 14.0 |
| Test Example 82 | Formic acid aqueous solution 2 | 0 | 80 | 20 | 3.5 | 76 | 12.9 |
| Comparative Example 4 | Methanol | 0 | 0 | 0 | 3.5 | 100 | 17.0 |

As shown in Table 14, in all the modified fibroin fibers produced by using, as a coagulation liquid, a mixed aqueous solution of a sodium chloride aqueous solution and formic acid (Test Examples 78 to 80), and the modified fibroin fibers produced by using, as a coagulation liquid, a mixed aqueous solution of water and formic acid (Test Examples 81 to 82), an excellent effect of reducing the shrinkage ratio relative to water was observed in any mixing ratio, compared to the modified fibroin fiber produced by using methacoagulation bath. The discharge temperature was 90° C. After completion of the coagulation, the obtained original yarn was wound up, and naturally dried to obtain a modified fibroin fiber (raw material fiber).

A knitted fabric (thickness: 180 denier, gauge number: 18) was produced by circular knitting a twisted yarn obtained by twisting the raw material fibers by using a circular knitting machine. 20 g of the obtained knitted fabric was cut out, and used as a test piece.

The combustion test was performed in accordance with the "test method of a particulate or low-melting point synthetic resin" specified in "Notice No. 50 of the Office of Hazardous Materials Regulation (May 31, 1995). The test was performed under conditions of a temperature of 22° C., a relative humidity of 45%, and an atmospheric pressure of 1,021 hPa. The measurement result (oxygen concentration (%), combustion rate (%), and converted combustion rate (%)) is shown in Table 15.

TABLE 15

| Oxygen concentration (%) | Combustion rate (%) | Converted combustion rate (%) |
| --- | --- | --- |
| 20.0 | 39.1 | 40.1 |
| 27.0 | 48.1 | 49.3 |
| 28.0 | 51.9 | 53.2 |
| 30.0 | 53.6 | 54.9 |
| 50.0 | 61.2 | 62.7 |
| 70.0 | 91.1 | 93.3 |
| 100.0 | 97.6 | 100.0 |

As a result of the combustion test, the limiting oxygen index (LOI) value of the knitted fabric obtained by knitting the modified fibroin (PRT799) fibers was 27.2. An LOI value of 26 or more is generally known to be flame retardant. The result shows that the modified fibroin is excellent in flame retardancy.

Reference Example 2: Evaluation of Moisture-Absorptive Heat Generation Property of Modified Fibroin A freeze-dried powder of a modified fibroin was added to a dimethyl sulfoxide solution of lithium chloride (concentration: 4.0% by mass) so that the concentration was 24% by mass, and then dissolved by mixing using a shaker for 3 hours. Thereafter, insoluble matters and foams were removed to obtain a modified fibroin solution (spinning dope).

The obtained spinning dope was heated to 60° C., and filtrated with a metal filter having an opening of 5 μm. Thereafter, the filtrate was allowed to stand in a 30 mL-stainless steel syringe to remove foams. The resulting spinning dope was discharged from a solid nozzle having a needle diameter of 0.2 mm into a 100% by mass methanol coagulation bath. The discharge temperature was 60° C. After completion of the coagulation, the obtained original yarn was wound up, and naturally dried to obtain a modified fibroin fiber (raw material fiber).

For comparison, commercially available wool fibers, cotton fibers, tencel fibers, rayon fibers, and polyester fibers were prepared as a raw material fiber.

A knitted fabric was produced by weft-knitting each of the raw material fibers by using a weft-knitting machine. The thickness and gauge number of the knitted fabric formed by using PRT918 fibers or PRT799 fibers are as shown in Table 16. The thickness and gauge number of each of the knitted fabrics formed by using other raw material fibers were adjusted so as to have a cover factor approximately the same as that of the knitted fabric of the modified fibroin fiber. Details are as follows.

TABLE 16

| Raw material fiber | Thickness [N] | Gauge number [GG] |
| --- | --- | --- |
| PRT918 | 1/30 (metric count single yarn) | 18 |
| PRT799 | 1/30 (metric count single yarn) | 16 |
| Wool | 2/30 (two ply yarn) | 14 |
| Cotton | 2/34 (two ply yarn) | 14 |
| Tencel | 2/30 (two ply yarn) | 15 |
| Rayon | 1/38 (single yarn) | 14 |
| Polyester | 1/60 (single yarn) | 14 |

Two pieces of knitted fabrics each cut with a size of 10 cm×10 cm were faced to each other, and four sides thereof were sewn to each other to prepare a test piece (sample). The test piece was left to stand in a low humidity environment (temperature: 20±2° C., relative humidity: 40±5%) for 4 hours or more, and then transferred to a high humidity environment (temperature: 20±2° C., relative humidity: 90±5%). Then, measurement of the temperature was performed with a temperature sensor attached to the center of inside of the test piece for 30 minutes at 1 minute intervals.

From the measurement result, the maximum moisture-absorptive heat generation was determined according to the following Equation A.

$$
\begin{aligned}
\text{maximum moisture-absorptive heat generation} = \{ \\
\text{(maximum value of a sample temperature when} \\
\text{a sample is placed in a low humidity environ-} \\
\text{ment until the sample temperature reaches the} \\
\text{equilibrium, and then transferred to a high} \\
\text{humidity environment)} - \text{(a sample temperature} \\
\text{when a sample is placed in a low humidity} \\
\text{environment until the sample temperature} \\
\text{reaches the equilibrium, and then transferred to} \\
\text{a high humidity environment)}\}(° \text{ C.})/\text{sample} \\
\text{weight(g)} \qquad\qquad \text{Equation A:}
\end{aligned}
$$

Figure 5:
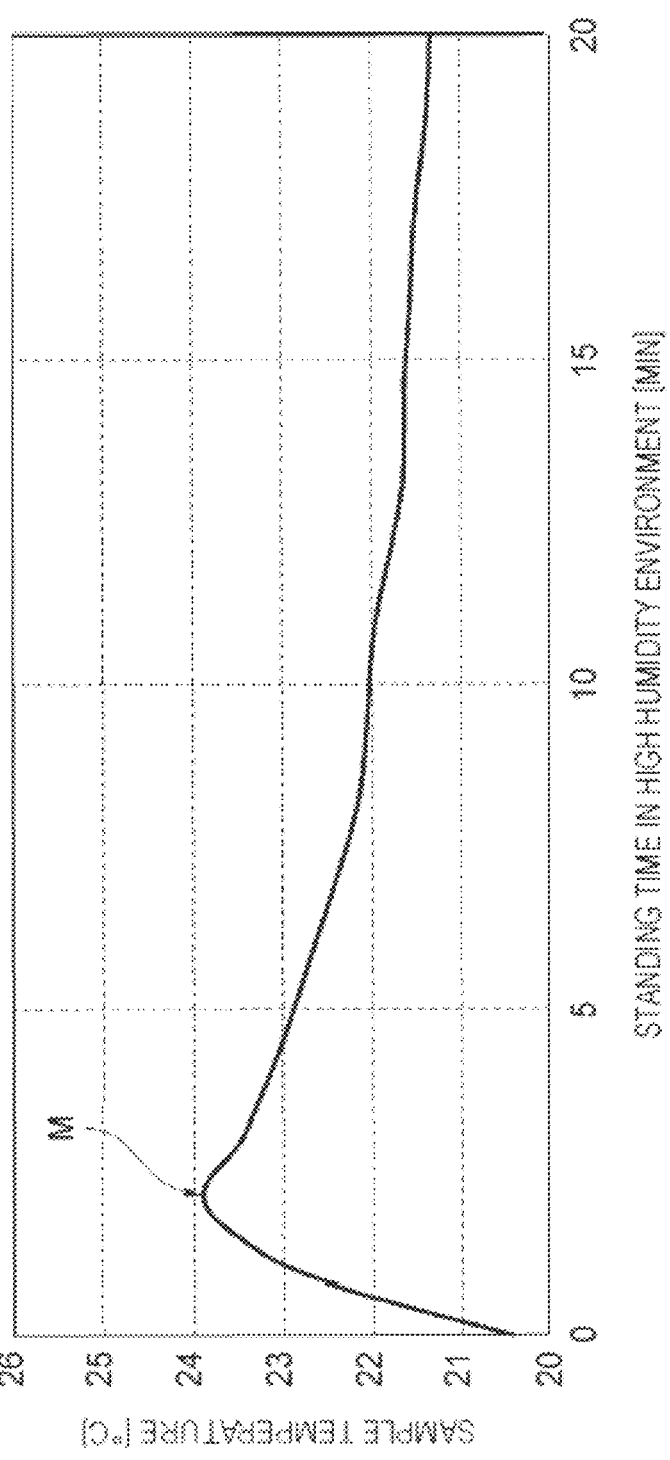
FIG. 5 is a graph showing an example of the result of a moisture-absorptive heat generation property test.

FIG. 5 is a graph showing an example of the result of a moisture-absorptive heat generation property test. In the horizontal axis of the graph, a time point at which the sample is transferred from a low humidity environment to a high humidity environment is defined as 0, and the horizontal axis represents a period of time during which the sample is left to stand in a high humidity environment (min). The vertical axis of the graph represents a temperature measured with a temperature sensor (sample temperature). In the graph shown in FIG. 5, the point indicated by M corresponds to the maximum value of the sample temperature.

The calculation result of the maximum moisture-absorptive heat generation of each of the knitted fabrics is shown in Table 16.

TABLE 17

| Raw material fiber | Maximum moisture-absorptive heat generation (° C./g) |
| --- | --- |
| PRT918 | 0.040 |
| PRT799 | 0.031 |
| Wool | 0.020 |
| Cotton | 0.021 |
| Tencel | 0.018 |
| Rayon | 0.025 |
| Polyester | 0.010 |

Table 17 shows that the modified fibroins (PRT918 and PRT799) have a high maximum moisture-absorptive heat generation compared to existing materials, and thus are excellent in the moisture-absorptive heat generation property.

Reference Example 3: Evaluation of Heat Retention Property of Modified Fibroin

A freeze-dried powder of a modified fibroin was added to a dimethyl sulfoxide solution of lithium chloride (concentration: 4.0% by mass) so that the concentration was 24% by mass, and then dissolved by mixing using a shaker for 3 hours. Thereafter, insoluble matters and foams were removed to obtain a modified fibroin solution (spinning dope).

The obtained spinning dope was heated to 60° C., and filtrated with a metal filter having an opening of 5 μm. Thereafter, the filtrate was allowed to stand in a 30 mL-stainless steel syringe to remove foams. The resulting spinning dope was discharged from a solid nozzle having a needle diameter of 0.2 mm into a 100% by mass methanol coagulation bath. The discharge temperature was 60° C. After completion of the coagulation, the obtained original yarn was wound up, and naturally dried to obtain a modified fibroin fiber (raw material fiber).

For comparison, commercially available wool fibers, silk fibers, cotton fibers, rayon fibers, and polyester fibers were prepared as a raw material fiber.

A knitted fabric was produced by weft-knitting each of the raw material fibers by using a weft-knitting machine. The yarn count, the number of twisted yarns, the gauge number, and the basis weight of the knitted fabric formed by using PRT966 fibers or PRT799 fibers are as shown in Table 18. Each of the knitted fabrics formed by using other raw material fibers was adjusted so as to have a cover factor approximately the same as that of the knitted fabric of the modified fibroin fiber. Details are as follows.

TABLE 18

| Raw material fiber | Count [Nm] | Number of twisted yarns | Gauge number [GG] | Basis weight [g/m²] |
|---|---|---|---|---|
| PRT966 | 30 | 1 | 18 | 90.1 |
| PRT799 | 30 | 1 | 16 | 111.0 |
| Wool | 30 | 2 | 14 | 242.6 |
| Silk | 60 | 2 | 14 | 225.2 |
| Cotton | 34 | 2 | 14 | 194.1 |
| Rayon | 38 | 1 | 14 | 181.8 |
| Polyester | 60 | 1 | 14 | 184.7 |

The heat retention property was evaluated by using a KES-F7 THERMO LABO II tester, manufactured by Kato Tech Co., Ltd., according to a dry contact method (a method based on an assumption that the skin and clothing are in direct contact in a dried state). One piece of square knitted fabric cut with a size of 20 cm×20 cm was used as a test piece (sample). The test piece was set on a hot plate set at a predetermined temperature (30° C.), and the amount of heat (a) dissipated via the test piece was measured under a condition of a wind speed of 30 cm/sec in a wind tunnel. The amount of heat (b) dissipated in a state in which the test piece was not set was determined under the same condition as described above. Then, the heat retention ratio (%) was calculated according to the following Equation B.

$$\text{heat retention ratio (\%)} = (1 - a/b) \times 100 \qquad \text{Equation B:}$$

From the measurement result, the heat retention index was determined according to the following Equation C.

$$\text{heat retention index} = \text{heat retention ratio (\%)/basis weight of sample(g/m}^2) \qquad \text{Equation C:}$$

The calculation result of the heat retention index is shown in Table 18. A higher heat retention index can be evaluated as being a material having an excellent heat retention property.

TABLE 19

| Raw material fiber | Moisture retainability index |
|---|---|
| PRT966 | 0.33 |
| PRT799 | 0.22 |
| Wool | 0.16 |
| Silk | 0.11 |
| Cotton | 0.13 |
| Rayon | 0.02 |
| Polyester | 0.18 |

Table 19 shows that the modified fibroins (PRT966 and PRT799) have a high heat retention index compared to existing materials, and thus are excellent in the heat retention property.

As shown in Reference Examples 1 to 3, when the modified fibroin is a modified spider silk fibroin, the heat retention property, moisture-absorptive heat generation property, and/or flame retardancy can be made even better. A fiber having a superior heat retention property, moisture-absorptive heat generation property, and/or flame retardancy, toughness, and elongation, and further having a reduced shrinkage ratio relative to water content can be obtained by using a modified spider silk fibroin as a protein and using water or an aqueous solution of pH 0.25 or more and pH 10.00 or less as a coagulation liquid (in particular, a sodium chloride aqueous solution, a sodium sulfate aqueous solution, an ammonium sulfate aqueous solution, a potassium chloride aqueous solution, a calcium chloride aqueous solution, a sodium formate aqueous solution, a sodium citrate aqueous solution, a formic acid aqueous solution, a mixed aqueous solution of formic acid, brackish water, and sea water) to form a fiber.

REFERENCE SIGNS LIST

1 Extrusion apparatus
2 Undrawn yarn producing apparatus
3 Wet heat drawing apparatus
4 Drying apparatus
6 Spinning dope
10 Spinning apparatus
20 Coagulation bath
21 Washing bath
36 Protein fiber

The invention claimed is:

1. A method for producing a protein fiber, the method comprising:

contacting a spinning dope containing a protein and an organic solvent with a coagulation liquid to coagulate the protein, wherein a content of the organic solvent in the spinning dope is more than 74% by mass based on a total amount of the spinning dope, a content of the protein in the spinning dope is more than 10% by mass and 26% by mass or less based on a total amount of the spinning dope, the coagulation liquid contains an aqueous solution of pH 0.25 or more and pH 4.00 or less, and the aqueous solution includes a mixed solution of a salt aqueous solution and a carboxylic acid aqueous solution.

2. The method according to claim 1, wherein a content of the aqueous solution in the coagulation liquid is 60% by mass or more based on a total amount of the coagulation liquid.

3. The method according to claim 1, wherein a content of salt in the coagulation liquid is 0.1% by mass or more based on a total amount of the coagulation liquid.

4. The method according to claim 3, wherein the salt includes at least one type selected from the group consisting of carboxylate and an inorganic salt.

5. The method according to claim 4, wherein the inorganic salt includes at least one type selected from the group consisting of a sulfate, a chloride, a nitrate, an iodide salt, a carbonate, a hydrogen sulfate, a hydrogen phosphate, a bicarbonate, and a thiocyanate.

6. The method according to claim 4, wherein the inorganic salt includes at least one type selected from the group consisting of a sulfate, a chloride, a hydrogen phosphate, and a bicarbonate.

7. The method according to claim 5, wherein the chloride includes at least one type selected from the group consisting of sodium chloride, calcium chloride, ammonium chloride, potassium chloride, lithium chloride, magnesium chloride, and guanidinium chloride.

8. The method according to claim 5, wherein the sulfate includes at least one type selected from the group consisting of ammonium sulfate, potassium sulfate, sodium sulfate, lithium sulfate, magnesium sulfate, and calcium sulfate.

9. The method according to claim 1, wherein the salt aqueous solution includes at least one type selected from the group consisting of a sodium sulfate aqueous solution, a sodium chloride aqueous solution, brackish water, and sea water.

10. The method according to claim 1, wherein a content of an organic solvent dissolved from a spinning dope in contact with a coagulation liquid in the coagulation liquid is 40% by mass or less based on 100% by mass of total content of the salt aqueous solution in the coagulation liquid and the organic solvent dissolved in the coagulation liquid.

11. The method according to claim 1, wherein an average hydropathy index of the protein is more than −1.3.

12. The method according to claim 1, wherein the protein includes at least one type selected from the group consisting of spider silk protein, silk protein, collagen protein, resilin protein, elastin protein, and keratin protein.

13. The method according to claim 1, wherein the protein is keratin protein or spider silk protein.

14. The method according to claim 1, wherein the protein is spider silk protein.

15. The method according to claim 1, wherein the organic solvent includes at least one type selected from the group consisting of formic acid and dimethyl sulfoxide.

16. The method according to claim 1, wherein the coagulation liquid contains the aqueous solution of pH 0.25 or more and pH 2.50 or less.

17. The method according to claim 6, wherein the chloride includes at least one type selected from the group consisting of sodium chloride, calcium chloride, ammonium chloride, potassium chloride, lithium chloride, magnesium chloride, and guanidinium chloride.

18. The method according to claim 1, wherein a content of salt in the coagulation liquid is 25% by mass or less based on a total amount of the coagulation liquid.

19. A method for producing a protein fiber, the method comprising:

bringing a spinning dope containing a protein and an organic solvent into contact with a coagulation liquid to coagulate the protein, wherein a content of the protein in the spinning dope is more than 10% by mass based on a total amount of the spinning dope, the coagulation liquid contains an aqueous solution of pH 0.25 or more and pH 4.00 or less, and the aqueous solution includes a mixed solution of a salt aqueous solution and a carboxylic acid aqueous solution.

20. The method according to claim 19, wherein the content of the protein in the spinning dope is 40% by mass or less based on a total amount of the spinning dope.

* * * * *

SEQUENCE LISTING

<160> NUMBER OF SEQ ID NOS: 64

<210> SEQ ID NO 1
<211> LENGTH: 50

```
<212> TYPE: PRT
<213> ORGANISM: Araneus diadematus

<400> SEQUENCE: 1

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn Tyr Gly
            20                  25                  30

Ala Ser Ala Gln Tyr Thr Gln Met Val Gly Gln Ser Val Ala Gln Ala
        35                  40                  45

Leu Ala
    50

<210> SEQ ID NO 2
<211> LENGTH: 30
<212> TYPE: PRT
<213> ORGANISM: Araneus diadematus

<400> SEQUENCE: 2

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn
            20                  25                  30

<210> SEQ ID NO 3
<211> LENGTH: 21
<212> TYPE: PRT
<213> ORGANISM: Araneus diadematus

<400> SEQUENCE: 3

Ser Gly Cys Asp Val Leu Val Gln Ala Leu Leu Glu Val Val Ser Ala
1               5                   10                  15

Leu Val Ser Ile Leu
            20

<210> SEQ ID NO 4
<211> LENGTH: 1154
<212> TYPE: PRT
<213> ORGANISM: Artificial Sequence
<220> FEATURE:
<223> OTHER INFORMATION: recombinant spider silk protein
      ADF3KaiLargeNRSH1

<400> SEQUENCE: 4

Met His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
            115                 120                 125
```

-continued

```
Ala Gly Gly Asn Gly Pro Gly Ser Gly Gln Gln Gly Ala Gly Gln Gln
    130              135              140

Gly Pro Gly Gln Gln Gly Pro Gly Ala Ser Ala Ala Ala Ala Ala Ala
145              150              155              160

Gly Gly Tyr Gly Pro Gly Ser Gly Gln Gln Gly Pro Gly Gln Gln Gly
                165              170              175

Pro Gly Gly Gln Gly Pro Tyr Gly Pro Gly Ala Ser Ala Ala Ala Ala
                180              185              190

Ala Ala Gly Gly Tyr Gly Pro Gly Ser Gly Gln Gly Pro Gly Gln Gln
                195              200              205

Gly Pro Gly Gly Gln Gly Pro Tyr Gly Pro Gly Ala Ser Ala Ala Ala
    210              215              220

Ala Ala Ala Gly Gly Tyr Gly Pro Gly Ser Gly Gln Gln Gly Pro Gly
225              230              235              240

Gln Gln Gly Pro Gly Gln Gln Gly Pro Gly Gly Gln Gly Pro Tyr Gly
                245              250              255

Pro Gly Ala Ser Ala Ala Ala Ala Ala Ala Gly Gly Tyr Gly Pro Gly
                260              265              270

Tyr Gly Gln Gln Gly Pro Gly Gln Gln Gly Pro Gly Gly Gln Gly Pro
    275              280              285

Tyr Gly Pro Gly Ala Ser Ala Ala Ser Ala Ala Ser Gly Gly Tyr Gly
    290              295              300

Pro Gly Ser Gly Gln Gln Gly Pro Gly Gln Gln Gly Pro Gly Gly Gln
305              310              315              320

Gly Pro Tyr Gly Pro Gly Ala Ser Ala Ala Ala Ala Ala Ala Gly Gly
                325              330              335

Tyr Gly Pro Gly Ser Gly Gln Gln Gly Pro Gly Gln Gln Gly Pro Gly
                340              345              350

Gln Gln Gly Pro Gly Gln Gln Gly Pro Gly Gly Gln Gly Pro Tyr Gly
                355              360              365

Pro Gly Ala Ser Ala Ala Ala Ala Ala Ala Gly Gly Tyr Gly Pro Gly
    370              375              380

Ser Gly Gln Gln Gly Pro Gly Gln Gln Gly Pro Gly Gln Gln Gly Pro
385              390              395              400

Gly Gln Gln Gly Pro Gly Gln Gln Gly Pro Gly Gln Gln Gly Pro Gly
                405              410              415

Gln Gln Gly Pro Gly Gln Gln Gly Pro Gly Gln Gln Gly Pro Gly Gly
                420              425              430

Gln Gly Ala Tyr Gly Pro Gly Ala Ser Ala Ala Ala Gly Ala Ala Gly
    435              440              445

Gly Tyr Gly Pro Gly Ser Gly Gln Gln Gly Pro Gly Gln Gln Gly Pro
    450              455              460

Gly Gln Gln Gly Pro Gly Gln Gln Gly Pro Gly Gln Gln Gly Pro Gly
465              470              475              480

Gln Gln Gly Pro Gly Gln Gln Gly Pro Gly Gln Gln Gly Pro Tyr Gly
                485              490              495

Pro Gly Ala Ser Ala Ala Ala Ala Ala Ala Gly Gly Tyr Gly Pro Gly
                500              505              510

Ser Gly Gln Gln Gly Pro Gly Gln Gln Gly Pro Gly Gln Gln Gly Pro
    515              520              525

Gly Gly Gln Gly Pro Tyr Gly Pro Gly Ala Ala Ser Ala Ala Val Ser
    530              535              540
```

```
Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
                565                 570                 575

Ala Ser Ala Ala Ala Ala Ala Ala Gly Gly Tyr Gly Pro Gly Ser Gly
                580                 585                 590

Gln Gln Gly Pro Ser Gln Gln Gly Pro Gly Gln Gln Gly Pro Gly Gly
                595                 600                 605

Gln Gly Pro Tyr Gly Pro Gly Ala Ser Ala Ala Ala Ala Ala Ala Gly
            610                 615                 620

Gly Tyr Gly Pro Gly Ser Gly Gln Gln Gly Pro Gly Gly Gln Gly Pro
625                 630                 635                 640

Tyr Gly Pro Gly Ser Ser Ala Ala Ala Ala Ala Gly Gly Asn Gly
                645                 650                 655

Pro Gly Ser Gly Gln Gln Gly Ala Gly Gln Gln Gly Pro Gly Gln Gln
                660                 665                 670

Gly Pro Gly Ala Ser Ala Ala Ala Ala Ala Gly Gly Tyr Gly Pro
            675                 680                 685

Gly Ser Gly Gln Gln Gly Pro Gly Gln Gln Gly Pro Gly Gly Gln Gly
            690                 695                 700

Pro Tyr Gly Pro Gly Ala Ser Ala Ala Ala Ala Ala Ala Gly Gly Tyr
705                 710                 715                 720

Gly Pro Gly Ser Gly Gln Gly Pro Gly Gln Gln Gly Pro Gly Gly Gln
                725                 730                 735

Gly Pro Tyr Gly Pro Gly Ala Ser Ala Ala Ala Ala Ala Ala Gly Gly
            740                 745                 750

Tyr Gly Pro Gly Ser Gly Gln Gln Gly Pro Gly Gln Gln Gly Pro Gly
            755                 760                 765

Gln Gln Gly Pro Gly Gly Gln Gly Pro Tyr Gly Pro Gly Ala Ser Ala
        770                 775                 780

Ala Ala Ala Ala Gly Gly Tyr Gly Pro Gly Tyr Gly Gln Gln Gly
785                 790                 795                 800

Pro Gly Gln Gln Gly Pro Gly Gly Gln Gly Pro Tyr Gly Pro Gly Ala
                805                 810                 815

Ser Ala Ala Ser Ala Ala Ser Gly Gly Tyr Gly Pro Gly Ser Gly Gln
                820                 825                 830

Gln Gly Pro Gly Gln Gln Gly Pro Gly Gly Gln Gly Pro Tyr Gly Pro
            835                 840                 845

Gly Ala Ser Ala Ala Ala Ala Ala Gly Gly Tyr Gly Pro Gly Ser
        850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
                885                 890                 895

Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
            915                 920                 925

Gly Gln Gln Gly Pro Gly Gln Gln Gly Pro Gly Gln Gln Gly Pro Gly
        930                 935                 940

Gln Gln Gly Pro Gly Gln Gln Gly Pro Gly Gly Gln Gly Ala Tyr Gly
945                 950                 955                 960

Pro Gly Ala Ser Ala Ala Ala Gly Ala Ala Gly Gly Tyr Gly Pro Gly
```

-continued

```
                 965              970               975
Ser Gly Gln Gln Gly Pro Gly Gln Gln Gly Pro Gly Gln Gln Gly Pro
             980              985               990

Gly Gln Gln Gly Pro Gly Gln Gln  Gly Pro Gly Gln Gln  Gly Pro Gly
         995             1000               1005

Gln Gln  Gly Pro Gly Gln Gln  Gly Pro Tyr Gly Pro  Gly Ala Ser
    1010             1015               1020

Ala Ala  Ala Ala Ala Ala Gly  Gly Tyr Gly Pro Gly  Ser Gly Gln
    1025             1030               1035

Gln Gly  Pro Gly Gln Gln Gly  Pro Gly Gln Gln Gly  Pro Gly Gly
    1040             1045               1050

Gln Gly  Pro Tyr Gly Pro Gly  Ala Ala Ser Ala Ala  Val Ser Val
    1055             1060               1065

Gly Gly  Tyr Gly Pro Gln Ser  Ser Ser Val Pro Val  Ala Ser Ala
    1070             1075               1080

Val Ala  Ser Arg Leu Ser Ser  Pro Ala Ala Ser Ser  Arg Val Ser
    1085             1090               1095

Ser Ala  Val Ser Ser Leu Val  Ser Ser Gly Pro Thr  Lys His Ala
    1100             1105               1110

Ala Leu  Ser Asn Thr Ile Ser  Ser Val Val Ser Gln  Val Ser Ala
    1115             1120               1125

Ser Asn  Pro Gly Leu Ser Gly  Cys Asp Val Leu Val  Gln Ala Leu
    1130             1135               1140

Leu Glu  Val Val Ser Ala Leu  Val Ser Ile Leu
    1145             1150

<210> SEQ ID NO 5
<211> LENGTH: 24
<212> TYPE: PRT
<213> ORGANISM: Artificial Sequence
<220> FEATURE:
<223> OTHER INFORMATION: His tag and start codon

<400> SEQUENCE: 5

Met His His His His His His His His His Ser Ser Gly Ser Ser
1               5                   10                  15

Leu Glu Val Leu Phe Gln Gly Pro
            20

<210> SEQ ID NO 6
<211> LENGTH: 597
<212> TYPE: PRT
<213> ORGANISM: Artificial Sequence
<220> FEATURE:
<223> OTHER INFORMATION: Met-PRT380

<400> SEQUENCE: 6

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20              25                  30

Gln Ser Ala Ala Ala Ala Ala Gly Gln Tyr Gly Pro Gly Gln Gln Gly
        35              40                  45

Pro Gly Gln Gln Gly Pro Gly Ser Ser Ala Ala Ala Ala Ala Gly Pro
    50              55                  60

Gly Gln Tyr Gly Pro Gly Gln Gln Gly Pro Ser Ala Ser Ala Ala Ala
65              70                  75                  80
```

-continued

```
Ala Ala Gly Pro Gly Ser Gly Gln Gln Gly Pro Gly Ala Ser Ala Ala
                85                  90                  95

Ala Ala Ala Gly Gln Tyr Gly Pro Gly Gln Gln Gly Pro Gly Gln Gln
            100                 105                 110

Gly Pro Gly Ser Ser Ala Ala Ala Ala Ala Gly Gln Tyr Gly Ser Gly
            115                 120                 125

Pro Gly Gln Gln Gly Pro Tyr Gly Ser Ala Ala Ala Ala Gly Pro
        130                 135                 140

Gly Ser Gly Gln Tyr Gly Gln Gly Pro Tyr Pro Gly Ala Ser Ala
145                 150                 155                 160

Ala Ala Ala Ala Gly Pro Gly Gln Tyr Gly Pro Gly Gln Gln Gly Pro
                165                 170                 175

Ser Ala Ser Ala Ala Ala Ala Ala Gly Ser Gly Gln Gln Gly Pro Gly
            180                 185                 190

Gln Tyr Gly Pro Tyr Ala Ser Ala Ala Ala Ala Gly Gln Tyr Gly
        195                 200                 205

Ser Gly Pro Gly Gln Gln Gly Pro Tyr Gly Pro Gly Gln Ser Ala Ala
    210                 215                 220

Ala Ala Ala Gly Ser Gly Gln Gln Gly Pro Gly Gln Gln Gly Pro Tyr
225                 230                 235                 240

Ala Ser Ala Ala Ala Ala Ala Gly Pro Gly Gln Gln Gly Pro Tyr Gly
            245                 250                 255

Pro Gly Ser Ser Ala Ala Ala Ala Ala Gly Gln Tyr Gly Tyr Gly Pro
            260                 265                 270

Gly Gln Gln Gly Pro Tyr Gly Pro Gly Ala Ser Ala Ala Ala Ala Ala
        275                 280                 285

Gly Gln Asn Gly Pro Gly Ser Gly Gln Tyr Gly Pro Gly Gln Gln Gly
    290                 295                 300

Pro Gly Gln Ser Ala Ala Ala Ala Ala Gly Pro Gly Gln Gln Gly Pro
305                 310                 315                 320

Tyr Gly Pro Gly Ala Ser Ala Ala Ala Ala Gly Gln Tyr Gly Pro
            325                 330                 335

Gly Gln Gln Gly Pro Gly Gln Tyr Gly Pro Gly Ser Ser Ala Ala Ala
            340                 345                 350

Ala Ala Gly Pro Gly Gln Gln Gly Pro Tyr Gly Pro Gly Ser Ser Ala
    355                 360                 365

Ala Ala Ala Gly Gln Tyr Gly Pro Gly Gln Gln Gly Pro Tyr Gly
    370                 375                 380

Pro Gly Gln Ser Ala Ala Ala Ala Ala Gly Gln Tyr Gln Gln Gly Pro
385                 390                 395                 400

Gly Gln Gln Gly Pro Tyr Gly Pro Gly Ala Ser Ala Ala Ala Ala
            405                 410                 415

Gly Pro Gly Gln Gln Gly Pro Tyr Gly Pro Gly Ala Ser Ala Ala Ala
            420                 425                 430

Ala Ala Gly Pro Gly Gln Tyr Gly Pro Gly Gln Gln Gly Pro Ser Ala
    435                 440                 445

Ser Ala Ala Ala Ala Ala Gly Gln Tyr Gly Ser Gly Pro Gly Gln Tyr
    450                 455                 460

Gly Pro Tyr Gly Pro Gly Gln Ser Ala Ala Ala Ala Ala Gly Pro Gly
465                 470                 475                 480

Ser Gly Gln Gln Gly Gln Gly Pro Tyr Gly Pro Gly Ala Ser Ala Ala
            485                 490                 495

Ala Ala Ala Gly Gln Tyr Gly Pro Gly Gln Gln Gly Pro Tyr Gly Pro
```

```
                 500                 505                 510

Gly Gln Ser Ala Ala Ala Ala Ala Gly Pro Gly Ser Gly Gln Tyr Gly
            515                 520                 525

Pro Gly Ala Ser Ala Ala Ala Ala Ala Gly Gln Asn Gly Pro Gly Ser
        530                 535                 540

Gly Gln Tyr Gly Pro Gly Gln Gln Gly Pro Gly Gln Ser Ala Ala Ala
545                 550                 555                 560

Ala Ala Gly Gln Tyr Gln Gln Gly Pro Gly Gln Gln Gly Pro Tyr Gly
                565                 570                 575

Pro Gly Ala Ser Ala Ala Ala Ala Ala Gly Pro Gly Ser Gly Gln Gln
            580                 585                 590

Gly Pro Gly Ala Ser
            595

<210> SEQ ID NO 7
<211> LENGTH: 590
<212> TYPE: PRT
<213> ORGANISM: Artificial Sequence
<220> FEATURE:
<223> OTHER INFORMATION: Met-PRT410

<400> SEQUENCE: 7

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
            35                  40                  45

Pro Gly Ser Ser Ala Ala Ala Ala Ala Gly Pro Gly Gln Tyr Gly Pro
        50                  55                  60

Gly Gln Gln Gly Pro Ser Ala Ser Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala Ala
            100                 105                 110

Gly Gln Tyr Gly Ser Gly Pro Gly Gln Gln Gly Pro Tyr Gly Ser Ala
        115                 120                 125

Ala Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Ala Gly Ser Gly Gln Gln Gly Pro
                165                 170                 175

Gly Gln Tyr Gly Pro Tyr Ala Ser Ala Ala Ala Ala Gly Gln Tyr
        180                 185                 190

Gly Ser Gly Pro Gly Gln Gln Gly Pro Tyr Gly Pro Gly Gln Ser Gly
        195                 200                 205

Ser Gly Gln Gln Gly Pro Gly Gln Gln Gly Pro Tyr Ala Ser Ala Ala
    210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
                245                 250                 255

Pro Tyr Gly Pro Gly Ala Ser Gly Gln Asn Gly Pro Gly Ser Gly Gln
```

-continued

```
              260               265               270

Tyr Gly Pro Gly Gln Gln Gly Pro Gly Gln Ser Ala Ala Ala Ala
        275               280               285

Gly Pro Gly Gln Gln Gly Pro Tyr Gly Pro Gly Ala Ser Ala Ala Ala
        290               295               300

Ala Ala Gly Gln Tyr Gly Pro Gly Gln Gln Gly Pro Gly Gln Tyr Gly
305               310               315               320

Pro Gly Ser Ser Gly Pro Gly Gln Gln Gly Pro Tyr Gly Pro Gly Ser
            325               330               335

Ser Ala Ala Ala Ala Ala Gly Gln Tyr Gly Pro Gly Gln Gln Gly Pro
            340               345               350

Tyr Gly Pro Gly Gln Ser Ala Ala Ala Ala Gly Gln Tyr Gln Gln
        355               360               365

Gly Pro Gly Gln Gln Gly Pro Tyr Gly Pro Gly Ala Ser Gly Pro Gly
        370               375               380

Gln Gln Gly Pro Tyr Gly Pro Gly Ala Ser Ala Ala Ala Ala Ala Gly
385               390               395               400

Pro Gly Gln Tyr Gly Pro Gly Gln Gln Gly Pro Ser Ala Ser Ala Ala
            405               410               415

Ala Ala Ala Gly Gln Tyr Gly Ser Gly Pro Gly Gln Tyr Gly Pro Tyr
            420               425               430

Gly Pro Gly Gln Ser Gly Pro Gly Ser Gly Gln Gln Gly Gln Gly Pro
            435               440               445

Tyr Gly Pro Gly Ala Ser Ala Ala Ala Ala Gly Gln Tyr Gly Pro
        450               455               460

Gly Gln Gln Gly Pro Tyr Gly Pro Gly Gln Ser Ala Ala Ala Ala Ala
465               470               475               480

Gly Pro Gly Ser Gly Gln Tyr Gly Pro Gly Ala Ser Gly Gln Asn Gly
            485               490               495

Pro Gly Ser Gly Gln Tyr Gly Pro Gly Gln Gln Gly Pro Gly Gln Ser
            500               505               510

Ala Ala Ala Ala Ala Gly Gln Tyr Gln Gln Gly Pro Gly Gln Gln Gly
            515               520               525

Pro Tyr Gly Pro Gly Ala Ser Ala Ala Ala Ala Gly Gln Tyr Gly
        530               535               540

Ser Gly Pro Gly Gln Gln Gly Pro Tyr Gly Pro Gly Gln Ser Gly Ser
545               550               555               560

Gly Gln Gln Gly Pro Gly Gln Gln Gly Pro Tyr Ala Ser Ala Ala Ala
            565               570               575

Ala Ala Gly Pro Gly Ser Gly Gln Gln Gly Pro Gly Ala Ser
            580               585               590
```

```
<210> SEQ ID NO 8
<211> LENGTH: 565
<212> TYPE: PRT
<213> ORGANISM: Artificial Sequence
<220> FEATURE:
<223> OTHER INFORMATION: Met-PRT468

<400> SEQUENCE: 8

Met Gly Pro Gly Gln Gln Gly Pro Tyr Gly Pro Gly Ala Ser Ala Ala
1               5               10               15

Ala Ala Ala Ala Ala Gly Ser Asn Gly Pro Gly Ser Gly Gln Gln Gly
            20               25               30

Pro Gly Gln Ser Gly Gln Tyr Gly Pro Gly Gln Gln Gly Pro Gly Gln
```

-continued

```
          35                  40                  45

Gln Gly Pro Gly Ser Ser Ala Ala Ala Ala Ala Ala Gly Pro Gly
          50                  55                  60

Gln Tyr Gly Pro Gly Gln Gln Gly Pro Ser Ala Ser Ala Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
                100                 105                 110

Ser Ala Ala Ala Ala Ala Ala Ala Gly Ser Tyr Gly Ser Gly Pro Gly
                115                 120                 125

Gln Gln Gly Pro Tyr Gly Ser Ala Ala Ala Ala Ala Ala Gly Pro
          130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Gln Gln Gly Pro Ser Ala Ser Ala Ala
                165                 170                 175

Ala Ala Ala Ala Ala Gly Ser Gly Gln Gln Gly Pro Gly Gln Tyr Gly
                180                 185                 190

Pro Tyr Ala Ser Ala Ala Ala Ala Ala Ala Gly Ser Tyr Gly Ser
          195                 200                 205

Gly Pro Gly Gln Gln Gly Pro Tyr Gly Pro Gly Gln Ser Gly Ser Gly
          210                 215                 220

Gln Gln Gly Pro Gly Gln Gln Gly Pro Tyr Ala Ser Ala Ala Ala Ala
225                 230                 235                 240

Ala Ala Ala Gly Pro Gly Gln Gln Gly Pro Tyr Gly Pro Gly Ser Ser
                245                 250                 255

Ala Ala Ala Ala Ala Ala Ala Gly Ser Tyr Gly Tyr Gly Pro Gly Gln
                260                 265                 270

Gln Gly Pro Tyr Gly Pro Gly Ala Ser Gly Gln Asn Gly Pro Gly Ser
          275                 280                 285

Gly Gln Tyr Gly Pro Gly Gln Gln Gly Pro Gly Pro Ser Ala Ala Ala
          290                 295                 300

Ala Ala Ala Ala Gly Pro Gly Gln Gln Gly Pro Tyr Gly Pro Gly Ala
305                 310                 315                 320

Ser Ala Ala Ala Ala Ala Ala Ala Gly Ser Tyr Gly Pro Gly Gln Gln
                325                 330                 335

Gly Pro Gly Gln Tyr Gly Pro Gly Ser Ser Gly Pro Gly Gln Gln Gly
                340                 345                 350

Pro Tyr Gly Pro Gly Ser Ser Ala Ala Ala Ala Ala Ala Ala Gly Ser
          355                 360                 365

Tyr Gly Pro Gly Gln Gln Gly Pro Tyr Gly Pro Gly Pro Ser Ala Ala
          370                 375                 380

Ala Ala Ala Ala Ala Gly Ser Tyr Gln Gln Gly Pro Gly Gln Gln Gly
385                 390                 395                 400

Pro Tyr Gly Pro Gly Ala Ser Gly Pro Gly Gln Gln Gly Pro Tyr Gly
                405                 410                 415

Pro Gly Ala Ser Ala Ala Ala Ala Ala Ala Gly Pro Gly Gln Tyr
                420                 425                 430

Gly Pro Gly Gln Gln Gly Pro Ser Ala Ser Ala Ala Ala Ala Ala Ala
          435                 440                 445

Ala Gly Ser Tyr Gly Ser Gly Pro Gly Gln Tyr Gly Pro Tyr Gly Pro
          450                 455                 460
```

```
Gly Gln Ser Gly Pro Gly Ser Gly Gln Gln Gly Gln Gly Pro Tyr Gly
465             470             475             480

Pro Gly Ala Ser Ala Ala Ala Ala Ala Ala Gly Ser Tyr Gly Pro
                485             490             495

Gly Gln Gln Gly Pro Tyr Gly Pro Gly Pro Ser Ala Ala Ala Ala Ala
            500             505             510

Ala Ala Gly Pro Gly Ser Gly Gln Tyr Gly Pro Gly Ala Ser Gly Gln
        515             520             525

Asn Gly Pro Gly Ser Gly Gln Tyr Gly Pro Gly Gln Gln Gly Pro Gly
    530             535             540

Pro Ser Ala Ala Ala Ala Ala Ala Ala Gly Pro Gly Ser Gly Gln Gln
545             550             555             560

Gly Pro Gly Ala Ser
            565

<210> SEQ ID NO 9
<211> LENGTH: 2364
<212> TYPE: PRT
<213> ORGANISM: Artificial Sequence
<220> FEATURE:
<223> OTHER INFORMATION: Met-PRT799

<400> SEQUENCE: 9

Met Gly Pro Gly Gln Gln Gly Pro Tyr Gly Pro Gly Ala Ser Ala Ala
1               5               10              15

Ala Ala Ala Gly Gln Asn Gly Pro Gly Ser Gly Gln Gln Gly Pro Gly
            20              25              30

Gln Ser Gly Gln Tyr Gly Pro Gly Gln Gln Gly Pro Gly Gln Gln Gly
        35              40              45

Pro Gly Ser Ser Ala Ala Ala Ala Gly Pro Gly Gln Tyr Gly Pro
    50              55              60

Gly Gln Gln Gly Pro Ser Ala Ser Ala Ala Ala Ala Ala Gly Pro Gly
65              70              75              80

Ser Gly Gln Gln Gly Pro Gly Ala Ser Gly Gln Tyr Gly Pro Gly Gln
                85              90              95

Gln Gly Pro Gly Gln Gln Gly Pro Gly Ser Ser Ala Ala Ala Ala Ala
            100             105             110

Gly Gln Tyr Gly Ser Gly Pro Gly Gln Gln Gly Pro Tyr Gly Ser Ala
        115             120             125

Ala Ala Ala Ala Gly Pro Gly Ser Gly Gln Tyr Gly Gln Gly Pro Tyr
    130             135             140

Gly Pro Gly Ala Ser Gly Pro Gly Gln Tyr Gly Pro Gly Gln Gln Gly
145             150             155             160

Pro Ser Ala Ser Ala Ala Ala Ala Ala Gly Ser Gly Gln Gln Gly Pro
                165             170             175

Gly Gln Tyr Gly Pro Tyr Ala Ser Ala Ala Ala Ala Gly Gln Tyr
        180             185             190

Gly Ser Gly Pro Gly Gln Gln Gly Pro Tyr Gly Pro Gly Gln Ser Gly
    195             200             205

Ser Gly Gln Gln Gly Pro Gly Gln Gln Gly Pro Tyr Ala Ser Ala Ala
    210             215             220

Ala Ala Ala Gly Pro Gly Gln Gln Gly Pro Tyr Gly Pro Gly Ser Ser
225             230             235             240

Ala Ala Ala Ala Ala Gly Gln Tyr Gly Tyr Gly Pro Gly Gln Gln Gly
            245             250             255
```

-continued

```
Pro Tyr Gly Pro Gly Ala Ser Gly Gln Asn Gly Pro Gly Ser Gly Gln
        260                 265             270

Tyr Gly Pro Gly Gln Gln Gly Pro Gly Gln Ser Ala Ala Ala Ala Ala
        275                 280             285

Gly Pro Gly Gln Gln Gly Pro Tyr Gly Pro Gly Ala Ser Ala Ala Ala
    290                 295             300

Ala Ala Gly Gln Tyr Gly Pro Gly Gln Gly Pro Gly Gln Tyr Gly
305                 310             315                 320

Pro Gly Ser Ser Gly Pro Gly Gln Gln Gly Pro Tyr Gly Pro Gly Ser
            325             330             335

Ser Ala Ala Ala Ala Ala Gly Gln Tyr Gly Pro Gly Gln Gln Gly Pro
        340                 345             350

Tyr Gly Pro Gly Gln Ser Ala Ala Ala Ala Ala Gly Gln Tyr Gln Gln
        355                 360             365

Gly Pro Gly Gln Gln Gly Pro Tyr Gly Pro Gly Ala Ser Gly Pro Gly
    370                 375             380

Gln Gln Gly Pro Tyr Gly Pro Gly Ala Ser Ala Ala Ala Ala Ala Gly
385                 390             395                 400

Pro Gly Gln Tyr Gly Pro Gly Gln Gln Gly Pro Ser Ala Ser Ala Ala
            405             410             415

Ala Ala Ala Gly Gln Tyr Gly Ser Gly Pro Gly Gln Tyr Gly Pro Tyr
        420                 425             430

Gly Pro Gly Gln Ser Gly Pro Gly Ser Gly Gln Gln Gly Gln Gly Pro
        435                 440             445

Tyr Gly Pro Gly Ala Ser Ala Ala Ala Ala Gly Gln Tyr Gly Pro
    450                 455             460

Gly Gln Gln Gly Pro Tyr Gly Pro Gly Gln Ser Ala Ala Ala Ala Ala
465                 470             475                 480

Gly Pro Gly Ser Gly Gln Tyr Gly Pro Gly Ala Ser Gly Gln Asn Gly
            485             490             495

Pro Gly Ser Gly Gln Tyr Gly Pro Gly Gln Gln Gly Pro Gly Gln Ser
        500                 505             510

Ala Ala Ala Ala Ala Gly Gln Tyr Gln Gln Gly Pro Gly Gln Gln Gly
        515                 520             525

Pro Tyr Gly Pro Gly Ala Ser Ala Ala Ala Ala Gly Gln Tyr Gly
    530                 535             540

Ser Gly Pro Gly Gln Gln Gly Pro Tyr Gly Pro Gly Gln Ser Gly Ser
545                 550             555                 560

Gly Gln Gln Gly Pro Gly Gln Gln Gly Pro Tyr Ala Ser Ala Ala Ala
            565             570             575

Ala Ala Gly Pro Gly Ser Gly Gln Gln Gly Pro Gly Ala Ser Gly Gln
            580             585             590

Gln Gly Pro Tyr Gly Pro Gly Ala Ser Ala Ala Ala Ala Gly Gln
        595             600             605

Asn Gly Pro Gly Ser Gly Gln Gln Gly Pro Gly Gln Ser Gly Gln Tyr
        610             615             620

Gly Pro Gly Gln Gln Gly Pro Gly Gln Gln Gly Pro Gly Ser Ser Ala
625                 630             635                 640

Ala Ala Ala Gly Pro Gly Gln Tyr Gly Pro Gly Gln Gln Gly Pro
            645             650             655

Ser Ala Ser Ala Ala Ala Ala Ala Gly Pro Gly Ser Gly Gln Gln Gly
            660             665             670
```

-continued

```
Pro Gly Ala Ser Gly Gln Tyr Gly Pro Gly Gln Gly Pro Gly Gln
        675             680             685

Gln Gly Pro Gly Ser Ser Ala Ala Ala Ala Gly Gln Tyr Gly Ser
        690             695             700

Gly Pro Gly Gln Gln Gly Pro Tyr Gly Ser Ala Ala Ala Ala Gly
705             710             715             720

Pro Gly Ser Gly Gln Tyr Gly Gln Gly Pro Tyr Gly Pro Gly Ala Ser
        725             730             735

Gly Pro Gly Gln Tyr Gly Pro Gly Gln Gly Pro Ser Ala Ser Ala
        740             745             750

Ala Ala Ala Ala Gly Ser Gly Gln Gln Gly Pro Gly Gln Tyr Gly Pro
        755             760             765

Tyr Ala Ser Ala Ala Ala Ala Ala Gly Gln Tyr Gly Ser Gly Pro Gly
        770             775             780

Gln Gln Gly Pro Tyr Gly Pro Gly Gln Ser Gly Ser Gly Gln Gln Gly
785             790             795             800

Pro Gly Gln Gln Gly Pro Tyr Ala Ser Ala Ala Ala Ala Gly Pro
        805             810             815

Gly Gln Gln Gly Pro Tyr Gly Pro Gly Ser Ser Ala Ala Ala Ala
        820             825             830

Gly Gln Tyr Gly Tyr Gly Pro Gly Gln Gln Gly Pro Tyr Gly Pro Gly
        835             840             845

Ala Ser Gly Gln Asn Gly Pro Gly Ser Gly Gln Tyr Gly Pro Gly Gln
        850             855             860

Gln Gly Pro Gly Gln Ser Ala Ala Ala Ala Gly Pro Gly Gln Gln
865             870             875             880

Gly Pro Tyr Gly Pro Gly Ala Ser Ala Ala Ala Ala Gly Gln Tyr
        885             890             895

Gly Pro Gly Gln Gln Gly Pro Gly Gln Tyr Gly Pro Gly Ser Ser Gly
        900             905             910

Pro Gly Gln Gln Gly Pro Tyr Gly Pro Gly Ser Ser Ala Ala Ala Ala
        915             920             925

Ala Gly Gln Tyr Gly Pro Gly Gln Gln Gly Pro Tyr Gly Pro Gly Gln
        930             935             940

Ser Ala Ala Ala Ala Ala Gly Gln Tyr Gln Gln Gly Pro Gly Gln Gln
945             950             955             960

Gly Pro Tyr Gly Pro Gly Ala Ser Gly Pro Gly Gln Gln Gly Pro Tyr
        965             970             975

Gly Pro Gly Ala Ser Ala Ala Ala Ala Gly Pro Gly Gln Tyr Gly
        980             985             990

Pro Gly Gln Gln Gly Pro Ser Ala  Ser Ala Ala Ala Ala  Ala Gly Gln
        995             1000            1005

Tyr Gly  Ser Gly Pro Gly Gln  Tyr Gly Pro Tyr Gly  Pro Gly Gln
    1010            1015            1020

Ser Gly  Pro Gly Ser Gly Gln  Gln Gly Gln Gly Pro  Tyr Gly Pro
    1025            1030            1035

Gly Ala  Ser Ala Ala Ala Ala  Ala Gly Gln Tyr Gly  Pro Gly Gln
    1040            1045            1050

Gln Gly  Pro Tyr Gly Pro Gly  Gln Ser Ala Ala Ala  Ala Ala Gly
    1055            1060            1065

Pro Gly  Ser Gly Gln Tyr Gly  Pro Gly Ala Ser Gly  Gln Asn Gly
    1070            1075            1080

Pro Gly  Ser Gly Gln Tyr Gly  Pro Gly Gln Gln Gly  Pro Gly Gln
```

-continued

```
      1085              1090              1095

Ser Ala  Ala Ala Ala Ala Gly  Gln Tyr Gln Gln Gly  Pro Gly Gln
    1100              1105              1110

Gln Gly  Pro Tyr Gly Pro Gly  Ala Ser Ala Ala Ala  Ala Ala Gly
    1115              1120              1125

Gln Tyr  Gly Ser Gly Pro Gly  Gln Gln Gly Pro Tyr  Gly Pro Gly
    1130              1135              1140

Gln Ser  Gly Ser Gly Gln Gln  Gly Pro Gly Gln Gln  Gly Pro Tyr
    1145              1150              1155

Ala Ser  Ala Ala Ala Ala Ala  Gly Pro Gly Ser Gly  Gln Gln Gly
    1160              1165              1170

Pro Gly  Ala Ser Gly Gln Gln  Gly Pro Tyr Gly Pro  Gly Ala Ser
    1175              1180              1185

Ala Ala  Ala Ala Ala Gly Gln  Asn Gly Pro Gly Ser  Gly Gln Gln
    1190              1195              1200

Gly Pro  Gly Gln Ser Gly Gln  Tyr Gly Pro Gly Gln  Gln Gly Pro
    1205              1210              1215

Gly Gln  Gln Gly Pro Gly Ser  Ser Ala Ala Ala Ala  Ala Gly Pro
    1220              1225              1230

Gly Gln  Tyr Gly Pro Gly Gln  Gln Gly Pro Ser Ala  Ser Ala Ala
    1235              1240              1245

Ala Ala  Ala Gly Pro Gly Ser  Gly Gln Gln Gly Pro  Gly Ala Ser
    1250              1255              1260

Gly Gln  Tyr Gly Pro Gly Gln  Gln Gly Pro Gly Gln  Gln Gly Pro
    1265              1270              1275

Gly Ser  Ser Ala Ala Ala Ala  Ala Gly Gln Tyr Gly  Ser Gly Pro
    1280              1285              1290

Gly Gln  Gln Gly Pro Tyr Gly  Ser Ala Ala Ala Ala  Ala Gly Pro
    1295              1300              1305

Gly Ser  Gly Gln Tyr Gly Gln  Gly Pro Tyr Gly Pro  Gly Ala Ser
    1310              1315              1320

Gly Pro  Gly Gln Tyr Gly Pro  Gly Gln Gln Gly Pro  Ser Ala Ser
    1325              1330              1335

Ala Ala  Ala Ala Ala Gly Ser  Gly Gln Gln Gly Pro  Gly Gln Tyr
    1340              1345              1350

Gly Pro  Tyr Ala Ser Ala Ala  Ala Ala Ala Gly Gln  Tyr Gly Ser
    1355              1360              1365

Gly Pro  Gly Gln Gln Gly Pro  Tyr Gly Pro Gly Gln  Ser Gly Ser
    1370              1375              1380

Gly Gln  Gln Gly Pro Gly Gln  Gln Gly Pro Tyr Ala  Ser Ala Ala
    1385              1390              1395

Ala Ala  Ala Gly Pro Gly Gln  Gln Gly Pro Tyr Gly  Pro Gly Ser
    1400              1405              1410

Ser Ala  Ala Ala Ala Ala Gly  Gln Tyr Gly Tyr Gly  Pro Gly Gln
    1415              1420              1425

Gln Gly  Pro Tyr Gly Pro Gly  Ala Ser Gly Gln Asn  Gly Pro Gly
    1430              1435              1440

Ser Gly  Gln Tyr Gly Pro Gly  Gln Gln Gly Pro Gly  Gln Ser Ala
    1445              1450              1455

Ala Ala  Ala Ala Gly Pro Gly  Gln Gln Gly Pro Tyr  Gly Pro Gly
    1460              1465              1470

Ala Ser  Ala Ala Ala Ala Ala  Gly Gln Tyr Gly Pro  Gly Gln Gln
    1475              1480              1485
```

-continued

```
Gly Pro  Gly Gln Tyr Gly Pro  Gly Ser Ser Gly Pro  Gly Gln Gln
    1490             1495             1500

Gly Pro  Tyr Gly Pro Gly Ser  Ser Ala Ala Ala Ala  Ala Gly Gln
    1505             1510             1515

Tyr Gly  Pro Gly Gln Gln Gly  Pro Tyr Gly Pro Gly  Gln Ser Ala
    1520             1525             1530

Ala Ala  Ala Ala Gly Gln Tyr  Gln Gln Gly Pro Gly  Gln Gln Gly
    1535             1540             1545

Pro Tyr  Gly Pro Gly Ala Ser  Gly Pro Gly Gln Gln  Gly Pro Tyr
    1550             1555             1560

Gly Pro  Gly Ala Ser Ala Ala  Ala Ala Ala Gly Pro  Gly Gln Tyr
    1565             1570             1575

Gly Pro  Gly Gln Gln Gly Pro  Ser Ala Ser Ala Ala  Ala Ala Ala
    1580             1585             1590

Gly Gln  Tyr Gly Ser Gly Pro  Gly Gln Tyr Gly Pro  Tyr Gly Pro
    1595             1600             1605

Gly Gln  Ser Gly Pro Gly Ser  Gly Gln Gln Gly Gln  Gly Pro Tyr
    1610             1615             1620

Gly Pro  Gly Ala Ser Ala Ala  Ala Ala Ala Gly Gln  Tyr Gly Pro
    1625             1630             1635

Gly Gln  Gln Gly Pro Tyr Gly  Pro Gly Gln Ser Ala  Ala Ala Ala
    1640             1645             1650

Ala Gly  Pro Gly Ser Gly Gln  Tyr Gly Pro Gly Ala  Ser Gly Gln
    1655             1660             1665

Asn Gly  Pro Gly Ser Gly Gln  Tyr Gly Pro Gly Gln  Gln Gly Pro
    1670             1675             1680

Gly Gln  Ser Ala Ala Ala Ala  Ala Gly Gln Tyr Gln  Gln Gly Pro
    1685             1690             1695

Gly Gln  Gln Gly Pro Tyr Gly  Pro Gly Ala Ser Ala  Ala Ala Ala
    1700             1705             1710

Ala Gly  Gln Tyr Gly Ser Gly  Pro Gly Gln Gln Gly  Pro Tyr Gly
    1715             1720             1725

Pro Gly  Gln Ser Gly Ser Gly  Gln Gln Gly Pro Gly  Gln Gln Gly
    1730             1735             1740

Pro Tyr  Ala Ser Ala Ala Ala  Ala Ala Gly Pro Gly  Ser Gly Gln
    1745             1750             1755

Gln Gly  Pro Gly Ala Ser Gly  Gln Gln Gly Pro Tyr  Gly Pro Gly
    1760             1765             1770

Ala Ser  Ala Ala Ala Ala Ala  Gly Gln Asn Gly Pro  Gly Ser Gly
    1775             1780             1785

Gln Gln  Gly Pro Gly Gln Ser  Gly Gln Tyr Gly Pro  Gly Gln Gln
    1790             1795             1800

Gly Pro  Gly Gln Gln Gly Pro  Gly Ser Ser Ala Ala  Ala Ala Ala
    1805             1810             1815

Gly Pro  Gly Gln Tyr Gly Pro  Gly Gln Gln Gly Pro  Ser Ala Ser
    1820             1825             1830

Ala Ala  Ala Ala Ala Gly Pro  Gly Ser Gly Gln Gln  Gly Pro Gly
    1835             1840             1845

Ala Ser  Gly Gln Tyr Gly Pro  Gly Gln Gln Gly Pro  Gly Gln Gln
    1850             1855             1860

Gly Pro  Gly Ser Ser Ala Ala  Ala Ala Ala Gly Gln  Tyr Gly Ser
    1865             1870             1875
```

-continued

```
Gly Pro  Gly Gln Gln Gly Pro  Tyr Gly Ser Ala Ala  Ala Ala Ala
    1880              1885              1890

Gly Pro  Gly Ser Gly Gln Tyr  Gly Gln Gly Pro Tyr  Gly Pro Gly
    1895              1900              1905

Ala Ser  Gly Pro Gly Gln Tyr  Gly Pro Gly Gln Gln  Gly Pro Ser
    1910              1915              1920

Ala Ser  Ala Ala Ala Ala Ala  Gly Ser Gly Gln Gln  Gly Pro Gly
    1925              1930              1935

Gln Tyr  Gly Pro Tyr Ala Ser  Ala Ala Ala Ala Ala  Gly Gln Tyr
    1940              1945              1950

Gly Ser  Gly Pro Gly Gln Gln  Gly Pro Tyr Gly Pro  Gly Gln Ser
    1955              1960              1965

Gly Ser  Gly Gln Gln Gly Pro  Gly Gln Gln Gly Pro  Tyr Ala Ser
    1970              1975              1980

Ala Ala  Ala Ala Ala Gly Pro  Gly Gln Gln Gly Pro  Tyr Gly Pro
    1985              1990              1995

Gly Ser  Ser Ala Ala Ala Ala  Ala Gly Gln Tyr Gly  Tyr Gly Pro
    2000              2005              2010

Gly Gln  Gln Gly Pro Tyr Gly  Pro Gly Ala Ser Gly  Gln Asn Gly
    2015              2020              2025

Pro Gly  Ser Gly Gln Tyr Gly  Pro Gly Gln Gln Gly  Pro Gly Gln
    2030              2035              2040

Ser Ala  Ala Ala Ala Ala Gly  Pro Gly Gln Gln Gly  Pro Tyr Gly
    2045              2050              2055

Pro Gly  Ala Ser Ala Ala Ala  Ala Ala Gly Gln Tyr  Gly Pro Gly
    2060              2065              2070

Gln Gln  Gly Pro Gly Gln Tyr  Gly Pro Gly Ser Ser  Gly Pro Gly
    2075              2080              2085

Gln Gln  Gly Pro Tyr Gly Pro  Gly Ser Ser Ala Ala  Ala Ala Ala
    2090              2095              2100

Gly Gln  Tyr Gly Pro Gly Gln  Gln Gly Pro Tyr Gly  Pro Gly Gln
    2105              2110              2115

Ser Ala  Ala Ala Ala Ala Gly  Gln Tyr Gln Gln Gly  Pro Gly Gln
    2120              2125              2130

Gln Gly  Pro Tyr Gly Pro Gly  Ala Ser Gly Pro Gly  Gln Gln Gly
    2135              2140              2145

Pro Tyr  Gly Pro Gly Ala Ser  Ala Ala Ala Ala Ala  Gly Pro Gly
    2150              2155              2160

Gln Tyr  Gly Pro Gly Gln Gln  Gly Pro Ser Ala Ser  Ala Ala Ala
    2165              2170              2175

Ala Ala  Gly Gln Tyr Gly Ser  Gly Pro Gly Gln Tyr  Gly Pro Tyr
    2180              2185              2190

Gly Pro  Gly Gln Ser Gly Pro  Gly Ser Gly Gln Gln  Gly Gln Gly
    2195              2200              2205

Pro Tyr  Gly Pro Gly Ala Ser  Ala Ala Ala Ala Ala  Gly Gln Tyr
    2210              2215              2220

Gly Pro  Gly Gln Gln Gly Pro  Tyr Gly Pro Gly Gln  Ser Ala Ala
    2225              2230              2235

Ala Ala  Ala Gly Pro Gly Ser  Gly Gln Tyr Gly Pro  Gly Ala Ser
    2240              2245              2250

Gly Gln  Asn Gly Pro Gly Ser  Gly Gln Tyr Gly Pro  Gly Gln Gln
    2255              2260              2265

Gly Pro  Gly Gln Ser Ala Ala  Ala Ala Ala Gly Gln  Tyr Gln Gln
```

```
              2270                2275                2280

Gly Pro  Gly Gln Gln Gly Pro  Tyr Gly Pro Gly Ala  Ser Ala Ala
    2285                2290                2295

Ala Ala  Ala Gly Gln Tyr Gly  Ser Gly Pro Gly Gln  Gln Gly Pro
    2300                2305                2310

Tyr Gly  Pro Gly Gln Ser Gly  Ser Gly Gln Gln Gly  Pro Gly Gln
    2315                2320                2325

Gln Gly  Pro Tyr Ala Ser Ala  Ala Ala Ala Ala Gly  Pro Gly Ser
    2330                2335                2340

Gly Gln  Gln Gly Ser Ser Val  Asp Lys Leu Ala Ala  Ala Leu Glu
    2345                2350                2355

His His  His His His His
    2360

<210> SEQ ID NO 10
<211> LENGTH: 597
<212> TYPE: PRT
<213> ORGANISM: Artificial Sequence
<220> FEATURE:
<223> OTHER INFORMATION: Met-PRT313

<400> SEQUENCE: 10

Met Gly Pro Gly Gly Gln Gly Pro  Tyr Gly Pro Gly Ala  Ser Ala Ala
1                5                10                15

Ala Ala Ala Gly Gly Asn Gly Pro  Gly Ser Gly Gln Gln Gly  Pro Gly
            20                25                30

Gly Ser Ala Ala Ala Ala Ala Gly  Gly Tyr Gly Pro Gly Gly Gln Gly
        35                40                45

Pro Gly Gln Gln Gly Pro  Gly Ser Ser Ala Ala Ala  Ala Ala Gly Pro
    50                55                60

Gly Gly Tyr Gly Pro Gly Gly Gln Gly Pro Ser Ala Ser Ala Ala Ala
65                70                75                80

Ala Ala Gly Pro Gly Ser  Gly Gln Gln Gly Pro Gly Ala Ser Ala Ala
            85                90                95

Ala Ala Ala Gly Gly Tyr  Gly Pro Gly Gly Gln Gly  Pro Gly Gln Gln
            100                105                110

Gly Pro Gly Ser Ser Ala  Ala Ala Ala Ala Gly Gly  Tyr Gly Ser Gly
        115                120                125

Pro Gly Gln Gln Gly Pro  Tyr Gly Ser Ala Ala Ala  Ala Ala Gly Pro
    130                135                140

Gly Ser Gly Gly Tyr Gly  Gln Gly Pro Tyr Gly Pro  Gly Ala Ser Ala
145                150                155                160

Ala Ala Ala Gly Pro Gly  Gly Tyr Gly Pro Gly Gly  Gln Gly Pro
            165                170                175

Ser Ala Ser Ala Ala Ala  Ala Ala Gly Ser Gly Gln  Gln Gly Pro Gly
            180                185                190

Gly Tyr Gly Pro Tyr Ala  Ser Ala Ala Ala Ala Ala  Gly Gly Tyr Gly
        195                200                205

Ser Gly Pro Gly Gln Gln  Gly Pro Tyr Gly Pro Gly  Gly Ser Ala Ala
    210                215                220

Ala Ala Ala Gly Ser Gly  Gln Gln Gly Pro Gly Gln  Gln Gly Pro Tyr
225                230                235                240

Ala Ser Ala Ala Ala Ala  Ala Gly Pro Gly Gly Gln  Gly Pro Tyr Gly
            245                250                255

Pro Gly Ser Ser Ala Ala  Ala Ala Ala Gly Gly Tyr  Gly Tyr Gly Pro
```

-continued

```
           260              265              270
Gly Gly Gln Gly Pro Tyr Gly Pro Gly Ala Ser Ala Ala Ala Ala
           275              280              285

Gly Gly Asn Gly Pro Gly Ser Gly Gly Tyr Gly Pro Gly Gln Gln Gly
           290              295              300

Pro Gly Gly Ser Ala Ala Ala Ala Gly Pro Gly Gly Gln Gly Pro
305              310              315              320

Tyr Gly Pro Gly Ala Ser Ala Ala Ala Ala Gly Gly Tyr Gly Pro
               325              330              335

Gly Gly Gln Gly Pro Gly Gly Tyr Gly Pro Gly Ser Ser Ala Ala Ala
               340              345              350

Ala Ala Gly Pro Gly Gly Gln Gly Pro Tyr Gly Pro Gly Ser Ser Ala
           355              360              365

Ala Ala Ala Gly Gly Tyr Gly Pro Gly Gln Gln Gly Pro Tyr Gly
           370              375              380

Pro Gly Gly Ser Ala Ala Ala Ala Gly Gly Tyr Gln Gln Gly Pro
385              390              395              400

Gly Gly Gln Gly Pro Tyr Gly Pro Gly Ala Ser Ala Ala Ala Ala
               405              410              415

Gly Pro Gly Gly Gln Gly Pro Tyr Gly Pro Gly Ala Ser Ala Ala Ala
               420              425              430

Ala Ala Gly Pro Gly Gly Tyr Gly Pro Gly Gly Gln Gly Pro Ser Ala
           435              440              445

Ser Ala Ala Ala Ala Ala Gly Gly Tyr Gly Ser Gly Pro Gly Gly Tyr
   450              455              460

Gly Pro Tyr Gly Pro Gly Gly Ser Ala Ala Ala Ala Gly Pro Gly
465              470              475              480

Ser Gly Gln Gln Gly Gln Gly Pro Tyr Gly Pro Gly Ala Ser Ala Ala
               485              490              495

Ala Ala Ala Gly Gly Tyr Gly Pro Gly Gln Gln Gly Pro Tyr Gly Pro
               500              505              510

Gly Gly Ser Ala Ala Ala Ala Ala Gly Pro Gly Ser Gly Gly Tyr Gly
           515              520              525

Pro Gly Ala Ser Ala Ala Ala Ala Gly Gly Asn Gly Pro Gly Ser
   530              535              540

Gly Gly Tyr Gly Pro Gly Gln Gln Gly Pro Gly Gly Ser Ala Ala Ala
545              550              555              560

Ala Ala Gly Gly Tyr Gln Gln Gly Pro Gly Gly Gln Gly Pro Tyr Gly
               565              570              575

Pro Gly Ala Ser Ala Ala Ala Ala Ala Gly Pro Gly Ser Gly Gln Gln
               580              585              590

Gly Pro Gly Ala Ser
           595
```

```
<210> SEQ ID NO 11
<211> LENGTH: 601
<212> TYPE: PRT
<213> ORGANISM: Artificial Sequence
<220> FEATURE:
<223> OTHER INFORMATION: PRT410

<400> SEQUENCE: 11

Met His His His His His His Ser Ser Gly Ser Ser Gly Pro Gly Gln
1               5               10              15

Gln Gly Pro Tyr Gly Pro Gly Ala Ser Ala Ala Ala Ala Ala Gly Gln
```

-continued

```
            20                25                30
Asn Gly Pro Gly Ser Gly Gln Gln Gly Pro Gly Gln Ser Gly Gln Tyr
            35                40                45
Gly Pro Gly Gln Gln Gly Pro Gly Gln Gln Gly Pro Gly Ser Ser Ala
        50                55                60
Ala Ala Ala Ala Gly Pro Gly Gln Tyr Gly Pro Gly Gln Gln Gly Pro
65                70                75                80
Ser Ala Ser Ala Ala Ala Ala Ala Gly Pro Gly Ser Gly Gln Gln Gly
                85                90                95
Pro Gly Ala Ser Gly Gln Tyr Gly Pro Gly Gln Gln Gly Pro Gly Gln
            100               105               110
Gln Gly Pro Gly Ser Ser Ala Ala Ala Ala Ala Gly Gln Tyr Gly Ser
        115               120               125
Gly Pro Gly Gln Gln Gly Pro Tyr Gly Ser Ala Ala Ala Ala Ala Gly
    130               135               140
Pro Gly Ser Gly Gln Tyr Gly Gln Gly Pro Tyr Gly Pro Gly Ala Ser
145               150               155               160
Gly Pro Gly Gln Tyr Gly Pro Gly Gln Gln Gly Pro Ser Ala Ser Ala
            165               170               175
Ala Ala Ala Ala Gly Ser Gly Gln Gln Gly Pro Gly Gln Tyr Gly Pro
        180               185               190
Tyr Ala Ser Ala Ala Ala Ala Ala Gly Gln Tyr Gly Ser Gly Pro Gly
        195               200               205
Gln Gln Gly Pro Tyr Gly Pro Gly Gln Ser Gly Ser Gly Gln Gln Gly
    210               215               220
Pro Gly Gln Gln Gly Pro Tyr Ala Ser Ala Ala Ala Ala Ala Gly Pro
225               230               235               240
Gly Gln Gln Gly Pro Tyr Gly Pro Gly Ser Ser Ala Ala Ala Ala Ala
            245               250               255
Gly Gln Tyr Gly Tyr Gly Pro Gly Gln Gln Gly Pro Tyr Gly Pro Gly
        260               265               270
Ala Ser Gly Gln Asn Gly Pro Gly Ser Gly Gln Tyr Gly Pro Gly Gln
        275               280               285
Gln Gly Pro Gly Gln Ser Ala Ala Ala Ala Gly Pro Gly Gln Gln
    290               295               300
Gly Pro Tyr Gly Pro Gly Ala Ser Ala Ala Ala Ala Gly Gln Tyr
305               310               315               320
Gly Pro Gly Gln Gln Gly Pro Gly Gln Tyr Gly Pro Gly Ser Ser Gly
            325               330               335
Pro Gly Gln Gln Gly Pro Tyr Gly Pro Gly Ser Ser Ala Ala Ala Ala
        340               345               350
Ala Gly Gln Tyr Gly Pro Gly Gln Gln Gly Pro Tyr Gly Pro Gly Gln
        355               360               365
Ser Ala Ala Ala Ala Ala Gly Gln Tyr Gln Gln Gly Pro Gly Gln Gln
    370               375               380
Gly Pro Tyr Gly Pro Gly Ala Ser Gly Pro Gly Gln Gln Gly Pro Tyr
385               390               395               400
Gly Pro Gly Ala Ser Ala Ala Ala Ala Gly Pro Gly Gln Tyr Gly
                405               410               415
Pro Gly Gln Gln Gly Pro Ser Ala Ser Ala Ala Ala Ala Gly Gln
            420               425               430
Tyr Gly Ser Gly Pro Gly Gln Tyr Gly Pro Tyr Gly Pro Gly Gln Ser
        435               440               445
```

```
Gly Pro Gly Ser Gly Gln Gln Gly Gln Gly Pro Tyr Gly Pro Gly Ala
    450                 455                 460

Ser Ala Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
                500                 505                 510

Tyr Gly Pro Gly Gln Gln Gly Pro Gly Gln Ser Ala Ala Ala Ala Ala
                515                 520                 525

Gly Gln Tyr Gln Gln Gly Pro Gly Gln Gln Gly Pro Tyr Gly Pro Gly
    530                 535                 540

Ala Ser Ala Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Gly Pro Gly
                580                 585                 590

Ser Gly Gln Gln Gly Pro Gly Ala Ser
        595                 600

<210> SEQ ID NO 12
<211> LENGTH: 12
<212> TYPE: PRT
<213> ORGANISM: Artificial Sequence
<220> FEATURE:
<223> OTHER INFORMATION: HisTag

<400> SEQUENCE: 12

Met His His His His His His Ser Ser Gly Ser Ser
1               5                   10

<210> SEQ ID NO 13
<211> LENGTH: 608
<212> TYPE: PRT
<213> ORGANISM: Artificial Sequence
<220> FEATURE:
<223> OTHER INFORMATION: PRT380

<400> SEQUENCE: 13

Met His His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
                20                  25                  30

Asn Gly Pro Gly Ser Gly Gln Gln Gly Pro Gly Gln Ser Ala Ala Ala
        35                  40                  45

Ala Ala Gly Gln Tyr Gly Pro Gly Gln Gln Gly Pro Gly Gln Gln Gly
    50                  55                  60

Pro Gly Ser Ser Ala Ala Ala Ala Ala Gly Pro Gly Gln Tyr Gly Pro
65                  70                  75                  80

Gly Gln Gln Gly Pro Ser Ala Ser Ala Ala Ala Ala Gly Pro Gly
                85                  90                  95

Ser Gly Gln Gln Gly Pro Gly Ala Ser Ala Ala Ala Ala Gly Gln
                100                 105                 110

Tyr Gly Pro Gly Gln Gln Gly Pro Gly Gln Gln Gly Pro Gly Ser Ser
        115                 120                 125

Ala Ala Ala Ala Ala Gly Gln Tyr Gly Ser Gly Pro Gly Gln Gln Gly
```

-continued

```
           130              135              140

Pro Tyr Gly Ser Ala Ala Ala Ala Ala Gly Pro Gly Ser Gly Gln Tyr
145              150              155              160

Gly Gln Gly Pro Tyr Gly Pro Gly Ala Ser Ala Ala Ala Ala Ala Gly
                 165              170              175

Pro Gly Gln Tyr Gly Pro Gly Gln Gln Gly Pro Ser Ala Ser Ala Ala
                 180              185              190

Ala Ala Ala Gly Ser Gly Gln Gln Gly Pro Gly Gln Tyr Gly Pro Tyr
                 195              200              205

Ala Ser Ala Ala Ala Ala Ala Gly Gln Tyr Gly Ser Gly Pro Gly Gln
         210              215              220

Gln Gly Pro Tyr Gly Pro Gly Gln Ser Ala Ala Ala Ala Gly Ser
225              230              235              240

Gly Gln Gln Gly Pro Gly Gln Gln Gly Pro Tyr Ala Ser Ala Ala Ala
                 245              250              255

Ala Ala Gly Pro Gly Gln Gln Gly Pro Tyr Gly Pro Gly Ser Ser Ala
                 260              265              270

Ala Ala Ala Ala Gly Gln Tyr Gly Tyr Gly Pro Gly Gln Gln Gly Pro
         275              280              285

Tyr Gly Pro Gly Ala Ser Ala Ala Ala Ala Gly Gln Asn Gly Pro
    290              295              300

Gly Ser Gly Gln Tyr Gly Pro Gly Gln Gln Gly Pro Gly Gln Ser Ala
305              310              315              320

Ala Ala Ala Gly Pro Gly Gln Gln Gly Pro Tyr Gly Pro Gly Ala
                 325              330              335

Ser Ala Ala Ala Ala Gly Gln Tyr Gly Pro Gly Gln Gln Gly Pro
         340              345              350

Gly Gln Tyr Gly Pro Gly Ser Ser Ala Ala Ala Ala Gly Pro Gly
         355              360              365

Gln Gln Gly Pro Tyr Gly Pro Gly Ser Ser Ala Ala Ala Ala Gly
    370              375              380

Gln Tyr Gly Pro Gly Gln Gln Gly Pro Tyr Gly Pro Gly Gln Ser Ala
385              390              395              400

Ala Ala Ala Gly Gln Tyr Gln Gln Gly Pro Gly Gln Gln Gly Pro
                 405              410              415

Tyr Gly Pro Gly Ala Ser Ala Ala Ala Ala Gly Pro Gly Gln Gln
    420              425              430

Gly Pro Tyr Gly Pro Gly Ala Ser Ala Ala Ala Ala Gly Pro Gly
    435              440              445

Gln Tyr Gly Pro Gly Gln Gln Gly Pro Ser Ala Ser Ala Ala Ala
    450              455              460

Ala Gly Gln Tyr Gly Ser Gly Pro Gly Gln Tyr Gly Pro Tyr Gly Pro
465              470              475              480

Gly Gln Ser Ala Ala Ala Ala Ala Gly Pro Gly Ser Gly Gln Gln Gly
                 485              490              495

Gln Gly Pro Tyr Gly Pro Gly Ala Ser Ala Ala Ala Ala Gly Gln
         500              505              510

Tyr Gly Pro Gly Gln Gln Gly Pro Tyr Gly Pro Gly Gln Ser Ala Ala
    515              520              525

Ala Ala Ala Gly Pro Gly Ser Gly Gln Tyr Gly Pro Gly Ala Ser Ala
    530              535              540

Ala Ala Ala Gly Gln Asn Gly Pro Gly Ser Gly Gln Tyr Gly Pro
545              550              555              560
```

```
Gly Gln Gln Gly Pro Gly Gln Ser Ala Ala Ala Ala Gly Gln Tyr
            565             570             575

Gln Gln Gly Pro Gly Gln Gln Gly Pro Tyr Gly Pro Gly Ala Ser Ala
            580             585             590

Ala Ala Ala Ala Gly Pro Gly Ser Gly Gln Gln Gly Pro Gly Ala Ser
        595             600             605

<210> SEQ ID NO 14
<211> LENGTH: 576
<212> TYPE: PRT
<213> ORGANISM: Artificial Sequence
<220> FEATURE:
<223> OTHER INFORMATION: PRT468

<400> SEQUENCE: 14

Met His His His His His His Ser Ser Gly Ser Ser Gly Pro Gly Gln
1               5               10              15

Gln Gly Pro Tyr Gly Pro Gly Ala Ser Ala Ala Ala Ala Ala Ala Ala
            20              25              30

Gly Ser Asn Gly Pro Gly Ser Gly Gln Gln Gly Pro Gly Gln Ser Gly
        35              40              45

Gln Tyr Gly Pro Gly Gln Gln Gly Pro Gly Gln Gln Gly Pro Gly Ser
    50              55              60

Ser Ala Ala Ala Ala Ala Ala Ala Gly Pro Gly Gln Tyr Gly Pro Gly
65              70              75              80

Gln Gln Gly Pro Ser Ala Ser Ala Ala Ala Ala Ala Ala Gly Pro
            85              90              95

Gly Ser Gly Gln Gln Gly Pro Gly Ala Ser Gly Gln Tyr Gly Pro Gly
        100             105             110

Gln Gln Gly Pro Gly Gln Gln Gly Pro Gly Ser Ser Ala Ala Ala Ala
        115             120             125

Ala Ala Ala Gly Ser Tyr Gly Ser Gly Pro Gly Gln Gln Gly Pro Tyr
    130             135             140

Gly Ser Ala Ala Ala Ala Ala Ala Ala Gly Pro Gly Ser Gly Gln Tyr
145             150             155             160

Gly Gln Gly Pro Tyr Gly Pro Gly Ala Ser Gly Pro Gly Gln Tyr Gly
            165             170             175

Pro Gly Gln Gln Gly Pro Ser Ala Ser Ala Ala Ala Ala Ala Ala Ala
        180             185             190

Gly Ser Gly Gln Gln Gly Pro Gly Gln Tyr Gly Pro Tyr Ala Ser Ala
        195             200             205

Ala Ala Ala Ala Ala Gly Ser Tyr Gly Ser Gly Pro Gly Gln Gln
    210             215             220

Gly Pro Tyr Gly Pro Gly Gln Ser Gly Ser Gly Gln Gln Gly Pro Gly
225             230             235             240

Gln Gln Gly Pro Tyr Ala Ser Ala Ala Ala Ala Ala Ala Gly Pro
            245             250             255

Gly Gln Gln Gly Pro Tyr Gly Pro Gly Ser Ser Ala Ala Ala Ala
            260             265             270

Ala Ala Gly Ser Tyr Gly Tyr Gly Pro Gly Gln Gln Gly Pro Tyr Gly
    275             280             285

Pro Gly Ala Ser Gly Gln Asn Gly Pro Gly Ser Gly Gln Tyr Gly Pro
    290             295             300

Gly Gln Gln Gly Pro Gly Pro Ser Ala Ala Ala Ala Ala Ala Ala Gly
305             310             315             320
```

```
Pro Gly Gln Gln Gly Pro Tyr Gly Pro Gly Ala Ser Ala Ala Ala
            325                 330             335

Ala Ala Ala Gly Ser Tyr Gly Pro Gly Gln Gln Gly Pro Gly Gln Tyr
            340                 345             350

Gly Pro Gly Ser Ser Gly Pro Gly Gln Gln Gly Pro Tyr Gly Pro Gly
            355                 360             365

Ser Ser Ala Ala Ala Ala Ala Ala Ala Gly Ser Tyr Gly Pro Gly Gln
        370                 375             380

Gln Gly Pro Tyr Gly Pro Gly Pro Ser Ala Ala Ala Ala Ala Ala
385                 390             395                 400

Gly Ser Tyr Gln Gln Gly Pro Gly Gln Gln Gly Pro Tyr Gly Pro Gly
            405                 410             415

Ala Ser Gly Pro Gly Gln Gln Gly Pro Tyr Gly Pro Gly Ala Ser Ala
            420                 425             430

Ala Ala Ala Ala Ala Gly Pro Gly Gln Tyr Gly Pro Gly Gln Gln
        435                 440             445

Gly Pro Ser Ala Ser Ala Ala Ala Ala Ala Ala Gly Ser Tyr Gly
    450                 455             460

Ser Gly Pro Gly Gln Tyr Gly Pro Tyr Gly Pro Gly Gln Ser Gly Pro
465                 470             475                 480

Gly Ser Gly Gln Gln Gly Gln Gly Pro Tyr Gly Pro Gly Ala Ser Ala
            485                 490             495

Ala Ala Ala Ala Ala Gly Ser Tyr Gly Pro Gly Gln Gln Gly Pro
            500                 505             510

Tyr Gly Pro Gly Pro Ser Ala Ala Ala Ala Ala Ala Gly Pro Gly
            515                 520             525

Ser Gly Gln Tyr Gly Pro Gly Ala Ser Gly Gln Asn Gly Pro Gly Ser
    530                 535             540

Gly Gln Tyr Gly Pro Gly Gln Gly Pro Gly Pro Ser Ala Ala Ala
545                 550             555                 560

Ala Ala Ala Ala Gly Pro Gly Ser Gly Gln Gln Gly Pro Gly Ala Ser
            565                 570             575
```

<210> SEQ ID NO 15
<211> LENGTH: 2375
<212> TYPE: PRT
<213> ORGANISM: Artificial Sequence
<220> FEATURE:
<223> OTHER INFORMATION: PRT799

<400> SEQUENCE: 15

```
Met His His His His His Ser Ser Gly Ser Ser Gly Pro Gly Gln
1               5               10              15

Gln Gly Pro Tyr Gly Pro Gly Ala Ser Ala Ala Ala Ala Ala Gly Gln
            20                  25              30

Asn Gly Pro Gly Ser Gly Gln Gln Gly Pro Gly Gln Ser Gly Gln Tyr
        35                  40              45

Gly Pro Gly Gln Gln Gly Pro Gly Gln Gln Gly Pro Gly Ser Ser Ala
    50                  55              60

Ala Ala Ala Ala Gly Pro Gly Gln Tyr Gly Pro Gly Gln Gln Gly Pro
65                  70                  75                  80

Ser Ala Ser Ala Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105             110
```

```
Gln Gly Pro Gly Ser Ser Ala Ala Ala Ala Gly Gln Tyr Gly Ser
        115                 120                 125

Gly Pro Gly Gln Gln Gly Pro Tyr Gly Ser Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Ala Gly Ser Gly Gln Gln Gly Pro Gly Gln Tyr Gly Pro
                180                 185                 190

Tyr Ala Ser Ala Ala Ala Ala Gly Gln Tyr Gly Ser Gly Pro Gly
        195                 200                 205

Gln Gln Gly Pro Tyr Gly Pro Gly Gln Ser Gly Ser Gly Gln Gln Gly
    210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala Ala
                245                 250                 255

Gly Gln Tyr Gly Tyr Gly Pro Gly Gln Gln Gly Pro Tyr Gly Pro Gly
        260                 265                 270

Ala Ser Gly Gln Asn Gly Pro Gly Ser Gly Gln Tyr Gly Pro Gly Gln
        275                 280                 285

Gln Gly Pro Gly Gln Ser Ala Ala Ala Ala Gly Pro Gly Gln Gln
    290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala Ala
                340                 345                 350

Ala Gly Gln Tyr Gly Pro Gly Gln Gln Gly Pro Tyr Gly Pro Gly Gln
        355                 360                 365

Ser Ala Ala Ala Ala Ala Gly Gln Tyr Gln Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
                405                 410                 415

Pro Gly Gln Gln Gly Pro Ser Ala Ser Ala Ala Ala Ala Gly Gln
        420                 425                 430

Tyr Gly Ser Gly Pro Gly Gln Tyr Gly Pro Tyr Gly Pro Gly Gln Ser
        435                 440                 445

Gly Pro Gly Ser Gly Gln Gln Gly Gln Gly Pro Tyr Gly Pro Gly Ala
    450                 455                 460

Ser Ala Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
        500                 505                 510

Tyr Gly Pro Gly Gln Gln Gly Pro Gly Gln Ser Ala Ala Ala Ala Ala
        515                 520                 525
```

-continued

```
Gly Gln Tyr Gln Gln Gly Pro Gly Gln Gln Gly Pro Tyr Gly Pro Gly
    530                 535                 540

Ala Ser Ala Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
            565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser Gly Gln Gln Gly Pro Tyr Gly
            595                 600                 605

Pro Gly Ala Ser Ala Ala Ala Ala Gly Gln Asn Gly Pro Gly Ser
    610                 615                 620

Gly Gln Gln Gly Pro Gly Gln Ser Gly Gln Tyr Gly Pro Gly Gln Gln
625                 630                 635                 640

Gly Pro Gly Gln Gln Gly Pro Gly Ser Ser Ala Ala Ala Ala Ala Gly
            645                 650                 655

Pro Gly Gln Tyr Gly Pro Gly Gln Gln Gly Pro Ser Ala Ser Ala Ala
            660                 665                 670

Ala Ala Ala Gly Pro Gly Ser Gly Gln Gln Gly Pro Gly Ala Ser Gly
            675                 680                 685

Gln Tyr Gly Pro Gly Gln Gln Gly Pro Gly Gln Gln Gly Pro Gly Ser
    690                 695                 700

Ser Ala Ala Ala Ala Ala Gly Gln Tyr Gly Ser Gly Pro Gly Gln Gln
705                 710                 715                 720

Gly Pro Tyr Gly Ser Ala Ala Ala Ala Gly Pro Gly Ser Gly Gln
            725                 730                 735

Tyr Gly Gln Gly Pro Tyr Gly Pro Gly Ala Ser Gly Pro Gly Gln Tyr
            740                 745                 750

Gly Pro Gly Gln Gln Gly Pro Ser Ala Ser Ala Ala Ala Ala Gly
            755                 760                 765

Ser Gly Gln Gln Gly Pro Gly Gln Tyr Gly Pro Tyr Ala Ser Ala Ala
    770                 775                 780

Ala Ala Ala Gly Gln Tyr Gly Ser Gly Pro Gly Gln Gln Gly Pro Tyr
785                 790                 795                 800

Gly Pro Gly Gln Ser Gly Ser Gly Gln Gln Gly Pro Gly Gln Gln Gly
            805                 810                 815

Pro Tyr Ala Ser Ala Ala Ala Ala Gly Pro Gly Gln Gln Gly Pro
            820                 825                 830

Tyr Gly Pro Gly Ser Ser Ala Ala Ala Ala Gly Gln Tyr Gly Tyr
            835                 840                 845

Gly Pro Gly Gln Gln Gly Pro Tyr Gly Pro Gly Ala Ser Gly Gln Asn
    850                 855                 860

Gly Pro Gly Ser Gly Gln Tyr Gly Pro Gly Gln Gln Gly Pro Gly Gln
865                 870                 875                 880

Ser Ala Ala Ala Ala Ala Gly Pro Gly Gln Gln Gly Pro Tyr Gly Pro
            885                 890                 895

Gly Ala Ser Ala Ala Ala Ala Ala Gly Gln Tyr Gly Pro Gly Gln Gln
            900                 905                 910

Gly Pro Gly Gln Tyr Gly Pro Gly Ser Ser Gly Pro Gly Gln Gln Gly
            915                 920                 925

Pro Tyr Gly Pro Gly Ser Ser Ala Ala Ala Ala Gly Gln Tyr Gly
    930                 935                 940

Pro Gly Gln Gln Gly Pro Tyr Gly Pro Gly Gln Ser Ala Ala Ala Ala
```

-continued

```
945              950              955              960

Ala Gly Gln Tyr Gln Gln Gly Pro Gly Gln Gln Gly Pro Tyr Gly Pro
                965              970              975

Gly Ala Ser Gly Pro Gly Gln Gln Gly Pro Tyr Gly Pro Gly Ala Ser
            980              985              990

Ala Ala Ala Ala Ala Gly Pro Gly  Gln Tyr Gly Pro Gly  Gln Gln Gly
         995              1000              1005

Pro Ser  Ala Ser Ala Ala Ala  Ala Ala Gly Gln Tyr  Gly Ser Gly
    1010              1015              1020

Pro Gly  Gln Tyr Gly Pro Tyr  Gly Pro Gly Gln Ser  Gly Pro Gly
    1025              1030              1035

Ser Gly  Gln Gln Gly Gln Gly  Pro Tyr Gly Pro Gly  Ala Ser Ala
    1040              1045              1050

Ala Ala  Ala Ala Gly Gln Tyr  Gly Pro Gly Gln Gln  Gly Pro Tyr
    1055              1060              1065

Gly Pro  Gly Gln Ser Ala Ala  Ala Ala Ala Gly Pro  Gly Ser Gly
    1070              1075              1080

Gln Tyr  Gly Pro Gly Ala Ser  Gly Gln Asn Gly Pro  Gly Ser Gly
    1085              1090              1095

Gln Tyr  Gly Pro Gly Gln Gln  Gly Pro Gly Gln Ser  Ala Ala Ala
    1100              1105              1110

Ala Ala  Gly Gln Tyr Gln Gln  Gly Pro Gly Gln Gln  Gly Pro Tyr
    1115              1120              1125

Gly Pro  Gly Ala Ser Ala Ala  Ala Ala Ala Gly Gln  Tyr Gly Ser
    1130              1135              1140

Gly Pro  Gly Gln Gln Gly Pro  Tyr Gly Pro Gly Gln  Ser Gly Ser
    1145              1150              1155

Gly Gln  Gln Gly Pro Gly Gln  Gln Gly Pro Tyr Ala  Ser Ala Ala
    1160              1165              1170

Ala Ala  Ala Gly Pro Gly Ser  Gly Gln Gln Gly Pro  Gly Ala Ser
    1175              1180              1185

Gly Gln  Gln Gly Pro Tyr Gly  Pro Gly Ala Ser Ala  Ala Ala Ala
    1190              1195              1200

Ala Gly  Gln Asn Gly Pro Gly  Ser Gly Gln Gln Gly  Pro Gly Gln
    1205              1210              1215

Ser Gly  Gln Tyr Gly Pro Gly  Gln Gln Gly Pro Gly  Gln Gln Gly
    1220              1225              1230

Pro Gly  Ser Ser Ala Ala Ala  Ala Ala Gly Pro Gly  Gln Tyr Gly
    1235              1240              1245

Pro Gly  Gln Gln Gly Pro Ser  Ala Ser Ala Ala Ala  Ala Ala Gly
    1250              1255              1260

Pro Gly  Ser Gly Gln Gln Gly  Pro Gly Ala Ser Gly  Gln Tyr Gly
    1265              1270              1275

Pro Gly  Gln Gln Gly Pro Gly  Gln Gln Gly Pro Gly  Ser Ser Ala
    1280              1285              1290

Ala Ala  Ala Ala Gly Gln Tyr  Gly Ser Gly Pro Gly  Gln Gln Gly
    1295              1300              1305

Pro Tyr  Gly Ser Ala Ala Ala  Ala Ala Gly Pro Gly  Ser Gly Gln
    1310              1315              1320

Tyr Gly  Gln Gly Pro Tyr Gly  Pro Gly Ala Ser Gly  Pro Gly Gln
    1325              1330              1335

Tyr Gly  Pro Gly Gln Gln Gly  Pro Ser Ala Ser Ala  Ala Ala Ala
    1340              1345              1350
```

```
Ala Gly  Ser Gly Gln Gln Gly  Pro Gly Gln Tyr Gly  Pro Tyr Ala
    1355             1360             1365

Ser Ala  Ala Ala Ala Ala Gly  Gln Tyr Gly Ser Gly  Pro Gly Gln
    1370             1375             1380

Gln Gly  Pro Tyr Gly Pro Gly  Gln Ser Gly Ser Gly  Gln Gln Gly
    1385             1390             1395

Pro Gly  Gln Gln Gly Pro Tyr  Ala Ser Ala Ala Ala  Ala Ala Gly
    1400             1405             1410

Pro Gly  Gln Gln Gly Pro Tyr  Gly Pro Gly Ser Ser  Ala Ala Ala
    1415             1420             1425

Ala Ala  Gly Gln Tyr Gly Tyr  Gly Pro Gly Gln Gln  Gly Pro Tyr
    1430             1435             1440

Gly Pro  Gly Ala Ser Gly Gln  Asn Gly Pro Gly Ser  Gly Gln Tyr
    1445             1450             1455

Gly Pro  Gly Gln Gln Gly Pro  Gly Gln Ser Ala Ala  Ala Ala Ala
    1460             1465             1470

Gly Pro  Gly Gln Gln Gly Pro  Tyr Gly Pro Gly Ala  Ser Ala Ala
    1475             1480             1485

Ala Ala  Ala Gly Gln Tyr Gly  Pro Gly Gln Gln Gly  Pro Gly Gln
    1490             1495             1500

Tyr Gly  Pro Gly Ser Ser Gly  Pro Gly Gln Gln Gly  Pro Tyr Gly
    1505             1510             1515

Pro Gly  Ser Ser Ala Ala Ala  Ala Ala Gly Gln Tyr  Gly Pro Gly
    1520             1525             1530

Gln Gln  Gly Pro Tyr Gly Pro  Gly Gln Ser Ala Ala  Ala Ala Ala
    1535             1540             1545

Gly Gln  Tyr Gln Gln Gly Pro  Gly Gln Gln Gly Pro  Tyr Gly Pro
    1550             1555             1560

Gly Ala  Ser Gly Pro Gly Gln  Gln Gly Pro Tyr Gly  Pro Gly Ala
    1565             1570             1575

Ser Ala  Ala Ala Ala Ala Gly  Pro Gly Gln Tyr Gly  Pro Gly Gln
    1580             1585             1590

Gln Gly  Pro Ser Ala Ser Ala  Ala Ala Ala Ala Gly  Gln Tyr Gly
    1595             1600             1605

Ser Gly  Pro Gly Gln Tyr Gly  Pro Tyr Gly Pro Gly  Gln Ser Gly
    1610             1615             1620

Pro Gly  Ser Gly Gln Gln Gly  Gln Gly Pro Tyr Gly  Pro Gly Ala
    1625             1630             1635

Ser Ala  Ala Ala Ala Ala Gly  Gln Tyr Gly Pro Gly  Gln Gln Gly
    1640             1645             1650

Pro Tyr  Gly Pro Gly Gln Ser  Ala Ala Ala Ala Ala  Gly Pro Gly
    1655             1660             1665

Ser Gly  Gln Tyr Gly Pro Gly  Ala Ser Gly Gln Asn  Gly Pro Gly
    1670             1675             1680

Ser Gly  Gln Tyr Gly Pro Gly  Gln Gln Gly Pro Gly  Gln Ser Ala
    1685             1690             1695

Ala Ala  Ala Ala Gly Gln Tyr  Gln Gln Gly Pro Gly  Gln Gln Gly
    1700             1705             1710

Pro Tyr  Gly Pro Gly Ala Ser  Ala Ala Ala Ala Ala  Gly Gln Tyr
    1715             1720             1725

Gly Ser  Gly Pro Gly Gln Gln  Gly Pro Tyr Gly Pro  Gly Gln Ser
    1730             1735             1740
```

-continued

```
Gly Ser Gly Gln Gln Gly Pro Gly Gln Gln Gly Pro Tyr Ala Ser
    1745                1750                1755

Ala Ala Ala Ala Ala Gly Pro Gly Ser Gly Gln Gln Gly Pro Gly
    1760                1765                1770

Ala Ser Gly Gln Gln Gly Pro Tyr Gly Pro Gly Ala Ser Ala Ala
    1775                1780                1785

Ala Ala Ala Gly Gln Asn Gly Pro Gly Ser Gly Gln Gln Gly Pro
    1790                1795                1800

Gly Gln Ser Gly Gln Tyr Gly Pro Gly Gln Gln Gly Pro Gly Gln
    1805                1810                1815

Gln Gly Pro Gly Ser Ser Ala Ala Ala Ala Ala Gly Pro Gly Gln
    1820                1825                1830

Tyr Gly Pro Gly Gln Gln Gly Pro Ser Ala Ser Ala Ala Ala Ala
    1835                1840                1845

Ala Gly Pro Gly Ser Gly Gln Gln Gly Pro Gly Ala Ser Gly Gln
    1850                1855                1860

Tyr Gly Pro Gly Gln Gln Gly Pro Gly Gln Gln Gly Pro Gly Ser
    1865                1870                1875

Ser Ala Ala Ala Ala Ala Gly Gln Tyr Gly Ser Gly Pro Gly Gln
    1880                1885                1890

Gln Gly Pro Tyr Gly Ser Ala Ala Ala Ala Gly Pro Gly Ser
    1895                1900                1905

Gly Gln Tyr Gly Gln Gly Pro Tyr Gly Pro Gly Ala Ser Gly Pro
    1910                1915                1920

Gly Gln Tyr Gly Pro Gly Gln Gln Gly Pro Ser Ala Ser Ala Ala
    1925                1930                1935

Ala Ala Ala Gly Ser Gly Gln Gln Gly Pro Gly Gln Tyr Gly Pro
    1940                1945                1950

Tyr Ala Ser Ala Ala Ala Ala Gly Gln Tyr Gly Ser Gly Pro
    1955                1960                1965

Gly Gln Gln Gly Pro Tyr Gly Pro Gly Gln Ser Gly Ser Gly Gln
    1970                1975                1980

Gln Gly Pro Gly Gln Gln Gly Pro Tyr Ala Ser Ala Ala Ala Ala
    1985                1990                1995

Ala Gly Pro Gly Gln Gln Gly Pro Tyr Gly Pro Gly Ser Ser Ala
    2000                2005                2010

Ala Ala Ala Ala Gly Gln Tyr Gly Tyr Gly Pro Gly Gln Gln Gly
    2015                2020                2025

Pro Tyr Gly Pro Gly Ala Ser Gly Gln Asn Gly Pro Gly Ser Gly
    2030                2035                2040

Gln Tyr Gly Pro Gly Gln Gln Gly Pro Gly Gln Ser Ala Ala Ala
    2045                2050                2055

Ala Ala Gly Pro Gly Gln Gln Gly Pro Tyr Gly Pro Gly Ala Ser
    2060                2065                2070

Ala Ala Ala Ala Ala Gly Gln Tyr Gly Pro Gly Gln Gln Gly Pro
    2075                2080                2085

Gly Gln Tyr Gly Pro Gly Ser Ser Gly Pro Gly Gln Gln Gly Pro
    2090                2095                2100

Tyr Gly Pro Gly Ser Ser Ala Ala Ala Ala Gly Gln Tyr Gly
    2105                2110                2115

Pro Gly Gln Gln Gly Pro Tyr Gly Pro Gly Gln Ser Ala Ala Ala
    2120                2125                2130

Ala Ala Gly Gln Tyr Gln Gln Gly Pro Gly Gln Gln Gly Pro Tyr
```

-continued

```
         2135              2140              2145

Gly Pro  Gly Ala Ser Gly Pro  Gly Gln Gln Gly Pro  Tyr Gly Pro
    2150              2155              2160

Gly Ala  Ser Ala Ala Ala Ala  Ala Gly Pro Gly Gln  Tyr Gly Pro
    2165              2170              2175

Gly Gln  Gln Gly Pro Ser Ala  Ser Ala Ala Ala Ala  Ala Gly Gln
    2180              2185              2190

Tyr Gly  Ser Gly Pro Gly Gln  Tyr Gly Pro Tyr Gly  Pro Gly Gln
    2195              2200              2205

Ser Gly  Pro Gly Ser Gly Gln  Gln Gly Gln Gly Pro  Tyr Gly Pro
    2210              2215              2220

Gly Ala  Ser Ala Ala Ala Ala  Ala Gly Gln Tyr Gly  Pro Gly Gln
    2225              2230              2235

Gln Gly  Pro Tyr Gly Pro Gly  Gln Ser Ala Ala Ala  Ala Ala Gly
    2240              2245              2250

Pro Gly  Ser Gly Gln Tyr Gly  Pro Gly Ala Ser Gly  Gln Asn Gly
    2255              2260              2265

Pro Gly  Ser Gly Gln Tyr Gly  Pro Gly Gln Gln Gly  Pro Gly Gln
    2270              2275              2280

Ser Ala  Ala Ala Ala Ala Gly  Gln Tyr Gln Gln Gly  Pro Gly Gln
    2285              2290              2295

Gln Gly  Pro Tyr Gly Pro Gly  Ala Ser Ala Ala Ala  Ala Ala Gly
    2300              2305              2310

Gln Tyr  Gly Ser Gly Pro Gly  Gln Gln Gly Pro Tyr  Gly Pro Gly
    2315              2320              2325

Gln Ser  Gly Ser Gly Gln Gln  Gly Pro Gly Gln Gln  Gly Pro Tyr
    2330              2335              2340

Ala Ser  Ala Ala Ala Ala Ala  Gly Pro Gly Ser Gly  Gln Gln Gly
    2345              2350              2355

Ser Ser  Val Asp Lys Leu Ala  Ala Ala Leu Glu His  His His His
    2360              2365              2370

His His
    2375

<210> SEQ ID NO 16
<211> LENGTH: 608
<212> TYPE: PRT
<213> ORGANISM: Artificial Sequence
<220> FEATURE:
<223> OTHER INFORMATION: PRT313

<400> SEQUENCE: 16

Met His His His His His His Ser Ser Gly Ser Ser Gly Pro Gly Gly
1               5                   10                  15

Gln Gly Pro Tyr Gly Pro Gly Ala Ser Ala Ala Ala Ala Gly Gly
            20                  25                  30

Asn Gly Pro Gly Ser Gly Gln Gln Gly Pro Gly Gly Ser Ala Ala Ala
        35                  40                  45

Ala Ala Gly Gly Tyr Gly Pro Gly Gln Gly Pro Gly Gln Gln Gly
        50                  55                  60

Pro Gly Ser Ser Ala Ala Ala Ala Ala Gly Pro Gly Gly Tyr Gly Pro
65                  70                  75                  80

Gly Gly Gln Gly Pro Ser Ala Ser Ala Ala Ala Ala Gly Pro Gly
                85                  90                  95

Ser Gly Gln Gln Gly Pro Gly Ala Ser Ala Ala Ala Ala Ala Gly Gly
```

-continued

```
                 100                 105                 110

Tyr Gly Pro Gly Gly Gln Gly Pro Gly Gln Gln Gly Pro Gly Ser Ser
            115                 120                 125

Ala Ala Ala Ala Ala Gly Gly Tyr Gly Ser Gly Pro Gly Gln Gln Gly
    130                 135                 140

Pro Tyr Gly Ser Ala Ala Ala Ala Gly Pro Gly Ser Gly Gly Tyr
145                 150                 155                 160

Gly Gln Gly Pro Tyr Gly Pro Gly Ala Ser Ala Ala Ala Ala Gly
            165                 170                 175

Pro Gly Gly Tyr Gly Pro Gly Gly Gln Gly Pro Ser Ala Ser Ala Ala
            180                 185                 190

Ala Ala Ala Gly Ser Gly Gln Gln Gly Pro Gly Gly Tyr Gly Pro Tyr
    195                 200                 205

Ala Ser Ala Ala Ala Ala Ala Gly Gly Tyr Gly Ser Gly Pro Gly Gln
    210                 215                 220

Gln Gly Pro Tyr Gly Pro Gly Gly Ser Ala Ala Ala Ala Gly Ser
225                 230                 235                 240

Gly Gln Gln Gly Pro Gly Gln Gln Gly Pro Tyr Ala Ser Ala Ala Ala
            245                 250                 255

Ala Ala Gly Pro Gly Gly Gln Gly Pro Tyr Gly Pro Gly Ser Ser Ala
            260                 265                 270

Ala Ala Ala Ala Gly Gly Tyr Gly Tyr Gly Pro Gly Gly Gln Gly Pro
            275                 280                 285

Tyr Gly Pro Gly Ala Ser Ala Ala Ala Ala Gly Gly Asn Gly Pro
    290                 295                 300

Gly Ser Gly Gly Tyr Gly Pro Gly Gln Gln Gly Pro Gly Gly Ser Ala
305                 310                 315                 320

Ala Ala Ala Gly Pro Gly Gly Gln Gly Pro Tyr Gly Pro Gly Ala
            325                 330                 335

Ser Ala Ala Ala Ala Gly Gly Tyr Gly Pro Gly Gly Gln Gly Pro
    340                 345                 350

Gly Gly Tyr Gly Pro Gly Ser Ser Ala Ala Ala Ala Gly Pro Gly
            355                 360                 365

Gly Gln Gly Pro Tyr Gly Pro Gly Ser Ser Ala Ala Ala Ala Ala Gly
    370                 375                 380

Gly Tyr Gly Pro Gly Gln Gln Gly Pro Tyr Gly Pro Gly Gly Ser Ala
385                 390                 395                 400

Ala Ala Ala Gly Gly Tyr Gln Gln Gly Pro Gly Gly Gln Gly Pro
            405                 410                 415

Tyr Gly Pro Gly Ala Ser Ala Ala Ala Ala Gly Pro Gly Gly Gln
            420                 425                 430

Gly Pro Tyr Gly Pro Gly Ala Ser Ala Ala Ala Ala Gly Pro Gly
            435                 440                 445

Gly Tyr Gly Pro Gly Gly Gln Gly Pro Ser Ala Ser Ala Ala Ala Ala
    450                 455                 460

Ala Gly Gly Tyr Gly Ser Gly Pro Gly Gly Tyr Gly Pro Tyr Gly Pro
465                 470                 475                 480

Gly Gly Ser Ala Ala Ala Ala Ala Gly Pro Gly Ser Gly Gln Gln Gly
            485                 490                 495

Gln Gly Pro Tyr Gly Pro Gly Ala Ser Ala Ala Ala Ala Gly Gly
            500                 505                 510

Tyr Gly Pro Gly Gln Gln Gly Pro Tyr Gly Pro Gly Gly Ser Ala Ala
            515                 520                 525
```

```
Ala Ala Ala Gly Pro Gly Ser Gly Gly Tyr Gly Pro Gly Ala Ser Ala
    530             535             540

Ala Ala Ala Ala Gly Gly Asn Gly Pro Gly Ser Gly Gly Tyr Gly Pro
545             550             555             560

Gly Gln Gln Gly Pro Gly Gly Ser Ala Ala Ala Ala Gly Gly Tyr
            565             570             575

Gln Gln Gly Pro Gly Gly Gln Gly Pro Tyr Gly Pro Gly Ala Ser Ala
            580             585             590

Ala Ala Ala Ala Gly Pro Gly Ser Gly Gln Gln Gly Pro Gly Ala Ser
        595             600             605

<210> SEQ ID NO 17
<211> LENGTH: 601
<212> TYPE: PRT
<213> ORGANISM: Artificial Sequence
<220> FEATURE:
<223> OTHER INFORMATION: PRT399

<400> SEQUENCE: 17

Met His His His His His Ser Ser Gly Ser Ser Gly Pro Gly Gly
1               5               10              15

Gln Gly Pro Tyr Gly Pro Gly Ala Ser Ala Ala Ala Ala Gly Gly
            20              25              30

Asn Gly Pro Gly Ser Gly Gln Gln Gly Pro Gly Gly Ser Gly Gly Tyr
        35              40              45

Gly Pro Gly Gly Gln Gly Pro Gly Gln Gln Gly Pro Gly Ser Ser Ala
    50              55              60

Ala Ala Ala Gly Pro Gly Gly Tyr Gly Pro Gly Gly Gln Gly Pro
65              70              75              80

Ser Ala Ser Ala Ala Ala Ala Gly Pro Gly Ser Gly Gln Gln Gly
            85              90              95

Pro Gly Ala Ser Gly Gly Tyr Gly Pro Gly Gly Gln Gly Pro Gly Gln
        100             105             110

Gln Gly Pro Gly Ser Ser Ala Ala Ala Ala Gly Gly Tyr Gly Ser
        115             120             125

Gly Pro Gly Gln Gln Gly Pro Tyr Gly Ser Ala Ala Ala Ala Gly
    130             135             140

Pro Gly Ser Gly Gly Tyr Gly Gln Gly Pro Tyr Gly Pro Gly Ala Ser
145             150             155             160

Gly Pro Gly Gly Tyr Gly Pro Gly Gly Gln Gly Pro Ser Ala Ser Ala
            165             170             175

Ala Ala Ala Gly Ser Gly Gln Gln Gly Pro Gly Gly Tyr Gly Pro
        180             185             190

Tyr Ala Ser Ala Ala Ala Ala Gly Gly Tyr Gly Ser Gly Pro Gly
        195             200             205

Gln Gln Gly Pro Tyr Gly Pro Gly Gly Ser Gly Ser Gly Gln Gln Gly
    210             215             220

Pro Gly Gln Gln Gly Pro Tyr Ala Ser Ala Ala Ala Ala Gly Pro
225             230             235             240

Gly Gly Gln Gly Pro Tyr Gly Pro Gly Ser Ser Ala Ala Ala Ala Ala
            245             250             255

Gly Gly Tyr Gly Tyr Gly Pro Gly Gly Gln Gly Pro Tyr Gly Pro Gly
        260             265             270

Ala Ser Gly Gly Asn Gly Pro Gly Ser Gly Gly Tyr Gly Pro Gly Gln
        275             280             285
```

```
Gln Gly Pro Gly Gly Ser Ala Ala Ala Ala Gly Pro Gly Gly Gln
    290             295             300

Gly Pro Tyr Gly Pro Gly Ala Ser Ala Ala Ala Ala Gly Gly Tyr
305             310             315             320

Gly Pro Gly Gly Gln Gly Pro Gly Gly Tyr Gly Pro Gly Ser Ser Gly
                325             330             335

Pro Gly Gly Gln Gly Pro Tyr Gly Pro Gly Ser Ser Ala Ala Ala Ala
                340             345             350

Ala Gly Gly Tyr Gly Pro Gly Gln Gln Gly Pro Tyr Gly Pro Gly Gly
                355             360             365

Ser Ala Ala Ala Ala Ala Gly Gly Tyr Gln Gln Gly Pro Gly Gly Gln
    370             375             380

Gly Pro Tyr Gly Pro Gly Ala Ser Gly Pro Gly Gly Gln Gly Pro Tyr
385             390             395             400

Gly Pro Gly Ala Ser Ala Ala Ala Ala Gly Pro Gly Gly Tyr Gly
                405             410             415

Pro Gly Gly Gln Gly Pro Ser Ala Ser Ala Ala Ala Ala Gly Gly
                420             425             430

Tyr Gly Ser Gly Pro Gly Gly Tyr Gly Pro Tyr Gly Pro Gly Gly Ser
                435             440             445

Gly Pro Gly Ser Gly Gln Gln Gly Gln Gly Pro Tyr Gly Pro Gly Ala
    450             455             460

Ser Ala Ala Ala Ala Ala Gly Gly Tyr Gly Pro Gly Gln Gln Gly Pro
465             470             475             480

Tyr Gly Pro Gly Gly Ser Ala Ala Ala Ala Gly Pro Gly Ser Gly
                485             490             495

Gly Tyr Gly Pro Gly Ala Ser Gly Gly Asn Gly Pro Gly Ser Gly Gly
                500             505             510

Tyr Gly Pro Gly Gln Gln Gly Pro Gly Gly Ser Ala Ala Ala Ala Ala
    515             520             525

Gly Gly Tyr Gln Gln Gly Pro Gly Gly Gln Gly Pro Tyr Gly Pro Gly
    530             535             540

Ala Ser Ala Ala Ala Ala Ala Gly Gly Tyr Gly Ser Gly Pro Gly Gln
545             550             555             560

Gln Gly Pro Tyr Gly Pro Gly Gly Ser Gly Ser Gly Gln Gln Gly Pro
                565             570             575

Gly Gln Gln Gly Pro Tyr Ala Ser Ala Ala Ala Ala Gly Pro Gly
                580             585             590

Ser Gly Gln Gln Gly Pro Gly Ala Ser
    595             600
```

```
<210> SEQ ID NO 18
<211> LENGTH: 590
<212> TYPE: PRT
<213> ORGANISM: Artificial Sequence
<220> FEATURE:
<223> OTHER INFORMATION: Met-PRT399

<400> SEQUENCE: 18

Met Gly Pro Gly Gly Gln Gly Pro Tyr Gly Pro Gly Ala Ser Ala Ala
1               5               10              15

Ala Ala Ala Gly Gly Asn Gly Pro Gly Ser Gly Gln Gln Gly Pro Gly
                20              25              30

Gly Ser Gly Gly Tyr Gly Pro Gly Gly Gln Gly Pro Gly Gln Gln Gly
    35              40              45
```

```
Pro Gly Ser Ser Ala Ala Ala Ala Gly Pro Gly Gly Tyr Gly Pro
    50              55              60

Gly Gly Gln Gly Pro Ser Ala Ser Ala Ala Ala Ala Gly Pro Gly
65              70              75              80

Ser Gly Gln Gln Gly Pro Gly Ala Ser Gly Gly Tyr Gly Pro Gly Gly
            85              90              95

Gln Gly Pro Gly Gln Gln Gly Pro Gly Ser Ser Ala Ala Ala Ala
            100             105             110

Gly Gly Tyr Gly Ser Gly Pro Gly Gln Gln Gly Pro Tyr Gly Ser Ala
            115             120             125

Ala Ala Ala Ala Gly Pro Gly Ser Gly Gly Tyr Gly Gln Gly Pro Tyr
    130             135             140

Gly Pro Gly Ala Ser Gly Pro Gly Gly Tyr Gly Pro Gly Gly Gln Gly
145             150             155             160

Pro Ser Ala Ser Ala Ala Ala Ala Gly Ser Gly Gln Gln Gly Pro
            165             170             175

Gly Gly Tyr Gly Pro Tyr Ala Ser Ala Ala Ala Ala Gly Gly Tyr
            180             185             190

Gly Ser Gly Pro Gly Gln Gln Gly Pro Tyr Gly Pro Gly Gly Ser Gly
            195             200             205

Ser Gly Gln Gln Gly Pro Gly Gln Gln Gly Pro Tyr Ala Ser Ala Ala
    210             215             220

Ala Ala Ala Gly Pro Gly Gly Gln Gly Pro Tyr Gly Pro Gly Ser Ser
225             230             235             240

Ala Ala Ala Ala Ala Gly Gly Tyr Gly Tyr Gly Pro Gly Gly Gln Gly
            245             250             255

Pro Tyr Gly Pro Gly Ala Ser Gly Gly Asn Gly Pro Gly Ser Gly Gly
            260             265             270

Tyr Gly Pro Gly Gln Gln Gly Pro Gly Gly Ser Ala Ala Ala Ala Ala
    275             280             285

Gly Pro Gly Gly Gln Gly Pro Tyr Gly Pro Gly Ala Ser Ala Ala Ala
    290             295             300

Ala Ala Gly Gly Tyr Gly Pro Gly Gly Gln Gly Pro Gly Gly Tyr Gly
305             310             315             320

Pro Gly Ser Ser Gly Pro Gly Gly Gln Gly Pro Tyr Gly Pro Gly Ser
            325             330             335

Ser Ala Ala Ala Ala Ala Gly Gly Tyr Gly Pro Gly Gln Gln Gly Pro
            340             345             350

Tyr Gly Pro Gly Gly Ser Ala Ala Ala Ala Gly Gly Tyr Gln Gln
    355             360             365

Gly Pro Gly Gly Gln Gly Pro Tyr Gly Pro Gly Ala Ser Gly Pro Gly
    370             375             380

Gly Gln Gly Pro Tyr Gly Pro Gly Ala Ser Ala Ala Ala Ala Ala Gly
385             390             395             400

Pro Gly Gly Tyr Gly Pro Gly Gly Gln Gly Pro Ser Ala Ser Ala Ala
            405             410             415

Ala Ala Ala Gly Gly Tyr Gly Ser Gly Pro Gly Gly Tyr Gly Pro Tyr
            420             425             430

Gly Pro Gly Gly Ser Gly Pro Gly Ser Gly Gln Gln Gly Gln Gly Pro
            435             440             445

Tyr Gly Pro Gly Ala Ser Ala Ala Ala Ala Ala Gly Gly Tyr Gly Pro
    450             455             460
```

-continued

```
Gly Gln Gln Gly Pro Tyr Gly Pro Gly Gly Ser Ala Ala Ala Ala
465                 470                 475                 480

Gly Pro Gly Ser Gly Gly Tyr Gly Pro Gly Ala Ser Gly Gly Asn Gly
                485             490                 495

Pro Gly Ser Gly Gly Tyr Gly Pro Gly Gln Gln Gly Pro Gly Gly Ser
            500             505                 510

Ala Ala Ala Ala Ala Gly Gly Tyr Gln Gln Gly Pro Gly Gly Gln Gly
        515             520                 525

Pro Tyr Gly Pro Gly Ala Ser Ala Ala Ala Ala Gly Gly Tyr Gly
    530             535                 540

Ser Gly Pro Gly Gln Gln Gly Pro Tyr Gly Pro Gly Gly Ser Gly Ser
545                 550                 555                 560

Gly Gln Gln Gly Pro Gly Gln Gln Gly Pro Tyr Ala Ser Ala Ala Ala
                565             570                 575

Ala Ala Gly Pro Gly Ser Gly Gln Gln Gly Pro Gly Ala Ser
            580             585                 590

<210> SEQ ID NO 19
<211> LENGTH: 612
<212> TYPE: PRT
<213> ORGANISM: Artificial Sequence
<220> FEATURE:
<223> OTHER INFORMATION: Met-PRT720

<400> SEQUENCE: 19

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Ala Gly Pro Gly Gln Tyr Val Leu
    50                  55                  60

Ile Gly Pro Gly Gln Gln Val Leu Ile Gly Pro Ser Ala Ser Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
            100                 105                 110

Ser Ala Ala Ala Ala Ala Gly Ser Tyr Gly Ser Val Leu Ile Gly Pro
        115                 120                 125

Gly Gln Gln Val Leu Ile Gly Pro Tyr Gly Ser Ala Ala Ala Ala Ala
        130                 135                 140

Gly Pro Gly Ser Gly Gln Tyr Gly Gln Gly Pro Tyr Gly Pro Gly Ala
145                 150                 155                 160

Ser Gly Pro Gly Gln Tyr Gly Pro Gly Gln Gln Gly Pro Ser Ala Ser
            165                 170                 175

Ala Ala Ala Ala Ala Gly Ser Gly Gln Gln Val Leu Ile Gly Pro Gly
            180                 185                 190

Gln Tyr Val Leu Ile Gly Pro Tyr Ala Ser Ala Ala Ala Ala Ala Gly
        195                 200                 205

Gln Tyr Gly Ser Gly Pro Gly Gln Gln Gly Pro Tyr Gly Pro Gly Gln
    210                 215                 220

Ser Gly Ser Gly Gln Gln Gly Pro Gly Gln Gln Gly Pro Tyr Ala Ser
225                 230                 235                 240
```

-continued

```
Ala Ala Ala Ala Ala Gly Pro Gly Gln Gln Val Leu Ile Gly Pro Tyr
             245             250                 255

Val Leu Ile Gly Pro Gly Ser Ser Ala Ala Ala Ala Gly Gln Tyr
             260             265                 270

Gly Tyr Gly Pro Gly Gln Gln Gly Pro Tyr Gly Pro Gly Ala Ser Gly
             275             280                 285

Gln Asn Gly Pro Gly Ser Gly Gln Tyr Gly Pro Gly Gln Gln Gly Pro
    290                 295             300

Gly Gln Ser Ala Ala Ala Ala Ala Gly Pro Gly Gln Gln Val Leu Ile
305             310             315                 320

Gly Pro Tyr Val Leu Ile Gly Pro Gly Ala Ser Ala Ala Ala Ala Ala
             325             330                 335

Gly Gln Tyr Gly Pro Gly Gln Gln Gly Pro Gly Gln Tyr Gly Pro Gly
             340             345                 350

Ser Ser Gly Pro Gly Gln Gln Gly Pro Tyr Gly Pro Gly Ser Ser Ala
             355             360                 365

Ala Ala Ala Gly Ser Tyr Gly Pro Gly Gln Gln Val Leu Ile Gly
    370                 375             380

Pro Tyr Val Leu Ile Gly Pro Gly Pro Ser Ala Ala Ala Ala Ala Gly
385             390             395                 400

Gln Tyr Gln Gln Gly Pro Gly Gln Gln Gly Pro Tyr Gly Pro Gly Ala
             405             410             415

Ser Gly Pro Gly Gln Gln Gly Pro Tyr Gly Pro Gly Ala Ser Ala Ala
             420             425             430

Ala Ala Ala Gly Pro Gly Gln Tyr Val Leu Ile Gly Pro Gly Gln Gln
    435                 440             445

Val Leu Ile Gly Pro Ser Ala Ser Ala Ala Ala Ala Gly Gln Tyr
    450                 455             460

Gly Ser Gly Pro Gly Gln Tyr Gly Pro Tyr Gly Pro Gly Gln Ser Gly
465                 470             475                 480

Pro Gly Ser Gly Gln Gln Gly Gln Gly Pro Tyr Gly Pro Gly Ala Ser
             485             490                 495

Ala Ala Ala Ala Ala Gly Ser Tyr Gly Pro Gly Gln Gln Val Leu Ile
             500             505             510

Gly Pro Tyr Val Leu Ile Gly Pro Gly Pro Ser Ala Ala Ala Ala Ala
             515             520             525

Gly Pro Gly Ser Gly Gln Tyr Gly Pro Gly Ala Ser Gly Gln Asn Gly
    530                 535             540

Pro Gly Ser Gly Gln Tyr Gly Pro Gly Gln Gln Gly Pro Gly Gln Ser
545                 550             555                 560

Ala Ala Ala Ala Ala Gly Gln Tyr Gln Gln Val Leu Ile Gly Pro Gly
             565             570                 575

Gln Gln Gly Pro Tyr Val Leu Ile Gly Pro Gly Ala Ser Ala Ala Ala
             580             585             590

Ala Ala Gly Pro Gly Ser Gly Gln Gln Val Leu Ile Gly Pro Gly Ala
    595                 600             605

Ser Val Leu Ile
    610
```

```
<210> SEQ ID NO 20
<211> LENGTH: 592
<212> TYPE: PRT
<213> ORGANISM: Artificial Sequence
<220> FEATURE:
<223> OTHER INFORMATION: Met-PRT665
```

-continued

<400> SEQUENCE: 20

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
                20                  25                  30

Pro Gly Gln Ser Gly Gln Tyr Gly Pro Gly Gln Gln Gly Pro Gly Gln
            35                  40                  45

Gln Gly Pro Gly Ser Ser Ala Ala Ala Ala Ala Ala Gly Pro Gly
        50                  55                  60

Gln Tyr Val Leu Ile Gly Pro Gly Gln Gln Gly Pro Ser Ala Ser Ala
65                  70                  75                  80

Ala Ala Ala Ala Ala Gly Pro Gly Ser Gly Gln Gln Gly Pro Gly
                85                  90                  95

Ala Ser Gly Gln Tyr Gly Pro Gly Gln Gln Gly Pro Gly Gln Gln Gly
            100                 105                 110

Pro Gly Ser Ser Ala Ala Ala Ala Ala Ala Gly Ser Tyr Gly Ser
            115                 120                 125

Val Leu Ile Gly Pro Gly Gln Gln Gly Pro Tyr Gly Ser Ala Ala Ala
        130                 135                 140

Ala Ala Ala Ala Gly Pro Gly Ser Gly Gln Tyr Gly Gln Gly Pro Tyr
145                 150                 155                 160

Gly Pro Gly Ala Ser Gly Pro Gly Gln Tyr Gly Pro Gly Gln Gln Gly
            165                 170                 175

Pro Ser Ala Ser Ala Ala Ala Ala Ala Ala Gly Ser Gly Gln Gln
            180                 185                 190

Val Leu Ile Gly Pro Gly Gln Tyr Gly Pro Tyr Ala Ser Ala Ala Ala
        195                 200                 205

Ala Ala Ala Ala Gly Ser Tyr Gly Ser Gly Pro Gly Gln Gln Gly Pro
    210                 215                 220

Tyr Gly Pro Gly Gln Ser Gly Ser Gly Gln Gln Gly Pro Gly Gln Gln
225                 230                 235                 240

Gly Pro Tyr Ala Ser Ala Ala Ala Ala Ala Ala Gly Pro Gly Gln
            245                 250                 255

Gln Val Leu Ile Gly Pro Tyr Gly Pro Gly Ser Ser Ala Ala Ala Ala
            260                 265                 270

Ala Ala Ala Gly Ser Tyr Gly Tyr Gly Pro Gly Gln Gln Gly Pro Tyr
    275                 280                 285

Gly Pro Gly Ala Ser Gly Gln Asn Gly Pro Gly Ser Gly Gln Tyr Gly
    290                 295                 300

Pro Gly Gln Gln Gly Pro Gly Pro Ser Ala Ala Ala Ala Ala Ala
305                 310                 315                 320

Gly Pro Gly Gln Gln Val Leu Ile Gly Pro Tyr Gly Pro Gly Ala Ser
            325                 330                 335

Ala Ala Ala Ala Ala Ala Ala Gly Ser Tyr Gly Pro Gly Gln Gln Gly
            340                 345                 350

Pro Gly Gln Tyr Gly Pro Gly Ser Ser Gly Pro Gly Gln Gln Gly Pro
            355                 360                 365

Tyr Gly Pro Gly Ser Ser Ala Ala Ala Ala Ala Ala Gly Ser Tyr
    370                 375                 380

Gly Pro Gly Gln Gln Val Leu Ile Gly Pro Tyr Gly Pro Gly Pro Ser
385                 390                 395                 400

Ala Ala Ala Ala Ala Ala Ala Gly Ser Tyr Gln Gln Gly Pro Gly Gln

-continued

```
              405               410               415

Gln Gly Pro Tyr Gly Pro Gly Ala Ser Gly Pro Gly Gln Gln Gly Pro
              420               425               430

Tyr Gly Pro Gly Ala Ser Ala Ala Ala Ala Ala Ala Gly Pro Gly
              435               440               445

Gln Tyr Val Leu Ile Gly Pro Gly Gln Gln Gly Pro Ser Ala Ser Ala
    450               455               460

Ala Ala Ala Ala Ala Ala Gly Ser Tyr Gly Ser Gly Pro Gly Gln Tyr
465               470               475               480

Gly Pro Tyr Gly Pro Gly Gln Ser Gly Pro Gly Ser Gly Gln Gln Gly
              485               490               495

Gln Gly Pro Tyr Gly Pro Gly Ala Ser Ala Ala Ala Ala Ala Ala
              500               505               510

Gly Ser Tyr Gly Pro Gly Gln Gln Val Leu Ile Gly Pro Tyr Gly Pro
              515               520               525

Gly Pro Ser Ala Ala Ala Ala Ala Ala Gly Pro Gly Ser Gly Gln
              530               535               540

Tyr Gly Pro Gly Ala Ser Gly Gln Asn Gly Pro Gly Ser Gly Gln Tyr
545               550               555               560

Gly Pro Gly Gln Gln Gly Pro Gly Pro Ser Ala Ala Ala Ala Ala Ala
              565               570               575

Ala Gly Pro Gly Ser Gly Gln Gln Gly Pro Gly Ala Ser Val Leu Ile
              580               585               590

<210> SEQ ID NO 21
<211> LENGTH: 619
<212> TYPE: PRT
<213> ORGANISM: Artificial Sequence
<220> FEATURE:
<223> OTHER INFORMATION: Met-PRT666

<400> SEQUENCE: 21

Met Gly Pro Gly Gln Gln Gly Pro Tyr Gly Pro Gly Ala Ser Ala Ala
1               5               10               15

Ala Ala Ala Ala Ala Gly Ser Asn Gly Pro Gly Ser Gly Gln Gln Gly
              20               25               30

Pro Gly Gln Ser Gly Gln Tyr Gly Pro Gly Gln Gln Gly Pro Gly Gln
         35               40               45

Gln Gly Pro Gly Ser Ser Ala Ala Ala Ala Ala Ala Gly Pro Gly
    50               55               60

Gln Tyr Val Leu Ile Gly Pro Gly Gln Gln Val Leu Ile Gly Pro Ser
65               70               75               80

Ala Ser Ala Ala Ala Ala Ala Ala Gly Pro Gly Ser Gly Gln Gln
              85               90               95

Gly Pro Gly Ala Ser Gly Gln Tyr Gly Pro Gly Gln Gln Gly Pro Gly
         100               105               110

Gln Gln Gly Pro Gly Ser Ser Ala Ala Ala Ala Ala Ala Gly Ser
         115               120               125

Tyr Gly Ser Val Leu Ile Gly Pro Gly Gln Gln Val Leu Ile Gly Pro
    130               135               140

Tyr Gly Ser Ala Ala Ala Ala Ala Ala Gly Pro Gly Ser Gly Gln
145               150               155               160

Tyr Gly Gln Gly Pro Tyr Gly Pro Gly Ala Ser Gly Pro Gly Gln Tyr
              165               170               175

Gly Pro Gly Gln Gln Gly Pro Ser Ala Ser Ala Ala Ala Ala Ala Ala
```

-continued

```
                180              185              190

Ala Gly Ser Gly Gln Gln Val Leu Ile Gly Pro Gly Gln Tyr Val Leu
            195              200              205

Ile Gly Pro Tyr Ala Ser Ala Ala Ala Ala Ala Ala Gly Ser Tyr
        210              215              220

Gly Ser Gly Pro Gly Gln Gln Gly Pro Tyr Gly Pro Gly Gln Ser Gly
225              230              235              240

Ser Gly Gln Gln Gly Pro Gly Gln Gln Gly Pro Tyr Ala Ser Ala Ala
            245              250              255

Ala Ala Ala Ala Ala Gly Pro Gly Gln Gln Val Leu Ile Gly Pro Tyr
            260              265              270

Val Leu Ile Gly Pro Gly Ser Ser Ala Ala Ala Ala Ala Ala Ala Gly
            275              280              285

Ser Tyr Gly Tyr Gly Pro Gly Gln Gln Gly Pro Tyr Gly Pro Gly Ala
            290              295              300

Ser Gly Gln Asn Gly Pro Gly Ser Gly Gln Tyr Gly Pro Gly Gln Gln
305              310              315              320

Gly Pro Gly Pro Ser Ala Ala Ala Ala Ala Ala Gly Pro Gly Gln
            325              330              335

Gln Val Leu Ile Gly Pro Tyr Val Leu Ile Gly Pro Gly Ala Ser Ala
            340              345              350

Ala Ala Ala Ala Ala Gly Ser Tyr Gly Pro Gly Gln Gln Gly Pro
            355              360              365

Gly Gln Tyr Gly Pro Gly Ser Ser Gly Pro Gly Gln Gln Gly Pro Tyr
            370              375              380

Gly Pro Gly Ser Ser Ala Ala Ala Ala Ala Ala Gly Ser Tyr Gly
385              390              395              400

Pro Gly Gln Gln Val Leu Ile Gly Pro Tyr Val Leu Ile Gly Pro Gly
                405              410              415

Pro Ser Ala Ala Ala Ala Ala Ala Gly Ser Tyr Gln Gln Gly Pro
            420              425              430

Gly Gln Gln Gly Pro Tyr Gly Pro Gly Ala Ser Gly Pro Gly Gln Gln
            435              440              445

Gly Pro Tyr Gly Pro Gly Ala Ser Ala Ala Ala Ala Ala Ala Gly
            450              455              460

Pro Gly Gln Tyr Val Leu Ile Gly Pro Gly Gln Gln Val Leu Ile Gly
465              470              475              480

Pro Ser Ala Ser Ala Ala Ala Ala Ala Ala Gly Ser Tyr Gly Ser
            485              490              495

Gly Pro Gly Gln Tyr Gly Pro Tyr Gly Pro Gly Gln Ser Gly Pro Gly
            500              505              510

Ser Gly Gln Gln Gly Gln Gly Pro Tyr Gly Pro Gly Ala Ser Ala Ala
            515              520              525

Ala Ala Ala Ala Ala Gly Ser Tyr Gly Pro Gly Gln Gln Val Leu Ile
            530              535              540

Gly Pro Tyr Val Leu Ile Gly Pro Gly Pro Ser Ala Ala Ala Ala Ala
545              550              555              560

Ala Ala Gly Pro Gly Ser Gly Gln Tyr Gly Pro Gly Ala Ser Gly Gln
                565              570              575

Asn Gly Pro Gly Ser Gly Gln Tyr Gly Pro Gly Gln Gln Gly Pro Gly
            580              585              590

Pro Ser Ala Ala Ala Ala Ala Ala Gly Pro Gly Ser Gly Gln Gln
            595              600              605
```

-continued

```
Val Leu Ile Gly Pro Gly Ala Ser Val Leu Ile
    610             615

<210> SEQ ID NO 22
<211> LENGTH: 590
<212> TYPE: PRT
<213> ORGANISM: Artificial Sequence
<220> FEATURE:
<223> OTHER INFORMATION: Met-PRT410

<400> SEQUENCE: 22

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Gly Pro Gly Gln Tyr Gly Pro
    50                  55                  60

Gly Gln Gln Gly Pro Ser Ala Ser Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala Ala
            100                 105                 110

Gly Gln Tyr Gly Ser Gly Pro Gly Gln Gln Gly Pro Tyr Gly Ser Ala
        115                 120                 125

Ala Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Gly Ser Gly Gln Gln Gly Pro
            165                 170                 175

Gly Gln Tyr Gly Pro Tyr Ala Ser Ala Ala Ala Ala Gly Gln Tyr
        180                 185                 190

Gly Ser Gly Pro Gly Gln Gln Gly Pro Tyr Gly Pro Gly Gln Ser Gly
        195                 200                 205

Ser Gly Gln Gln Gly Pro Gly Gln Gln Gly Pro Tyr Ala Ser Ala Ala
    210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
            245                 250                 255

Pro Tyr Gly Pro Gly Ala Ser Gly Gln Asn Gly Pro Gly Ser Gly Gln
            260                 265                 270

Tyr Gly Pro Gly Gln Gln Gly Pro Gly Gln Ser Ala Ala Ala Ala Ala
        275                 280                 285

Gly Pro Gly Gln Gln Gly Pro Tyr Gly Pro Gly Ala Ser Ala Ala Ala
    290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
            325                 330                 335

Ser Ala Ala Ala Ala Ala Gly Gln Tyr Gly Pro Gly Gln Gln Gly Pro
            340                 345                 350
```

-continued

```
Tyr Gly Pro Gly Gln Ser Ala Ala Ala Ala Gly Gln Tyr Gln Gln
        355                 360                 365

Gly Pro Gly Gln Gln Gly Pro Tyr Gly Pro Gly Ala Ser Gly Pro Gly
        370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gln Gly Pro Ser Ala Ser Ala Ala
                405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
        435                 440                 445

Tyr Gly Pro Gly Ala Ser Ala Ala Ala Ala Gly Gln Tyr Gly Pro
    450                 455                 460

Gly Gln Gln Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
                485                 490                 495

Pro Gly Ser Gly Gln Tyr Gly Pro Gly Gln Gln Gly Pro Gly Gln Ser
            500                 505                 510

Ala Ala Ala Ala Ala Gly Gln Tyr Gln Gln Gly Pro Gly Gln Gln Gly
            515                 520                 525

Pro Tyr Gly Pro Gly Ala Ser Ala Ala Ala Ala Gly Gln Tyr Gly
    530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gln Gly Pro Tyr Ala Ser Ala Ala Ala
            565                 570                 575

Ala Ala Gly Pro Gly Ser Gly Gln Gln Gly Pro Gly Ala Ser
            580                 585                 590

<210> SEQ ID NO 23
<211> LENGTH: 565
<212> TYPE: PRT
<213> ORGANISM: Artificial Sequence
<220> FEATURE:
<223> OTHER INFORMATION: Met-PRT468

<400> SEQUENCE: 23

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Ala Gly Pro Gly
        50                  55                  60

Gln Tyr Gly Pro Gly Gln Gln Gly Pro Ser Ala Ser Ala Ala Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
            100                 105                 110

Ser Ala Ala Ala Ala Ala Ala Ala Gly Ser Tyr Gly Ser Gly Pro Gly
            115                 120                 125
```

-continued

```
Gln Gln Gly Pro Tyr Gly Ser Ala Ala Ala Ala Ala Ala Gly Pro
    130             135             140

Gly Ser Gly Gln Tyr Gly Gln Gly Pro Tyr Gly Pro Gly Ala Ser Gly
145             150             155             160

Pro Gly Gln Tyr Gly Pro Gly Gln Gln Gly Pro Ser Ala Ser Ala Ala
                165             170             175

Ala Ala Ala Ala Ala Gly Ser Gly Gln Gln Gly Pro Gly Gln Tyr Gly
            180             185             190

Pro Tyr Ala Ser Ala Ala Ala Ala Ala Ala Gly Ser Tyr Gly Ser
    195             200             205

Gly Pro Gly Gln Gln Gly Pro Tyr Gly Pro Gly Gln Ser Gly Ser Gly
    210             215             220

Gln Gln Gly Pro Gly Gln Gln Gly Pro Tyr Ala Ser Ala Ala Ala Ala
225             230             235             240

Ala Ala Ala Gly Pro Gly Gln Gln Gly Pro Tyr Gly Pro Gly Ser Ser
            245             250             255

Ala Ala Ala Ala Ala Ala Ala Gly Ser Tyr Gly Tyr Gly Pro Gly Gln
            260             265             270

Gln Gly Pro Tyr Gly Pro Gly Ala Ser Gly Gln Asn Gly Pro Gly Ser
    275             280             285

Gly Gln Tyr Gly Pro Gly Gln Gln Gly Pro Gly Pro Ser Ala Ala Ala
    290             295             300

Ala Ala Ala Ala Gly Pro Gly Gln Gln Gly Pro Tyr Gly Pro Gly Ala
305             310             315             320

Ser Ala Ala Ala Ala Ala Ala Gly Ser Tyr Gly Pro Gly Gln Gln
            325             330             335

Gly Pro Gly Gln Tyr Gly Pro Gly Ser Ser Gly Pro Gly Gln Gln Gly
            340             345             350

Pro Tyr Gly Pro Gly Ser Ser Ala Ala Ala Ala Ala Ala Ala Gly Ser
    355             360             365

Tyr Gly Pro Gly Gln Gln Gly Pro Tyr Gly Pro Gly Pro Ser Ala Ala
    370             375             380

Ala Ala Ala Ala Ala Gly Ser Tyr Gln Gln Gly Pro Gly Gln Gln Gly
385             390             395             400

Pro Tyr Gly Pro Gly Ala Ser Gly Pro Gly Gln Gln Gly Pro Tyr Gly
            405             410             415

Pro Gly Ala Ser Ala Ala Ala Ala Ala Ala Gly Pro Gly Gln Tyr
            420             425             430

Gly Pro Gly Gln Gln Gly Pro Ser Ala Ser Ala Ala Ala Ala Ala Ala
    435             440             445

Ala Gly Ser Tyr Gly Ser Gly Pro Gly Gln Tyr Gly Pro Tyr Gly Pro
    450             455             460

Gly Gln Ser Gly Pro Gly Ser Gly Gln Gln Gly Gln Gly Pro Tyr Gly
465             470             475             480

Pro Gly Ala Ser Ala Ala Ala Ala Ala Ala Gly Ser Tyr Gly Pro
            485             490             495

Gly Gln Gln Gly Pro Tyr Gly Pro Gly Pro Ser Ala Ala Ala Ala Ala
            500             505             510

Ala Ala Gly Pro Gly Ser Gly Gln Tyr Gly Pro Gly Ala Ser Gly Gln
            515             520             525

Asn Gly Pro Gly Ser Gly Gln Tyr Gly Pro Gly Gln Gln Gly Pro Gly
    530             535             540
```

-continued

```
Pro Ser Ala Ala Ala Ala Ala Ala Gly Pro Gly Ser Gly Gln Gln
545                 550                 555                 560

Gly Pro Gly Ala Ser
                565

<210> SEQ ID NO 24
<211> LENGTH: 623
<212> TYPE: PRT
<213> ORGANISM: Artificial Sequence
<220> FEATURE:
<223> OTHER INFORMATION: PRT468

<400> SEQUENCE: 24

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gly Gln Gln Gly Pro Gly Ser Ser Ala
    50                  55                  60

Ala Ala Ala Ala Gly Pro Gly Gln Tyr Val Leu Ile Gly Pro Gly Gln
65                  70                  75                  80

Gln Val Leu Ile Gly Pro Ser Ala Ser Ala Ala Ala Ala Gly Pro
            85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala Ala
        115                 120                 125

Ala Gly Ser Tyr Gly Ser Val Leu Ile Gly Pro Gly Gln Gln Val Leu
    130                 135                 140

Ile Gly Pro Tyr Gly Ser Ala Ala Ala Ala Ala Gly Pro Gly Ser Gly
145                 150                 155                 160

Gln Tyr Gly Gln Gly Pro Tyr Gly Pro Gly Ala Ser Gly Pro Gly Gln
            165                 170                 175

Tyr Gly Pro Gly Gln Gln Gly Pro Ser Ala Ser Ala Ala Ala Ala Ala
            180                 185                 190

Gly Ser Gly Gln Gln Val Leu Ile Gly Pro Gly Gln Tyr Val Leu Ile
            195                 200                 205

Gly Pro Tyr Ala Ser Ala Ala Ala Ala Gly Gln Tyr Gly Ser Gly
    210                 215                 220

Pro Gly Gln Gln Gly Pro Tyr Gly Pro Gly Gln Ser Gly Ser Gly Gln
225                 230                 235                 240

Gln Gly Pro Gly Gln Gln Gly Pro Tyr Ala Ser Ala Ala Ala Ala Ala
            245                 250                 255

Gly Pro Gly Gln Gln Val Leu Ile Gly Pro Tyr Val Leu Ile Gly Pro
            260                 265                 270

Gly Ser Ser Ala Ala Ala Ala Ala Gly Gln Tyr Gly Tyr Gly Pro Gly
            275                 280                 285

Gln Gln Gly Pro Tyr Gly Pro Gly Ala Ser Gly Gln Asn Gly Pro Gly
        290                 295                 300

Ser Gly Gln Tyr Gly Pro Gly Gln Gln Gly Pro Gly Gln Ser Ala Ala
305                 310                 315                 320

Ala Ala Ala Gly Pro Gly Gln Gln Val Leu Ile Gly Pro Tyr Val Leu
            325                 330                 335
```

-continued

```
Ile Gly Pro Gly Ala Ser Ala Ala Ala Ala Gly Gln Tyr Gly Pro
            340                 345                 350

Gly Gln Gln Gly Pro Gly Gln Tyr Gly Pro Gly Ser Ser Gly Pro Gly
            355                 360                 365

Gln Gln Gly Pro Tyr Gly Pro Gly Ser Ser Ala Ala Ala Ala Gly
            370                 375                 380

Ser Tyr Gly Pro Gly Gln Gln Val Leu Ile Gly Pro Tyr Val Leu Ile
385                 390                 395                 400

Gly Pro Gly Pro Ser Ala Ala Ala Ala Gly Gln Tyr Gln Gln Gly
            405                 410                 415

Pro Gly Gln Gln Gly Pro Tyr Gly Pro Gly Ala Ser Gly Pro Gly Gln
            420                 425                 430

Gln Gly Pro Tyr Gly Pro Gly Ala Ser Ala Ala Ala Ala Gly Pro
            435                 440                 445

Gly Gln Tyr Val Leu Ile Gly Pro Gly Gln Gln Val Leu Ile Gly Pro
            450                 455                 460

Ser Ala Ser Ala Ala Ala Ala Ala Gly Gln Tyr Gly Ser Gly Pro Gly
465                 470                 475                 480

Gln Tyr Gly Pro Tyr Gly Pro Gly Gln Ser Gly Pro Gly Ser Gly Gln
            485                 490                 495

Gln Gly Gln Gly Pro Tyr Gly Pro Gly Ala Ser Ala Ala Ala Ala Ala
            500                 505                 510

Gly Ser Tyr Gly Pro Gly Gln Gln Val Leu Ile Gly Pro Tyr Val Leu
            515                 520                 525

Ile Gly Pro Gly Pro Ser Ala Ala Ala Ala Gly Pro Gly Ser Gly
            530                 535                 540

Gln Tyr Gly Pro Gly Ala Ser Gly Gln Asn Gly Pro Gly Ser Gly Gln
545                 550                 555                 560

Tyr Gly Pro Gly Gln Gln Gly Pro Gly Gln Ser Ala Ala Ala Ala
            565                 570                 575

Gly Gln Tyr Gln Gln Val Leu Ile Gly Pro Gly Gln Gln Gly Pro Tyr
            580                 585                 590

Val Leu Ile Gly Pro Gly Ala Ser Ala Ala Ala Ala Ala Gly Pro Gly
            595                 600                 605

Ser Gly Gln Gln Val Leu Ile Gly Pro Gly Ala Ser Val Leu Ile
            610                 615                 620
```

```
<210> SEQ ID NO 25
<211> LENGTH: 603
<212> TYPE: PRT
<213> ORGANISM: Artificial Sequence
<220> FEATURE:
<223> OTHER INFORMATION: PRT665

<400> SEQUENCE: 25
```

```
Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
            20                  25                  30

Gly Ser Asn Gly Pro Gly Ser Gly Gln Gln Gly Pro Gly Gln Ser Gly
            35                  40                  45

Gln Tyr Gly Pro Gly Gln Gln Gly Pro Gly Gln Gln Gly Pro Gly Ser
            50                  55                  60

Ser Ala Ala Ala Ala Ala Ala Ala Gly Pro Gly Gln Tyr Val Leu Ile
65                  70                  75                  80
```

-continued

Gly Pro Gly Gln Gln Gly Pro Ser Ala Ser Ala Ala Ala Ala Ala Ala
                85                      90                      95

Ala Gly Pro Gly Ser Gly Gln Gln Gly Pro Gly Ala Ser Gly Gln Tyr
            100                 105                 110

Gly Pro Gly Gln Gln Gly Pro Gly Gln Gln Gly Pro Gly Ser Ser Ala
            115                 120                 125

Ala Ala Ala Ala Ala Ala Gly Ser Tyr Gly Ser Val Leu Ile Gly Pro
    130                 135                 140

Gly Gln Gln Gly Pro Tyr Gly Ser Ala Ala Ala Ala Ala Ala Ala Gly
145                 150                 155                 160

Pro Gly Ser Gly Gln Tyr Gly Gln Gly Pro Tyr Gly Pro Gly Ala Ser
                165                 170                 175

Gly Pro Gly Gln Tyr Gly Pro Gly Gln Gln Gly Pro Ser Ala Ser Ala
            180                 185                 190

Ala Ala Ala Ala Ala Ala Gly Ser Gly Gln Gln Val Leu Ile Gly Pro
            195                 200                 205

Gly Gln Tyr Gly Pro Tyr Ala Ser Ala Ala Ala Ala Ala Ala Ala Gly
    210                 215                 220

Ser Tyr Gly Ser Gly Pro Gly Gln Gln Gly Pro Tyr Gly Pro Gly Gln
225                 230                 235                 240

Ser Gly Ser Gly Gln Gln Gly Pro Gly Gln Gln Gly Pro Tyr Ala Ser
            245                 250                 255

Ala Ala Ala Ala Ala Ala Ala Gly Pro Gly Gln Gln Val Leu Ile Gly
            260                 265                 270

Pro Tyr Gly Pro Gly Ser Ser Ala Ala Ala Ala Ala Ala Gly Ser
            275                 280                 285

Tyr Gly Tyr Gly Pro Gly Gln Gln Gly Pro Tyr Gly Pro Gly Ala Ser
    290                 295                 300

Gly Gln Asn Gly Pro Gly Ser Gly Gln Tyr Gly Pro Gly Gln Gln Gly
305                 310                 315                 320

Pro Gly Pro Ser Ala Ala Ala Ala Ala Ala Gly Pro Gly Gln Gln
            325                 330                 335

Val Leu Ile Gly Pro Tyr Gly Pro Gly Ala Ser Ala Ala Ala Ala Ala
            340                 345                 350

Ala Ala Gly Ser Tyr Gly Pro Gly Gln Gln Gly Pro Gly Gln Tyr Gly
            355                 360                 365

Pro Gly Ser Ser Gly Pro Gly Gln Gln Gly Pro Tyr Gly Pro Gly Ser
    370                 375                 380

Ser Ala Ala Ala Ala Ala Ala Ala Gly Ser Tyr Gly Pro Gly Gln Gln
385                 390                 395                 400

Val Leu Ile Gly Pro Tyr Gly Pro Gly Pro Ser Ala Ala Ala Ala Ala
            405                 410                 415

Ala Ala Gly Ser Tyr Gln Gln Gly Pro Gly Gln Gln Gly Pro Tyr Gly
            420                 425                 430

Pro Gly Ala Ser Gly Pro Gly Gln Gln Gly Pro Tyr Gly Pro Gly Ala
            435                 440                 445

Ser Ala Ala Ala Ala Ala Ala Ala Gly Pro Gly Gln Tyr Val Leu Ile
    450                 455                 460

Gly Pro Gly Gln Gln Gly Pro Ser Ala Ser Ala Ala Ala Ala Ala Ala
465                 470                 475                 480

Ala Gly Ser Tyr Gly Ser Gly Pro Gly Gln Tyr Gly Pro Tyr Gly Pro
            485                 490                 495

Gly Gln Ser Gly Pro Gly Ser Gly Gln Gln Gly Gln Gly Pro Tyr Gly

-continued

```
            500              505              510

Pro Gly Ala Ser Ala Ala Ala Ala Ala Ala Gly Ser Tyr Gly Pro
        515              520              525

Gly Gln Gln Val Leu Ile Gly Pro Tyr Gly Pro Gly Pro Ser Ala Ala
    530              535              540

Ala Ala Ala Ala Ala Gly Pro Gly Ser Gly Gln Tyr Gly Pro Gly Ala
545              550              555              560

Ser Gly Gln Asn Gly Pro Gly Ser Gly Gln Tyr Gly Pro Gly Gln Gln
            565              570              575

Gly Pro Gly Pro Ser Ala Ala Ala Ala Ala Ala Gly Pro Gly Ser
            580              585              590

Gly Gln Gln Gly Pro Gly Ala Ser Val Leu Ile
        595              600
```

```
<210> SEQ ID NO 26
<211> LENGTH: 630
<212> TYPE: PRT
<213> ORGANISM: Artificial Sequence
<220> FEATURE:
<223> OTHER INFORMATION: PRT666

<400> SEQUENCE: 26

Met His His His His His Ser Ser Gly Ser Ser Gly Pro Gly Gln
1               5               10              15

Gln Gly Pro Tyr Gly Pro Gly Ala Ser Ala Ala Ala Ala Ala Ala
            20              25              30

Gly Ser Asn Gly Pro Gly Ser Gly Gln Gln Gly Pro Gly Gln Ser Gly
        35              40              45

Gln Tyr Gly Pro Gly Gln Gln Gly Pro Gly Gln Gln Gly Pro Gly Ser
    50              55              60

Ser Ala Ala Ala Ala Ala Ala Gly Pro Gly Gln Tyr Val Leu Ile
65              70              75              80

Gly Pro Gly Gln Gln Val Leu Ile Gly Pro Ser Ala Ser Ala Ala Ala
            85              90              95

Ala Ala Ala Ala Gly Pro Gly Ser Gly Gln Gln Gly Pro Gly Ala Ser
            100             105             110

Gly Gln Tyr Gly Pro Gly Gln Gln Gly Pro Gly Gln Gln Gly Pro Gly
        115             120             125

Ser Ser Ala Ala Ala Ala Ala Ala Gly Ser Tyr Gly Ser Val Leu
    130             135             140

Ile Gly Pro Gly Gln Gln Val Leu Ile Gly Pro Tyr Gly Ser Ala Ala
145             150             155             160

Ala Ala Ala Ala Ala Gly Pro Gly Ser Gly Gln Tyr Gly Gln Gly Pro
            165             170             175

Tyr Gly Pro Gly Ala Ser Gly Pro Gly Gln Tyr Gly Pro Gly Gln Gln
            180             185             190

Gly Pro Ser Ala Ser Ala Ala Ala Ala Ala Ala Gly Ser Gly Gln
        195             200             205

Gln Val Leu Ile Gly Pro Gly Gln Tyr Val Leu Ile Gly Pro Tyr Ala
    210             215             220

Ser Ala Ala Ala Ala Ala Ala Gly Ser Tyr Gly Ser Gly Pro Gly
225             230             235             240

Gln Gln Gly Pro Tyr Gly Pro Gly Gln Ser Gly Ser Gly Gln Gln Gly
            245             250             255

Pro Gly Gln Gln Gly Pro Tyr Ala Ser Ala Ala Ala Ala Ala Ala Ala
```

-continued

```
                  260                 265                 270

Gly Pro Gly Gln Gln Val Leu Ile Gly Pro Tyr Val Leu Ile Gly Pro
            275                 280                 285

Gly Ser Ser Ala Ala Ala Ala Ala Ala Gly Ser Tyr Gly Tyr Gly
            290                 295                 300

Pro Gly Gln Gln Gly Pro Tyr Gly Pro Gly Ala Ser Gly Gln Asn Gly
305                 310                 315                 320

Pro Gly Ser Gly Gln Tyr Gly Pro Gly Gln Gln Gly Pro Gly Pro Ser
                325                 330                 335

Ala Ala Ala Ala Ala Ala Ala Gly Pro Gly Gln Gln Val Leu Ile Gly
                340                 345                 350

Pro Tyr Val Leu Ile Gly Pro Gly Ala Ser Ala Ala Ala Ala Ala Ala
                355                 360                 365

Ala Gly Ser Tyr Gly Pro Gly Gln Gln Gly Pro Gly Gln Tyr Gly Pro
            370                 375                 380

Gly Ser Ser Gly Pro Gly Gln Gln Gly Pro Tyr Gly Pro Gly Ser Ser
385                 390                 395                 400

Ala Ala Ala Ala Ala Ala Ala Gly Ser Tyr Gly Pro Gly Gln Gln Val
                405                 410                 415

Leu Ile Gly Pro Tyr Val Leu Ile Gly Pro Gly Pro Ser Ala Ala Ala
                420                 425                 430

Ala Ala Ala Ala Gly Ser Tyr Gln Gln Gly Pro Gly Gln Gln Gly Pro
                435                 440                 445

Tyr Gly Pro Gly Ala Ser Gly Pro Gly Gln Gln Gly Pro Tyr Gly Pro
            450                 455                 460

Gly Ala Ser Ala Ala Ala Ala Ala Ala Gly Pro Gly Gln Tyr Val
465                 470                 475                 480

Leu Ile Gly Pro Gly Gln Gln Val Leu Ile Gly Pro Ser Ala Ser Ala
                485                 490                 495

Ala Ala Ala Ala Ala Gly Ser Tyr Gly Ser Gly Pro Gly Gln Tyr
                500                 505                 510

Gly Pro Tyr Gly Pro Gly Gln Ser Gly Pro Gly Ser Gly Gln Gln Gly
            515                 520                 525

Gln Gly Pro Tyr Gly Pro Gly Ala Ser Ala Ala Ala Ala Ala Ala Ala
            530                 535                 540

Gly Ser Tyr Gly Pro Gly Gln Gln Val Leu Ile Gly Pro Tyr Val Leu
545                 550                 555                 560

Ile Gly Pro Gly Pro Ser Ala Ala Ala Ala Ala Ala Ala Gly Pro Gly
                565                 570                 575

Ser Gly Gln Tyr Gly Pro Gly Ala Ser Gly Gln Asn Gly Pro Gly Ser
                580                 585                 590

Gly Gln Tyr Gly Pro Gly Gln Gln Gly Pro Gly Pro Ser Ala Ala Ala
                595                 600                 605

Ala Ala Ala Ala Gly Pro Gly Ser Gly Gln Gln Val Leu Ile Gly Pro
            610                 615                 620

Gly Ala Ser Val Leu Ile
625                 630
```

<210> SEQ ID NO 27
<211> LENGTH: 593
<212> TYPE: PRT
<213> ORGANISM: Artificial Sequence
<220> FEATURE:
<223> OTHER INFORMATION: M_PRT888

```
<400> SEQUENCE: 27

Met Gly Ser Ser Gly Pro Gly Val Leu Gly Pro Tyr Gly Pro Gly Ala
1               5                   10                  15

Ser Ala Ala Ala Ala Ala Gly Gln Asn Gly Pro Gly Ser Gly Val Leu
                20                  25                  30

Gly Pro Gly Gln Ser Gly Gln Tyr Gly Pro Gly Val Leu Gly Pro Gly
            35                  40                  45

Val Leu Gly Pro Gly Ser Ser Ala Ala Ala Ala Ala Gly Pro Gly Gln
    50                  55                  60

Tyr Gly Pro Gly Val Leu Gly Pro Ser Ala Ser Ala Ala Ala Ala Ala
65                  70                  75                  80

Gly Pro Gly Ser Gly Val Leu Gly Pro Gly Ala Ser Gly Gln Tyr Gly
                85                  90                  95

Pro Gly Val Leu Gly Pro Gly Val Leu Gly Pro Gly Ser Ser Ala Ala
            100                 105                 110

Ala Ala Ala Gly Gln Tyr Gly Ser Gly Pro Gly Val Leu Gly Pro Tyr
        115                 120                 125

Gly Ser Ala Ala Ala Ala Ala Gly Pro Gly Ser Gly Gln Tyr Gly Gln
    130                 135                 140

Gly Pro Tyr Gly Pro Gly Ala Ser Gly Pro Gly Gln Tyr Gly Pro Gly
145                 150                 155                 160

Val Leu Gly Pro Ser Ala Ser Ala Ala Ala Ala Gly Ser Gly Val
                165                 170                 175

Leu Gly Pro Gly Gln Tyr Gly Pro Tyr Ala Ser Ala Ala Ala Ala Ala
            180                 185                 190

Gly Gln Tyr Gly Ser Gly Pro Gly Val Leu Gly Pro Tyr Gly Pro Gly
        195                 200                 205

Gln Ser Gly Ser Gly Val Leu Gly Pro Gly Val Leu Gly Pro Tyr Ala
    210                 215                 220

Ser Ala Ala Ala Ala Gly Pro Gly Val Leu Gly Pro Tyr Gly Pro
225                 230                 235                 240

Gly Ser Ser Ala Ala Ala Ala Ala Gly Gln Tyr Gly Tyr Gly Pro Gly
                245                 250                 255

Val Leu Gly Pro Tyr Gly Pro Gly Ala Ser Gly Gln Asn Gly Pro Gly
            260                 265                 270

Ser Gly Gln Tyr Gly Pro Gly Val Leu Gly Pro Gly Gln Ser Ala Ala
    275                 280                 285

Ala Ala Ala Gly Pro Gly Val Leu Gly Pro Tyr Gly Pro Gly Ala Ser
    290                 295                 300

Ala Ala Ala Ala Ala Gly Gln Tyr Gly Pro Gly Val Leu Gly Pro Gly
305                 310                 315                 320

Gln Tyr Gly Pro Gly Ser Ser Gly Pro Gly Val Leu Gly Pro Tyr Gly
            325                 330                 335

Pro Gly Ser Ser Ala Ala Ala Ala Ala Gly Gln Tyr Gly Pro Gly Val
            340                 345                 350

Leu Gly Pro Tyr Gly Pro Gly Gln Ser Ala Ala Ala Ala Gly Gln
        355                 360                 365

Tyr Val Leu Gly Pro Gly Val Leu Gly Pro Tyr Gly Pro Gly Ala Ser
    370                 375                 380

Gly Pro Gly Val Leu Gly Pro Tyr Gly Pro Gly Ala Ser Ala Ala Ala
385                 390                 395                 400

Ala Ala Gly Pro Gly Gln Tyr Gly Pro Gly Val Leu Gly Pro Ser Ala
            405                 410                 415
```

-continued

Ser Ala Ala Ala Ala Ala Gly Gln Tyr Gly Ser Gly Pro Gly Gln Tyr
            420                 425                 430

Gly Pro Tyr Gly Pro Gly Gln Ser Gly Pro Gly Ser Gly Val Leu Gly
            435                 440                 445

Gln Gly Pro Tyr Gly Pro Gly Ala Ser Ala Ala Ala Ala Gly Gln
    450                 455                 460

Tyr Gly Pro Gly Val Leu Gly Pro Tyr Gly Pro Gly Gln Ser Ala Ala
465                 470                 475                 480

Ala Ala Ala Gly Pro Gly Ser Gly Gln Tyr Gly Pro Gly Ala Ser Gly
            485                 490                 495

Gln Asn Gly Pro Gly Ser Gly Gln Tyr Gly Pro Gly Val Leu Gly Pro
            500                 505                 510

Gly Gln Ser Ala Ala Ala Ala Ala Gly Gln Tyr Val Leu Gly Pro Gly
            515                 520                 525

Val Leu Gly Pro Tyr Gly Pro Gly Ala Ser Ala Ala Ala Ala Ala Gly
            530                 535                 540

Gln Tyr Gly Ser Gly Pro Gly Val Leu Gly Pro Tyr Gly Pro Gly Gln
545                 550                 555                 560

Ser Gly Ser Gly Val Leu Gly Pro Gly Val Leu Gly Pro Tyr Ala Ser
                565                 570                 575

Ala Ala Ala Ala Ala Gly Pro Gly Ser Gly Val Leu Gly Pro Gly Ala
            580                 585                 590

Ser

<210> SEQ ID NO 28
<211> LENGTH: 590
<212> TYPE: PRT
<213> ORGANISM: Artificial Sequence
<220> FEATURE:
<223> OTHER INFORMATION: M_PRT965

<400> SEQUENCE: 28

Met Gly Pro Gly Thr Ser Gly Pro Tyr Gly Pro Gly Ala Ser Ala Ala
1               5                   10                  15

Ala Ala Ala Gly Ala Asn Gly Pro Gly Ser Gly Thr Ser Gly Pro Gly
            20                  25                  30

Ala Ser Gly Ala Tyr Gly Pro Gly Thr Ser Gly Pro Gly Thr Ser Gly
        35                  40                  45

Pro Gly Ser Ser Ala Ala Ala Ala Gly Pro Gly Ala Tyr Gly Pro
    50                  55                  60

Gly Thr Ser Gly Pro Ser Ala Ser Ala Ala Ala Ala Gly Pro Gly
65                  70                  75                  80

Ser Gly Thr Ser Gly Pro Gly Ala Ser Gly Ala Tyr Gly Pro Gly Thr
                85                  90                  95

Ser Gly Pro Gly Thr Ser Gly Pro Gly Ser Ser Ala Ala Ala Ala
            100                 105                 110

Gly Ala Tyr Gly Ser Gly Pro Gly Thr Ser Gly Pro Tyr Gly Ser Ala
            115                 120                 125

Ala Ala Ala Ala Gly Pro Gly Ser Gly Ala Tyr Gly Ala Gly Pro Tyr
    130                 135                 140

Gly Pro Gly Ala Ser Gly Pro Gly Ala Tyr Gly Pro Gly Thr Ser Gly
145                 150                 155                 160

Pro Ser Ala Ser Ala Ala Ala Ala Ala Gly Ser Gly Thr Ser Gly Pro
            165                 170                 175

-continued

```
Gly Ala Tyr Gly Pro Tyr Ala Ser Ala Ala Ala Ala Gly Ala Tyr
            180                 185                 190

Gly Ser Gly Pro Gly Thr Ser Gly Pro Tyr Gly Pro Gly Ala Ser Gly
        195                 200                 205

Ser Gly Thr Ser Gly Pro Gly Thr Ser Gly Pro Tyr Ala Ser Ala Ala
    210                 215                 220

Ala Ala Ala Gly Pro Gly Thr Ser Gly Pro Tyr Gly Pro Gly Ser Ser
225                 230                 235                 240

Ala Ala Ala Ala Ala Gly Ala Tyr Gly Tyr Gly Pro Gly Thr Ser Gly
                245                 250                 255

Pro Tyr Gly Pro Gly Ala Ser Gly Ala Asn Gly Pro Gly Ser Gly Ala
        260                 265                 270

Tyr Gly Pro Gly Thr Ser Gly Pro Gly Ala Ser Ala Ala Ala Ala Ala
        275                 280                 285

Gly Pro Gly Thr Ser Gly Pro Tyr Gly Pro Gly Ala Ser Ala Ala Ala
    290                 295                 300

Ala Ala Gly Ala Tyr Gly Pro Gly Thr Ser Gly Pro Gly Ala Tyr Gly
305                 310                 315                 320

Pro Gly Ser Ser Gly Pro Gly Thr Ser Gly Pro Tyr Gly Pro Gly Ser
                325                 330                 335

Ser Ala Ala Ala Ala Ala Gly Ala Tyr Gly Pro Gly Thr Ser Gly Pro
        340                 345                 350

Tyr Gly Pro Gly Ala Ser Ala Ala Ala Ala Ala Gly Ala Tyr Thr Ser
        355                 360                 365

Gly Pro Gly Thr Ser Gly Pro Tyr Gly Pro Gly Ala Ser Gly Pro Gly
    370                 375                 380

Thr Ser Gly Pro Tyr Gly Pro Gly Ala Ser Ala Ala Ala Ala Ala Gly
385                 390                 395                 400

Pro Gly Ala Tyr Gly Pro Gly Thr Ser Gly Pro Ser Ala Ser Ala Ala
                405                 410                 415

Ala Ala Ala Gly Ala Tyr Gly Ser Gly Pro Gly Ala Tyr Gly Pro Tyr
        420                 425                 430

Gly Pro Gly Ala Ser Gly Pro Gly Ser Gly Thr Ser Gly Ala Gly Pro
    435                 440                 445

Tyr Gly Pro Gly Ala Ser Ala Ala Ala Ala Gly Ala Tyr Gly Pro
    450                 455                 460

Gly Thr Ser Gly Pro Tyr Gly Pro Gly Ala Ser Ala Ala Ala Ala Ala
465                 470                 475                 480

Gly Pro Gly Ser Gly Ala Tyr Gly Pro Gly Ala Ser Gly Ala Asn Gly
                485                 490                 495

Pro Gly Ser Gly Ala Tyr Gly Pro Gly Thr Ser Gly Pro Gly Ala Ser
            500                 505                 510

Ala Ala Ala Ala Ala Gly Ala Tyr Thr Ser Gly Pro Gly Thr Ser Gly
        515                 520                 525

Pro Tyr Gly Pro Gly Ala Ser Ala Ala Ala Ala Gly Ala Tyr Gly
        530                 535                 540

Ser Gly Pro Gly Thr Ser Gly Pro Tyr Gly Pro Gly Ala Ser Gly Ser
545                 550                 555                 560

Gly Thr Ser Gly Pro Gly Thr Ser Gly Pro Tyr Ala Ser Ala Ala Ala
                565                 570                 575

Ala Ala Gly Pro Gly Ser Gly Thr Ser Gly Pro Gly Ala Ser
        580                 585                 590
```

```
<210> SEQ ID NO 29
<211> LENGTH: 593
<212> TYPE: PRT
<213> ORGANISM: Artificial Sequence
<220> FEATURE:
<223> OTHER INFORMATION: M_PRT889

<400> SEQUENCE: 29

Met Gly Ser Ser Gly Pro Gly Val Leu Gly Pro Tyr Gly Pro Gly Ala
1               5                   10                  15

Ser Ala Ala Ala Ala Gly Ile Asn Gly Pro Gly Ser Gly Val Leu
            20                  25                  30

Gly Pro Gly Ile Ser Gly Ile Tyr Gly Pro Gly Val Leu Gly Pro Gly
            35                  40                  45

Val Leu Gly Pro Gly Ser Ser Ala Ala Ala Ala Gly Pro Gly Ile
        50                  55                  60

Tyr Gly Pro Gly Val Leu Gly Pro Ser Ala Ser Ala Ala Ala Ala
65                  70                  75                  80

Gly Pro Gly Ser Gly Val Leu Gly Pro Gly Ala Ser Gly Ile Tyr Gly
                85                  90                  95

Pro Gly Val Leu Gly Pro Gly Val Leu Gly Pro Gly Ser Ser Ala Ala
            100                 105                 110

Ala Ala Ala Gly Ile Tyr Gly Ser Gly Pro Gly Val Leu Gly Pro Tyr
            115                 120                 125

Gly Ser Ala Ala Ala Ala Ala Gly Pro Gly Ser Gly Ile Tyr Gly Ile
        130                 135                 140

Gly Pro Tyr Gly Pro Gly Ala Ser Gly Pro Gly Ile Tyr Gly Pro Gly
145                 150                 155                 160

Val Leu Gly Pro Ser Ala Ser Ala Ala Ala Ala Gly Ser Gly Val
                165                 170                 175

Leu Gly Pro Gly Ile Tyr Gly Pro Tyr Ala Ser Ala Ala Ala Ala
            180                 185                 190

Gly Ile Tyr Gly Ser Gly Pro Gly Val Leu Gly Pro Tyr Gly Pro Gly
            195                 200                 205

Ile Ser Gly Ser Gly Val Leu Gly Pro Gly Val Leu Gly Pro Tyr Ala
        210                 215                 220

Ser Ala Ala Ala Ala Ala Gly Pro Gly Val Leu Gly Pro Tyr Gly Pro
225                 230                 235                 240

Gly Ser Ser Ala Ala Ala Ala Gly Ile Tyr Gly Tyr Gly Pro Gly
            245                 250                 255

Val Leu Gly Pro Tyr Gly Pro Gly Ala Ser Gly Ile Asn Gly Pro Gly
            260                 265                 270

Ser Gly Ile Tyr Gly Pro Gly Val Leu Gly Pro Gly Ile Ser Ala Ala
            275                 280                 285

Ala Ala Ala Gly Pro Gly Val Leu Gly Pro Tyr Gly Pro Gly Ala Ser
    290                 295                 300

Ala Ala Ala Ala Ala Gly Ile Tyr Gly Pro Gly Val Leu Gly Pro Gly
305                 310                 315                 320

Ile Tyr Gly Pro Gly Ser Ser Gly Pro Gly Val Leu Gly Pro Tyr Gly
                325                 330                 335

Pro Gly Ser Ser Ala Ala Ala Ala Gly Ile Tyr Gly Pro Gly Val
            340                 345                 350

Leu Gly Pro Tyr Gly Pro Gly Ile Ser Ala Ala Ala Ala Gly Ile
            355                 360                 365

Tyr Val Leu Gly Pro Gly Val Leu Gly Pro Tyr Gly Pro Gly Ala Ser
```

-continued

```
            370             375             380
Gly Pro Gly Val Leu Gly Pro Tyr Gly Pro Gly Ala Ser Ala Ala Ala
385             390             395             400

Ala Ala Gly Pro Gly Ile Tyr Gly Pro Gly Val Leu Gly Pro Ser Ala
            405             410             415

Ser Ala Ala Ala Ala Ala Gly Ile Tyr Gly Ser Gly Pro Gly Ile Tyr
            420             425             430

Gly Pro Tyr Gly Pro Gly Ile Ser Gly Pro Gly Ser Gly Val Leu Gly
            435             440             445

Ile Gly Pro Tyr Gly Pro Gly Ala Ser Ala Ala Ala Ala Gly Ile
            450             455             460

Tyr Gly Pro Gly Val Leu Gly Pro Tyr Gly Pro Gly Ile Ser Ala Ala
465             470             475             480

Ala Ala Ala Gly Pro Gly Ser Gly Ile Tyr Gly Pro Gly Ala Ser Gly
            485             490             495

Ile Asn Gly Pro Gly Ser Gly Ile Tyr Gly Pro Gly Val Leu Gly Pro
            500             505             510

Gly Ile Ser Ala Ala Ala Ala Gly Ile Tyr Val Leu Gly Pro Gly
            515             520             525

Val Leu Gly Pro Tyr Gly Pro Gly Ala Ser Ala Ala Ala Ala Ala Gly
            530             535             540

Ile Tyr Gly Ser Gly Pro Gly Val Leu Gly Pro Tyr Gly Pro Gly Ile
545             550             555             560

Ser Gly Ser Gly Val Leu Gly Pro Gly Val Leu Gly Pro Tyr Ala Ser
            565             570             575

Ala Ala Ala Ala Ala Gly Pro Gly Ser Gly Val Leu Gly Pro Gly Ala
            580             585             590

Ser
```

```
<210> SEQ ID NO 30
<211> LENGTH: 590
<212> TYPE: PRT
<213> ORGANISM: Artificial Sequence
<220> FEATURE:
<223> OTHER INFORMATION: M_PRT916

<400> SEQUENCE: 30
```

```
Met Gly Pro Gly Val Ile Gly Pro Tyr Gly Pro Gly Ala Ser Ala Ala
1               5               10              15

Ala Ala Ala Gly Leu Asn Gly Pro Gly Ser Gly Val Ile Gly Pro Gly
            20              25              30

Leu Ser Gly Leu Tyr Gly Pro Gly Val Ile Gly Pro Gly Val Ile Gly
            35              40              45

Pro Gly Ser Ser Ala Ala Ala Ala Gly Pro Gly Leu Tyr Gly Pro
            50              55              60

Gly Val Ile Gly Pro Ser Ala Ser Ala Ala Ala Ala Gly Pro Gly
65              70              75              80

Ser Gly Val Ile Gly Pro Gly Ala Ser Gly Leu Tyr Gly Pro Gly Val
            85              90              95

Ile Gly Pro Gly Val Ile Gly Pro Gly Ser Ser Ala Ala Ala Ala Ala
            100             105             110

Gly Leu Tyr Gly Ser Gly Pro Gly Val Ile Gly Pro Tyr Gly Ser Ala
            115             120             125

Ala Ala Ala Ala Gly Pro Gly Ser Gly Leu Tyr Gly Leu Gly Pro Tyr
            130             135             140
```

-continued

```
Gly Pro Gly Ala Ser Gly Pro Gly Leu Tyr Gly Pro Gly Val Ile Gly
145                 150                 155                 160

Pro Ser Ala Ser Ala Ala Ala Ala Gly Ser Gly Val Ile Gly Pro
                165                 170                 175

Gly Leu Tyr Gly Pro Tyr Ala Ser Ala Ala Ala Ala Gly Leu Tyr
            180                 185                 190

Gly Ser Gly Pro Gly Val Ile Gly Pro Tyr Gly Pro Gly Leu Ser Gly
            195                 200                 205

Ser Gly Val Ile Gly Pro Gly Val Ile Gly Pro Tyr Ala Ser Ala Ala
    210                 215                 220

Ala Ala Ala Gly Pro Gly Val Ile Gly Pro Tyr Gly Pro Gly Ser Ser
225                 230                 235                 240

Ala Ala Ala Ala Ala Gly Leu Tyr Gly Tyr Gly Pro Gly Val Ile Gly
                245                 250                 255

Pro Tyr Gly Pro Gly Ala Ser Gly Leu Asn Gly Pro Gly Ser Gly Leu
            260                 265                 270

Tyr Gly Pro Gly Val Ile Gly Pro Gly Leu Ser Ala Ala Ala Ala Ala
            275                 280                 285

Gly Pro Gly Val Ile Gly Pro Tyr Gly Pro Gly Ala Ser Ala Ala Ala
    290                 295                 300

Ala Ala Gly Leu Tyr Gly Pro Gly Val Ile Gly Pro Gly Leu Tyr Gly
305                 310                 315                 320

Pro Gly Ser Ser Gly Pro Gly Val Ile Gly Pro Tyr Gly Pro Gly Ser
            325                 330                 335

Ser Ala Ala Ala Ala Ala Gly Leu Tyr Gly Pro Gly Val Ile Gly Pro
            340                 345                 350

Tyr Gly Pro Gly Leu Ser Ala Ala Ala Ala Gly Leu Tyr Val Ile
            355                 360                 365

Gly Pro Gly Val Ile Gly Pro Tyr Gly Pro Gly Ala Ser Gly Pro Gly
    370                 375                 380

Val Ile Gly Pro Tyr Gly Pro Gly Ala Ser Ala Ala Ala Ala Ala Gly
385                 390                 395                 400

Pro Gly Leu Tyr Gly Pro Gly Val Ile Gly Pro Ser Ala Ser Ala Ala
            405                 410                 415

Ala Ala Ala Gly Leu Tyr Gly Ser Gly Pro Gly Leu Tyr Gly Pro Tyr
            420                 425                 430

Gly Pro Gly Leu Ser Gly Pro Gly Ser Gly Val Ile Gly Leu Gly Pro
            435                 440                 445

Tyr Gly Pro Gly Ala Ser Ala Ala Ala Ala Ala Gly Leu Tyr Gly Pro
    450                 455                 460

Gly Val Ile Gly Pro Tyr Gly Pro Gly Leu Ser Ala Ala Ala Ala Ala
465                 470                 475                 480

Gly Pro Gly Ser Gly Leu Tyr Gly Pro Gly Ala Ser Gly Leu Asn Gly
            485                 490                 495

Pro Gly Ser Gly Leu Tyr Gly Pro Gly Val Ile Gly Pro Gly Leu Ser
            500                 505                 510

Ala Ala Ala Ala Ala Gly Leu Tyr Val Ile Gly Pro Gly Val Ile Gly
            515                 520                 525

Pro Tyr Gly Pro Gly Ala Ser Ala Ala Ala Ala Gly Leu Tyr Gly
            530                 535                 540

Ser Gly Pro Gly Val Ile Gly Pro Tyr Gly Pro Gly Leu Ser Gly Ser
545                 550                 555                 560
```

-continued

```
Gly Val Ile Gly Pro Gly Val Ile Gly Pro Tyr Ala Ser Ala Ala Ala
            565             570                 575

Ala Ala Gly Pro Gly Ser Gly Val Ile Gly Pro Gly Ala Ser
            580             585                 590

<210> SEQ ID NO 31
<211> LENGTH: 590
<212> TYPE: PRT
<213> ORGANISM: Artificial Sequence
<220> FEATURE:
<223> OTHER INFORMATION: M_ PRT918

<400> SEQUENCE: 31

Met Gly Pro Gly Val Phe Gly Pro Tyr Gly Pro Gly Ala Ser Ala Ala
1               5                   10                  15

Ala Ala Ala Gly Ile Asn Gly Pro Gly Ser Gly Val Phe Gly Pro Gly
            20                  25                  30

Ile Ser Gly Ile Tyr Gly Pro Gly Val Phe Gly Pro Gly Val Phe Gly
            35                  40                  45

Pro Gly Ser Ser Ala Ala Ala Ala Ala Gly Pro Gly Ile Tyr Gly Pro
    50                  55                  60

Gly Val Phe Gly Pro Ser Ala Ser Ala Ala Ala Ala Gly Pro Gly
65                  70                  75                  80

Ser Gly Val Phe Gly Pro Gly Ala Ser Gly Ile Tyr Gly Pro Gly Val
                85                  90                  95

Phe Gly Pro Gly Val Phe Gly Pro Gly Ser Ser Ala Ala Ala Ala Ala
            100                 105                 110

Gly Ile Tyr Gly Ser Gly Pro Gly Val Phe Gly Pro Tyr Gly Ser Ala
            115                 120                 125

Ala Ala Ala Gly Pro Gly Ser Gly Ile Tyr Gly Ile Gly Pro Tyr
            130                 135                 140

Gly Pro Gly Ala Ser Gly Pro Gly Ile Tyr Gly Pro Gly Val Phe Gly
145                 150                 155                 160

Pro Ser Ala Ser Ala Ala Ala Ala Ala Gly Ser Gly Val Phe Gly Pro
                165                 170                 175

Gly Ile Tyr Gly Pro Tyr Ala Ser Ala Ala Ala Ala Ala Gly Ile Tyr
            180                 185                 190

Gly Ser Gly Pro Gly Val Phe Gly Pro Tyr Gly Pro Gly Ile Ser Gly
            195                 200                 205

Ser Gly Val Phe Gly Pro Gly Val Phe Gly Pro Tyr Ala Ser Ala Ala
    210                 215                 220

Ala Ala Ala Gly Pro Gly Val Phe Gly Pro Tyr Gly Pro Gly Ser Ser
225                 230                 235                 240

Ala Ala Ala Ala Ala Gly Ile Tyr Gly Tyr Gly Pro Gly Val Phe Gly
                245                 250                 255

Pro Tyr Gly Pro Gly Ala Ser Gly Ile Asn Gly Pro Gly Ser Gly Ile
            260                 265                 270

Tyr Gly Pro Gly Val Phe Gly Pro Gly Ile Ser Ala Ala Ala Ala Ala
            275                 280                 285

Gly Pro Gly Val Phe Gly Pro Tyr Gly Pro Gly Ala Ser Ala Ala Ala
    290                 295                 300

Ala Ala Gly Ile Tyr Gly Pro Gly Val Phe Gly Pro Gly Ile Tyr Gly
305                 310                 315                 320

Pro Gly Ser Ser Gly Pro Gly Val Phe Gly Pro Tyr Gly Pro Gly Ser
            325                 330                 335
```

Ser Ala Ala Ala Ala Ala Gly Ile Tyr Gly Pro Gly Val Phe Gly Pro
            340                 345                 350

Tyr Gly Pro Gly Ile Ser Ala Ala Ala Ala Gly Ile Tyr Val Phe
            355                 360                 365

Gly Pro Gly Val Phe Gly Pro Tyr Gly Pro Gly Ala Ser Gly Pro Gly
            370                 375                 380

Val Phe Gly Pro Tyr Gly Pro Gly Ala Ser Ala Ala Ala Ala Gly
385                 390                 395                 400

Pro Gly Ile Tyr Gly Pro Gly Val Phe Gly Pro Ser Ala Ser Ala Ala
                405                 410                 415

Ala Ala Ala Gly Ile Tyr Gly Ser Gly Pro Gly Ile Tyr Gly Pro Tyr
            420                 425                 430

Gly Pro Gly Ile Ser Gly Pro Gly Ser Gly Val Phe Gly Ile Gly Pro
            435                 440                 445

Tyr Gly Pro Gly Ala Ser Ala Ala Ala Ala Gly Ile Tyr Gly Pro
    450                 455                 460

Gly Val Phe Gly Pro Tyr Gly Pro Gly Ile Ser Ala Ala Ala Ala Ala
465                 470                 475                 480

Gly Pro Gly Ser Gly Ile Tyr Gly Pro Gly Ala Ser Gly Ile Asn Gly
            485                 490                 495

Pro Gly Ser Gly Ile Tyr Gly Pro Gly Val Phe Gly Pro Gly Ile Ser
            500                 505                 510

Ala Ala Ala Ala Ala Gly Ile Tyr Val Phe Gly Pro Gly Val Phe Gly
            515                 520                 525

Pro Tyr Gly Pro Gly Ala Ser Ala Ala Ala Ala Gly Ile Tyr Gly
    530                 535                 540

Ser Gly Pro Gly Val Phe Gly Pro Tyr Gly Pro Gly Ile Ser Gly Ser
545                 550                 555                 560

Gly Val Phe Gly Pro Gly Val Phe Gly Pro Tyr Ala Ser Ala Ala Ala
            565                 570                 575

Ala Ala Gly Pro Gly Ser Gly Val Phe Gly Pro Gly Ala Ser
            580                 585                 590

<210> SEQ ID NO 32
<211> LENGTH: 565
<212> TYPE: PRT
<213> ORGANISM: Artificial Sequence
<220> FEATURE:
<223> OTHER INFORMATION: M_PRT699

<400> SEQUENCE: 32

Met Gly Pro Gly Val Leu Gly Pro Tyr Gly Pro Gly Ala Ser Ala Ala
1               5                   10                  15

Ala Ala Ala Ala Ala Gly Ser Asn Gly Pro Gly Ser Gly Val Leu Gly
            20                  25                  30

Pro Gly Gln Ser Gly Gln Tyr Gly Pro Gly Val Leu Gly Pro Gly Val
        35                  40                  45

Leu Gly Pro Gly Ser Ser Ala Ala Ala Ala Ala Ala Gly Pro Gly
    50                  55                  60

Gln Tyr Gly Pro Gly Val Leu Gly Pro Ser Ala Ser Ala Ala Ala Ala
65                  70                  75                  80

Ala Ala Ala Gly Pro Gly Ser Gly Val Leu Gly Pro Gly Ala Ser Gly
            85                  90                  95

Gln Tyr Gly Pro Gly Val Leu Gly Pro Gly Val Leu Gly Pro Gly Ser
            100                 105                 110

```
Ser Ala Ala Ala Ala Ala Ala Gly Ser Tyr Gly Ser Gly Pro Gly
        115                 120             125

Val Leu Gly Pro Tyr Gly Ser Ala Ala Ala Ala Ala Ala Gly Pro
    130                 135             140

Gly Ser Gly Gln Tyr Gly Gln Gly Pro Tyr Gly Pro Gly Ala Ser Gly
145                 150             155             160

Pro Gly Gln Tyr Gly Pro Gly Val Leu Gly Pro Ser Ala Ser Ala Ala
            165             170             175

Ala Ala Ala Ala Ala Gly Ser Gly Val Leu Gly Pro Gly Gln Tyr Gly
            180             185             190

Pro Tyr Ala Ser Ala Ala Ala Ala Ala Ala Gly Ser Tyr Gly Ser
    195                 200             205

Gly Pro Gly Val Leu Gly Pro Tyr Gly Pro Gly Gln Ser Gly Ser Gly
    210                 215             220

Val Leu Gly Pro Gly Val Leu Gly Pro Tyr Ala Ser Ala Ala Ala Ala
225                 230             235             240

Ala Ala Ala Gly Pro Gly Val Leu Gly Pro Tyr Gly Pro Gly Ser Ser
            245             250             255

Ala Ala Ala Ala Ala Ala Ala Gly Ser Tyr Gly Tyr Gly Pro Gly Val
            260             265             270

Leu Gly Pro Tyr Gly Pro Gly Ala Ser Gly Gln Asn Gly Pro Gly Ser
    275             280             285

Gly Gln Tyr Gly Pro Gly Val Leu Gly Pro Gly Pro Ser Ala Ala Ala
    290             295             300

Ala Ala Ala Ala Gly Pro Gly Val Leu Gly Pro Tyr Gly Pro Gly Ala
305             310             315             320

Ser Ala Ala Ala Ala Ala Ala Ala Gly Ser Tyr Gly Pro Gly Val Leu
        325             330             335

Gly Pro Gly Gln Tyr Gly Pro Gly Ser Ser Gly Pro Gly Val Leu Gly
        340             345             350

Pro Tyr Gly Pro Gly Ser Ser Ala Ala Ala Ala Ala Ala Gly Ser
    355             360             365

Tyr Gly Pro Gly Val Leu Gly Pro Tyr Gly Pro Gly Pro Ser Ala Ala
    370             375             380

Ala Ala Ala Ala Ala Gly Ser Tyr Val Leu Gly Pro Gly Val Leu Gly
385             390             395             400

Pro Tyr Gly Pro Gly Ala Ser Gly Pro Gly Val Leu Gly Pro Tyr Gly
            405             410             415

Pro Gly Ala Ser Ala Ala Ala Ala Ala Ala Gly Pro Gly Gln Tyr
            420             425             430

Gly Pro Gly Val Leu Gly Pro Ser Ala Ser Ala Ala Ala Ala Ala
        435             440             445

Ala Gly Ser Tyr Gly Ser Gly Pro Gly Gln Tyr Gly Pro Tyr Gly Pro
    450             455             460

Gly Gln Ser Gly Pro Gly Ser Gly Val Leu Gly Gln Gly Pro Tyr Gly
465                 470             475             480

Pro Gly Ala Ser Ala Ala Ala Ala Ala Ala Gly Ser Tyr Gly Pro
            485             490             495

Gly Val Leu Gly Pro Tyr Gly Pro Gly Pro Ser Ala Ala Ala Ala Ala
        500             505             510

Ala Ala Gly Pro Gly Ser Gly Gln Tyr Gly Pro Gly Ala Ser Gly Gln
    515             520             525

Asn Gly Pro Gly Ser Gly Gln Tyr Gly Pro Gly Val Leu Gly Pro Gly
```

-continued

```
        530              535              540

Pro Ser Ala Ala Ala Ala Ala Ala Ala Gly Pro Gly Ser Gly Val Leu
545              550              555              560

Gly Pro Gly Ala Ser
            565

<210> SEQ ID NO 33
<211> LENGTH: 565
<212> TYPE: PRT
<213> ORGANISM: Artificial Sequence
<220> FEATURE:
<223> OTHER INFORMATION: M_PRT698

<400> SEQUENCE: 33

Met Gly Pro Gly Val Leu Gly Pro Tyr Gly Pro Gly Ala Ser Ala Ala
1               5               10              15

Ala Ala Ala Ala Ala Gly Ser Asn Gly Pro Gly Ser Gly Val Leu Gly
            20              25              30

Pro Gly Ile Ser Gly Ile Tyr Gly Pro Gly Val Leu Gly Pro Gly Val
            35              40              45

Leu Gly Pro Gly Ser Ser Ala Ala Ala Ala Ala Ala Gly Pro Gly
    50              55              60

Ile Tyr Gly Pro Gly Val Leu Gly Pro Ser Ala Ser Ala Ala Ala Ala
65              70              75              80

Ala Ala Ala Gly Pro Gly Ser Gly Val Leu Gly Pro Gly Ala Ser Gly
            85              90              95

Ile Tyr Gly Pro Gly Val Leu Gly Pro Gly Val Leu Gly Pro Gly Ser
            100             105             110

Ser Ala Ala Ala Ala Ala Ala Ala Gly Ser Tyr Gly Ser Gly Pro Gly
        115             120             125

Val Leu Gly Pro Tyr Gly Ser Ala Ala Ala Ala Ala Ala Gly Pro
    130             135             140

Gly Ser Gly Ile Tyr Gly Ile Gly Pro Tyr Gly Pro Gly Ala Ser Gly
145             150             155             160

Pro Gly Ile Tyr Gly Pro Gly Val Leu Gly Pro Ser Ala Ser Ala Ala
            165             170             175

Ala Ala Ala Ala Ala Gly Ser Gly Val Leu Gly Pro Gly Ile Tyr Gly
            180             185             190

Pro Tyr Ala Ser Ala Ala Ala Ala Ala Ala Gly Ser Tyr Gly Ser
        195             200             205

Gly Pro Gly Val Leu Gly Pro Tyr Gly Pro Gly Ile Ser Gly Ser Gly
    210             215             220

Val Leu Gly Pro Gly Val Leu Gly Pro Tyr Ala Ser Ala Ala Ala Ala
225             230             235             240

Ala Ala Ala Gly Pro Gly Val Leu Gly Pro Tyr Gly Pro Gly Ser Ser
            245             250             255

Ala Ala Ala Ala Ala Ala Ala Gly Ser Tyr Gly Tyr Gly Pro Gly Val
            260             265             270

Leu Gly Pro Tyr Gly Pro Gly Ala Ser Gly Ile Asn Gly Pro Gly Ser
        275             280             285

Gly Ile Tyr Gly Pro Gly Val Leu Gly Pro Gly Pro Ser Ala Ala Ala
    290             295             300

Ala Ala Ala Ala Gly Pro Gly Val Leu Gly Pro Tyr Gly Pro Gly Ala
305             310             315             320

Ser Ala Ala Ala Ala Ala Ala Ala Gly Ser Tyr Gly Pro Gly Val Leu
```

-continued

```
                325               330               335
Gly Pro Gly Ile Tyr Gly Pro Gly Ser Ser Gly Pro Gly Val Leu Gly
                340               345               350

Pro Tyr Gly Pro Gly Ser Ser Ala Ala Ala Ala Ala Ala Ala Gly Ser
                355               360               365

Tyr Gly Pro Gly Val Leu Gly Pro Tyr Gly Pro Gly Pro Ser Ala Ala
    370               375               380

Ala Ala Ala Ala Ala Gly Ser Tyr Val Leu Gly Pro Gly Val Leu Gly
385               390               395               400

Pro Tyr Gly Pro Gly Ala Ser Gly Pro Gly Val Leu Gly Pro Tyr Gly
                405               410               415

Pro Gly Ala Ser Ala Ala Ala Ala Ala Ala Gly Pro Gly Ile Tyr
                420               425               430

Gly Pro Gly Val Leu Gly Pro Ser Ala Ser Ala Ala Ala Ala Ala Ala
                435               440               445

Ala Gly Ser Tyr Gly Ser Gly Pro Gly Ile Tyr Gly Pro Tyr Gly Pro
    450               455               460

Gly Ile Ser Gly Pro Gly Ser Gly Val Leu Gly Ile Gly Pro Tyr Gly
465               470               475               480

Pro Gly Ala Ser Ala Ala Ala Ala Ala Ala Gly Ser Tyr Gly Pro
                485               490               495

Gly Val Leu Gly Pro Tyr Gly Pro Gly Pro Ser Ala Ala Ala Ala Ala
                500               505               510

Ala Ala Gly Pro Gly Ser Gly Ile Tyr Gly Pro Gly Ala Ser Gly Ile
                515               520               525

Asn Gly Pro Gly Ser Gly Ile Tyr Gly Pro Gly Val Leu Gly Pro Gly
    530               535               540

Pro Ser Ala Ala Ala Ala Ala Ala Gly Pro Gly Ser Gly Val Leu
545               550               555               560

Gly Pro Gly Ala Ser
                565
```

```
<210> SEQ ID NO 34
<211> LENGTH: 565
<212> TYPE: PRT
<213> ORGANISM: Artificial Sequence
<220> FEATURE:
<223> OTHER INFORMATION: M_PRT525

<400> SEQUENCE: 34

Met Gly Pro Gly Gln Gln Gly Pro Tyr Gly Pro Gly Ala Ser Ala Ala
1               5               10               15

Ala Ala Ala Ala Ala Gly Ser Asn Gly Pro Gly Ser Gly Gln Gln Gly
                20               25               30

Pro Gly Gln Ser Gly Gln Tyr Gly Pro Gly Gln Gln Gly Pro Gly Gln
                35               40               45

Gln Gly Pro Gly Ser Ser Ala Ala Ala Ala Ala Ala Gly Pro Gly
    50               55               60

Gln Tyr Gly Pro Gly Gln Gln Gly Pro Ser Ala Ser Ala Ala Ala Ala
65               70               75               80

Ala Ala Ala Gly Pro Gly Ser Gly Gln Gln Gly Pro Gly Ala Ser Gly
                85               90               95

Gln Tyr Gly Pro Gly Gln Gln Gly Pro Gly Gln Gln Gly Pro Gly Ser
                100               105               110

Ser Ala Ala Ala Ala Ala Ala Ala Gly Ser Tyr Gly Ser Gly Pro Gly
```

-continued

```
                115                 120                 125

Gln Gln Gly Pro Tyr Gly Ser Ala Ala Ala Ala Ala Ala Gly Pro
    130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Gln Gln Gly Pro Ser Ala Ser Ala Ala
                165                 170                 175

Ala Ala Ala Ala Ala Gly Ser Gly Gln Gln Gly Pro Gly Gln Tyr Gly
                180                 185                 190

Pro Tyr Ala Ser Ala Ala Ala Ala Ala Ala Gly Ser Tyr Gly Ser
                195                 200                 205

Gly Pro Gly Gln Gln Gly Pro Tyr Gly Pro Gly Gln Ser Gly Ser Gly
    210                 215                 220

Gln Gln Gly Pro Gly Gln Gln Gly Pro Tyr Ala Ser Ala Ala Ala Ala
225                 230                 235                 240

Ala Ala Ala Gly Pro Gly Gln Gln Gly Pro Tyr Gly Pro Gly Ser Ser
                245                 250                 255

Ala Ala Ala Ala Ala Ala Ala Gly Ser Tyr Gly Tyr Gly Pro Gly Gln
                260                 265                 270

Gln Gly Pro Tyr Gly Pro Gly Ala Ser Gly Gln Asn Gly Pro Gly Ser
                275                 280                 285

Gly Gln Tyr Gly Pro Gly Gln Gln Gly Pro Gly Pro Ser Ala Ala Ala
    290                 295                 300

Ala Ala Ala Ala Gly Pro Gly Gln Gln Gly Pro Tyr Gly Pro Gly Ala
305                 310                 315                 320

Ser Ala Ala Ala Ala Ala Ala Ala Gly Ser Tyr Gly Pro Gly Gln Gln
                325                 330                 335

Gly Pro Gly Gln Tyr Gly Pro Gly Ser Ser Gly Pro Gly Gln Gln Gly
    340                 345                 350

Pro Tyr Gly Pro Gly Ser Ser Ala Ala Ala Ala Ala Ala Ala Gly Ser
    355                 360                 365

Tyr Gly Pro Gly Gln Gln Gly Pro Tyr Gly Pro Gly Pro Ser Ala Ala
    370                 375                 380

Ala Ala Ala Ala Ala Gly Ser Tyr Gln Gln Gly Pro Gly Gln Gln Gly
385                 390                 395                 400

Pro Tyr Gly Pro Gly Ala Ser Gly Pro Gly Gln Gln Gly Pro Tyr Gly
                405                 410                 415

Pro Gly Ala Ser Ala Ala Ala Ala Ala Ala Ala Gly Pro Gly Gln Tyr
                420                 425                 430

Gly Pro Gly Gln Gln Gly Pro Ser Ala Ser Ala Ala Ala Ala Ala Ala
    435                 440                 445

Ala Gly Ser Tyr Gly Ser Gly Pro Gly Gln Tyr Gly Pro Tyr Gly Pro
    450                 455                 460

Gly Gln Ser Gly Pro Gly Ser Gly Gln Gln Gly Gln Gly Pro Tyr Gly
465                 470                 475                 480

Pro Gly Ala Ser Ala Ala Ala Ala Ala Ala Gly Ser Tyr Gly Pro
                485                 490                 495

Gly Gln Gln Gly Pro Tyr Gly Pro Gly Pro Ser Ala Ala Ala Ala Ala
                500                 505                 510

Ala Ala Gly Pro Gly Ser Gly Gln Tyr Gly Pro Gly Ala Ser Gly Gln
    515                 520                 525

Asn Gly Pro Gly Ser Gly Gln Tyr Gly Pro Gly Gln Gln Gly Pro Gly
    530                 535                 540
```

-continued

```
Pro Ser Ala Ala Ala Ala Ala Ala Ala Gly Pro Gly Ser Gly Gln Gln
545                 550                 555                 560

Gly Pro Gly Ala Ser
                565

<210> SEQ ID NO 35
<211> LENGTH: 601
<212> TYPE: PRT
<213> ORGANISM: Artificial Sequence
<220> FEATURE:
<223> OTHER INFORMATION: PRT888

<400> SEQUENCE: 35

Met His His His His His Ser Ser Gly Ser Ser Gly Pro Gly Val
1                 5                   10                  15

Leu Gly Pro Tyr Gly Pro Gly Ala Ser Ala Ala Ala Ala Gly Gln
                20                  25                  30

Asn Gly Pro Gly Ser Gly Val Leu Gly Pro Gly Gln Ser Gly Gln Tyr
            35                  40                  45

Gly Pro Gly Val Leu Gly Pro Gly Val Leu Gly Pro Gly Ser Ser Ala
        50                  55                  60

Ala Ala Ala Ala Gly Pro Gly Gln Tyr Gly Pro Gly Val Leu Gly Pro
65                  70                  75                  80

Ser Ala Ser Ala Ala Ala Ala Ala Gly Pro Gly Ser Gly Val Leu Gly
                85                  90                  95

Pro Gly Ala Ser Gly Gln Tyr Gly Pro Gly Val Leu Gly Pro Gly Val
            100                 105                 110

Leu Gly Pro Gly Ser Ser Ala Ala Ala Ala Gly Gln Tyr Gly Ser
        115                 120                 125

Gly Pro Gly Val Leu Gly Pro Tyr Gly Ser Ala Ala Ala Ala Gly
        130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Val Leu Gly Pro Ser Ala Ser Ala
                165                 170                 175

Ala Ala Ala Gly Ser Gly Val Leu Gly Pro Gly Gln Tyr Gly Pro
            180                 185                 190

Tyr Ala Ser Ala Ala Ala Ala Gly Gln Tyr Gly Ser Gly Pro Gly
            195                 200                 205

Val Leu Gly Pro Tyr Gly Pro Gly Gln Ser Gly Ser Gly Val Leu Gly
    210                 215                 220

Pro Gly Val Leu Gly Pro Tyr Ala Ser Ala Ala Ala Ala Gly Pro
225                 230                 235                 240

Gly Val Leu Gly Pro Tyr Gly Pro Gly Ser Ser Ala Ala Ala Ala
                245                 250                 255

Gly Gln Tyr Gly Tyr Gly Pro Gly Val Leu Gly Pro Tyr Gly Pro Gly
            260                 265                 270

Ala Ser Gly Gln Asn Gly Pro Gly Ser Gly Gln Tyr Gly Pro Gly Val
        275                 280                 285

Leu Gly Pro Gly Gln Ser Ala Ala Ala Ala Gly Pro Gly Val Leu
    290                 295                 300

Gly Pro Tyr Gly Pro Gly Ala Ser Ala Ala Ala Ala Gly Gln Tyr
305                 310                 315                 320

Gly Pro Gly Val Leu Gly Pro Gly Gln Tyr Gly Pro Gly Ser Ser Gly
            325                 330                 335
```

-continued

```
Pro Gly Val Leu Gly Pro Tyr Gly Pro Gly Ser Ser Ala Ala Ala Ala
        340                 345                 350

Ala Gly Gln Tyr Gly Pro Gly Val Leu Gly Pro Tyr Gly Pro Gly Gln
        355                 360                 365

Ser Ala Ala Ala Ala Ala Gly Gln Tyr Val Leu Gly Pro Gly Val Leu
        370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Gly Pro Gly Gln Tyr Gly
        405                 410                 415

Pro Gly Val Leu Gly Pro Ser Ala Ser Ala Ala Ala Ala Gly Gln
        420                 425                 430

Tyr Gly Ser Gly Pro Gly Gln Tyr Gly Pro Tyr Gly Pro Gly Gln Ser
        435                 440                 445

Gly Pro Gly Ser Gly Val Leu Gly Gln Gly Pro Tyr Gly Pro Gly Ala
        450                 455                 460

Ser Ala Ala Ala Ala Ala Gly Gln Tyr Gly Pro Gly Val Leu Gly Pro
465                 470                 475                 480

Tyr Gly Pro Gly Gln Ser Ala Ala Ala Ala Gly Pro Gly Ser Gly
        485                 490                 495

Gln Tyr Gly Pro Gly Ala Ser Gly Gln Asn Gly Pro Gly Ser Gly Gln
        500                 505                 510

Tyr Gly Pro Gly Val Leu Gly Pro Gly Gln Ser Ala Ala Ala Ala Ala
        515                 520                 525

Gly Gln Tyr Val Leu Gly Pro Gly Val Leu Gly Pro Tyr Gly Pro Gly
        530                 535                 540

Ala Ser Ala Ala Ala Ala Ala Gly Gln Tyr Gly Ser Gly Pro Gly Val
545                 550                 555                 560

Leu Gly Pro Tyr Gly Pro Gly Gln Ser Gly Ser Gly Val Leu Gly Pro
        565                 570                 575

Gly Val Leu Gly Pro Tyr Ala Ser Ala Ala Ala Ala Gly Pro Gly
        580                 585                 590

Ser Gly Val Leu Gly Pro Gly Ala Ser
        595                 600
```

```
<210> SEQ ID NO 36
<211> LENGTH: 601
<212> TYPE: PRT
<213> ORGANISM: Artificial Sequence
<220> FEATURE:
<223> OTHER INFORMATION: PRT965

<400> SEQUENCE: 36

Met His His His His His His Ser Ser Gly Ser Ser Gly Pro Gly Thr
1               5                   10                  15

Ser Gly Pro Tyr Gly Pro Gly Ala Ser Ala Ala Ala Ala Gly Ala
        20                  25                  30

Asn Gly Pro Gly Ser Gly Thr Ser Gly Pro Gly Ala Ser Gly Ala Tyr
        35                  40                  45

Gly Pro Gly Thr Ser Gly Pro Gly Thr Ser Gly Pro Gly Ser Ser Ala
        50                  55                  60

Ala Ala Ala Ala Gly Pro Gly Ala Tyr Gly Pro Gly Thr Ser Gly Pro
65                  70                  75                  80

Ser Ala Ser Ala Ala Ala Ala Ala Gly Pro Gly Ser Gly Thr Ser Gly
        85                  90                  95
```

-continued

```
Pro Gly Ala Ser Gly Ala Tyr Gly Pro Gly Thr Ser Gly Pro Gly Thr
        100                 105             110

Ser Gly Pro Gly Ser Ser Ala Ala Ala Ala Gly Ala Tyr Gly Ser
        115             120             125

Gly Pro Gly Thr Ser Gly Pro Tyr Gly Ser Ala Ala Ala Ala Ala Gly
        130             135             140

Pro Gly Ser Gly Ala Tyr Gly Ala Gly Pro Tyr Gly Pro Gly Ala Ser
145             150             155             160

Gly Pro Gly Ala Tyr Gly Pro Gly Thr Ser Gly Pro Ser Ala Ser Ala
            165             170             175

Ala Ala Ala Ala Gly Ser Gly Thr Ser Gly Pro Gly Ala Tyr Gly Pro
        180             185             190

Tyr Ala Ser Ala Ala Ala Ala Ala Gly Ala Tyr Gly Ser Gly Pro Gly
        195             200             205

Thr Ser Gly Pro Tyr Gly Pro Gly Ala Ser Gly Ser Gly Thr Ser Gly
    210             215             220

Pro Gly Thr Ser Gly Pro Tyr Ala Ser Ala Ala Ala Ala Ala Gly Pro
225             230             235             240

Gly Thr Ser Gly Pro Tyr Gly Pro Gly Ser Ser Ala Ala Ala Ala Ala
            245             250             255

Gly Ala Tyr Gly Tyr Gly Pro Gly Thr Ser Gly Pro Tyr Gly Pro Gly
            260             265             270

Ala Ser Gly Ala Asn Gly Pro Gly Ser Gly Ala Tyr Gly Pro Gly Thr
        275             280             285

Ser Gly Pro Gly Ala Ser Ala Ala Ala Ala Gly Pro Gly Thr Ser
        290             295             300

Gly Pro Tyr Gly Pro Gly Ala Ser Ala Ala Ala Ala Gly Ala Tyr
305             310             315             320

Gly Pro Gly Thr Ser Gly Pro Gly Ala Tyr Gly Pro Gly Ser Ser Gly
            325             330             335

Pro Gly Thr Ser Gly Pro Tyr Gly Pro Gly Ser Ser Ala Ala Ala Ala
            340             345             350

Ala Gly Ala Tyr Gly Pro Gly Thr Ser Gly Pro Tyr Gly Pro Gly Ala
        355             360             365

Ser Ala Ala Ala Ala Ala Gly Ala Tyr Thr Ser Gly Pro Gly Thr Ser
    370             375             380

Gly Pro Tyr Gly Pro Gly Ala Ser Gly Pro Gly Thr Ser Gly Pro Tyr
385             390             395             400

Gly Pro Gly Ala Ser Ala Ala Ala Ala Gly Pro Gly Ala Tyr Gly
            405             410             415

Pro Gly Thr Ser Gly Pro Ser Ala Ser Ala Ala Ala Ala Gly Ala
            420             425             430

Tyr Gly Ser Gly Pro Gly Ala Tyr Gly Pro Tyr Gly Pro Gly Ala Ser
        435             440             445

Gly Pro Gly Ser Gly Thr Ser Gly Ala Gly Pro Tyr Gly Pro Gly Ala
    450             455             460

Ser Ala Ala Ala Ala Ala Gly Ala Tyr Gly Pro Gly Thr Ser Gly Pro
465             470             475             480

Tyr Gly Pro Gly Ala Ser Ala Ala Ala Ala Gly Pro Gly Ser Gly
            485             490             495

Ala Tyr Gly Pro Gly Ala Ser Gly Ala Asn Gly Pro Gly Ser Gly Ala
            500             505             510
```

```
Tyr Gly Pro Gly Thr Ser Gly Pro Gly Ala Ser Ala Ala Ala Ala Ala
        515                 520             525

Gly Ala Tyr Thr Ser Gly Pro Gly Thr Ser Gly Pro Tyr Gly Pro Gly
        530                 535             540

Ala Ser Ala Ala Ala Ala Ala Gly Ala Tyr Gly Ser Gly Pro Gly Thr
545                 550             555                 560

Ser Gly Pro Tyr Gly Pro Gly Ala Ser Gly Ser Gly Thr Ser Gly Pro
                565             570             575

Gly Thr Ser Gly Pro Tyr Ala Ser Ala Ala Ala Ala Gly Pro Gly
        580             585                 590

Ser Gly Thr Ser Gly Pro Gly Ala Ser
        595                 600

<210> SEQ ID NO 37
<211> LENGTH: 601
<212> TYPE: PRT
<213> ORGANISM: Artificial Sequence
<220> FEATURE:
<223> OTHER INFORMATION: PRT889

<400> SEQUENCE: 37

Met His His His His His His Ser Ser Gly Ser Ser Gly Pro Gly Val
1               5                   10                  15

Leu Gly Pro Tyr Gly Pro Gly Ala Ser Ala Ala Ala Ala Gly Ile
            20                  25                  30

Asn Gly Pro Gly Ser Gly Val Leu Gly Pro Gly Ile Ser Gly Ile Tyr
        35                  40                  45

Gly Pro Gly Val Leu Gly Pro Gly Val Leu Gly Pro Gly Ser Ser Ala
        50                  55                  60

Ala Ala Ala Ala Gly Pro Gly Ile Tyr Gly Pro Gly Val Leu Gly Pro
65                  70                  75                  80

Ser Ala Ser Ala Ala Ala Ala Gly Pro Gly Ser Gly Val Leu Gly
                85                  90                  95

Pro Gly Ala Ser Gly Ile Tyr Gly Pro Gly Val Leu Gly Pro Gly Val
            100                 105                 110

Leu Gly Pro Gly Ser Ser Ala Ala Ala Ala Gly Ile Tyr Gly Ser
            115                 120                 125

Gly Pro Gly Val Leu Gly Pro Tyr Gly Ser Ala Ala Ala Ala Gly
        130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Leu Gly Pro Ser Ala Ser Ala
                165                 170                 175

Ala Ala Ala Gly Ser Gly Val Leu Gly Pro Gly Ile Tyr Gly Pro
            180                 185                 190

Tyr Ala Ser Ala Ala Ala Ala Gly Ile Tyr Gly Ser Gly Pro Gly
            195                 200                 205

Val Leu Gly Pro Tyr Gly Pro Gly Ile Ser Gly Ser Gly Val Leu Gly
        210                 215                 220

Pro Gly Val Leu Gly Pro Tyr Ala Ser Ala Ala Ala Ala Gly Pro
225                 230                 235                 240

Gly Val Leu Gly Pro Tyr Gly Pro Gly Ser Ser Ala Ala Ala Ala
            245                 250                 255

Gly Ile Tyr Gly Tyr Gly Pro Gly Val Leu Gly Pro Tyr Gly Pro Gly
        260                 265                 270
```

-continued

```
Ala Ser Gly Ile Asn Gly Pro Gly Ser Gly Ile Tyr Gly Pro Gly Val
        275                 280                 285

Leu Gly Pro Gly Ile Ser Ala Ala Ala Ala Gly Pro Gly Val Leu
        290                 295                 300

Gly Pro Tyr Gly Pro Gly Ala Ser Ala Ala Ala Ala Gly Ile Tyr
305                 310                 315                 320

Gly Pro Gly Val Leu Gly Pro Gly Ile Tyr Gly Pro Gly Ser Ser Gly
                325                 330                 335

Pro Gly Val Leu Gly Pro Tyr Gly Pro Gly Ser Ser Ala Ala Ala
                340                 345                 350

Ala Gly Ile Tyr Gly Pro Gly Val Leu Gly Pro Tyr Gly Pro Gly Ile
            355                 360                 365

Ser Ala Ala Ala Ala Ala Gly Ile Tyr Val Leu Gly Pro Gly Val Leu
    370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Gly Pro Gly Ile Tyr Gly
                405                 410                 415

Pro Gly Val Leu Gly Pro Ser Ala Ser Ala Ala Ala Ala Gly Ile
                420                 425                 430

Tyr Gly Ser Gly Pro Gly Ile Tyr Gly Pro Tyr Gly Pro Gly Ile Ser
            435                 440                 445

Gly Pro Gly Ser Gly Val Leu Gly Ile Gly Pro Tyr Gly Pro Gly Ala
        450                 455                 460

Ser Ala Ala Ala Ala Ala Gly Ile Tyr Gly Pro Gly Val Leu Gly Pro
465                 470                 475                 480

Tyr Gly Pro Gly Ile Ser Ala Ala Ala Ala Gly Pro Gly Ser Gly
                485                 490                 495

Ile Tyr Gly Pro Gly Ala Ser Gly Ile Asn Gly Pro Gly Ser Gly Ile
            500                 505                 510

Tyr Gly Pro Gly Val Leu Gly Pro Gly Ile Ser Ala Ala Ala Ala Ala
            515                 520                 525

Gly Ile Tyr Val Leu Gly Pro Gly Val Leu Gly Pro Tyr Gly Pro Gly
        530                 535                 540

Ala Ser Ala Ala Ala Ala Ala Gly Ile Tyr Gly Ser Gly Pro Gly Val
545                 550                 555                 560

Leu Gly Pro Tyr Gly Pro Gly Ile Ser Gly Ser Gly Val Leu Gly Pro
                565                 570                 575

Gly Val Leu Gly Pro Tyr Ala Ser Ala Ala Ala Ala Gly Pro Gly
                580                 585                 590

Ser Gly Val Leu Gly Pro Gly Ala Ser
        595                 600

<210> SEQ ID NO 38
<211> LENGTH: 601
<212> TYPE: PRT
<213> ORGANISM: Artificial Sequence
<220> FEATURE:
<223> OTHER INFORMATION: PRT916

<400> SEQUENCE: 38

Met His His His His His Ser Ser Gly Ser Ser Gly Pro Gly Val
1               5                   10                  15

Ile Gly Pro Tyr Gly Pro Gly Ala Ser Ala Ala Ala Ala Ala Gly Leu
            20                  25                  30
```

-continued

```
Asn Gly Pro Gly Ser Gly Val Ile Gly Pro Gly Leu Ser Gly Leu Tyr
        35              40              45

Gly Pro Gly Val Ile Gly Pro Gly Val Ile Gly Pro Gly Ser Ser Ala
    50              55              60

Ala Ala Ala Ala Gly Pro Gly Leu Tyr Gly Pro Gly Val Ile Gly Pro
65              70              75              80

Ser Ala Ser Ala Ala Ala Ala Ala Gly Pro Gly Ser Gly Val Ile Gly
            85              90              95

Pro Gly Ala Ser Gly Leu Tyr Gly Pro Gly Val Ile Gly Pro Gly Val
            100             105             110

Ile Gly Pro Gly Ser Ser Ala Ala Ala Ala Gly Leu Tyr Gly Ser
            115             120             125

Gly Pro Gly Val Ile Gly Pro Tyr Gly Ser Ala Ala Ala Ala Gly
    130             135             140

Pro Gly Ser Gly Leu Tyr Gly Leu Gly Pro Tyr Gly Pro Gly Ala Ser
145             150             155             160

Gly Pro Gly Leu Tyr Gly Pro Gly Val Ile Gly Pro Ser Ala Ser Ala
            165             170             175

Ala Ala Ala Ala Gly Ser Gly Val Ile Gly Pro Gly Leu Tyr Gly Pro
            180             185             190

Tyr Ala Ser Ala Ala Ala Ala Gly Leu Tyr Gly Ser Gly Pro Gly
    195             200             205

Val Ile Gly Pro Tyr Gly Pro Gly Leu Ser Gly Ser Gly Val Ile Gly
    210             215             220

Pro Gly Val Ile Gly Pro Tyr Ala Ser Ala Ala Ala Ala Gly Pro
225             230             235             240

Gly Val Ile Gly Pro Tyr Gly Pro Gly Ser Ser Ala Ala Ala Ala
            245             250             255

Gly Leu Tyr Gly Tyr Gly Pro Gly Val Ile Gly Pro Tyr Gly Pro Gly
            260             265             270

Ala Ser Gly Leu Asn Gly Pro Gly Ser Gly Leu Tyr Gly Pro Gly Val
            275             280             285

Ile Gly Pro Gly Leu Ser Ala Ala Ala Ala Gly Pro Gly Val Ile
    290             295             300

Gly Pro Tyr Gly Pro Gly Ala Ser Ala Ala Ala Ala Gly Leu Tyr
305             310             315             320

Gly Pro Gly Val Ile Gly Pro Gly Leu Tyr Gly Pro Gly Ser Ser Gly
            325             330             335

Pro Gly Val Ile Gly Pro Tyr Gly Pro Gly Ser Ser Ala Ala Ala Ala
            340             345             350

Ala Gly Leu Tyr Gly Pro Gly Val Ile Gly Pro Tyr Gly Pro Gly Leu
            355             360             365

Ser Ala Ala Ala Ala Gly Leu Tyr Val Ile Gly Pro Gly Val Ile
    370             375             380

Gly Pro Tyr Gly Pro Gly Ala Ser Gly Pro Gly Val Ile Gly Pro Tyr
385             390             395             400

Gly Pro Gly Ala Ser Ala Ala Ala Ala Gly Pro Gly Leu Tyr Gly
            405             410             415

Pro Gly Val Ile Gly Pro Ser Ala Ser Ala Ala Ala Ala Gly Leu
            420             425             430

Tyr Gly Ser Gly Pro Gly Leu Tyr Gly Pro Tyr Gly Pro Gly Leu Ser
    435             440             445

Gly Pro Gly Ser Gly Val Ile Gly Leu Gly Pro Tyr Gly Pro Gly Ala
```

```
         450              455              460

Ser Ala Ala Ala Ala Ala Gly Leu Tyr Gly Pro Gly Val Ile Gly Pro
465              470              475              480

Tyr Gly Pro Gly Leu Ser Ala Ala Ala Ala Gly Pro Gly Ser Gly
             485              490              495

Leu Tyr Gly Pro Gly Ala Ser Gly Leu Asn Gly Pro Gly Ser Gly Leu
             500              505              510

Tyr Gly Pro Gly Val Ile Gly Pro Gly Leu Ser Ala Ala Ala Ala Ala
             515              520              525

Gly Leu Tyr Val Ile Gly Pro Gly Val Ile Gly Pro Tyr Gly Pro Gly
             530              535              540

Ala Ser Ala Ala Ala Ala Ala Gly Leu Tyr Gly Ser Gly Pro Gly Val
545              550              555              560

Ile Gly Pro Tyr Gly Pro Gly Leu Ser Gly Ser Gly Val Ile Gly Pro
             565              570              575

Gly Val Ile Gly Pro Tyr Ala Ser Ala Ala Ala Ala Gly Pro Gly
             580              585              590

Ser Gly Val Ile Gly Pro Gly Ala Ser
         595              600

<210> SEQ ID NO 39
<211> LENGTH: 601
<212> TYPE: PRT
<213> ORGANISM: Artificial Sequence
<220> FEATURE:
<223> OTHER INFORMATION: PRT918

<400> SEQUENCE: 39

Met His His His His His Ser Ser Gly Ser Ser Gly Pro Gly Val
1               5               10              15

Phe Gly Pro Tyr Gly Pro Gly Ala Ser Ala Ala Ala Ala Gly Ile
             20              25              30

Asn Gly Pro Gly Ser Gly Val Phe Gly Pro Gly Ile Ser Gly Ile Tyr
         35              40              45

Gly Pro Gly Val Phe Gly Pro Gly Val Phe Gly Pro Gly Ser Ser Ala
     50              55              60

Ala Ala Ala Ala Gly Pro Gly Ile Tyr Gly Pro Gly Val Phe Gly Pro
65              70              75              80

Ser Ala Ser Ala Ala Ala Ala Gly Pro Gly Ser Gly Val Phe Gly
             85              90              95

Pro Gly Ala Ser Gly Ile Tyr Gly Pro Gly Val Phe Gly Pro Gly Val
             100             105             110

Phe Gly Pro Gly Ser Ser Ala Ala Ala Ala Gly Ile Tyr Gly Ser
             115             120             125

Gly Pro Gly Val Phe Gly Pro Tyr Gly Ser Ala Ala Ala Ala Gly
             130             135             140

Pro Gly Ser Gly Ile Tyr Gly Ile Gly Pro Tyr Gly Pro Gly Ala Ser
145             150             155             160

Gly Pro Gly Ile Tyr Gly Pro Gly Val Phe Gly Pro Ser Ala Ser Ala
             165             170             175

Ala Ala Ala Gly Ser Gly Val Phe Gly Pro Gly Ile Tyr Gly Pro
             180             185             190

Tyr Ala Ser Ala Ala Ala Ala Gly Ile Tyr Gly Ser Gly Pro Gly
             195             200             205

Val Phe Gly Pro Tyr Gly Pro Gly Ile Ser Gly Ser Gly Val Phe Gly
```

-continued

```
            210             215             220

Pro Gly Val Phe Gly Pro Tyr Ala Ser Ala Ala Ala Ala Ala Gly Pro
225                 230                 235                 240

Gly Val Phe Gly Pro Tyr Gly Pro Gly Ser Ser Ala Ala Ala Ala
                245                 250                 255

Gly Ile Tyr Gly Tyr Gly Pro Gly Val Phe Gly Pro Tyr Gly Pro Gly
            260                 265                 270

Ala Ser Gly Ile Asn Gly Pro Gly Ser Gly Ile Tyr Gly Pro Gly Val
            275                 280                 285

Phe Gly Pro Gly Ile Ser Ala Ala Ala Ala Gly Pro Gly Val Phe
            290                 295                 300

Gly Pro Tyr Gly Pro Gly Ala Ser Ala Ala Ala Ala Gly Ile Tyr
305                 310                 315                 320

Gly Pro Gly Val Phe Gly Pro Gly Ile Tyr Gly Pro Gly Ser Ser Gly
                325                 330                 335

Pro Gly Val Phe Gly Pro Tyr Gly Pro Gly Ser Ser Ala Ala Ala Ala
                340                 345                 350

Ala Gly Ile Tyr Gly Pro Gly Val Phe Gly Pro Tyr Gly Pro Gly Ile
                355                 360                 365

Ser Ala Ala Ala Ala Ala Gly Ile Tyr Val Phe Gly Pro Gly Val Phe
            370                 375                 380

Gly Pro Tyr Gly Pro Gly Ala Ser Gly Pro Gly Val Phe Gly Pro Tyr
385                 390                 395                 400

Gly Pro Gly Ala Ser Ala Ala Ala Ala Gly Pro Gly Ile Tyr Gly
                405                 410                 415

Pro Gly Val Phe Gly Pro Ser Ala Ser Ala Ala Ala Ala Gly Ile
                420                 425                 430

Tyr Gly Ser Gly Pro Gly Ile Tyr Gly Pro Tyr Gly Pro Gly Ile Ser
            435                 440                 445

Gly Pro Gly Ser Gly Val Phe Gly Ile Gly Pro Tyr Gly Pro Gly Ala
            450                 455                 460

Ser Ala Ala Ala Ala Ala Gly Ile Tyr Gly Pro Gly Val Phe Gly Pro
465                 470                 475                 480

Tyr Gly Pro Gly Ile Ser Ala Ala Ala Ala Gly Pro Gly Ser Gly
                485                 490                 495

Ile Tyr Gly Pro Gly Ala Ser Gly Ile Asn Gly Pro Gly Ser Gly Ile
                500                 505                 510

Tyr Gly Pro Gly Val Phe Gly Pro Gly Ile Ser Ala Ala Ala Ala Ala
                515                 520                 525

Gly Ile Tyr Val Phe Gly Pro Gly Val Phe Gly Pro Tyr Gly Pro Gly
            530                 535                 540

Ala Ser Ala Ala Ala Ala Gly Ile Tyr Gly Ser Gly Pro Gly Val
545                 550                 555                 560

Phe Gly Pro Tyr Gly Pro Gly Ile Ser Gly Ser Gly Val Phe Gly Pro
                565                 570                 575

Gly Val Phe Gly Pro Tyr Ala Ser Ala Ala Ala Ala Gly Pro Gly
                580                 585                 590

Ser Gly Val Phe Gly Pro Gly Ala Ser
            595                 600

<210> SEQ ID NO 40
<211> LENGTH: 576
<212> TYPE: PRT
<213> ORGANISM: Artificial Sequence
```

<220> FEATURE:
<223> OTHER INFORMATION: PRT699

<400> SEQUENCE: 40

```
Met His His His His His Ser Ser Gly Ser Ser Gly Pro Gly Val
1               5                   10                  15

Leu Gly Pro Tyr Gly Pro Gly Ala Ser Ala Ala Ala Ala Ala Ala
            20              25              30

Gly Ser Asn Gly Pro Gly Ser Gly Val Leu Gly Pro Gly Gln Ser Gly
        35              40                  45

Gln Tyr Gly Pro Gly Val Leu Gly Pro Gly Val Leu Gly Pro Gly Ser
    50              55              60

Ser Ala Ala Ala Ala Ala Ala Gly Pro Gly Gln Tyr Gly Pro Gly
65                  70              75                  80

Val Leu Gly Pro Ser Ala Ser Ala Ala Ala Ala Ala Ala Gly Pro
                85              90                  95

Gly Ser Gly Val Leu Gly Pro Gly Ala Ser Gly Gln Tyr Gly Pro Gly
            100             105             110

Val Leu Gly Pro Gly Val Leu Gly Pro Gly Ser Ser Ala Ala Ala Ala
            115             120             125

Ala Ala Ala Gly Ser Tyr Gly Ser Gly Pro Gly Val Leu Gly Pro Tyr
    130             135             140

Gly Ser Ala Ala Ala Ala Ala Ala Ala Gly Pro Gly Ser Gly Gln Tyr
145                 150             155                 160

Gly Gln Gly Pro Tyr Gly Pro Gly Ala Ser Gly Pro Gly Gln Tyr Gly
            165             170             175

Pro Gly Val Leu Gly Pro Ser Ala Ser Ala Ala Ala Ala Ala Ala
            180             185             190

Gly Ser Gly Val Leu Gly Pro Gly Gln Tyr Gly Pro Tyr Ala Ser Ala
            195             200             205

Ala Ala Ala Ala Ala Gly Ser Tyr Gly Ser Gly Pro Gly Val Leu
    210             215             220

Gly Pro Tyr Gly Pro Gly Gln Ser Gly Ser Gly Val Leu Gly Pro Gly
225             230             235                 240

Val Leu Gly Pro Tyr Ala Ser Ala Ala Ala Ala Ala Ala Gly Pro
            245             250             255

Gly Val Leu Gly Pro Tyr Gly Pro Gly Ser Ser Ala Ala Ala Ala
            260             265             270

Ala Ala Gly Ser Tyr Gly Tyr Gly Pro Gly Val Leu Gly Pro Tyr Gly
    275             280             285

Pro Gly Ala Ser Gly Gln Asn Gly Pro Gly Ser Gly Gln Tyr Gly Pro
    290             295             300

Gly Val Leu Gly Pro Gly Pro Ser Ala Ala Ala Ala Ala Ala Gly
305             310             315             320

Pro Gly Val Leu Gly Pro Tyr Gly Pro Gly Ala Ser Ala Ala Ala Ala
            325             330             335

Ala Ala Ala Gly Ser Tyr Gly Pro Gly Val Leu Gly Pro Gly Gln Tyr
            340             345             350

Gly Pro Gly Ser Ser Gly Pro Gly Val Leu Gly Pro Tyr Gly Pro Gly
            355             360             365

Ser Ser Ala Ala Ala Ala Ala Ala Ala Gly Ser Tyr Gly Pro Gly Val
    370             375             380

Leu Gly Pro Tyr Gly Pro Gly Pro Ser Ala Ala Ala Ala Ala Ala Ala
385             390             395             400
```

-continued

```
Gly Ser Tyr Val Leu Gly Pro Gly Val Leu Gly Pro Tyr Gly Pro Gly
            405                 410                 415

Ala Ser Gly Pro Gly Val Leu Gly Pro Tyr Gly Pro Gly Ala Ser Ala
            420                 425                 430

Ala Ala Ala Ala Ala Ala Gly Pro Gly Gln Tyr Gly Pro Gly Val Leu
            435                 440                 445

Gly Pro Ser Ala Ser Ala Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Val Leu Gly Gln Gly Pro Tyr Gly Pro Gly Ala Ser Ala
            485                 490                 495

Ala Ala Ala Ala Ala Gly Ser Tyr Gly Pro Gly Val Leu Gly Pro
            500                 505                 510

Tyr Gly Pro Gly Pro Ser Ala Ala Ala Ala Ala Ala Gly Pro Gly
            515                 520                 525

Ser Gly Gln Tyr Gly Pro Gly Ala Ser Gly Gln Asn Gly Pro Gly Ser
    530                 535                 540

Gly Gln Tyr Gly Pro Gly Val Leu Gly Pro Gly Pro Ser Ala Ala Ala
545                 550                 555                 560

Ala Ala Ala Ala Gly Pro Gly Ser Gly Val Leu Gly Pro Gly Ala Ser
            565                 570                 575
```

```
<210> SEQ ID NO 41
<211> LENGTH: 576
<212> TYPE: PRT
<213> ORGANISM: Artificial Sequence
<220> FEATURE:
<223> OTHER INFORMATION: PRT698

<400> SEQUENCE: 41
```

```
Met His His His His His His Ser Ser Gly Ser Ser Gly Pro Gly Val
1               5                   10                  15

Leu Gly Pro Tyr Gly Pro Gly Ala Ser Ala Ala Ala Ala Ala Ala Ala
            20                  25                  30

Gly Ser Asn Gly Pro Gly Ser Gly Val Leu Gly Pro Gly Ile Ser Gly
            35                  40                  45

Ile Tyr Gly Pro Gly Val Leu Gly Pro Gly Val Leu Gly Pro Gly Ser
    50                  55                  60

Ser Ala Ala Ala Ala Ala Ala Gly Pro Gly Ile Tyr Gly Pro Gly
65                  70                  75                  80

Val Leu Gly Pro Ser Ala Ser Ala Ala Ala Ala Ala Ala Gly Pro
            85                  90                  95

Gly Ser Gly Val Leu Gly Pro Gly Ala Ser Gly Ile Tyr Gly Pro Gly
            100                 105                 110

Val Leu Gly Pro Gly Val Leu Gly Pro Gly Ser Ser Ala Ala Ala Ala
            115                 120                 125

Ala Ala Ala Gly Ser Tyr Gly Ser Gly Pro Gly Val Leu Gly Pro Tyr
    130                 135                 140

Gly Ser Ala Ala Ala Ala Ala Ala Ala Gly Pro Gly Ser Gly Ile Tyr
145                 150                 155                 160

Gly Ile Gly Pro Tyr Gly Pro Gly Ala Ser Gly Pro Gly Ile Tyr Gly
            165                 170                 175

Pro Gly Val Leu Gly Pro Ser Ala Ser Ala Ala Ala Ala Ala Ala Ala
            180                 185                 190
```

-continued

Gly Ser Gly Val Leu Gly Pro Gly Ile Tyr Gly Pro Tyr Ala Ser Ala
        195                 200                 205

Ala Ala Ala Ala Ala Ala Gly Ser Tyr Gly Ser Gly Pro Gly Val Leu
        210                 215                 220

Gly Pro Tyr Gly Pro Gly Ile Ser Gly Ser Gly Val Leu Gly Pro Gly
225                 230                 235                 240

Val Leu Gly Pro Tyr Ala Ser Ala Ala Ala Ala Ala Ala Ala Gly Pro
                245                 250                 255

Gly Val Leu Gly Pro Tyr Gly Pro Gly Ser Ser Ala Ala Ala Ala Ala
                260                 265                 270

Ala Ala Gly Ser Tyr Gly Tyr Gly Pro Gly Val Leu Gly Pro Tyr Gly
                275                 280                 285

Pro Gly Ala Ser Gly Ile Asn Gly Pro Gly Ser Gly Ile Tyr Gly Pro
        290                 295                 300

Gly Val Leu Gly Pro Gly Pro Ser Ala Ala Ala Ala Ala Ala Gly
305                 310                 315                 320

Pro Gly Val Leu Gly Pro Tyr Gly Pro Gly Ala Ser Ala Ala Ala Ala
                325                 330                 335

Ala Ala Ala Gly Ser Tyr Gly Pro Gly Val Leu Gly Pro Gly Ile Tyr
                340                 345                 350

Gly Pro Gly Ser Ser Gly Pro Gly Val Leu Gly Pro Tyr Gly Pro Gly
                355                 360                 365

Ser Ser Ala Ala Ala Ala Ala Ala Gly Ser Tyr Gly Pro Gly Val
        370                 375                 380

Leu Gly Pro Tyr Gly Pro Gly Pro Ser Ala Ala Ala Ala Ala Ala Ala
385                 390                 395                 400

Gly Ser Tyr Val Leu Gly Pro Gly Val Leu Gly Pro Tyr Gly Pro Gly
                405                 410                 415

Ala Ser Gly Pro Gly Val Leu Gly Pro Tyr Gly Pro Gly Ala Ser Ala
                420                 425                 430

Ala Ala Ala Ala Ala Gly Pro Gly Ile Tyr Gly Pro Gly Val Leu
        435                 440                 445

Gly Pro Ser Ala Ser Ala Ala Ala Ala Ala Ala Gly Ser Tyr Gly
        450                 455                 460

Ser Gly Pro Gly Ile Tyr Gly Pro Tyr Gly Pro Gly Ile Ser Gly Pro
465                 470                 475                 480

Gly Ser Gly Val Leu Gly Ile Gly Pro Tyr Gly Pro Gly Ala Ser Ala
                485                 490                 495

Ala Ala Ala Ala Ala Gly Ser Tyr Gly Pro Gly Val Leu Gly Pro
        500                 505                 510

Tyr Gly Pro Gly Pro Ser Ala Ala Ala Ala Ala Ala Gly Pro Gly
        515                 520                 525

Ser Gly Ile Tyr Gly Pro Gly Ala Ser Gly Ile Asn Gly Pro Gly Ser
        530                 535                 540

Gly Ile Tyr Gly Pro Gly Val Leu Gly Pro Gly Pro Ser Ala Ala Ala
545                 550                 555                 560

Ala Ala Ala Ala Gly Pro Gly Ser Gly Val Leu Gly Pro Gly Ala Ser
                565                 570                 575

<210> SEQ ID NO 42
<211> LENGTH: 17
<212> TYPE: PRT
<213> ORGANISM: Artificial Sequence
<220> FEATURE:

```
<223> OTHER INFORMATION: Hinge+His-tag

<400> SEQUENCE: 42

Ser Ser Val Asp Lys Leu Ala Ala Ala Leu Glu His His His His His
1               5                   10                  15

His

<210> SEQ ID NO 43
<211> LENGTH: 1179
<212> TYPE: PRT
<213> ORGANISM: Artificial Sequence
<220> FEATURE:
<223> OTHER INFORMATION: Met-PRT966

<400> SEQUENCE: 43

Met Gly Pro Gly Val Phe Gly Pro Tyr Gly Pro Gly Ala Ser Ala Ala
1               5                   10                  15

Ala Ala Ala Gly Ile Asn Gly Pro Gly Ser Gly Val Phe Gly Pro Gly
                20                  25                  30

Ile Ser Gly Ile Tyr Gly Pro Gly Val Phe Gly Pro Gly Val Phe Gly
            35                  40                  45

Pro Gly Ser Ser Ala Ala Ala Ala Ala Gly Pro Gly Ile Tyr Gly Pro
        50                  55                  60

Gly Val Phe Gly Pro Ser Ala Ser Ala Ala Ala Ala Gly Pro Gly
65                  70                  75                  80

Ser Gly Val Phe Gly Pro Gly Ala Ser Gly Ile Tyr Gly Pro Gly Val
                85                  90                  95

Phe Gly Pro Gly Val Phe Gly Pro Gly Ser Ser Ala Ala Ala Ala Ala
            100                 105                 110

Gly Ile Tyr Gly Ser Gly Pro Gly Val Phe Gly Pro Tyr Gly Ser Ala
            115                 120                 125

Ala Ala Ala Ala Gly Pro Gly Ser Gly Ile Tyr Gly Ile Gly Pro Tyr
    130                 135                 140

Gly Pro Gly Ala Ser Gly Pro Gly Ile Tyr Gly Pro Gly Val Phe Gly
145                 150                 155                 160

Pro Ser Ala Ser Ala Ala Ala Ala Gly Ser Gly Val Phe Gly Pro
                165                 170                 175

Gly Ile Tyr Gly Pro Tyr Ala Ser Ala Ala Ala Ala Gly Ile Tyr
            180                 185                 190

Gly Ser Gly Pro Gly Val Phe Gly Pro Tyr Gly Pro Gly Ile Ser Gly
            195                 200                 205

Ser Gly Val Phe Gly Pro Gly Val Phe Gly Pro Tyr Ala Ser Ala Ala
    210                 215                 220

Ala Ala Ala Gly Pro Gly Val Phe Gly Pro Tyr Gly Pro Gly Ser Ser
225                 230                 235                 240

Ala Ala Ala Ala Ala Gly Ile Tyr Gly Tyr Gly Pro Gly Val Phe Gly
                245                 250                 255

Pro Tyr Gly Pro Gly Ala Ser Gly Ile Asn Gly Pro Gly Ser Gly Ile
            260                 265                 270

Tyr Gly Pro Gly Val Phe Gly Pro Gly Ile Ser Ala Ala Ala Ala Ala
            275                 280                 285

Gly Pro Gly Val Phe Gly Pro Tyr Gly Pro Gly Ala Ser Ala Ala Ala
    290                 295                 300

Ala Ala Gly Ile Tyr Gly Pro Gly Val Phe Gly Pro Gly Ile Tyr Gly
305                 310                 315                 320
```

-continued

```
Pro Gly Ser Ser Gly Pro Gly Val Phe Gly Pro Tyr Gly Pro Gly Ser
              325             330             335

Ser Ala Ala Ala Ala Ala Gly Ile Tyr Gly Pro Gly Val Phe Gly Pro
              340             345             350

Tyr Gly Pro Gly Ile Ser Ala Ala Ala Ala Gly Ile Tyr Val Phe
              355             360             365

Gly Pro Gly Val Phe Gly Pro Tyr Gly Pro Gly Ala Ser Gly Pro Gly
              370             375             380

Val Phe Gly Pro Tyr Gly Pro Gly Ala Ser Ala Ala Ala Ala Gly
      385             390             395             400

Pro Gly Ile Tyr Gly Pro Gly Val Phe Gly Pro Ser Ala Ser Ala Ala
              405             410             415

Ala Ala Ala Gly Ile Tyr Gly Ser Gly Pro Gly Ile Tyr Gly Pro Tyr
              420             425             430

Gly Pro Gly Ile Ser Gly Pro Gly Ser Gly Val Phe Gly Ile Gly Pro
              435             440             445

Tyr Gly Pro Gly Ala Ser Ala Ala Ala Ala Gly Ile Tyr Gly Pro
      450             455             460

Gly Val Phe Gly Pro Tyr Gly Pro Gly Ile Ser Ala Ala Ala Ala
      465             470             475             480

Gly Pro Gly Ser Gly Ile Tyr Gly Pro Gly Ala Ser Gly Ile Asn Gly
              485             490             495

Pro Gly Ser Gly Ile Tyr Gly Pro Gly Val Phe Gly Pro Gly Ile Ser
              500             505             510

Ala Ala Ala Ala Ala Gly Ile Tyr Val Phe Gly Pro Gly Val Phe Gly
              515             520             525

Pro Tyr Gly Pro Gly Ala Ser Ala Ala Ala Ala Gly Ile Tyr Gly
      530             535             540

Ser Gly Pro Gly Val Phe Gly Pro Tyr Gly Pro Gly Ile Ser Gly Ser
545             550             555             560

Gly Val Phe Gly Pro Gly Val Phe Gly Pro Tyr Ala Ser Ala Ala Ala
              565             570             575

Ala Ala Gly Pro Gly Ser Gly Val Phe Gly Pro Gly Ala Ser Gly Pro
              580             585             590

Gly Val Phe Gly Pro Tyr Gly Pro Gly Ala Ser Ala Ala Ala Ala Ala
      595             600             605

Gly Ile Asn Gly Pro Gly Ser Gly Val Phe Gly Pro Gly Ile Ser Gly
      610             615             620

Ile Tyr Gly Pro Gly Val Phe Gly Pro Gly Val Phe Gly Pro Gly Ser
625             630             635             640

Ser Ala Ala Ala Ala Ala Gly Pro Gly Ile Tyr Gly Pro Gly Val Phe
              645             650             655

Gly Pro Ser Ala Ser Ala Ala Ala Ala Gly Pro Gly Ser Gly Val
              660             665             670

Phe Gly Pro Gly Ala Ser Gly Ile Tyr Gly Pro Gly Val Phe Gly Pro
              675             680             685

Gly Val Phe Gly Pro Gly Ser Ser Ala Ala Ala Ala Gly Ile Tyr
      690             695             700

Gly Ser Gly Pro Gly Val Phe Gly Pro Tyr Gly Ser Ala Ala Ala Ala
705             710             715             720

Ala Gly Pro Gly Ser Gly Ile Tyr Gly Ile Gly Pro Tyr Gly Pro Gly
              725             730             735

Ala Ser Gly Pro Gly Ile Tyr Gly Pro Gly Val Phe Gly Pro Ser Ala
```

-continued

```
              740              745              750
Ser Ala Ala Ala Ala Ala Gly Ser Gly Val Phe Gly Pro Gly Ile Tyr
       755              760              765

Gly Pro Tyr Ala Ser Ala Ala Ala Ala Ala Gly Ile Tyr Gly Ser Gly
   770              775              780

Pro Gly Val Phe Gly Pro Tyr Gly Pro Gly Ile Ser Gly Ser Gly Val
785              790              795              800

Phe Gly Pro Gly Val Phe Gly Pro Tyr Ala Ser Ala Ala Ala Ala Ala
           805              810              815

Gly Pro Gly Val Phe Gly Pro Tyr Gly Pro Gly Ser Ser Ala Ala Ala
           820              825              830

Ala Ala Gly Ile Tyr Gly Tyr Gly Pro Gly Val Phe Gly Pro Tyr Gly
       835              840              845

Pro Gly Ala Ser Gly Ile Asn Gly Pro Gly Ser Gly Ile Tyr Gly Pro
   850              855              860

Gly Val Phe Gly Pro Gly Ile Ser Ala Ala Ala Ala Ala Gly Pro Gly
865              870              875              880

Val Phe Gly Pro Tyr Gly Pro Gly Ala Ser Ala Ala Ala Ala Ala Gly
           885              890              895

Ile Tyr Gly Pro Gly Val Phe Gly Pro Gly Ile Tyr Gly Pro Gly Ser
           900              905              910

Ser Gly Pro Gly Val Phe Gly Pro Tyr Gly Pro Gly Ser Ser Ala Ala
           915              920              925

Ala Ala Ala Gly Ile Tyr Gly Pro Gly Val Phe Gly Pro Tyr Gly Pro
   930              935              940

Gly Ile Ser Ala Ala Ala Ala Ala Gly Ile Tyr Val Phe Gly Pro Gly
945              950              955              960

Val Phe Gly Pro Tyr Gly Pro Gly Ala Ser Gly Pro Gly Val Phe Gly
           965              970              975

Pro Tyr Gly Pro Gly Ala Ser Ala Ala Ala Ala Gly Pro Gly Ile
           980              985              990

Tyr Gly Pro Gly Val Phe Gly Pro  Ser Ala Ser Ala Ala  Ala Ala Ala
           995              1000              1005

Gly Ile  Tyr Gly Ser Gly Pro  Gly Ile Tyr Gly Pro  Tyr Gly Pro
   1010              1015              1020

Gly Ile  Ser Gly Pro Gly Ser  Gly Val Phe Gly Ile  Gly Pro Tyr
   1025              1030              1035

Gly Pro  Gly Ala Ser Ala Ala  Ala Ala Ala Gly Ile  Tyr Gly Pro
   1040              1045              1050

Gly Val  Phe Gly Pro Tyr Gly  Pro Gly Ile Ser Ala  Ala Ala Ala
   1055              1060              1065

Ala Gly  Pro Gly Ser Gly Ile  Tyr Gly Pro Gly Ala  Ser Gly Ile
   1070              1075              1080

Asn Gly  Pro Gly Ser Gly Ile  Tyr Gly Pro Gly Val  Phe Gly Pro
   1085              1090              1095

Gly Ile  Ser Ala Ala Ala Ala  Ala Gly Ile Tyr Val  Phe Gly Pro
   1100              1105              1110

Gly Val  Phe Gly Pro Tyr Gly  Pro Gly Ala Ser Ala  Ala Ala Ala
   1115              1120              1125

Ala Gly  Ile Tyr Gly Ser Gly  Pro Gly Val Phe Gly  Pro Tyr Gly
   1130              1135              1140

Pro Gly  Ile Ser Gly Ser Gly  Val Phe Gly Pro Gly  Val Phe Gly
   1145              1150              1155
```

-continued

```
Pro Tyr  Ala Ser Ala Ala Ala  Ala Ala Gly Pro Gly  Ser Gly Val
    1160             1165             1170

Phe Gly  Pro Gly Ala Ser
    1175

<210> SEQ ID NO 44
<211> LENGTH: 1190
<212> TYPE: PRT
<213> ORGANISM: Artificial Sequence
<220> FEATURE:
<223> OTHER INFORMATION: PRT966

<400> SEQUENCE: 44

Met His His His His His Ser Ser Gly Ser Ser Gly Pro Gly Val
1               5               10              15

Phe Gly Pro Tyr Gly Pro Gly Ala Ser Ala Ala Ala Ala Gly Ile
            20              25              30

Asn Gly Pro Gly Ser Gly Val Phe Gly Pro Gly Ile Ser Gly Ile Tyr
        35              40              45

Gly Pro Gly Val Phe Gly Pro Gly Val Phe Gly Pro Gly Ser Ser Ala
    50              55              60

Ala Ala Ala Ala Gly Pro Gly Ile Tyr Gly Pro Gly Val Phe Gly Pro
65              70              75              80

Ser Ala Ser Ala Ala Ala Ala Ala Gly Pro Gly Ser Gly Val Phe Gly
            85              90              95

Pro Gly Ala Ser Gly Ile Tyr Gly Pro Gly Val Phe Gly Pro Gly Val
            100             105             110

Phe Gly Pro Gly Ser Ser Ala Ala Ala Ala Gly Ile Tyr Gly Ser
    115             120             125

Gly Pro Gly Val Phe Gly Pro Tyr Gly Ser Ala Ala Ala Ala Ala Gly
    130             135             140

Pro Gly Ser Gly Ile Tyr Gly Ile Gly Pro Tyr Gly Pro Gly Ala Ser
145             150             155             160

Gly Pro Gly Ile Tyr Gly Pro Gly Val Phe Gly Pro Ser Ala Ser Ala
            165             170             175

Ala Ala Ala Ala Gly Ser Gly Val Phe Gly Pro Gly Ile Tyr Gly Pro
            180             185             190

Tyr Ala Ser Ala Ala Ala Ala Ala Gly Ile Tyr Gly Ser Gly Pro Gly
            195             200             205

Val Phe Gly Pro Tyr Gly Pro Gly Ile Ser Gly Ser Gly Val Phe Gly
    210             215             220

Pro Gly Val Phe Gly Pro Tyr Ala Ser Ala Ala Ala Ala Gly Pro
225             230             235             240

Gly Val Phe Gly Pro Tyr Gly Pro Gly Ser Ser Ala Ala Ala Ala Ala
            245             250             255

Gly Ile Tyr Gly Tyr Gly Pro Gly Val Phe Gly Pro Tyr Gly Pro Gly
            260             265             270

Ala Ser Gly Ile Asn Gly Pro Gly Ser Gly Ile Tyr Gly Pro Gly Val
        275             280             285

Phe Gly Pro Gly Ile Ser Ala Ala Ala Ala Gly Pro Gly Val Phe
    290             295             300

Gly Pro Tyr Gly Pro Gly Ala Ser Ala Ala Ala Ala Gly Ile Tyr
305             310             315             320

Gly Pro Gly Val Phe Gly Pro Gly Ile Tyr Gly Pro Gly Ser Ser Gly
            325             330             335
```

-continued

```
Pro Gly Val Phe Gly Pro Tyr Gly Pro Gly Ser Ser Ala Ala Ala Ala
            340                 345                 350

Ala Gly Ile Tyr Gly Pro Gly Val Phe Gly Pro Tyr Gly Pro Gly Ile
            355                 360                 365

Ser Ala Ala Ala Ala Ala Gly Ile Tyr Val Phe Gly Pro Gly Val Phe
    370                 375                 380

Gly Pro Tyr Gly Pro Gly Ala Ser Gly Pro Gly Val Phe Gly Pro Tyr
385                 390                 395                 400

Gly Pro Gly Ala Ser Ala Ala Ala Ala Ala Gly Pro Gly Ile Tyr Gly
                405                 410                 415

Pro Gly Val Phe Gly Pro Ser Ala Ser Ala Ala Ala Ala Ala Gly Ile
            420                 425                 430

Tyr Gly Ser Gly Pro Gly Ile Tyr Gly Pro Tyr Gly Pro Gly Ile Ser
            435                 440                 445

Gly Pro Gly Ser Gly Val Phe Gly Ile Gly Pro Tyr Gly Pro Gly Ala
    450                 455                 460

Ser Ala Ala Ala Ala Ala Gly Ile Tyr Gly Pro Gly Val Phe Gly Pro
465                 470                 475                 480

Tyr Gly Pro Gly Ile Ser Ala Ala Ala Ala Ala Gly Pro Gly Ser Gly
                485                 490                 495

Ile Tyr Gly Pro Gly Ala Ser Gly Ile Asn Gly Pro Gly Ser Gly Ile
            500                 505                 510

Tyr Gly Pro Gly Val Phe Gly Pro Gly Ile Ser Ala Ala Ala Ala Ala
            515                 520                 525

Gly Ile Tyr Val Phe Gly Pro Gly Val Phe Gly Pro Tyr Gly Pro Gly
    530                 535                 540

Ala Ser Ala Ala Ala Ala Ala Gly Ile Tyr Gly Ser Gly Pro Gly Val
545                 550                 555                 560

Phe Gly Pro Tyr Gly Pro Gly Ile Ser Gly Ser Gly Val Phe Gly Pro
                565                 570                 575

Gly Val Phe Gly Pro Tyr Ala Ser Ala Ala Ala Ala Gly Pro Gly
            580                 585                 590

Ser Gly Val Phe Gly Pro Gly Ala Ser Gly Pro Gly Val Phe Gly Pro
            595                 600                 605

Tyr Gly Pro Gly Ala Ser Ala Ala Ala Ala Gly Ile Asn Gly Pro
    610                 615                 620

Gly Ser Gly Val Phe Gly Pro Gly Ile Ser Gly Ile Tyr Gly Pro Gly
625                 630                 635                 640

Val Phe Gly Pro Gly Val Phe Gly Pro Gly Ser Ser Ala Ala Ala Ala
                645                 650                 655

Ala Gly Pro Gly Ile Tyr Gly Pro Gly Val Phe Gly Pro Ser Ala Ser
            660                 665                 670

Ala Ala Ala Ala Ala Gly Pro Gly Ser Gly Val Phe Gly Pro Gly Ala
    675                 680                 685

Ser Gly Ile Tyr Gly Pro Gly Val Phe Gly Pro Gly Val Phe Gly Pro
    690                 695                 700

Gly Ser Ser Ala Ala Ala Ala Ala Gly Ile Tyr Gly Ser Gly Pro Gly
705                 710                 715                 720

Val Phe Gly Pro Tyr Gly Ser Ala Ala Ala Ala Gly Pro Gly Ser
            725                 730                 735

Gly Ile Tyr Gly Ile Gly Pro Tyr Gly Pro Gly Ala Ser Gly Pro Gly
            740                 745                 750
```

-continued

```
Ile Tyr Gly Pro Gly Val Phe Gly Pro Ser Ala Ser Ala Ala Ala Ala
        755                 760                 765

Ala Gly Ser Gly Val Phe Gly Pro Gly Ile Tyr Gly Pro Tyr Ala Ser
    770                 775                 780

Ala Ala Ala Ala Ala Gly Ile Tyr Gly Ser Gly Pro Gly Val Phe Gly
785                 790                 795                 800

Pro Tyr Gly Pro Gly Ile Ser Gly Ser Gly Val Phe Gly Pro Gly Val
            805                 810                 815

Phe Gly Pro Tyr Ala Ser Ala Ala Ala Ala Gly Pro Gly Val Phe
        820                 825                 830

Gly Pro Tyr Gly Pro Gly Ser Ser Ala Ala Ala Ala Gly Ile Tyr
        835                 840                 845

Gly Tyr Gly Pro Gly Val Phe Gly Pro Tyr Gly Pro Gly Ala Ser Gly
    850                 855                 860

Ile Asn Gly Pro Gly Ser Gly Ile Tyr Gly Pro Gly Val Phe Gly Pro
865                 870                 875                 880

Gly Ile Ser Ala Ala Ala Ala Ala Gly Pro Gly Val Phe Gly Pro Tyr
            885                 890                 895

Gly Pro Gly Ala Ser Ala Ala Ala Ala Gly Ile Tyr Gly Pro Gly
        900                 905                 910

Val Phe Gly Pro Gly Ile Tyr Gly Pro Gly Ser Ser Gly Pro Gly Val
        915                 920                 925

Phe Gly Pro Tyr Gly Pro Gly Ser Ser Ala Ala Ala Ala Gly Ile
    930                 935                 940

Tyr Gly Pro Gly Val Phe Gly Pro Tyr Gly Pro Gly Ile Ser Ala Ala
945                 950                 955                 960

Ala Ala Ala Gly Ile Tyr Val Phe Gly Pro Gly Val Phe Gly Pro Tyr
            965                 970                 975

Gly Pro Gly Ala Ser Gly Pro Gly Val Phe Gly Pro Tyr Gly Pro Gly
        980                 985                 990

Ala Ser Ala Ala Ala Ala Ala Gly  Pro Gly Ile Tyr Gly  Pro Gly Val
        995                 1000                1005

Phe Gly  Pro Ser Ala Ser Ala  Ala Ala Ala Ala Gly  Ile Tyr Gly
    1010                1015                1020

Ser Gly  Pro Gly Ile Tyr Gly  Pro Tyr Gly Pro Gly  Ile Ser Gly
    1025                1030                1035

Pro Gly  Ser Gly Val Phe Gly  Ile Gly Pro Tyr Gly  Pro Gly Ala
    1040                1045                1050

Ser Ala  Ala Ala Ala Ala Gly  Ile Tyr Gly Pro Gly  Val Phe Gly
    1055                1060                1065

Pro Tyr  Gly Pro Gly Ile Ser  Ala Ala Ala Ala Ala  Gly Pro Gly
    1070                1075                1080

Ser Gly  Ile Tyr Gly Pro Gly  Ala Ser Gly Ile Asn  Gly Pro Gly
    1085                1090                1095

Ser Gly  Ile Tyr Gly Pro Gly  Val Phe Gly Pro Gly  Ile Ser Ala
    1100                1105                1110

Ala Ala  Ala Ala Gly Ile Tyr  Val Phe Gly Pro Gly  Val Phe Gly
    1115                1120                1125

Pro Tyr  Gly Pro Gly Ala Ser  Ala Ala Ala Ala Ala  Gly Ile Tyr
    1130                1135                1140

Gly Ser  Gly Pro Gly Val Phe  Gly Pro Tyr Gly Pro  Gly Ile Ser
    1145                1150                1155

Gly Ser  Gly Val Phe Gly Pro  Gly Val Phe Gly Pro  Tyr Ala Ser
```

-continued

```
          1160              1165              1170

Ala Ala  Ala Ala Ala Gly Pro  Gly Ser Gly Val Phe  Gly Pro Gly
    1175              1180              1185

Ala Ser
    1190

<210> SEQ ID NO 45
<211> LENGTH: 252
<212> TYPE: PRT
<213> ORGANISM: Artificial Sequence
<220> FEATURE:
<223> OTHER INFORMATION: Collagen-type4-Kai

<400> SEQUENCE: 45

Met His His His His His His Ser Ser Gly Ser Ser Lys Asp Gly Val
1               5               10              15

Pro Gly Phe Pro Gly Ser Glu Gly Val Lys Gly Asn Arg Gly Phe Pro
            20              25              30

Gly Leu Met Gly Glu Asp Gly Ile Lys Gly Gln Lys Gly Asp Ile Gly
        35              40              45

Pro Pro Gly Phe Arg Gly Pro Thr Glu Tyr Tyr Asp Thr Tyr Gln Glu
    50              55              60

Lys Gly Asp Glu Gly Thr Pro Gly Pro Pro Gly Pro Arg Gly Ala Arg
65              70              75              80

Gly Pro Gln Gly Pro Ser Gly Pro Pro Gly Val Pro Gly Ser Pro Gly
                85              90              95

Ser Ser Arg Pro Gly Leu Arg Gly Ala Pro Gly Trp Pro Gly Leu Lys
            100             105             110

Gly Ser Lys Gly Glu Arg Gly Arg Pro Gly Lys Asp Ala Met Gly Thr
            115             120             125

Pro Gly Ser Pro Gly Cys Ala Gly Ser Pro Gly Leu Pro Gly Ser Pro
    130             135             140

Gly Pro Pro Gly Pro Pro Gly Asp Ile Val Phe Arg Lys Gly Pro Pro
145             150             155             160

Gly Asp His Gly Leu Pro Gly Tyr Leu Gly Ser Pro Gly Ile Pro Gly
            165             170             175

Val Asp Gly Pro Lys Gly Glu Pro Gly Leu Leu Cys Thr Gln Cys Pro
            180             185             190

Tyr Ile Pro Gly Pro Pro Gly Leu Pro Gly Leu Pro Gly Leu His Gly
        195             200             205

Val Lys Gly Ile Pro Gly Arg Gln Gly Ala Ala Gly Leu Lys Gly Ser
    210             215             220

Pro Gly Ser Pro Gly Asn Thr Gly Leu Pro Gly Phe Pro Gly Phe Pro
225             230             235             240

Gly Ala Gln Gly Asp Pro Gly Leu Lys Gly Glu Lys
            245             250

<210> SEQ ID NO 46
<211> LENGTH: 12
<212> TYPE: PRT
<213> ORGANISM: Artificial Sequence
<220> FEATURE:
<223> OTHER INFORMATION: HisTag

<400> SEQUENCE: 46

Met His His His His His His Ser Ser Gly Ser Ser
1               5               10
```

```
<210> SEQ ID NO 47
<211> LENGTH: 310
<212> TYPE: PRT
<213> ORGANISM: Artificial Sequence
<220> FEATURE:
<223> OTHER INFORMATION: Resilin-Kai

<400> SEQUENCE: 47

Met His His His His His His Pro Glu Pro Pro Val Asn Ser Tyr Leu
1               5                   10                  15

Pro Pro Ser Asp Ser Tyr Gly Ala Pro Gly Gln Ser Gly Pro Gly Gly
            20                  25                  30

Arg Pro Ser Asp Ser Tyr Gly Ala Pro Gly Gly Gly Asn Gly Gly Arg
            35                  40                  45

Pro Ser Asp Ser Tyr Gly Ala Pro Gly Gln Gly Gln Gly Gln Gly Gln
        50                  55                  60

Gly Gln Gly Gly Tyr Ala Gly Lys Pro Ser Asp Ser Tyr Gly Ala Pro
65                  70                  75                  80

Gly Gly Gly Asp Gly Asn Gly Gly Arg Pro Ser Ser Ser Tyr Gly Ala
                85                  90                  95

Pro Gly Gly Gly Asn Gly Gly Arg Pro Ser Asp Thr Tyr Gly Ala Pro
            100                 105                 110

Gly Gly Gly Asn Gly Gly Arg Pro Ser Asp Thr Tyr Gly Ala Pro Gly
            115                 120                 125

Gly Gly Gly Asn Gly Asn Gly Gly Arg Pro Ser Ser Ser Tyr Gly Ala
        130                 135                 140

Pro Gly Gln Gly Gln Gly Asn Gly Asn Gly Gly Arg Pro Ser Ser Ser
145                 150                 155                 160

Tyr Gly Ala Pro Gly Gly Gly Asn Gly Gly Arg Pro Ser Asp Thr Tyr
                165                 170                 175

Gly Ala Pro Gly Gly Gly Asn Gly Gly Arg Pro Ser Asp Thr Tyr Gly
            180                 185                 190

Ala Pro Gly Gly Gly Asn Asn Gly Gly Arg Pro Ser Ser Ser Tyr Gly
            195                 200                 205

Ala Pro Gly Gly Gly Asn Gly Gly Arg Pro Ser Asp Thr Tyr Gly Ala
        210                 215                 220

Pro Gly Gly Gly Asn Gly Asn Gly Ser Gly Gly Arg Pro Ser Ser Ser
225                 230                 235                 240

Tyr Gly Ala Pro Gly Gln Gly Gln Gly Gly Phe Gly Gly Arg Pro Ser
                245                 250                 255

Asp Ser Tyr Gly Ala Pro Gly Gln Asn Gln Lys Pro Ser Asp Ser Tyr
            260                 265                 270

Gly Ala Pro Gly Ser Gly Asn Gly Asn Gly Gly Arg Pro Ser Ser Ser
            275                 280                 285

Tyr Gly Ala Pro Gly Ser Gly Pro Gly Gly Arg Pro Ser Asp Ser Tyr
    290                 295                 300

Gly Pro Pro Ala Ser Gly
305                 310

<210> SEQ ID NO 48
<211> LENGTH: 282
<212> TYPE: PRT
<213> ORGANISM: Artificial Sequence
<220> FEATURE:
<223> OTHER INFORMATION: elastin short

<400> SEQUENCE: 48
```

```
Met His His His His His Ser Ser Gly Ser Ser Leu Gly Val Ser
1               5                   10                  15

Ala Gly Ala Val Val Pro Gln Pro Gly Ala Gly Val Lys Pro Gly Lys
                20                  25                  30

Val Pro Gly Val Gly Leu Pro Gly Val Tyr Pro Gly Gly Val Leu Pro
            35                  40                  45

Gly Ala Arg Phe Pro Gly Val Gly Val Leu Pro Gly Val Pro Thr Gly
    50                  55                  60

Ala Gly Val Lys Pro Lys Ala Pro Gly Val Gly Gly Ala Phe Ala Gly
65                  70                  75                  80

Ile Pro Gly Val Gly Pro Phe Gly Gly Pro Gln Pro Gly Val Pro Leu
                85                  90                  95

Gly Tyr Pro Ile Lys Ala Pro Lys Leu Pro Gly Gly Tyr Gly Leu Pro
            100                 105                 110

Tyr Thr Thr Gly Lys Leu Pro Tyr Gly Tyr Gly Pro Gly Gly Val Ala
            115                 120                 125

Gly Ala Ala Gly Lys Ala Gly Tyr Pro Thr Gly Thr Gly Val Gly Pro
    130                 135                 140

Gln Ala Ala Ala Ala Ala Ala Ala Lys Ala Ala Ala Lys Phe Gly Ala
145                 150                 155                 160

Gly Ala Ala Gly Val Leu Pro Gly Val Gly Gly Ala Gly Val Pro Gly
                165                 170                 175

Val Pro Gly Ala Ile Pro Gly Ile Gly Gly Ile Ala Gly Val Gly Thr
                180                 185                 190

Pro Ala Ala Ala Ala Ala Ala Ala Ala Ala Lys Ala Ala Lys Tyr
                195                 200                 205

Gly Ala Ala Ala Gly Leu Val Pro Gly Gly Pro Gly Phe Gly Pro Gly
    210                 215                 220

Val Val Gly Val Pro Gly Ala Gly Val Pro Gly Val Gly Val Pro Gly
225                 230                 235                 240

Ala Gly Ile Pro Val Val Pro Gly Ala Gly Ile Pro Gly Ala Ala Val
                245                 250                 255

Pro Gly Val Val Ser Pro Glu Ala Ala Ala Lys Ala Ala Ala Lys Ala
                260                 265                 270

Ala Lys Tyr Gly Ala Arg Pro Gly Val Gly
            275                 280
```

```
<210> SEQ ID NO 49
<211> LENGTH: 535
<212> TYPE: PRT
<213> ORGANISM: Artificial Sequence
<220> FEATURE:
<223> OTHER INFORMATION: type I keratin 26

<400> SEQUENCE: 49
```

```
Met Ser Phe Arg Leu Ser Gly Val Ser Arg Arg Leu Cys Ser Gln Ala
1               5                   10                  15

Gly Thr Gly Arg Leu Thr Gly Gly Arg Thr Gly Phe Arg Ala Gly Asn
                20                  25                  30

Val Cys Ser Gly Leu Gly Ala Gly Ser Ser Phe Ser Gly Pro Leu Gly
            35                  40                  45

Ser Val Ser Ser Lys Gly Ser Phe Ser His Gly Gly Gly Gly Leu Gly
    50                  55                  60

Ser Gly Val Cys Thr Gly Phe Leu Glu Asn Glu His Gly Leu Leu Pro
65                  70                  75                  80
```

```
Gly Asn Glu Lys Val Thr Leu Gln Asn Leu Asn Asp Arg Leu Ala Ser
                85                  90                  95

Tyr Leu Asp His Val Cys Thr Leu Glu Glu Ala Asn Ala Asp Leu Glu
            100                 105                 110

Gln Lys Ile Lys Gly Trp Tyr Glu Lys Tyr Gly Pro Gly Ser Gly Arg
            115                 120                 125

Gln Leu Ala His Asp Tyr Ser Lys Tyr Phe Ser Val Thr Glu Asp Leu
        130                 135                 140

Lys Arg Gln Ile Ile Ser Val Thr Thr Cys Asn Ala Ser Ile Val Leu
145                 150                 155                 160

Gln Asn Glu Asn Ala Arg Leu Thr Ala Asp Asp Phe Arg Leu Lys Cys
                165                 170                 175

Glu Asn Glu Leu Ala Leu His Gln Ser Val Glu Ala Asp Ile Asn Gly
            180                 185                 190

Leu His Arg Val Met Asp Glu Leu Thr Leu Cys Thr Ser Asp Leu Glu
            195                 200                 205

Met Gln Cys Glu Ala Leu Ser Glu Glu Leu Thr Tyr Leu Lys Lys Asn
        210                 215                 220

His Gln Glu Glu Met Lys Val Met Gln Gly Ala Ala Arg Gly Asn Val
225                 230                 235                 240

Leu Lys Cys Glu Asn Glu Leu Ala Leu His Gln Ser Val Glu Ala Asp
                245                 250                 255

Ile Asn Gly Leu His Arg Val Met Asp Glu Leu Thr Leu Cys Thr Ser
            260                 265                 270

Asp Leu Glu Met Gln Cys Glu Ala Leu Ser Glu Glu Leu Thr Tyr Leu
            275                 280                 285

Lys Lys Asn His Gln Glu Glu Met Lys Val Met Gln Gly Ala Ala Arg
        290                 295                 300

Gly Asn Val Asn Val Glu Ile Asn Ala Ala Pro Gly Val Asp Leu Thr
305                 310                 315                 320

Val Leu Leu Asn Asn Met Arg Ala Glu Tyr Glu Asp Leu Ala Glu Gln
                325                 330                 335

Asn His Glu Asp Ala Glu Ala Trp Phe Ser Glu Lys Ser Thr Ser Leu
            340                 345                 350

His Gln Gln Ile Ser Asp Asp Ala Gly Ala Ala Met Ala Ala Arg Asn
        355                 360                 365

Glu Leu Met Glu Leu Lys Arg Asn Leu Gln Thr Leu Glu Ile Glu Leu
    370                 375                 380

Gln Ser Leu Leu Ala Met Lys His Ser Tyr Glu Cys Ser Leu Ala Glu
385                 390                 395                 400

Thr Glu Ser Asn Tyr Cys His Gln Leu Gln Gln Ile Gln Glu Gln Ile
                405                 410                 415

Gly Ala Met Glu Asp Gln Leu Gln Gln Ile Arg Met Glu Thr Glu Gly
            420                 425                 430

Gln Lys Leu Glu His Glu Arg Leu Leu Asp Val Lys Ile Phe Leu Glu
        435                 440                 445

Lys Glu Ile Glu Met Tyr Cys Lys Leu Ile Asp Gly Glu Gly Arg Lys
    450                 455                 460

Ser Lys Ser Thr Cys Tyr Lys Ser Glu Gly Arg Gly Pro Lys Asn Ser
465                 470                 475                 480

Glu Asn Gln Val Lys Asp Ser Lys Glu Glu Ala Val Val Lys Thr Val
                485                 490                 495
```

```
Val Gly Glu Leu Asp Gln Leu Gly Ser Val Leu Ser Leu Arg Val His
            500             505             510

Ser Val Glu Glu Lys Ser Ser Lys Ile Ser Asn Ile Thr Met Glu Gln
        515             520             525

Arg Leu Pro Ser Lys Val Pro
    530             535

<210> SEQ ID NO 50
<211> LENGTH: 2268
<212> TYPE: PRT
<213> ORGANISM: Artificial Sequence
<220> FEATURE:
<223> OTHER INFORMATION: PRT705

<400> SEQUENCE: 50

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
            20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Gly Pro Gly Gln Tyr Gly Pro Gly
65                  70                  75                  80

Gln Gln Gly Pro Ser Ala Ser Ala Ala Ala Ala Ala Ala Gly Pro
            85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala
            115                 120                 125

Ala Ala Ala Gly Ser Tyr Gly Ser Gly Pro Gly Gln Gln Gly Pro Tyr
    130                 135                 140

Gly Ser Ala Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Gln Gln Gly Pro Ser Ala Ser Ala Ala Ala Ala Ala Ala Ala
            180                 185                 190

Gly Ser Gly Gln Gln Gly Pro Gly Gln Tyr Gly Pro Tyr Ala Ser Ala
            195                 200                 205

Ala Ala Ala Ala Ala Gly Ser Tyr Gly Ser Gly Pro Gly Gln Gln
    210                 215                 220

Gly Pro Tyr Gly Pro Gly Gln Ser Gly Ser Gly Gln Gln Gly Pro Gly
225                 230                 235                 240

Gln Gln Gly Pro Tyr Ala Ser Ala Ala Ala Ala Ala Ala Gly Pro
            245                 250                 255

Gly Gln Gln Gly Pro Tyr Gly Pro Gly Ser Ser Ala Ala Ala Ala Ala
            260                 265                 270

Ala Ala Gly Ser Tyr Gly Tyr Gly Pro Gly Gln Gln Gly Pro Tyr Gly
        275                 280                 285

Pro Gly Ala Ser Gly Gln Asn Gly Pro Gly Ser Gly Gln Tyr Gly Pro
    290                 295                 300

Gly Gln Gln Gly Pro Gly Pro Ser Ala Ala Ala Ala Ala Ala Ala Gly
305                 310                 315                 320
```

-continued

```
Pro Gly Gln Gln Gly Pro Tyr Gly Pro Gly Ala Ser Ala Ala Ala Ala
                325                 330                 335

Ala Ala Ala Gly Ser Tyr Gly Pro Gly Gln Gln Gly Pro Gly Gln Tyr
            340                 345                 350

Gly Pro Gly Ser Ser Gly Pro Gly Gln Gln Gly Pro Tyr Gly Pro Gly
        355                 360                 365

Ser Ser Ala Ala Ala Ala Ala Ala Ala Gly Ser Tyr Gly Pro Gly Gln
    370                 375                 380

Gln Gly Pro Tyr Gly Pro Gly Pro Ser Ala Ala Ala Ala Ala Ala Ala
385                 390                 395                 400

Gly Ser Tyr Gln Gln Gly Pro Gly Gln Gln Gly Pro Tyr Gly Pro Gly
                405                 410                 415

Ala Ser Gly Pro Gly Gln Gln Gly Pro Tyr Gly Pro Gly Ala Ser Ala
            420                 425                 430

Ala Ala Ala Ala Ala Ala Gly Pro Gly Gln Tyr Gly Pro Gly Gln Gln
            435                 440                 445

Gly Pro Ser Ala Ser Ala Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Gln Gln Gly Gln Gly Pro Tyr Gly Pro Gly Ala Ser Ala
            485                 490                 495

Ala Ala Ala Ala Ala Gly Ser Tyr Gly Pro Gly Gln Gln Gly Pro
            500                 505                 510

Tyr Gly Pro Gly Pro Ser Ala Ala Ala Ala Ala Ala Gly Pro Gly
        515                 520                 525

Ser Gly Gln Tyr Gly Pro Gly Ala Ser Gly Gln Asn Gly Pro Gly Ser
    530                 535                 540

Gly Gln Tyr Gly Pro Gly Gln Gly Pro Gly Pro Ser Ala Ala Ala
545                 550                 555                 560

Ala Ala Ala Ala Gly Pro Gly Ser Gly Gln Gln Gly Pro Gly Ala Ser
            565                 570                 575

Gly Gln Gln Gly Pro Tyr Gly Pro Gly Ala Ser Ala Ala Ala Ala Ala
        580                 585                 590

Ala Ala Gly Ser Asn Gly Pro Gly Ser Gly Gln Gln Gly Pro Gly Gln
        595                 600                 605

Ser Gly Gln Tyr Gly Pro Gly Gln Gln Gly Pro Gly Gln Gln Gly Pro
    610                 615                 620

Gly Ser Ser Ala Ala Ala Ala Ala Ala Gly Pro Gly Gln Tyr Gly
625                 630                 635                 640

Pro Gly Gln Gln Gly Pro Ser Ala Ser Ala Ala Ala Ala Ala Ala
                645                 650                 655

Gly Pro Gly Ser Gly Gln Gln Gly Pro Gly Ala Ser Gly Gln Tyr Gly
        660                 665                 670

Pro Gly Gln Gln Gly Pro Gly Gln Gln Gly Pro Gly Ser Ser Ala Ala
        675                 680                 685

Ala Ala Ala Ala Ala Gly Ser Tyr Gly Ser Gly Pro Gly Gln Gln Gly
    690                 695                 700

Pro Tyr Gly Ser Ala Ala Ala Ala Ala Ala Gly Pro Gly Ser Gly
705                 710                 715                 720

Gln Tyr Gly Gln Gly Pro Tyr Gly Pro Gly Ala Ser Gly Pro Gly Gln
            725                 730                 735

Tyr Gly Pro Gly Gln Gln Gly Pro Ser Ala Ser Ala Ala Ala Ala Ala
```

-continued

```
             740              745              750

Ala Ala Gly Ser Gly Gln Gln Gly Pro Gly Gln Tyr Gly Pro Tyr Ala
         755              760              765

Ser Ala Ala Ala Ala Ala Ala Ala Gly Ser Tyr Gly Ser Gly Pro Gly
     770              775              780

Gln Gln Gly Pro Tyr Gly Pro Gly Gln Ser Gly Ser Gly Gln Gln Gly
785              790              795              800

Pro Gly Gln Gln Gly Pro Tyr Ala Ser Ala Ala Ala Ala Ala Ala Ala
             805              810              815

Gly Pro Gly Gln Gln Gly Pro Tyr Gly Pro Gly Ser Ser Ala Ala Ala
             820              825              830

Ala Ala Ala Ala Gly Ser Tyr Gly Tyr Gly Pro Gly Gln Gln Gly Pro
         835              840              845

Tyr Gly Pro Gly Ala Ser Gly Gln Asn Gly Pro Gly Ser Gly Gln Tyr
     850              855              860

Gly Pro Gly Gln Gln Gly Pro Gly Pro Ser Ala Ala Ala Ala Ala Ala
865              870              875              880

Ala Gly Pro Gly Gln Gln Gly Pro Tyr Gly Pro Gly Ala Ser Ala Ala
             885              890              895

Ala Ala Ala Ala Ala Gly Ser Tyr Gly Pro Gly Gln Gln Gly Pro Gly
         900              905              910

Gln Tyr Gly Pro Gly Ser Ser Gly Pro Gly Gln Gln Gly Pro Tyr Gly
     915              920              925

Pro Gly Ser Ser Ala Ala Ala Ala Ala Ala Ala Gly Ser Tyr Gly Pro
     930              935              940

Gly Gln Gln Gly Pro Tyr Gly Pro Gly Pro Ser Ala Ala Ala Ala Ala
945              950              955              960

Ala Ala Gly Ser Tyr Gln Gln Gly Pro Gly Gln Gln Gly Pro Tyr Gly
             965              970              975

Pro Gly Ala Ser Gly Pro Gly Gln Gln Gly Pro Tyr Gly Pro Gly Ala
         980              985              990

Ser Ala Ala Ala Ala Ala Ala Ala  Gly Pro Gly Gln Tyr  Gly Pro Gly
         995              1000              1005

Gln Gln  Gly Pro Ser Ala Ser  Ala Ala Ala Ala Ala  Ala Ala Gly
     1010              1015              1020

Ser Tyr  Gly Ser Gly Pro Gly  Gln Tyr Gly Pro Tyr  Gly Pro Gly
     1025              1030              1035

Gln Ser  Gly Pro Gly Ser Gly  Gln Gln Gly Gln Gly  Pro Tyr Gly
     1040              1045              1050

Pro Gly  Ala Ser Ala Ala Ala  Ala Ala Ala Ala Gly  Ser Tyr Gly
     1055              1060              1065

Pro Gly  Gln Gln Gly Pro Tyr  Gly Pro Gly Pro Ser  Ala Ala Ala
     1070              1075              1080

Ala Ala  Ala Ala Gly Pro Gly  Ser Gly Gln Tyr Gly  Pro Gly Ala
     1085              1090              1095

Ser Gly  Gln Asn Gly Pro Gly  Ser Gly Gln Tyr Gly  Pro Gly Gln
     1100              1105              1110

Gln Gly  Pro Gly Pro Ser Ala  Ala Ala Ala Ala Ala  Ala Gly Pro
     1115              1120              1125

Gly Ser  Gly Gln Gln Gly Pro  Gly Ala Ser Glu Phe  Glu Leu Val
     1130              1135              1140

Asp Gly  Gln Gln Gly Pro Tyr  Gly Pro Gly Ala Ser  Ala Ala Ala
     1145              1150              1155
```

-continued

```
Ala Ala  Ala Ala Gly Ser Asn  Gly Pro Gly Ser Gly  Gln Gln Gly
    1160             1165              1170

Pro Gly  Gln Ser Gly Gln Tyr  Gly Pro Gly Gln Gln  Gly Pro Gly
    1175             1180              1185

Gln Gln  Gly Pro Gly Ser Ser  Ala Ala Ala Ala Ala  Ala Ala Gly
    1190             1195              1200

Pro Gly  Gln Tyr Gly Pro Gly  Gln Gln Gly Pro Ser  Ala Ser Ala
    1205             1210              1215

Ala Ala  Ala Ala Ala Ala Gly  Pro Gly Ser Gly Gln  Gln Gly Pro
    1220             1225              1230

Gly Ala  Ser Gly Gln Tyr Gly  Pro Gly Gln Gln Gly  Pro Gly Gln
    1235             1240              1245

Gln Gly  Pro Gly Ser Ser Ala  Ala Ala Ala Ala Ala  Ala Gly Ser
    1250             1255              1260

Tyr Gly  Ser Gly Pro Gly Gln  Gln Gly Pro Tyr Gly  Ser Ala Ala
    1265             1270              1275

Ala Ala  Ala Ala Ala Gly Pro  Gly Ser Gly Gln Tyr  Gly Gln Gly
    1280             1285              1290

Pro Tyr  Gly Pro Gly Ala Ser  Gly Pro Gly Gln Tyr  Gly Pro Gly
    1295             1300              1305

Gln Gln  Gly Pro Ser Ala Ser  Ala Ala Ala Ala Ala  Ala Ala Gly
    1310             1315              1320

Ser Gly  Gln Gln Gly Pro Gly  Gln Tyr Gly Pro Tyr  Ala Ser Ala
    1325             1330              1335

Ala Ala  Ala Ala Ala Ala Gly  Ser Tyr Gly Ser Gly  Pro Gly Gln
    1340             1345              1350

Gln Gly  Pro Tyr Gly Pro Gly  Gln Ser Gly Ser Gly  Gln Gln Gly
    1355             1360              1365

Pro Gly  Gln Gln Gly Pro Tyr  Ala Ser Ala Ala Ala  Ala Ala Ala
    1370             1375              1380

Ala Gly  Pro Gly Gln Gln Gly  Pro Tyr Gly Pro Gly  Ser Ser Ala
    1385             1390              1395

Ala Ala  Ala Ala Ala Ala Gly  Ser Tyr Gly Tyr Gly  Pro Gly Gln
    1400             1405              1410

Gln Gly  Pro Tyr Gly Pro Gly  Ala Ser Gly Gln Asn  Gly Pro Gly
    1415             1420              1425

Ser Gly  Gln Tyr Gly Pro Gly  Gln Gln Gly Pro Gly  Pro Ser Ala
    1430             1435              1440

Ala Ala  Ala Ala Ala Ala Gly  Pro Gly Gln Gln Gly  Pro Tyr Gly
    1445             1450              1455

Pro Gly  Ala Ser Ala Ala Ala  Ala Ala Ala Ala Gly  Ser Tyr Gly
    1460             1465              1470

Pro Gly  Gln Gln Gly Pro Gly  Gln Tyr Gly Pro Gly  Ser Ser Gly
    1475             1480              1485

Pro Gly  Gln Gln Gly Pro Tyr  Gly Pro Gly Ser Ser  Ala Ala Ala
    1490             1495              1500

Ala Ala  Ala Ala Gly Ser Tyr  Gly Pro Gly Gln Gln  Gly Pro Tyr
    1505             1510              1515

Gly Pro  Gly Pro Ser Ala Ala  Ala Ala Ala Ala Ala  Gly Ser Tyr
    1520             1525              1530

Gln Gln  Gly Pro Gly Gln Gln  Gly Pro Tyr Gly Pro  Gly Ala Ser
    1535             1540              1545
```

-continued

```
Gly Pro  Gly Gln Gln Gly Pro  Tyr Gly Pro Gly  Ser Ala Ala
    1550             1555             1560

Ala Ala  Ala Ala Ala Gly Pro  Gly Gln Tyr Gly  Pro Gly Gln Gln
    1565             1570             1575

Gly Pro  Ser Ala Ser Ala Ala  Ala Ala Ala Ala  Ala Gly Ser Tyr
    1580             1585             1590

Gly Ser  Gly Pro Gly Gln Tyr  Gly Pro Tyr Gly  Pro Gly Gln Ser
    1595             1600             1605

Gly Pro  Gly Ser Gly Gln Gln  Gly Gln Gly Pro  Tyr Gly Pro Gly
    1610             1615             1620

Ala Ser  Ala Ala Ala Ala Ala  Ala Ala Gly Ser  Tyr Gly Pro Gly
    1625             1630             1635

Gln Gln  Gly Pro Tyr Gly Pro  Gly Pro Ser Ala  Ala Ala Ala Ala
    1640             1645             1650

Ala Ala  Gly Pro Gly Ser Gly  Gln Tyr Gly Pro  Gly Ala Ser Gly
    1655             1660             1665

Gln Asn  Gly Pro Gly Ser Gly  Gln Tyr Gly Pro  Gly Gln Gln Gly
    1670             1675             1680

Pro Gly  Pro Ser Ala Ala Ala  Ala Ala Ala Gly  Pro Gly Ser
    1685             1690             1695

Gly Gln  Gln Gly Pro Gly Ala  Ser Gly Gln Gln  Gly Pro Tyr Gly
    1700             1705             1710

Pro Gly  Ala Ser Ala Ala Ala  Ala Ala Ala Gly  Ser Asn Gly
    1715             1720             1725

Pro Gly  Ser Gly Gln Gln Gly  Pro Gly Gln Ser  Gly Gln Tyr Gly
    1730             1735             1740

Pro Gly  Gln Gln Gly Pro Gly  Gln Gln Gly Pro  Gly Ser Ser Ala
    1745             1750             1755

Ala Ala  Ala Ala Ala Ala Gly  Pro Gly Gln Tyr  Gly Pro Gly Gln
    1760             1765             1770

Gln Gly  Pro Ser Ala Ser Ala  Ala Ala Ala Ala  Ala Gly Pro
    1775             1780             1785

Gly Ser  Gly Gln Gln Gly Pro  Gly Ala Ser Gly  Gln Tyr Gly Pro
    1790             1795             1800

Gly Gln  Gln Gly Pro Gly Gln  Gln Gly Pro Gly  Ser Ser Ala Ala
    1805             1810             1815

Ala Ala  Ala Ala Ala Gly Ser  Tyr Gly Ser Gly  Pro Gly Gln Gln
    1820             1825             1830

Gly Pro  Tyr Gly Ser Ala Ala  Ala Ala Ala Ala  Gly Pro Gly
    1835             1840             1845

Ser Gly  Gln Tyr Gly Gln Gly  Pro Tyr Gly Pro  Gly Ala Ser Gly
    1850             1855             1860

Pro Gly  Gln Tyr Gly Pro Gly  Gln Gln Gly Pro  Ser Ala Ser Ala
    1865             1870             1875

Ala Ala  Ala Ala Ala Ala Gly  Ser Gly Gln Gln  Gly Pro Gly Gln
    1880             1885             1890

Tyr Gly  Pro Tyr Ala Ser Ala  Ala Ala Ala Ala  Ala Gly Ser
    1895             1900             1905

Tyr Gly  Ser Gly Pro Gly Gln  Gln Gly Pro Tyr  Gly Pro Gly Gln
    1910             1915             1920

Ser Gly  Ser Gly Gln Gln Gly  Pro Gly Gln Gln  Gly Pro Tyr Ala
    1925             1930             1935

Ser Ala  Ala Ala Ala Ala Ala  Ala Gly Pro Gly Gln  Gln Gly Pro
```

-continued

```
        1940              1945              1950

Tyr Gly  Pro Gly Ser Ser Ala  Ala Ala Ala Ala  Ala Gly Ser
    1955              1960              1965

Tyr Gly  Tyr Gly Pro Gly Gln  Gln Gly Pro Tyr  Gly Pro Gly Ala
    1970              1975              1980

Ser Gly  Gln Asn Gly Pro Gly  Ser Gly Gln Tyr  Gly Pro Gly Gln
    1985              1990              1995

Gln Gly  Pro Gly Pro Ser Ala  Ala Ala Ala Ala  Ala Gly Pro
    2000              2005              2010

Gly Gln  Gln Gly Pro Tyr Gly  Pro Gly Ala Ser  Ala Ala Ala
    2015              2020              2025

Ala Ala  Ala Gly Ser Tyr Gly  Pro Gly Gln Gln  Gly Pro Gly Gln
    2030              2035              2040

Tyr Gly  Pro Gly Ser Ser Gly  Pro Gly Gln Gln  Gly Pro Tyr Gly
    2045              2050              2055

Pro Gly  Ser Ser Ala Ala Ala  Ala Ala Ala Gly  Ser Tyr Gly
    2060              2065              2070

Pro Gly  Gln Gln Gly Pro Tyr  Gly Pro Gly Pro  Ser Ala Ala Ala
    2075              2080              2085

Ala Ala  Ala Ala Gly Ser Tyr  Gln Gln Gly Pro  Gly Gln Gln Gly
    2090              2095              2100

Pro Tyr  Gly Pro Gly Ala Ser  Gly Pro Gly Gln  Gln Gly Pro Tyr
    2105              2110              2115

Gly Pro  Gly Ala Ser Ala Ala  Ala Ala Ala Ala  Gly Pro Gly
    2120              2125              2130

Gln Tyr  Gly Pro Gly Gln Gln  Gly Pro Ser Ala  Ser Ala Ala Ala
    2135              2140              2145

Ala Ala  Ala Ala Gly Ser Tyr  Gly Ser Gly Pro  Gly Gln Tyr Gly
    2150              2155              2160

Pro Tyr  Gly Pro Gly Gln Ser  Gly Pro Gly Ser  Gly Gln Gln Gly
    2165              2170              2175

Gln Gly  Pro Tyr Gly Pro Gly  Ala Ser Ala Ala  Ala Ala Ala Ala
    2180              2185              2190

Ala Gly  Ser Tyr Gly Pro Gly  Gln Gln Gly Pro  Tyr Gly Pro Gly
    2195              2200              2205

Pro Ser  Ala Ala Ala Ala Ala  Ala Ala Gly Pro  Gly Ser Gly Gln
    2210              2215              2220

Tyr Gly  Pro Gly Ala Ser Gly  Gln Asn Gly Pro  Gly Ser Gly Gln
    2225              2230              2235

Tyr Gly  Pro Gly Gln Gln Gly  Pro Gly Pro Ser  Ala Ala Ala Ala
    2240              2245              2250

Ala Ala  Ala Gly Pro Gly Ser  Gly Gln Gln Gly  Pro Gly Ala Ser
    2255              2260              2265
```

<210> SEQ ID NO 51
<211> LENGTH: 601
<212> TYPE: PRT
<213> ORGANISM: Artificial Sequence
<220> FEATURE:
<223> OTHER INFORMATION: PRT826

<400> SEQUENCE: 51

```
Met His His His His His His Thr Thr Gly Thr Thr Gly Pro Gly Gln
1               5                   10                  15

Gln Gly Pro Tyr Gly Pro Gly Ala Thr Ala Ala Ala Ala Ala Gly Gln
```

-continued

```
                  20                  25                  30

Asn Gly Pro Gly Thr Gly Gln Gln Gly Pro Gly Gln Thr Gly Gln Tyr
              35                  40                  45

Gly Pro Gly Gln Gln Gly Pro Gly Gln Gln Gly Pro Gly Thr Thr Ala
          50                  55                  60

Ala Ala Ala Ala Gly Pro Gly Gln Tyr Gly Pro Gly Gln Gln Gly Pro
65                  70                  75                  80

Thr Ala Thr Ala Ala Ala Ala Ala Gly Pro Gly Thr Gly Gln Gln Gly
                  85                  90                  95

Pro Gly Ala Thr Gly Gln Tyr Gly Pro Gly Gln Gln Gly Pro Gly Gln
              100                 105                 110

Gln Gly Pro Gly Thr Thr Ala Ala Ala Ala Gly Gln Tyr Gly Thr
          115                 120                 125

Gly Pro Gly Gln Gln Gly Pro Tyr Gly Thr Ala Ala Ala Ala Ala Gly
          130                 135                 140

Pro Gly Thr Gly Gln Tyr Gly Gln Gly Pro Tyr Gly Pro Gly Ala Thr
145                 150                 155                 160

Gly Pro Gly Gln Tyr Gly Pro Gly Gln Gln Gly Pro Thr Ala Thr Ala
              165                 170                 175

Ala Ala Ala Ala Gly Thr Gly Gln Gln Gly Pro Gly Gln Tyr Gly Pro
              180                 185                 190

Tyr Ala Thr Ala Ala Ala Ala Ala Gly Gln Tyr Gly Thr Gly Pro Gly
              195                 200                 205

Gln Gln Gly Pro Tyr Gly Pro Gly Gln Thr Gly Thr Gly Gln Gln Gly
          210                 215                 220

Pro Gly Gln Gln Gly Pro Tyr Ala Thr Ala Ala Ala Ala Gly Pro
225                 230                 235                 240

Gly Gln Gln Gly Pro Tyr Gly Pro Gly Thr Thr Ala Ala Ala Ala Ala
              245                 250                 255

Gly Gln Tyr Gly Tyr Gly Pro Gly Gln Gln Gly Pro Tyr Gly Pro Gly
              260                 265                 270

Ala Thr Gly Gln Asn Gly Pro Gly Thr Gly Gln Tyr Gly Pro Gly Gln
              275                 280                 285

Gln Gly Pro Gly Gln Thr Ala Ala Ala Ala Gly Pro Gly Gln Gln
          290                 295                 300

Gly Pro Tyr Gly Pro Gly Ala Thr Ala Ala Ala Ala Gly Gln Tyr
305                 310                 315                 320

Gly Pro Gly Gln Gln Gly Pro Gly Gln Tyr Gly Pro Gly Thr Thr Gly
              325                 330                 335

Pro Gly Gln Gln Gly Pro Tyr Gly Pro Gly Thr Thr Ala Ala Ala Ala
              340                 345                 350

Ala Gly Gln Tyr Gly Pro Gly Gln Gln Gly Pro Tyr Gly Pro Gly Gln
              355                 360                 365

Thr Ala Ala Ala Ala Gly Gln Tyr Gln Gln Gly Pro Gly Gln Gln
          370                 375                 380

Gly Pro Tyr Gly Pro Gly Ala Thr Gly Pro Gly Gln Gln Gly Pro Tyr
385                 390                 395                 400

Gly Pro Gly Ala Thr Ala Ala Ala Ala Gly Pro Gly Gln Tyr Gly
              405                 410                 415

Pro Gly Gln Gln Gly Pro Thr Ala Thr Ala Ala Ala Ala Gly Gln
          420                 425                 430

Tyr Gly Thr Gly Pro Gly Gln Tyr Gly Pro Tyr Gly Pro Gly Gln Thr
          435                 440                 445
```

```
Gly Pro Gly Thr Gly Gln Gln Gly Gln Gly Pro Tyr Gly Pro Gly Ala
    450                 455             460

Thr Ala Ala Ala Ala Ala Gly Gln Tyr Gly Pro Gly Gln Gln Gly Pro
465             470             475             480

Tyr Gly Pro Gly Gln Thr Ala Ala Ala Ala Gly Pro Gly Thr Gly
            485             490             495

Gln Tyr Gly Pro Gly Ala Thr Gly Gln Asn Gly Pro Gly Thr Gly Gln
            500             505             510

Tyr Gly Pro Gly Gln Gln Gly Pro Gly Gln Thr Ala Ala Ala Ala Ala
            515             520             525

Gly Gln Tyr Gln Gln Gly Pro Gly Gln Gln Gly Pro Tyr Gly Pro Gly
    530             535             540

Ala Thr Ala Ala Ala Ala Ala Gly Gln Tyr Gly Thr Gly Pro Gly Gln
545             550             555             560

Gln Gly Pro Tyr Gly Pro Gly Gln Thr Gly Thr Gly Gln Gln Gly Pro
            565             570             575

Gly Gln Gln Gly Pro Tyr Ala Thr Ala Ala Ala Ala Ala Gly Pro Gly
            580             585             590

Thr Gly Gln Gln Gly Pro Gly Ala Thr
            595             600
```

<210> SEQ ID NO 52
<211> LENGTH: 2476
<212> TYPE: PRT
<213> ORGANISM: Artificial Sequence
<220> FEATURE:
<223> OTHER INFORMATION: PRT853

<400> SEQUENCE: 52

```
Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Ala Gly
            20              25              30

Gln Asn Gly Pro Gly Ser Gly Gln Gln Gly Pro Gly Gln Ser Gly Gln
        35              40              45

Tyr Gly Pro Gly Gln Gln Gly Pro Gly Gln Gln Gly Pro Gly Ser Ser
    50              55              60

Ala Ala Ala Ala Ala Ala Gly Pro Gly Gln Tyr Gly Pro Gly Gln Gln
65              70              75              80

Gly Pro Ser Ala Ser Ala Ala Ala Ala Ala Gly Pro Gly Ser Gly
            85              90              95

Gln Gln Gly Pro Gly Ala Ser Gly Gln Tyr Gly Pro Gly Gln Gln Gly
            100             105             110

Pro Gly Gln Gln Gly Pro Gly Ser Ser Ala Ala Ala Ala Ala Ala Gly
            115             120             125

Gln Tyr Gly Ser Gly Pro Gly Gln Gln Gly Pro Tyr Gly Ser Ala Ala
    130             135             140

Ala Ala Ala Ala Gly Pro Gly Ser Gly Gln Tyr Gly Gln Gly Pro Tyr
145             150             155             160

Gly Pro Gly Ala Ser Gly Pro Gly Gln Tyr Gly Pro Gly Gln Gln Gly
            165             170             175

Pro Ser Ala Ser Ala Ala Ala Ala Ala Ala Gly Ser Gly Gln Gln Gly
            180             185             190

Pro Gly Gln Tyr Gly Pro Tyr Ala Ser Ala Ala Ala Ala Ala Ala Gly
            195             200             205
```

-continued

```
Gln Tyr Gly Ser Gly Pro Gly Gln Gln Gly Pro Tyr Gly Pro Gly Gln
    210             215             220

Ser Gly Ser Gly Gln Gln Gly Pro Gly Gln Gln Gly Pro Tyr Ala Ser
225             230             235             240

Ala Ala Ala Ala Ala Ala Gly Pro Gly Gln Gln Gly Pro Tyr Gly Pro
            245             250             255

Gly Ser Ser Ala Ala Ala Ala Ala Ala Gly Gln Tyr Gly Tyr Gly Pro
            260             265             270

Gly Gln Gln Gly Pro Tyr Gly Pro Gly Ala Ser Gly Gln Asn Gly Pro
            275             280             285

Gly Ser Gly Gln Tyr Gly Pro Gly Gln Gln Gly Pro Gly Gln Ser Ala
    290             295             300

Ala Ala Ala Ala Gly Pro Gly Gln Gln Gly Pro Tyr Gly Pro Gly
305             310             315             320

Ala Ser Ala Ala Ala Ala Ala Ala Gly Gln Tyr Gly Pro Gly Gln Gln
            325             330             335

Gly Pro Gly Gln Tyr Gly Pro Gly Ser Ser Gly Pro Gly Gln Gln Gly
            340             345             350

Pro Tyr Gly Pro Gly Ser Ser Ala Ala Ala Ala Ala Ala Gly Gln Tyr
    355             360             365

Gly Pro Gly Gln Gln Gly Pro Tyr Gly Pro Gly Gln Ser Ala Ala Ala
    370             375             380

Ala Ala Ala Gly Gln Tyr Gln Gln Gly Pro Gly Gln Gln Gly Pro Tyr
385             390             395             400

Gly Pro Gly Ala Ser Gly Pro Gly Gln Gln Gly Pro Tyr Gly Pro Gly
            405             410             415

Ala Ser Ala Ala Ala Ala Ala Ala Gly Pro Gly Gln Tyr Gly Pro Gly
            420             425             430

Gln Gln Gly Pro Ser Ala Ser Ala Ala Ala Ala Ala Gly Gln Tyr
    435             440             445

Gly Ser Gly Pro Gly Gln Tyr Gly Pro Tyr Gly Pro Gly Gln Ser Gly
    450             455             460

Pro Gly Ser Gly Gln Gln Gly Gln Gly Pro Tyr Gly Pro Gly Ala Ser
465             470             475             480

Ala Ala Ala Ala Ala Ala Gly Gln Tyr Gly Pro Gly Gln Gln Gly Pro
            485             490             495

Tyr Gly Pro Gly Gln Ser Ala Ala Ala Ala Ala Gly Pro Gly Ser
            500             505             510

Gly Gln Tyr Gly Pro Gly Ala Ser Gly Gln Asn Gly Pro Gly Ser Gly
            515             520             525

Gln Tyr Gly Pro Gly Gln Gln Gly Pro Gly Gln Ser Ala Ala Ala Ala
    530             535             540

Ala Ala Gly Gln Tyr Gln Gln Gly Pro Gly Gln Gln Gly Pro Tyr Gly
545             550             555             560

Pro Gly Ala Ser Ala Ala Ala Ala Ala Ala Gly Gln Tyr Gly Ser Gly
            565             570             575

Pro Gly Gln Gln Gly Pro Tyr Gly Pro Gly Gln Ser Gly Ser Gly Gln
            580             585             590

Gln Gly Pro Gly Gln Gln Gly Pro Tyr Ala Ser Ala Ala Ala Ala Ala
    595             600             605

Ala Gly Pro Gly Ser Gly Gln Gln Gly Pro Gly Ala Ser Ala Ala Ala
    610             615             620
```

-continued

Ala Ala Ala Ala Glu Phe Gly Gln Gln Gly Pro Tyr Gly Pro Gly Ala
625              630              635              640

Ser Ala Ala Ala Ala Ala Ala Gly Gln Asn Gly Pro Gly Ser Gly Gln
                645              650              655

Gln Gly Pro Gly Gln Ser Gly Gln Tyr Gly Pro Gly Gln Gln Gly Pro
              660              665              670

Gly Gln Gln Gly Pro Gly Ser Ser Ala Ala Ala Ala Ala Ala Gly Pro
      675              680              685

Gly Gln Tyr Gly Pro Gly Gln Gln Gly Pro Ser Ala Ser Ala Ala Ala
      690              695              700

Ala Ala Ala Gly Pro Gly Ser Gly Gln Gln Gly Pro Gly Ala Ser Gly
705              710              715              720

Gln Tyr Gly Pro Gly Gln Gln Gly Pro Gly Gln Gln Gly Pro Gly Ser
              725              730              735

Ser Ala Ala Ala Ala Ala Ala Gly Gln Tyr Gly Ser Gly Pro Gly Gln
              740              745              750

Gln Gly Pro Tyr Gly Ser Ala Ala Ala Ala Ala Gly Pro Gly Ser
      755              760              765

Gly Gln Tyr Gly Gln Gly Pro Tyr Gly Pro Gly Ala Ser Gly Pro Gly
      770              775              780

Gln Tyr Gly Pro Gly Gln Gln Gly Pro Ser Ala Ser Ala Ala Ala Ala
785              790              795              800

Ala Ala Gly Ser Gly Gln Gln Gly Pro Gly Gln Tyr Gly Pro Tyr Ala
              805              810              815

Ser Ala Ala Ala Ala Ala Ala Gly Gln Tyr Gly Ser Gly Pro Gly Gln
              820              825              830

Gln Gly Pro Tyr Gly Pro Gly Gln Ser Gly Ser Gly Gln Gln Gly Pro
      835              840              845

Gly Gln Gln Gly Pro Tyr Ala Ser Ala Ala Ala Ala Ala Ala Gly Pro
      850              855              860

Gly Gln Gln Gly Pro Tyr Gly Pro Gly Ser Ser Ala Ala Ala Ala Ala
865              870              875              880

Ala Gly Gln Tyr Gly Tyr Gly Pro Gly Gln Gln Gly Pro Tyr Gly Pro
              885              890              895

Gly Ala Ser Gly Gln Asn Gly Pro Gly Ser Gly Gln Tyr Gly Pro Gly
              900              905              910

Gln Gln Gly Pro Gly Gln Ser Ala Ala Ala Ala Ala Ala Gly Pro Gly
      915              920              925

Gln Gln Gly Pro Tyr Gly Pro Gly Ala Ser Ala Ala Ala Ala Ala Ala
      930              935              940

Gly Gln Tyr Gly Pro Gly Gln Gln Gly Pro Gly Gln Tyr Gly Pro Gly
945              950              955              960

Ser Ser Gly Pro Gly Gln Gln Gly Pro Tyr Gly Pro Gly Ser Ser Ala
              965              970              975

Ala Ala Ala Ala Gly Gln Tyr Gly Pro Gly Gln Gln Gly Pro Tyr
      980              985              990

Gly Pro Gly Gln Ser Ala Ala Ala  Ala Ala Ala Gly Gln  Tyr Gln Gln
      995              1000              1005

Gly Pro  Gly Gln Gln Gly Pro  Tyr Gly Pro Gly Ala  Ser Gly Pro
      1010              1015              1020

Gly Gln  Gln Gly Pro Tyr Gly  Pro Gly Ala Ser Ala  Ala Ala Ala
      1025              1030              1035

Ala Ala  Gly Pro Gly Gln Tyr  Gly Pro Gly Gln Gln  Gly Pro Ser

-continued

```
          1040                1045                1050

Ala Ser  Ala Ala Ala Ala Ala  Ala Gly Gln Tyr Gly  Ser Gly Pro
    1055                1060                1065

Gly Gln  Tyr Gly Pro Tyr Gly  Pro Gly Gln Ser Gly  Pro Gly Ser
    1070                1075                1080

Gly Gln  Gln Gly Gln Gly Pro  Tyr Gly Pro Gly Ala  Ser Ala Ala
    1085                1090                1095

Ala Ala  Ala Ala Gly Gln Tyr  Gly Pro Gly Gln Gln  Gly Pro Tyr
    1100                1105                1110

Gly Pro  Gly Gln Ser Ala Ala  Ala Ala Ala Ala Gly  Pro Gly Ser
    1115                1120                1125

Gly Gln  Tyr Gly Pro Gly Ala  Ser Gly Gln Asn Gly  Pro Gly Ser
    1130                1135                1140

Gly Gln  Tyr Gly Pro Gly Gln  Gln Gly Pro Gly Gln  Ser Ala Ala
    1145                1150                1155

Ala Ala  Ala Ala Gly Gln Tyr  Gln Gln Gly Pro Gly  Gln Gln Gly
    1160                1165                1170

Pro Tyr  Gly Pro Gly Ala Ser  Ala Ala Ala Ala Ala  Ala Gly Gln
    1175                1180                1185

Tyr Gly  Ser Gly Pro Gly Gln  Gln Gly Pro Tyr Gly  Pro Gly Gln
    1190                1195                1200

Ser Gly  Ser Gly Gln Gln Gly  Pro Gly Gln Gln Gly  Pro Tyr Ala
    1205                1210                1215

Ser Ala  Ala Ala Ala Ala Ala  Gly Pro Gly Ser Gly  Gln Gln Gly
    1220                1225                1230

Pro Gly  Ala Ser Ala Ala Ala  Ala Ala Ala Glu Leu  Gly Gln
    1235                1240                1245

Gln Gly  Pro Tyr Gly Pro Gly  Ala Ser Ala Ala Ala  Ala Ala Ala
    1250                1255                1260

Gly Gln  Asn Gly Pro Gly Ser  Gly Gln Gln Gly Pro  Gly Gln Ser
    1265                1270                1275

Gly Gln  Tyr Gly Pro Gly Gln  Gln Gly Pro Gly Gln  Gln Gly Pro
    1280                1285                1290

Gly Ser  Ser Ala Ala Ala Ala  Ala Ala Gly Pro Gly  Gln Tyr Gly
    1295                1300                1305

Pro Gly  Gln Gln Gly Pro Ser  Ala Ser Ala Ala Ala  Ala Ala Ala
    1310                1315                1320

Gly Pro  Gly Ser Gly Gln Gln  Gly Pro Gly Ala Ser  Gly Gln Tyr
    1325                1330                1335

Gly Pro  Gly Gln Gln Gly Pro  Gly Gln Gln Gly Pro  Gly Ser Ser
    1340                1345                1350

Ala Ala  Ala Ala Ala Ala Gly  Gln Tyr Gly Ser Gly  Pro Gly Gln
    1355                1360                1365

Gln Gly  Pro Tyr Gly Ser Ala  Ala Ala Ala Ala Ala  Gly Pro Gly
    1370                1375                1380

Ser Gly  Gln Tyr Gly Gln Gly  Pro Tyr Gly Pro Gly  Ala Ser Gly
    1385                1390                1395

Pro Gly  Gln Tyr Gly Pro Gly  Gln Gln Gly Pro Ser  Ala Ser Ala
    1400                1405                1410

Ala Ala  Ala Ala Ala Gly Ser  Gly Gln Gln Gly Pro  Gly Gln Tyr
    1415                1420                1425

Gly Pro  Tyr Ala Ser Ala Ala  Ala Ala Ala Ala Gly  Gln Tyr Gly
    1430                1435                1440
```

-continued

```
Ser Gly  Pro Gly Gln Gln Gly  Pro Tyr Gly Pro Gly  Gln Ser Gly
    1445              1450              1455

Ser Gly  Gln Gln Gly Pro Gly  Gln Gln Gly Pro Tyr  Ala Ser Ala
    1460              1465              1470

Ala Ala  Ala Ala Ala Gly Pro  Gly Gln Gln Gly Pro  Tyr Gly Pro
    1475              1480              1485

Gly Ser  Ser Ala Ala Ala Ala  Ala Ala Gly Gln Tyr  Gly Tyr Gly
    1490              1495              1500

Pro Gly  Gln Gln Gly Pro Tyr  Gly Pro Gly Ala Ser  Gly Gln Asn
    1505              1510              1515

Gly Pro  Gly Ser Gly Gln Tyr  Gly Pro Gly Gln Gln  Gly Pro Gly
    1520              1525              1530

Gln Ser  Ala Ala Ala Ala Ala  Ala Gly Pro Gly Gln  Gln Gly Pro
    1535              1540              1545

Tyr Gly  Pro Gly Ala Ser Ala  Ala Ala Ala Ala Ala  Gly Gln Tyr
    1550              1555              1560

Gly Pro  Gly Gln Gln Gly Pro  Gly Gln Tyr Gly Pro  Gly Ser Ser
    1565              1570              1575

Gly Pro  Gly Gln Gln Gly Pro  Tyr Gly Pro Gly Ser  Ser Ala Ala
    1580              1585              1590

Ala Ala  Ala Ala Gly Gln Tyr  Gly Pro Gly Gln Gln  Gly Pro Tyr
    1595              1600              1605

Gly Pro  Gly Gln Ser Ala Ala  Ala Ala Ala Ala Gly  Gln Tyr Gln
    1610              1615              1620

Gln Gly  Pro Gly Gln Gln Gly  Pro Tyr Gly Pro Gly  Ala Ser Gly
    1625              1630              1635

Pro Gly  Gln Gln Gly Pro Tyr  Gly Pro Gly Ala Ser  Ala Ala Ala
    1640              1645              1650

Ala Ala  Ala Gly Pro Gly Gln  Tyr Gly Pro Gly Gln  Gln Gly Pro
    1655              1660              1665

Ser Ala  Ser Ala Ala Ala Ala  Ala Ala Gly Gln Tyr  Gly Ser Gly
    1670              1675              1680

Pro Gly  Gln Tyr Gly Pro Tyr  Gly Pro Gly Gln Ser  Gly Pro Gly
    1685              1690              1695

Ser Gly  Gln Gln Gly Gln Gly  Pro Tyr Gly Pro Gly  Ala Ser Ala
    1700              1705              1710

Ala Ala  Ala Ala Ala Gly Gln  Tyr Gly Pro Gly Gln  Gln Gly Pro
    1715              1720              1725

Tyr Gly  Pro Gly Gln Ser Ala  Ala Ala Ala Ala Ala  Gly Pro Gly
    1730              1735              1740

Ser Gly  Gln Tyr Gly Pro Gly  Ala Ser Gly Gln Asn  Gly Pro Gly
    1745              1750              1755

Ser Gly  Gln Tyr Gly Pro Gly  Gln Gln Gly Pro Gly  Gln Ser Ala
    1760              1765              1770

Ala Ala  Ala Ala Gly Gln Tyr  Gln Gln Gly Pro Gly  Gln Gln
    1775              1780              1785

Gly Pro  Tyr Gly Pro Gly Ala  Ser Ala Ala Ala Ala  Ala Ala Gly
    1790              1795              1800

Gln Tyr  Gly Ser Gly Pro Gly  Gln Gln Gly Pro Tyr  Gly Pro Gly
    1805              1810              1815

Gln Ser  Gly Ser Gly Gln Gln  Gly Pro Gly Gln Gln  Gly Pro Tyr
    1820              1825              1830
```

-continued

```
Ala Ser  Ala Ala Ala Ala Ala  Ala Gly Pro Gly Ser  Gly Gln Gln
    1835               1840               1845

Gly Pro  Gly Ala Ser Ala Ala  Ala Ala Ala Ala Ala  Lys Leu Gly
    1850               1855               1860

Gln Gln  Gly Pro Tyr Gly Pro  Gly Ala Ser Ala Ala  Ala Ala Ala
    1865               1870               1875

Ala Gly  Gln Asn Gly Pro Gly  Ser Gly Gln Gln Gly  Pro Gly Gln
    1880               1885               1890

Ser Gly  Gln Tyr Gly Pro Gly  Gln Gln Gly Pro Gly  Gln Gln Gly
    1895               1900               1905

Pro Gly  Ser Ser Ala Ala Ala  Ala Ala Ala Gly Pro  Gly Gln Tyr
    1910               1915               1920

Gly Pro  Gly Gln Gln Gly Pro  Ser Ala Ser Ala Ala  Ala Ala Ala
    1925               1930               1935

Ala Gly  Pro Gly Ser Gly Gln  Gln Gly Pro Gly Ala  Ser Gly Gln
    1940               1945               1950

Tyr Gly  Pro Gly Gln Gln Gly  Pro Gly Gln Gly  Pro Gly Ser
    1955               1960               1965

Ser Ala  Ala Ala Ala Ala Ala  Gly Gln Tyr Gly Ser  Gly Pro Gly
    1970               1975               1980

Gln Gln  Gly Pro Tyr Gly Ser  Ala Ala Ala Ala Ala  Ala Gly Pro
    1985               1990               1995

Gly Ser  Gly Gln Tyr Gly Gln  Gly Pro Tyr Gly Pro  Gly Ala Ser
    2000               2005               2010

Gly Pro  Gly Gln Tyr Gly Pro  Gly Gln Gln Gly Pro  Ser Ala Ser
    2015               2020               2025

Ala Ala  Ala Ala Ala Ala Gly  Ser Gly Gln Gln Gly  Pro Gly Gln
    2030               2035               2040

Tyr Gly  Pro Tyr Ala Ser Ala  Ala Ala Ala Ala  Gly Gln Tyr
    2045               2050               2055

Gly Ser  Gly Pro Gly Gln Gln  Gly Pro Tyr Gly Pro  Gly Gln Ser
    2060               2065               2070

Gly Ser  Gly Gln Gln Gly Pro  Gly Gln Gln Gly Pro  Tyr Ala Ser
    2075               2080               2085

Ala Ala  Ala Ala Ala Ala Gly  Pro Gly Gln Gln Gly  Pro Tyr Gly
    2090               2095               2100

Pro Gly  Ser Ser Ala Ala Ala  Ala Ala Ala Gly Gln  Tyr Gly Tyr
    2105               2110               2115

Gly Pro  Gly Gln Gln Gly Pro  Tyr Gly Pro Gly Ala  Ser Gly Gln
    2120               2125               2130

Asn Gly  Pro Gly Ser Gly Gln  Tyr Gly Pro Gly Gln  Gln Gly Pro
    2135               2140               2145

Gly Gln  Ser Ala Ala Ala Ala  Ala Ala Gly Pro Gly  Gln Gln Gly
    2150               2155               2160

Pro Tyr  Gly Pro Gly Ala Ser  Ala Ala Ala Ala Ala  Ala Gly Gln
    2165               2170               2175

Tyr Gly  Pro Gly Gln Gln Gly  Pro Gly Gln Tyr Gly  Pro Gly Ser
    2180               2185               2190

Ser Gly  Pro Gly Gln Gln Gly  Pro Tyr Gly Pro Gly  Ser Ser Ala
    2195               2200               2205

Ala Ala  Ala Ala Ala Gly Gln  Tyr Gly Pro Gly Gln  Gln Gly Pro
    2210               2215               2220

Tyr Gly  Pro Gly Gln Ser Ala  Ala Ala Ala Ala Ala  Gly Gln Tyr
```

-continued

```
          2225              2230              2235

Gln Gln  Gly Pro Gly Gln Gln  Gly Pro Tyr Gly Pro  Gly Ala Ser
    2240              2245              2250

Gly Pro  Gly Gln Gln Gly Pro  Tyr Gly Pro Gly Ala  Ser Ala Ala
    2255              2260              2265

Ala Ala  Ala Ala Gly Pro Gly  Gln Tyr Gly Pro Gly  Gln Gln Gly
    2270              2275              2280

Pro Ser  Ala Ser Ala Ala Ala  Ala Ala Ala Gly Gln  Tyr Gly Ser
    2285              2290              2295

Gly Pro  Gly Gln Tyr Gly Pro  Tyr Gly Pro Gly Gln  Ser Gly Pro
    2300              2305              2310

Gly Ser  Gly Gln Gln Gly Gln  Gly Pro Tyr Gly Pro  Gly Ala Ser
    2315              2320              2325

Ala Ala  Ala Ala Ala Ala Gly  Gln Tyr Gly Pro Gly  Gln Gln Gly
    2330              2335              2340

Pro Tyr  Gly Pro Gly Gln Ser  Ala Ala Ala Ala Ala  Ala Gly Pro
    2345              2350              2355

Gly Ser  Gly Gln Tyr Gly Pro  Gly Ala Ser Gly Gln  Asn Gly Pro
    2360              2365              2370

Gly Ser  Gly Gln Tyr Gly Pro  Gly Gln Gln Gly Pro  Gly Gln Ser
    2375              2380              2385

Ala Ala  Ala Ala Ala Ala Gly  Gln Tyr Gln Gln Gly  Pro Gly Gln
    2390              2395              2400

Gln Gly  Pro Tyr Gly Pro Gly  Ala Ser Ala Ala Ala  Ala Ala Ala
    2405              2410              2415

Gly Gln  Tyr Gly Ser Gly Pro  Gly Gln Gln Gly Pro  Tyr Gly Pro
    2420              2425              2430

Gly Gln  Ser Gly Ser Gly Gln  Gln Gly Pro Gly Gln  Gln Gly Pro
    2435              2440              2445

Tyr Ala  Ser Ala Ala Ala Ala  Ala Ala Gly Pro Gly  Ser Gly Gln
    2450              2455              2460

Gln Gly  Pro Gly Ala Ser Ala  Ala Ala Ala Ala Ala  Ala
    2465              2470              2475

<210> SEQ ID NO 53
<211> LENGTH: 601
<212> TYPE: PRT
<213> ORGANISM: Artificial Sequence
<220> FEATURE:
<223> OTHER INFORMATION: PRT1103

<400> SEQUENCE: 53

Met His His His His His His Ala Ala Gly Ala Ala Gly Pro Gly Gln
1               5                  10                  15

Gln Gly Pro Phe Gly Pro Gly Ala Gly Ala Ala Ala Ala Gly Gln
            20              25                  30

Asn Gly Pro Gly Ala Gly Gln Gln Gly Pro Gly Gln Ala Gly Gln Phe
        35              40                  45

Gly Pro Gly Gln Gln Gly Pro Gly Gln Gln Gly Pro Gly Ala Gly Ala
    50              55                  60

Ala Ala Ala Ala Gly Pro Gly Gln Phe Gly Pro Gly Gln Gln Gly Pro
65              70              75                  80

Ser Ala Gly Ala Ala Ala Ala Ala Gly Pro Gly Ala Gly Gln Gln Gly
                85              90                  95

Pro Gly Ala Ala Gly Gln Phe Gly Pro Gly Gln Gln Gly Pro Gly Gln
```

-continued

```
                100                 105                 110

Gln Gly Pro Gly Ala Gly Ala Ala Ala Ala Ala Gly Gln Phe Gly Ala
            115                 120                 125

Gly Pro Gly Gln Gln Gly Pro Phe Gly Gly Ala Ala Ala Ala Ala Gly
        130                 135                 140

Pro Gly Ala Gly Gln Phe Gly Gln Gly Pro Phe Gly Pro Gly Ala Ala
145                 150                 155                 160

Gly Pro Gly Gln Phe Gly Pro Gly Gln Gln Gly Pro Ser Ala Gly Ala
                165                 170                 175

Ala Ala Ala Ala Gly Ala Gly Gln Gln Gly Pro Gly Gln Phe Gly Pro
            180                 185                 190

Phe Ala Gly Ala Ala Ala Ala Ala Gly Gln Phe Gly Ala Gly Pro Gly
        195                 200                 205

Gln Gln Gly Pro Phe Gly Pro Gly Gln Ala Gly Ala Gly Gln Gln Gly
        210                 215                 220

Pro Gly Gln Gln Gly Pro Phe Ala Gly Ala Ala Ala Ala Ala Gly Pro
225                 230                 235                 240

Gly Gln Gln Gly Pro Phe Gly Pro Gly Ala Gly Ala Ala Ala Ala Ala
            245                 250                 255

Gly Gln Phe Gly Phe Gly Pro Gly Gln Gln Gly Pro Phe Gly Pro Gly
            260                 265                 270

Ala Ala Gly Gln Asn Gly Pro Gly Ala Gly Gln Phe Gly Pro Gly Gln
            275                 280                 285

Gln Gly Pro Gly Gln Gly Ala Ala Ala Ala Ala Gly Pro Gly Gln Gln
        290                 295                 300

Gly Pro Phe Gly Pro Gly Ala Gly Ala Ala Ala Ala Gly Gln Phe
305                 310                 315                 320

Gly Pro Gly Gln Gln Gly Pro Gly Gln Phe Gly Pro Gly Ala Ala Gly
            325                 330                 335

Pro Gly Gln Gln Gly Pro Phe Gly Pro Gly Ala Gly Ala Ala Ala Ala
            340                 345                 350

Ala Gly Gln Phe Gly Pro Gly Gln Gln Gly Pro Phe Gly Pro Gly Gln
            355                 360                 365

Gly Ala Ala Ala Ala Ala Gly Gln Phe Gln Gln Gly Pro Gly Gln Gln
        370                 375                 380

Gly Pro Phe Gly Pro Gly Ala Ala Gly Pro Gly Gln Gln Gly Pro Phe
385                 390                 395                 400

Gly Pro Gly Ala Gly Ala Ala Ala Ala Gly Pro Gly Gln Phe Gly
            405                 410                 415

Pro Gly Gln Gln Gly Pro Ser Ala Gly Ala Ala Ala Ala Gly Gln
            420                 425                 430

Phe Gly Ala Gly Pro Gly Gln Phe Gly Pro Phe Gly Pro Gly Gln Ala
            435                 440                 445

Gly Pro Gly Ala Gly Gln Gln Gly Gln Gly Pro Phe Gly Pro Gly Ala
        450                 455                 460

Gly Ala Ala Ala Ala Ala Gly Gln Phe Gly Pro Gly Gln Gln Gly Pro
465                 470                 475                 480

Phe Gly Pro Gly Gln Gly Ala Ala Ala Ala Gly Pro Gly Ala Gly
            485                 490                 495

Gln Phe Gly Pro Gly Ala Ala Gly Gln Asn Gly Pro Gly Ala Gly Gln
            500                 505                 510

Phe Gly Pro Gly Gln Gln Gly Pro Gly Gln Gly Ala Ala Ala Ala Ala
            515                 520                 525
```

```
Gly Gln Phe Gln Gln Gly Pro Gly Gln Gln Gly Pro Phe Gly Pro Gly
    530                 535                 540

Ala Gly Ala Ala Ala Ala Ala Gly Gln Phe Gly Ala Gly Pro Gly Gln
545                 550                 555                 560

Gln Gly Pro Phe Gly Pro Gly Gln Ala Gly Ala Gly Gln Gln Gly Pro
                565                 570                 575

Gly Gln Gln Gly Pro Phe Ala Gly Ala Ala Ala Ala Gly Pro Gly
            580                 585                 590

Ala Gly Gln Gln Gly Pro Gly Ala Ser
        595                 600

<210> SEQ ID NO 54
<211> LENGTH: 601
<212> TYPE: PRT
<213> ORGANISM: Artificial Sequence
<220> FEATURE:
<223> OTHER INFORMATION: PRT1104

<400> SEQUENCE: 54

Met His His His His His Ala Ala Gly Ala Ala Gly Pro Gly Gln
1               5                   10                  15

Gln Gly Pro Tyr Gly Pro Gly Ala Gly Ala Ala Ala Ala Gly Gln
            20                  25                  30

Asn Gly Pro Gly Ala Gly Gln Gln Gly Pro Gly Gln Ala Gly Gln Tyr
        35                  40                  45

Gly Pro Gly Gln Gln Gly Pro Gly Gln Gln Gly Pro Gly Ala Gly Ala
    50                  55                  60

Ala Ala Ala Ala Gly Pro Gly Gln Tyr Gly Pro Gly Gln Gln Gly Pro
65                  70                  75                  80

Ser Ala Gly Ala Ala Ala Ala Ala Gly Pro Gly Ala Gly Gln Gln Gly
                85                  90                  95

Pro Gly Ala Ala Gly Gln Tyr Gly Pro Gly Gln Gln Gly Pro Gly Gln
            100                 105                 110

Gln Gly Pro Gly Ala Gly Ala Ala Ala Ala Gly Gln Tyr Gly Ala
        115                 120                 125

Gly Pro Gly Gln Gln Gly Pro Tyr Gly Gly Ala Ala Ala Ala Ala Gly
    130                 135                 140

Pro Gly Ala Gly Gln Tyr Gly Gln Gly Pro Tyr Gly Pro Gly Ala Ala
145                 150                 155                 160

Gly Pro Gly Gln Tyr Gly Pro Gly Gln Gln Gly Pro Ser Ala Gly Ala
            165                 170                 175

Ala Ala Ala Gly Ala Gly Gln Gln Gly Pro Gly Gln Tyr Gly Pro
        180                 185                 190

Tyr Ala Gly Ala Ala Ala Ala Ala Gly Gln Tyr Gly Ala Gly Pro Gly
        195                 200                 205

Gln Gln Gly Pro Tyr Gly Pro Gly Gln Ala Gly Ala Gly Gln Gln Gly
    210                 215                 220

Pro Gly Gln Gln Gly Pro Tyr Ala Gly Ala Ala Ala Ala Gly Pro
225                 230                 235                 240

Gly Gln Gln Gly Pro Tyr Gly Pro Gly Ala Gly Ala Ala Ala Ala Ala
            245                 250                 255

Gly Gln Tyr Gly Tyr Gly Pro Gly Gln Gln Gly Pro Tyr Gly Pro Gly
        260                 265                 270

Ala Ala Gly Gln Asn Gly Pro Gly Ala Gly Gln Tyr Gly Pro Gly Gln
        275                 280                 285
```

-continued

```
Gln Gly Pro Gly Gln Gly Ala Ala Ala Ala Gly Pro Gly Gln Gln
    290                 295                 300

Gly Pro Tyr Gly Pro Gly Ala Gly Ala Ala Ala Ala Ala Gly Gln Tyr
305                 310                 315                 320

Gly Pro Gly Gln Gln Gly Pro Gly Gln Tyr Gly Pro Gly Ala Ala Gly
                325                 330                 335

Pro Gly Gln Gln Gly Pro Tyr Gly Pro Gly Ala Gly Ala Ala Ala Ala
                340                 345                 350

Ala Gly Gln Tyr Gly Pro Gly Gln Gln Gly Pro Tyr Gly Pro Gly Gln
                355                 360                 365

Gly Ala Ala Ala Ala Ala Gly Gln Tyr Gln Gln Gly Pro Gly Gln Gln
    370                 375                 380

Gly Pro Tyr Gly Pro Gly Ala Ala Gly Pro Gly Gln Gln Gly Pro Tyr
385                 390                 395                 400

Gly Pro Gly Ala Gly Ala Ala Ala Ala Ala Gly Pro Gly Gln Tyr Gly
                405                 410                 415

Pro Gly Gln Gln Gly Pro Ser Ala Gly Ala Ala Ala Ala Ala Gly Gln
                420                 425                 430

Tyr Gly Ala Gly Pro Gly Gln Tyr Gly Pro Tyr Gly Pro Gly Gln Ala
                435                 440                 445

Gly Pro Gly Ala Gly Gln Gln Gly Gln Gly Pro Tyr Gly Pro Gly Ala
    450                 455                 460

Gly Ala Ala Ala Ala Ala Gly Gln Tyr Gly Pro Gly Gln Gln Gly Pro
465                 470                 475                 480

Tyr Gly Pro Gly Gln Gly Ala Ala Ala Ala Gly Pro Gly Ala Gly
                485                 490                 495

Gln Tyr Gly Pro Gly Ala Ala Gly Gln Asn Gly Pro Gly Ala Gly Gln
                500                 505                 510

Tyr Gly Pro Gly Gln Gln Gly Pro Gly Gln Gly Ala Ala Ala Ala Ala
                515                 520                 525

Gly Gln Tyr Gln Gln Gly Pro Gly Gln Gln Gly Pro Tyr Gly Pro Gly
    530                 535                 540

Ala Gly Ala Ala Ala Ala Ala Gly Gln Tyr Gly Ala Gly Pro Gly Gln
545                 550                 555                 560

Gln Gly Pro Tyr Gly Pro Gly Gln Ala Gly Ala Gly Gln Gln Gly Pro
                565                 570                 575

Gly Gln Gln Gly Pro Tyr Ala Gly Ala Ala Ala Ala Gly Pro Gly
                580                 585                 590

Ala Gly Gln Gln Gly Pro Gly Ala Ser
    595                 600
```

```
<210> SEQ ID NO 55
<211> LENGTH: 601
<212> TYPE: PRT
<213> ORGANISM: Artificial Sequence
<220> FEATURE:
<223> OTHER INFORMATION: PRT1107

<400> SEQUENCE: 55

Met His His His His His His Ala Ala Gly Ala Ala Gly Pro Gly Val
1               5                   10                  15

Phe Gly Pro Tyr Gly Pro Gly Ala Val Ala Ala Ala Ala Ala Gly Ile
                20                  25                  30

Asn Gly Pro Gly Ala Gly Val Phe Gly Pro Gly Ile Leu Gly Ile Tyr
                35                  40                  45
```

-continued

```
Gly Pro Gly Val Phe Gly Pro Gly Val Phe Gly Pro Gly Ala Leu Ala
    50                  55                  60

Ala Ala Ala Ala Gly Pro Gly Ile Tyr Gly Pro Gly Val Phe Gly Pro
65                  70                  75                  80

Ile Ala Val Ala Ala Ala Ala Ala Gly Pro Gly Ala Gly Val Phe Gly
                85                  90                  95

Pro Gly Ala Leu Gly Ile Tyr Gly Pro Gly Val Phe Gly Pro Gly Val
            100                 105                 110

Phe Gly Pro Gly Ala Leu Ala Ala Ala Ala Gly Ile Tyr Gly Ala
            115                 120                 125

Gly Pro Gly Val Phe Gly Pro Tyr Gly Leu Ala Ala Ala Ala Ala Gly
    130                 135                 140

Pro Gly Ala Gly Ile Tyr Gly Ile Gly Pro Tyr Gly Pro Gly Ala Leu
145                 150                 155                 160

Gly Pro Gly Ile Tyr Gly Pro Gly Val Phe Gly Pro Ile Ala Val Ala
                165                 170                 175

Ala Ala Ala Ala Gly Ala Gly Val Phe Gly Pro Gly Ile Tyr Gly Pro
                180                 185                 190

Tyr Ala Val Ala Ala Ala Ala Ala Gly Ile Tyr Gly Ala Gly Pro Gly
                195                 200                 205

Val Phe Gly Pro Tyr Gly Pro Gly Ile Leu Gly Ala Gly Val Phe Gly
    210                 215                 220

Pro Gly Val Phe Gly Pro Tyr Ala Val Ala Ala Ala Ala Gly Pro
225                 230                 235                 240

Gly Val Phe Gly Pro Tyr Gly Pro Gly Ala Leu Ala Ala Ala Ala Ala
                245                 250                 255

Gly Ile Tyr Gly Tyr Gly Pro Gly Val Phe Gly Pro Tyr Gly Pro Gly
            260                 265                 270

Ala Leu Gly Ile Asn Gly Pro Gly Ala Gly Ile Tyr Gly Pro Gly Val
    275                 280                 285

Phe Gly Pro Gly Ile Leu Ala Ala Ala Ala Gly Pro Gly Val Phe
    290                 295                 300

Gly Pro Tyr Gly Pro Gly Ala Val Ala Ala Ala Ala Gly Ile Tyr
305                 310                 315                 320

Gly Pro Gly Val Phe Gly Pro Gly Ile Tyr Gly Pro Gly Ala Leu Gly
            325                 330                 335

Pro Gly Val Phe Gly Pro Tyr Gly Pro Gly Ala Leu Ala Ala Ala Ala
            340                 345                 350

Ala Gly Ile Tyr Gly Pro Gly Val Phe Gly Pro Tyr Gly Pro Gly Ile
    355                 360                 365

Leu Ala Ala Ala Ala Gly Ile Tyr Val Phe Gly Pro Gly Val Phe
    370                 375                 380

Gly Pro Tyr Gly Pro Gly Ala Leu Gly Pro Gly Val Phe Gly Pro Tyr
385                 390                 395                 400

Gly Pro Gly Ala Val Ala Ala Ala Ala Gly Pro Gly Ile Tyr Gly
            405                 410                 415

Pro Gly Val Phe Gly Pro Ile Ala Val Ala Ala Ala Ala Gly Ile
            420                 425                 430

Tyr Gly Ala Gly Pro Gly Ile Tyr Gly Pro Tyr Gly Pro Gly Ile Leu
    435                 440                 445

Gly Pro Gly Ala Gly Val Phe Gly Ile Gly Pro Tyr Gly Pro Gly Ala
    450                 455                 460
```

-continued

```
Val Ala Ala Ala Ala Ala Gly Ile Tyr Gly Pro Gly Val Phe Gly Pro
465                 470                 475                 480

Tyr Gly Pro Gly Ile Leu Ala Ala Ala Ala Gly Pro Gly Ala Gly
                485                 490                 495

Ile Tyr Gly Pro Gly Ala Leu Gly Ile Asn Gly Pro Gly Ala Gly Ile
            500                 505                 510

Tyr Gly Pro Gly Val Phe Gly Pro Gly Ile Leu Ala Ala Ala Ala
            515                 520                 525

Gly Ile Tyr Val Phe Gly Pro Gly Val Phe Gly Pro Tyr Gly Pro Gly
        530                 535                 540

Ala Val Ala Ala Ala Ala Ala Gly Ile Tyr Gly Ala Gly Pro Gly Val
545                 550                 555                 560

Phe Gly Pro Tyr Gly Pro Gly Ile Leu Gly Ala Gly Val Phe Gly Pro
                565                 570                 575

Gly Val Phe Gly Pro Tyr Ala Val Ala Ala Ala Ala Gly Pro Gly
                580                 585                 590

Ala Gly Val Phe Gly Pro Gly Ala Ile
        595                 600

<210> SEQ ID NO 56
<211> LENGTH: 601
<212> TYPE: PRT
<213> ORGANISM: Artificial Sequence
<220> FEATURE:
<223> OTHER INFORMATION: PRT1083

<400> SEQUENCE: 56

Met His His His His His His Ser Ser Gly Ser Ser Gly Leu Gly Val
1               5                   10                  15

Phe Gly Leu Tyr Gly Thr Gly Ala Ser Ala Ala Ala Ala Gly Ile
                20                  25                  30

Ala Gly Thr Gly Ser Gly Val Phe Gly Thr Gly Ile Ser Gly Ile Tyr
            35                  40                  45

Gly Leu Gly Val Phe Gly Leu Gly Val Phe Gly Thr Gly Ser Ser Ala
        50                  55                  60

Ala Ala Ala Ala Gly Thr Gly Ile Tyr Gly Leu Gly Val Phe Gly Leu
65                  70                  75                  80

Ser Ala Ser Ala Ala Ala Ala Ala Gly Thr Gly Ser Gly Val Phe Gly
                85                  90                  95

Thr Gly Ala Ser Gly Ile Tyr Gly Leu Gly Val Phe Gly Leu Gly Val
            100                 105                 110

Phe Gly Thr Gly Ser Ser Ala Ala Ala Ala Gly Ile Tyr Gly Ser
            115                 120                 125

Gly Leu Gly Val Phe Gly Leu Tyr Gly Ser Ala Ala Ala Ala Gly
        130                 135                 140

Thr Gly Ser Gly Ile Tyr Gly Ile Gly Leu Tyr Gly Thr Gly Ala Ser
145                 150                 155                 160

Gly Thr Gly Ile Tyr Gly Leu Gly Val Phe Gly Leu Ser Ala Ser Ala
                165                 170                 175

Ala Ala Ala Ala Gly Ser Gly Val Phe Gly Thr Gly Ile Tyr Gly Leu
            180                 185                 190

Tyr Ala Ser Ala Ala Ala Ala Gly Ile Tyr Gly Ser Gly Leu Gly
        195                 200                 205

Val Phe Gly Leu Tyr Gly Thr Gly Ile Ser Gly Ser Gly Val Phe Gly
        210                 215                 220
```

-continued

```
Leu Gly Val Phe Gly Leu Tyr Ala Ser Ala Ala Ala Ala Gly Leu
225             230             235             240

Gly Val Phe Gly Leu Tyr Gly Thr Gly Ser Ser Ala Ala Ala Ala
            245             250             255

Gly Ile Tyr Gly Tyr Gly Leu Gly Val Phe Gly Leu Tyr Gly Thr Gly
        260             265             270

Ala Ser Gly Ile Ala Gly Thr Gly Ser Gly Ile Tyr Gly Leu Gly Val
        275             280             285

Phe Gly Thr Gly Ile Ser Ala Ala Ala Ala Gly Leu Gly Val Phe
    290             295             300

Gly Leu Tyr Gly Thr Gly Ala Ser Ala Ala Ala Ala Gly Ile Tyr
305             310             315             320

Gly Leu Gly Val Phe Gly Thr Gly Ile Tyr Gly Thr Gly Ser Ser Gly
            325             330             335

Leu Gly Val Phe Gly Leu Tyr Gly Thr Gly Ser Ser Ala Ala Ala Ala
            340             345             350

Ala Gly Ile Tyr Gly Leu Gly Val Phe Gly Leu Tyr Gly Thr Gly Ile
        355             360             365

Ser Ala Ala Ala Ala Ala Gly Ile Tyr Val Phe Gly Leu Gly Val Phe
    370             375             380

Gly Leu Tyr Gly Thr Gly Ala Ser Gly Leu Gly Val Phe Gly Leu Tyr
385             390             395             400

Gly Thr Gly Ala Ser Ala Ala Ala Ala Gly Thr Gly Ile Tyr Gly
            405             410             415

Leu Gly Val Phe Gly Leu Ser Ala Ser Ala Ala Ala Ala Gly Ile
            420             425             430

Tyr Gly Ser Gly Thr Gly Ile Tyr Gly Leu Tyr Gly Thr Gly Ile Ser
        435             440             445

Gly Thr Gly Ser Gly Val Phe Gly Ile Gly Leu Tyr Gly Thr Gly Ala
    450             455             460

Ser Ala Ala Ala Ala Ala Gly Ile Tyr Gly Leu Gly Val Phe Gly Leu
465             470             475             480

Tyr Gly Thr Gly Ile Ser Ala Ala Ala Ala Gly Thr Gly Ser Gly
        485             490             495

Ile Tyr Gly Thr Gly Ala Ser Gly Ile Ala Gly Thr Gly Ser Gly Ile
        500             505             510

Tyr Gly Leu Gly Val Phe Gly Thr Gly Ile Ser Ala Ala Ala Ala
        515             520             525

Gly Ile Tyr Val Phe Gly Leu Gly Val Phe Gly Leu Tyr Gly Thr Gly
    530             535             540

Ala Ser Ala Ala Ala Ala Ala Gly Ile Tyr Gly Ser Gly Leu Gly Val
545             550             555             560

Phe Gly Leu Tyr Gly Thr Gly Ile Ser Gly Ser Gly Val Phe Gly Leu
            565             570             575

Gly Val Phe Gly Leu Tyr Ala Ser Ala Ala Ala Ala Gly Thr Gly
            580             585             590

Ser Gly Val Phe Gly Thr Gly Ala Ser
        595             600
```

<210> SEQ ID NO 57
<211> LENGTH: 2266
<212> TYPE: PRT
<213> ORGANISM: Artificial Sequence
<220> FEATURE:
<223> OTHER INFORMATION: PRT1125

-continued

```
<400> SEQUENCE: 57

Met His His His His His Ser Ser Gly Ser Ser Gly Pro Gly Gln
1               5               10              15

Gln Gly Pro Tyr Gly Pro Gly Ala Ser Ala Ala Ala Ala Ala Ala
            20              25              30

Gly Ser Asn Gly Pro Gly Ser Gly Gln Gln Gly Pro Gly Gln Ser Gly
        35              40              45

Gln Tyr Gly Pro Gly Gln Gln Gly Pro Gly Gln Gln Gly Pro Gly Ser
    50              55              60

Ser Ala Ala Ala Ala Ala Ala Gly Pro Gly Gln Tyr Gly Pro Gly
65              70              75              80

Gln Gln Gly Pro Ser Ala Ser Ala Ala Ala Ala Ala Ala Gly Pro
                85              90              95

Gly Ser Gly Gln Gln Gly Pro Gly Ala Ser Gly Gln Tyr Gly Pro Gly
            100             105             110

Gln Gln Gly Pro Gly Gln Gln Gly Pro Gly Ser Ser Ala Ala Ala Ala
            115             120             125

Ala Ala Ala Gly Ser Tyr Gly Ser Gly Pro Gly Gln Gln Gly Pro Tyr
    130             135             140

Gly Ser Ala Ala Ala Ala Ala Ala Gly Pro Gly Ser Gly Gln Tyr
145             150             155             160

Gly Gln Gly Pro Tyr Gly Pro Gly Ala Ser Gly Pro Gly Gln Tyr Gly
            165             170             175

Pro Gly Gln Gln Gly Pro Ser Ala Ser Ala Ala Ala Ala Ala Ala
            180             185             190

Gly Ser Gly Gln Gln Gly Pro Gly Gln Tyr Gly Pro Tyr Ala Ser Ala
            195             200             205

Ala Ala Ala Ala Ala Gly Ser Tyr Gly Ser Gly Pro Gly Gln Gln
    210             215             220

Gly Pro Tyr Gly Pro Gly Gln Ser Gly Ser Gly Gln Gln Gly Pro Gly
225             230             235             240

Gln Gln Gly Pro Tyr Ala Ser Ala Ala Ala Ala Ala Ala Gly Pro
            245             250             255

Gly Gln Gln Gly Pro Tyr Gly Pro Gly Ser Ser Ala Ala Ala Ala
            260             265             270

Ala Ala Gly Ser Tyr Gly Tyr Gly Pro Gly Gln Gln Gly Pro Tyr Gly
    275             280             285

Pro Gly Ala Ser Gly Gln Asn Gly Pro Gly Ser Gly Gln Tyr Gly Pro
    290             295             300

Gly Gln Gln Gly Pro Gly Pro Ser Ala Ala Ala Ala Ala Ala Gly
305             310             315             320

Pro Gly Gln Gln Gly Pro Tyr Gly Pro Gly Ala Ser Ala Ala Ala
            325             330             335

Ala Ala Ala Gly Ser Tyr Gly Pro Gly Gln Gln Gly Pro Gly Gln Tyr
            340             345             350

Gly Pro Gly Ser Ser Gly Pro Gly Gln Gln Gly Pro Tyr Gly Pro Gly
            355             360             365

Ser Ser Ala Ala Ala Ala Ala Ala Gly Ser Tyr Gly Pro Gly Gln
    370             375             380

Gln Gly Pro Tyr Gly Pro Gly Pro Ser Ala Ala Ala Ala Ala Ala Ala
385             390             395             400

Gly Ser Tyr Gln Gln Gly Pro Gly Gln Gln Gly Pro Tyr Gly Pro Gly
```

```
                    405              410              415

Ala Ser Gly Pro Gly Gln Gln Gly Pro Tyr Gly Pro Gly Ala Ser Ala
            420              425              430

Ala Ala Ala Ala Ala Ala Gly Pro Gly Gln Tyr Gly Pro Gly Gln Gln
            435              440              445

Gly Pro Ser Ala Ser Ala Ala Ala Ala Ala Ala Gly Ser Tyr Gly
    450              455              460

Ser Gly Pro Gly Gln Tyr Gly Pro Tyr Gly Pro Gly Gln Ser Gly Pro
465              470              475              480

Gly Ser Gly Gln Gln Gly Gln Gly Pro Tyr Gly Pro Gly Ala Ser Ala
            485              490              495

Ala Ala Ala Ala Ala Ala Gly Ser Tyr Gly Pro Gly Gln Gln Gly Pro
            500              505              510

Tyr Gly Pro Gly Pro Ser Ala Ala Ala Ala Ala Ala Gly Pro Gly
    515              520              525

Ser Gly Gln Tyr Gly Pro Gly Ala Ser Gly Gln Asn Gly Pro Gly Ser
    530              535              540

Gly Gln Tyr Gly Pro Gly Gln Gln Gly Pro Gly Pro Ser Ala Ala Ala
545              550              555              560

Ala Ala Ala Ala Gly Pro Gly Ser Gly Gln Gln Gly Pro Gly Ala Ser
            565              570              575

Glu Leu Gly Gln Gln Gly Pro Tyr Gly Pro Gly Ala Ser Ala Ala Ala
            580              585              590

Ala Ala Ala Ala Gly Ser Asn Gly Pro Gly Ser Gly Gln Gln Gly Pro
            595              600              605

Gly Gln Ser Gly Gln Tyr Gly Pro Gly Gln Gln Gly Pro Gly Gln Gln
    610              615              620

Gly Pro Gly Ser Ser Ala Ala Ala Ala Ala Ala Gly Pro Gly Gln
625              630              635              640

Tyr Gly Pro Gly Gln Gln Gly Pro Ser Ala Ser Ala Ala Ala Ala Ala
            645              650              655

Ala Ala Gly Pro Gly Ser Gly Gln Gln Gly Pro Gly Ala Ser Gly Gln
            660              665              670

Tyr Gly Pro Gly Gln Gln Gly Pro Gly Gln Gln Gly Pro Gly Ser Ser
    675              680              685

Ala Ala Ala Ala Ala Ala Ala Gly Ser Tyr Gly Ser Gly Pro Gly Gln
    690              695              700

Gln Gly Pro Tyr Gly Ser Ala Ala Ala Ala Ala Ala Gly Pro Gly
705              710              715              720

Ser Gly Gln Tyr Gly Gln Gly Pro Tyr Gly Pro Gly Ala Ser Gly Pro
            725              730              735

Gly Gln Tyr Gly Pro Gly Gln Gln Gly Pro Ser Ala Ser Ala Ala Ala
            740              745              750

Ala Ala Ala Ala Gly Ser Gly Gln Gln Gly Pro Gly Gln Tyr Gly Pro
            755              760              765

Tyr Ala Ser Ala Ala Ala Ala Ala Ala Ala Gly Ser Tyr Gly Ser Gly
    770              775              780

Pro Gly Gln Gln Gly Pro Tyr Gly Pro Gly Gln Ser Gly Ser Gly Gln
785              790              795              800

Gln Gly Pro Gly Gln Gln Gly Pro Tyr Ala Ser Ala Ala Ala Ala Ala
            805              810              815

Ala Ala Gly Pro Gly Gln Gln Gly Pro Tyr Gly Pro Gly Ser Ser Ala
            820              825              830
```

-continued

```
Ala Ala Ala Ala Ala Ala Gly Ser Tyr Gly Tyr Gly Pro Gly Gln Gln
        835             840             845

Gly Pro Tyr Gly Pro Gly Ala Ser Gly Gln Asn Gly Pro Gly Ser Gly
    850             855             860

Gln Tyr Gly Pro Gly Gln Gln Gly Pro Gly Pro Ser Ala Ala Ala Ala
865             870             875             880

Ala Ala Ala Gly Pro Gly Gln Gln Gly Pro Tyr Gly Pro Gly Ala Ser
            885             890             895

Ala Ala Ala Ala Ala Ala Ala Gly Ser Tyr Gly Pro Gly Gln Gln Gly
        900             905             910

Pro Gly Gln Tyr Gly Pro Gly Ser Ser Gly Pro Gly Gln Gln Gly Pro
    915             920             925

Tyr Gly Pro Gly Ser Ser Ala Ala Ala Ala Ala Ala Gly Ser Tyr
    930             935             940

Gly Pro Gly Gln Gln Gly Pro Tyr Gly Pro Gly Pro Ser Ala Ala Ala
945             950             955             960

Ala Ala Ala Ala Gly Ser Tyr Gln Gln Gly Pro Gly Gln Gln Gly Pro
            965             970             975

Tyr Gly Pro Gly Ala Ser Gly Pro Gly Gln Gln Gly Pro Tyr Gly Pro
            980             985             990

Gly Ala Ser Ala Ala Ala Ala Ala  Ala Ala Gly Pro Gly  Gln Tyr Gly
        995             1000            1005

Pro Gly  Gln Gln Gly Pro Ser  Ala Ser Ala Ala Ala  Ala Ala Ala
    1010            1015            1020

Ala Gly  Ser Tyr Gly Ser Gly  Pro Gly Gln Tyr Gly  Pro Tyr Gly
    1025            1030            1035

Pro Gly  Gln Ser Gly Pro Gly  Ser Gly Gln Gln Gly  Gln Gly Pro
    1040            1045            1050

Tyr Gly  Pro Gly Ala Ser Ala  Ala Ala Ala Ala Ala  Ala Gly Ser
    1055            1060            1065

Tyr Gly  Pro Gly Gln Gln Gly  Pro Tyr Gly Pro Gly  Pro Ser Ala
    1070            1075            1080

Ala Ala  Ala Ala Ala Ala Gly  Pro Gly Ser Gly Gln  Tyr Gly Pro
    1085            1090            1095

Gly Ala  Ser Gly Gln Asn Gly  Pro Gly Ser Gly Gln  Tyr Gly Pro
    1100            1105            1110

Gly Gln  Gln Gly Pro Gly Pro  Ser Ala Ala Ala Ala  Ala Ala Ala
    1115            1120            1125

Gly Pro  Gly Ser Gly Gln Gln  Gly Pro Gly Ala Ser  Gly Pro Gly
    1130            1135            1140

Gln Gln  Gly Pro Tyr Gly Pro  Gly Ala Ser Ala Ala  Ala Ala Ala
    1145            1150            1155

Ala Ala  Gly Ser Asn Gly Pro  Gly Ser Gly Gln Gln  Gly Pro Gly
    1160            1165            1170

Gln Ser  Gly Gln Tyr Gly Pro  Gly Gln Gln Gly Pro  Gly Gln Gln
    1175            1180            1185

Gly Pro  Gly Ser Ser Ala Ala  Ala Ala Ala Ala Ala  Gly Pro Gly
    1190            1195            1200

Gln Tyr  Gly Pro Gly Gln Gln  Gly Pro Ser Ala Ser  Ala Ala Ala
    1205            1210            1215

Ala Ala  Ala Ala Gly Pro Gly  Ser Gly Gln Gln Gly  Pro Gly Ala
    1220            1225            1230
```

-continued

```
Ser Gly  Gln Tyr Gly Pro Gly  Gln Gln Gly Pro  Gly  Gln Gln Gly
    1235              1240              1245

Pro Gly  Ser Ser Ala Ala Ala  Ala Ala Ala Gly  Ser  Tyr Gly
    1250              1255              1260

Ser Gly  Pro Gly Gln Gln Gly  Pro Tyr Gly Ser Ala  Ala Ala Ala
    1265              1270              1275

Ala Ala  Ala Gly Pro Gly Ser  Gly Gln Tyr Gly Gln  Gly Pro Tyr
    1280              1285              1290

Gly Pro  Gly Ala Ser Gly Pro  Gly Gln Tyr Gly Pro  Gly Gln Gln
    1295              1300              1305

Gly Pro  Ser Ala Ser Ala Ala  Ala Ala Ala Ala Ala  Gly Ser Gly
    1310              1315              1320

Gln Gln  Gly Pro Gly Gln Tyr  Gly Pro Tyr Ala Ser  Ala Ala Ala
    1325              1330              1335

Ala Ala  Ala Ala Gly Ser Tyr  Gly Ser Gly Pro Gly  Gln Gln Gly
    1340              1345              1350

Pro Tyr  Gly Pro Gly Gln Ser  Gly Ser Gly Gln Gln  Gly Pro Gly
    1355              1360              1365

Gln Gln  Gly Pro Tyr Ala Ser  Ala Ala Ala Ala Ala  Ala Ala Gly
    1370              1375              1380

Pro Gly  Gln Gln Gly Pro Tyr  Gly Pro Gly Ser Ser  Ala Ala Ala
    1385              1390              1395

Ala Ala  Ala Ala Gly Ser Tyr  Gly Tyr Gly Pro Gly  Gln Gln Gly
    1400              1405              1410

Pro Tyr  Gly Pro Gly Ala Ser  Gly Gln Asn Gly Pro  Gly Ser Gly
    1415              1420              1425

Gln Tyr  Gly Pro Gly Gln Gln  Gly Pro Gly Pro Ser  Ala Ala Ala
    1430              1435              1440

Ala Ala  Ala Ala Gly Pro Gly  Gln Gln Gly Pro Tyr  Gly Pro Gly
    1445              1450              1455

Ala Ser  Ala Ala Ala Ala Ala  Ala Ala Gly Ser Tyr  Gly Pro Gly
    1460              1465              1470

Gln Gln  Gly Pro Gly Gln Tyr  Gly Pro Gly Ser Ser  Gly Pro Gly
    1475              1480              1485

Gln Gln  Gly Pro Tyr Gly Pro  Gly Ser Ser Ala Ala  Ala Ala Ala
    1490              1495              1500

Ala Ala  Gly Ser Tyr Gly Pro  Gly Gln Gln Gly Pro  Tyr Gly Pro
    1505              1510              1515

Gly Pro  Ser Ala Ala Ala Ala  Ala Ala Ala Gly Ser  Tyr Gln Gln
    1520              1525              1530

Gly Pro  Gly Gln Gln Gly Pro  Tyr Gly Pro Gly Ala  Ser Gly Pro
    1535              1540              1545

Gly Gln  Gln Gly Pro Tyr Gly  Pro Gly Ala Ser Ala  Ala Ala Ala
    1550              1555              1560

Ala Ala  Ala Gly Pro Gly Gln  Tyr Gly Pro Gly Gln  Gln Gly Pro
    1565              1570              1575

Ser Ala  Ser Ala Ala Ala Ala  Ala Ala Ala Gly Ser  Tyr Gly Ser
    1580              1585              1590

Gly Pro  Gly Gln Tyr Gly Pro  Tyr Gly Pro Gly Gln  Ser Gly Pro
    1595              1600              1605

Gly Ser  Gly Gln Gln Gly Gln  Gly Pro Tyr Gly Pro  Gly Ala Ser
    1610              1615              1620

Ala Ala  Ala Ala Ala Ala Ala  Gly Ser Tyr Gly Pro  Gly Gln Gln
```

-continued

```
      1625              1630              1635

Gly Pro  Tyr Gly Pro Gly Pro  Ser Ala Ala Ala  Ala Ala Ala
    1640              1645              1650

Gly Pro  Gly Ser Gly Gln Tyr  Gly Pro Gly Ala Ser  Gly Gln Asn
    1655              1660              1665

Gly Pro  Gly Ser Gly Gln Tyr  Gly Pro Gly Gln Gln  Gly Pro Gly
    1670              1675              1680

Pro Ser  Ala Ala Ala Ala Ala  Ala Ala Gly Pro Gly  Ser Gly Gln
    1685              1690              1695

Gln Gly  Pro Gly Ala Ser Gly  Gln Gln Gly Pro Tyr  Gly Pro Gly
    1700              1705              1710

Ala Ser  Ala Ala Ala Ala Ala  Ala Ala Gly Ser Asn  Gly Pro Gly
    1715              1720              1725

Ser Gly  Gln Gln Gly Pro Gly  Gln Ser Gly Gln Tyr  Gly Pro Gly
    1730              1735              1740

Gln Gln  Gly Pro Gly Gln Gln  Gly Pro Gly Ser Ser  Ala Ala Ala
    1745              1750              1755

Ala Ala  Ala Ala Gly Pro Gly  Gln Tyr Gly Pro Gly  Gln Gln Gly
    1760              1765              1770

Pro Ser  Ala Ser Ala Ala Ala  Ala Ala Ala Gly  Pro Gly Ser
    1775              1780              1785

Gly Gln  Gln Gly Pro Gly Ala  Ser Gly Gln Tyr Gly  Pro Gly Gln
    1790              1795              1800

Gln Gly  Pro Gly Gln Gln Gly  Pro Gly Ser Ser Ala  Ala Ala Ala
    1805              1810              1815

Ala Ala  Ala Gly Ser Tyr Gly  Ser Gly Pro Gly Gln  Gln Gly Pro
    1820              1825              1830

Tyr Gly  Ser Ala Ala Ala Ala  Ala Ala Ala Gly Pro  Gly Ser Gly
    1835              1840              1845

Gln Tyr  Gly Gln Gly Pro Tyr  Gly Pro Gly Ala Ser  Gly Pro Gly
    1850              1855              1860

Gln Tyr  Gly Pro Gly Gln Gln  Gly Pro Ser Ala Ser  Ala Ala Ala
    1865              1870              1875

Ala Ala  Ala Ala Gly Ser Gly  Gln Gln Gly Pro Gly  Gln Tyr Gly
    1880              1885              1890

Pro Tyr  Ala Ser Ala Ala Ala  Ala Ala Ala Ala Gly  Ser Tyr Gly
    1895              1900              1905

Ser Gly  Pro Gly Gln Gln Gly  Pro Tyr Gly Pro Gly  Gln Ser Gly
    1910              1915              1920

Ser Gly  Gln Gln Gly Pro Gly  Gln Gln Gly Pro Tyr  Ala Ser Ala
    1925              1930              1935

Ala Ala  Ala Ala Ala Ala Gly  Pro Gly Gln Gln Gly  Pro Tyr Gly
    1940              1945              1950

Pro Gly  Ser Ser Ala Ala Ala  Ala Ala Ala Ala Gly  Ser Tyr Gly
    1955              1960              1965

Tyr Gly  Pro Gly Gln Gln Gly  Pro Tyr Gly Pro Gly  Ala Ser Gly
    1970              1975              1980

Gln Asn  Gly Pro Gly Ser Gly  Gln Tyr Gly Pro Gly  Gln Gln Gly
    1985              1990              1995

Pro Gly  Pro Ser Ala Ala Ala  Ala Ala Ala Ala Gly  Pro Gly Gln
    2000              2005              2010

Gln Gly  Pro Tyr Gly Pro Gly  Ala Ser Ala Ala Ala  Ala Ala Ala
    2015              2020              2025
```

-continued

```
Ala Gly  Ser Tyr Gly Pro Gly  Gln Gln Gly Pro Gly  Gln Tyr Gly
    2030              2035              2040

Pro Gly  Ser Ser Gly Pro Gly  Gln Gln Gly Pro Tyr  Gly Pro Gly
    2045              2050              2055

Ser Ser  Ala Ala Ala Ala Ala  Ala Ala Gly Ser Tyr  Gly Pro Gly
    2060              2065              2070

Gln Gln  Gly Pro Tyr Gly Pro  Gly Pro Ser Ala Ala  Ala Ala Ala
    2075              2080              2085

Ala Ala  Gly Ser Tyr Gln Gln  Gly Pro Gly Gln Gln  Gly Pro Tyr
    2090              2095              2100

Gly Pro  Gly Ala Ser Gly Pro  Gly Gln Gln Gly Pro  Tyr Gly Pro
    2105              2110              2115

Gly Ala  Ser Ala Ala Ala Ala  Ala Ala Ala Gly Pro  Gly Gln Tyr
    2120              2125              2130

Gly Pro  Gly Gln Gln Gly Pro  Ser Ala Ser Ala Ala  Ala Ala Ala
    2135              2140              2145

Ala Ala  Gly Ser Tyr Gly Ser  Gly Pro Gly Gln Tyr  Gly Pro Tyr
    2150              2155              2160

Gly Pro  Gly Gln Ser Gly Pro  Gly Ser Gly Gln Gln  Gly Gln Gly
    2165              2170              2175

Pro Tyr  Gly Pro Gly Ala Ser  Ala Ala Ala Ala Ala  Ala Ala Gly
    2180              2185              2190

Ser Tyr  Gly Pro Gly Gln Gln  Gly Pro Tyr Gly Pro  Gly Pro Ser
    2195              2200              2205

Ala Ala  Ala Ala Ala Ala Ala  Gly Pro Gly Ser Gly  Gln Tyr Gly
    2210              2215              2220

Pro Gly  Ala Ser Gly Gln Asn  Gly Pro Gly Ser Gly  Gln Tyr Gly
    2225              2230              2235

Pro Gly  Gln Gln Gly Pro Gly  Pro Ser Ala Ala Ala  Ala Ala Ala
    2240              2245              2250

Ala Gly  Pro Gly Ser Gly Gln  Gln Gly Pro Gly Ala  Ser
    2255              2260              2265
```

```
<210> SEQ ID NO 58
<211> LENGTH: 560
<212> TYPE: PRT
<213> ORGANISM: Artificial Sequence
<220> FEATURE:
<223> OTHER INFORMATION: PRT855

<400> SEQUENCE: 58

Met His His His His His Ser Ser Gly Ser Ser Gly Glu Gly Ala
1               5               10              15

Phe Gln Gly Pro Ser Phe Arg Gly Ser Gly Ala Ser Arg Gly Ala Ala
            20              25              30

Ala Ala Ala Gly Ser Gln Ala Gly Thr Gly Arg Gly Thr Gly Gly Arg
        35              40              45

Thr Gly Phe Arg Ala Gly Asn Gly Cys Ser Gly Ala Gly Ala Ala Ala
    50              55              60

Ala Ala Gly Ser Ser Phe Ser Gly Pro Gly Gly Ser Ala Ser Ser Lys
65              70              75              80

Gly Ser Phe Ser His Gly Gly Ala Ala Ala Ala Gly Gly Ala Gly
                85              90              95

Ser Gly Gly Cys Thr Gly Phe Gly Glu Asn Glu His Gly Ala Ala Ala
            100             105             110
```

-continued

```
Ala Ala Gly Gly Asn Glu Lys Ala Thr Gly Gln Asn Ala Asn Asp Arg
        115             120             125

Gly Ala Ala Ala Ala Ala Gly Tyr Ala Asp His Gly Cys Thr Gly Glu
        130             135             140

Glu Ala Asn Ala Gly Ala Ala Ala Ala Gly Gln Lys Ile Lys Gly
145             150             155             160

Trp Tyr Glu Lys Tyr Gly Pro Gly Ser Gly Arg Gln Gly Ala Ala Ala
            165             170             175

Ala Ala Gly Asp Tyr Ser Lys Tyr Phe Ser Ala Thr Glu Asp Ala Lys
            180             185             190

Arg Gln Ser Gly Thr Thr Cys Gly Ala Ala Ala Ala Gly Ala Gly
            195             200             205

Gln Asn Glu Asn Ala Arg Ala Thr Ala Asp Asp Phe Arg Gly Lys Cys
        210             215             220

Glu Asn Gly Ala Ala Ala Ala Ala Gly His Gln Ser Gly Glu Ala Asp
225             230             235             240

Ile Asn Gly Ala His Arg Ala Met Asp Glu Gly Gly Ala Ala Ala Ala
            245             250             255

Ala Gly Thr Ser Asp Gly Glu Met Gln Cys Glu Ala Ala Ser Glu Glu
            260             265             270

Gly Thr Gly Ala Ala Ala Ala Ala Gly Lys Asn His Gln Glu Glu Met
            275             280             285

Lys Gly Ser Phe Arg Gly Ser Gly Ala Ser Arg Gly Ala Ala Ala Ala
        290             295             300

Ala Gly Ser Gln Ala Gly Thr Gly Arg Gly Thr Gly Gly Arg Thr Gly
305             310             315             320

Phe Arg Ala Gly Asn Gly Cys Ser Gly Ala Gly Ala Ala Ala Ala Ala
            325             330             335

Gly Ser Ser Phe Ser Gly Pro Gly Gly Ser Ala Ser Ser Lys Gly Ser
            340             345             350

Phe Ser His Gly Gly Ala Ala Ala Ala Gly Gly Ala Gly Ser Gly
        355             360             365

Gly Cys Thr Gly Phe Gly Glu Asn Glu His Gly Ala Ala Ala Ala Ala
        370             375             380

Gly Gly Asn Glu Lys Ala Thr Gly Gln Asn Ala Asn Asp Arg Gly Ala
385             390             395             400

Ala Ala Ala Gly Tyr Ala Asp His Gly Cys Thr Gly Glu Glu Ala
            405             410             415

Asn Ala Gly Ala Ala Ala Ala Gly Gln Lys Ile Lys Gly Trp Tyr
            420             425             430

Glu Lys Tyr Gly Pro Gly Ser Gly Arg Gln Gly Ala Ala Ala Ala Ala
        435             440             445

Gly Asp Tyr Ser Lys Tyr Phe Ser Ala Thr Glu Asp Ala Lys Arg Gln
    450             455             460

Ser Gly Thr Thr Cys Gly Ala Ala Ala Ala Gly Ala Gly Gln Asn
465             470             475             480

Glu Asn Ala Arg Ala Thr Ala Asp Asp Phe Arg Gly Lys Cys Glu Asn
            485             490             495

Gly Ala Ala Ala Ala Ala Gly His Gln Ser Gly Glu Ala Asp Ile Asn
            500             505             510

Gly Ala His Arg Ala Met Asp Glu Gly Gly Ala Ala Ala Ala Ala Gly
            515             520             525
```

-continued

```
Thr Ser Asp Gly Glu Met Gln Cys Glu Ala Ala Ser Glu Glu Gly Thr
    530             535             540

Gly Ala Ala Ala Ala Ala Gly Lys Asn His Gln Glu Glu Met Lys Gly
545             550             555             560

<210> SEQ ID NO 59
<211> LENGTH: 252
<212> TYPE: PRT
<213> ORGANISM: Artificial Sequence
<220> FEATURE:
<223> OTHER INFORMATION: PRT537

<400> SEQUENCE: 59

Met His His His His His His Ser Ser Gly Ser Ser Lys Asp Gly Val
1               5               10              15

Pro Gly Phe Pro Gly Ser Glu Gly Val Lys Gly Asn Arg Gly Phe Pro
            20              25              30

Gly Leu Met Gly Glu Asp Gly Ile Lys Gly Gln Lys Gly Asp Ile Gly
        35              40              45

Pro Pro Gly Phe Arg Gly Pro Thr Glu Tyr Tyr Asp Thr Tyr Gln Glu
    50              55              60

Lys Gly Asp Glu Gly Thr Pro Gly Pro Pro Gly Pro Arg Gly Ala Arg
65              70              75              80

Gly Pro Gln Gly Pro Ser Gly Pro Pro Gly Val Pro Gly Ser Pro Gly
            85              90              95

Ser Ser Arg Pro Gly Leu Arg Gly Ala Pro Gly Trp Pro Gly Leu Lys
            100             105             110

Gly Ser Lys Gly Glu Arg Gly Arg Pro Gly Lys Asp Ala Met Gly Thr
            115             120             125

Pro Gly Ser Pro Gly Cys Ala Gly Ser Pro Gly Leu Pro Gly Ser Pro
    130             135             140

Gly Pro Pro Gly Pro Pro Gly Asp Ile Val Phe Arg Lys Gly Pro Pro
145             150             155             160

Gly Asp His Gly Leu Pro Gly Tyr Leu Gly Ser Pro Gly Ile Pro Gly
            165             170             175

Val Asp Gly Pro Lys Gly Glu Pro Gly Leu Leu Cys Thr Gln Cys Pro
            180             185             190

Tyr Ile Pro Gly Pro Pro Gly Leu Pro Gly Leu Pro Gly Leu His Gly
            195             200             205

Val Lys Gly Ile Pro Gly Arg Gln Gly Ala Ala Gly Leu Lys Gly Ser
    210             215             220

Pro Gly Ser Pro Gly Asn Thr Gly Leu Pro Gly Phe Pro Gly Phe Pro
225             230             235             240

Gly Ala Gln Gly Asp Pro Gly Leu Lys Gly Glu Lys
            245             250

<210> SEQ ID NO 60
<211> LENGTH: 310
<212> TYPE: PRT
<213> ORGANISM: Artificial Sequence
<220> FEATURE:
<223> OTHER INFORMATION: PRT366

<400> SEQUENCE: 60

Met His His His His His His Pro Glu Pro Pro Val Asn Ser Tyr Leu
1               5               10              15

Pro Pro Ser Asp Ser Tyr Gly Ala Pro Gly Gln Ser Gly Pro Gly Gly
            20              25              30
```

```
Arg Pro Ser Asp Ser Tyr Gly Ala Pro Gly Gly Gly Asn Gly Gly Arg
        35                  40                  45

Pro Ser Asp Ser Tyr Gly Ala Pro Gly Gln Gly Gln Gly Gln Gly Gln
    50                  55                  60

Gly Gln Gly Gly Tyr Ala Gly Lys Pro Ser Asp Ser Tyr Gly Ala Pro
65                  70                  75                  80

Gly Gly Gly Asp Gly Asn Gly Gly Arg Pro Ser Ser Ser Tyr Gly Ala
                85                  90                  95

Pro Gly Gly Gly Asn Gly Gly Arg Pro Ser Asp Thr Tyr Gly Ala Pro
                100                 105                 110

Gly Gly Gly Asn Gly Gly Arg Pro Ser Asp Thr Tyr Gly Ala Pro Gly
            115                 120                 125

Gly Gly Gly Asn Gly Asn Gly Gly Arg Pro Ser Ser Ser Tyr Gly Ala
        130                 135                 140

Pro Gly Gln Gly Gln Gly Asn Gly Asn Gly Gly Arg Pro Ser Ser Ser
145                 150                 155                 160

Tyr Gly Ala Pro Gly Gly Gly Asn Gly Gly Arg Pro Ser Asp Thr Tyr
                165                 170                 175

Gly Ala Pro Gly Gly Gly Asn Gly Gly Arg Pro Ser Asp Thr Tyr Gly
            180                 185                 190

Ala Pro Gly Gly Gly Asn Asn Gly Gly Arg Pro Ser Ser Ser Tyr Gly
        195                 200                 205

Ala Pro Gly Gly Gly Asn Gly Gly Arg Pro Ser Asp Thr Tyr Gly Ala
    210                 215                 220

Pro Gly Gly Gly Asn Gly Asn Gly Ser Gly Gly Arg Pro Ser Ser Ser
225                 230                 235                 240

Tyr Gly Ala Pro Gly Gln Gly Gln Gly Gly Phe Gly Gly Arg Pro Ser
                245                 250                 255

Asp Ser Tyr Gly Ala Pro Gly Gln Asn Gln Lys Pro Ser Asp Ser Tyr
            260                 265                 270

Gly Ala Pro Gly Ser Gly Asn Gly Asn Gly Gly Arg Pro Ser Ser Ser
        275                 280                 285

Tyr Gly Ala Pro Gly Ser Gly Pro Gly Gly Arg Pro Ser Asp Ser Tyr
    290                 295                 300

Gly Pro Pro Ala Ser Gly
305                 310

<210> SEQ ID NO 61
<211> LENGTH: 150
<212> TYPE: PRT
<213> ORGANISM: Artificial Sequence
<220> FEATURE:
<223> OTHER INFORMATION: PRT662

<400> SEQUENCE: 61

Met His His His His His His Gln Asp Pro Tyr Val Lys Glu Ala Glu
1               5                   10                  15

Asn Leu Lys Lys Tyr Phe Asn Ala Gly His Ser Asp Val Ala Asp Asn
            20                  25                  30

Gly Thr Leu Phe Leu Gly Ile Leu Lys Asn Trp Lys Glu Glu Ser Asp
        35                  40                  45

Arg Lys Ile Met Gln Ser Gln Ile Val Ser Phe Tyr Phe Lys Leu Phe
    50                  55                  60

Lys Asn Phe Lys Asp Asp Gln Ser Ile Gln Lys Ser Val Glu Thr Ile
65                  70                  75                  80
```

-continued

```
Lys Glu Asp Met Asn Val Lys Phe Phe Asn Ser Asn Lys Lys Lys Arg
                85                  90                  95

Asp Asp Phe Glu Lys Leu Thr Asn Tyr Ser Val Thr Asp Leu Asn Val
               100                 105                 110

Gln Arg Lys Ala Ile His Glu Leu Ile Gln Val Met Ala Glu Leu Ser
           115                 120                 125

Pro Ala Ala Lys Thr Gly Lys Arg Lys Arg Ser Gln Met Leu Phe Arg
        130                 135                 140

Gly Arg Arg Ala Ser Gln
145                 150

<210> SEQ ID NO 62
<211> LENGTH: 7
<212> TYPE: PRT
<213> ORGANISM: Artificial Sequence
<220> FEATURE:
<223> OTHER INFORMATION: Amino acid sequence

<400> SEQUENCE: 62

Gly Ala Ala Ala Ala Ala Gly
1               5

<210> SEQ ID NO 63
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 63

Ala Ala Ala Ala
1

<210> SEQ ID NO 64
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (4)..(5)
<223> OTHER INFORMATION: Xaa can be any naturally occurring amino acid

<400> SEQUENCE: 64

Gly Pro Gly Xaa Xaa
1               5
```